US012582724B2

(12) United States Patent
Kishnani et al.

(10) Patent No.: US 12,582,724 B2
(45) Date of Patent: Mar. 24, 2026

(54) COMPOSITIONS COMPRISING MICROBIAL POLYPEPTIDES FOR DEGRADING GLYCOGEN AND METHODS FOR THE TREATMENT OF GLYCOGEN STORAGE DISEASES

(71) Applicant: Duke University, Durham, NC (US)

(72) Inventors: Priya Kishnani, Durham, NC (US); Baodong Sun, Durham, NC (US); Jeong-A Lim, Durham, NC (US)

(73) Assignee: Duke University, Durham, NC (US)

( * ) Notice: Subject to any disclaimer, the term of this patent is extended or adjusted under 35 U.S.C. 154(b) by 1252 days.

(21) Appl. No.: 17/432,011

(22) PCT Filed: Feb. 20, 2020

(86) PCT No.: PCT/US2020/019114
§ 371 (c)(1),
(2) Date: Aug. 18, 2021

(87) PCT Pub. No.: WO2020/172465
PCT Pub. Date: Aug. 27, 2020

(65) Prior Publication Data
US 2022/0105204 A1 Apr. 7, 2022

Related U.S. Application Data

(60) Provisional application No. 62/823,894, filed on Mar. 26, 2019, provisional application No. 62/807,790, filed on Feb. 20, 2019.

(51) Int. Cl.
| | |
|---|---|
| *A61K 48/00* | (2006.01) |
| *A61K 38/45* | (2006.01) |
| *A61K 45/06* | (2006.01) |
| *C12N 9/44* | (2006.01) |
| *C12N 15/86* | (2006.01) |

(52) U.S. Cl.
CPC .......... *A61K 48/0058* (2013.01); *A61K 38/45* (2013.01); *A61K 45/06* (2013.01); *C12N 9/2457* (2013.01); *C12N 15/86* (2013.01); *C12Y 302/01041* (2013.01); *C12N 2750/14143* (2013.01); *C12N 2800/22* (2013.01); *C12N 2830/008* (2013.01)

(58) Field of Classification Search
CPC .. A61K 48/0058; C12N 9/2457; C12N 15/86; C12N 2800/22; C12N 9/2451; C12Y 302/01041
See application file for complete search history.

(56) References Cited

U.S. PATENT DOCUMENTS

| | | |
|---|---|---|
| 2008/0227174 A1 | 9/2008 | Bisgard-Frantzen |
| 2011/0281326 A1 | 11/2011 | England |
| 2012/0232133 A1 | 9/2012 | Balazs |
| 2013/0022637 A1 | 1/2013 | Yoshida |
| 2016/0089451 A1 | 3/2016 | Armstrong |

FOREIGN PATENT DOCUMENTS

| | | |
|---|---|---|
| WO | 2009/075815 | 6/2009 |

OTHER PUBLICATIONS

Colella et al. AAV Gene Transfer with Tandem Promoter Design Prevents Anti-transgene Immunity and Provides Persistent Efficacy in Neonate Pompe Mice. Molecular Therapy: Methods & Clinical Development vol. 12,Mar. 15, 2019, p. 85-101 (Year: 2019).*
Shim JH, et al. (2009) Role of maltogenic amylase and pullulanase in maltodextrin and glycogen metabolism of Bacillus subtilis 168. J Bacteriol. 191(15):4835-4844.
Sun B, et al. (2005) Correction of glycogen storage disease type II by an adeno-associated virus vector containing a muscle-specific promoter. Mol Ther. 11(6):889-898.
Sun B, et al. (2007) Enhanced response to enzyme replacement therapy in Pompe disease after the induction of immune tolerance. Am J Hum Genet. 81(5):1042-1049.
Sun B, et al. (2008) Correction of multiple striated muscles in murine Pompe disease through adeno-associated virus-mediated gene therapy. Mol Ther. 16(8):1366-1371.
Sun B, et al. (2010) Immunomodulatory gene therapy prevents antibody formation and lethal hypersensitivity reactions in murine pompe disease. Mol Ther. 18(2):353-360.
Sun B, et al. (2013) Alglucosidase alfa enzyme replacement therapy as a therapeutic approach for glycogen storage disease type III. Mol Genet Metab. 108(2):145-147.
Sun BD, et al. (2003) Long-term correction of glycogen storage disease type II with a hybrid Ad-AAV vector. Mol. Ther. 7(2):193-201.
Taksir TV, et al. (2007) Optimized preservation of CNS morphology for the identification of glycogen in the Pompe mouse model. J. Histochem. Cytochem. 55:991-998.
Thomas J, et al. (2018) Pegvaliase for the treatment of phenylketonuria: Results of a long-term phase 3 clinical trial program (PRISM). Mol Genet Metab. 124(1):27-38.
Vidal P, et al. (2018) Rescue of GSDIII Phenotype with Gene Transfer Requires Liver- and Muscle-Targeted GDE Expression. Mol Ther. 26(3):890-901.
Yi H, et al. (2012) Characterization of a canine model of glycogen storage disease type IIIa. Dis Model Mech. 5(6):804-811.
Yi H, et al. (2014) Correction of glycogen storage disease type III with rapamycin in a canine model. J Mol Med (Berl). 92(6):641-650.
Yi H, et al. (2017) Systemic Correction of Murine Glycogen Storage Disease Type IV by an AAV-Mediated Gene Therapy. Hum Gene Ther. 28(3)286-294.
Young SP, et al. (2003) Analysis of a glucose tetrasaccharide elevated in Pompe disease by stable isotope dilution-electrospray ionization tandem mass spectrometry. Anal Biochem. 316(2):175-180.

(Continued)

*Primary Examiner* — Taeyoon Kim
(74) *Attorney, Agent, or Firm* — Polsinelli PC

(57) ABSTRACT

This disclosure provides isolated nucleic acid molecules comprising nucleic acid sequences encoding microbial polypeptides that are codon optimized for expression in mammalian cells, vectors comprising an immunotolerant dual promoter system, and methods using these polynucleotides and polypeptides to treat glycogen storage diseases and other inherited diseases.

14 Claims, 49 Drawing Sheets

Specification includes a Sequence Listing.

(56) References Cited

OTHER PUBLICATIONS

Zhang P, et al. (2012) Immunodominant liver-specific expression suppresses transgene-directed immune responses in murine pompe disease. Hum Gene Ther. 23(5):460-472.

Zincarelli C, et al. (2008) Analysis of AAV serotypes 1-9 mediated gene expression and tropism in mice after systemic injection. Mol Ther. 16(6):1073-1080.

International Search Report mailed Jul. 1, 2020 for PCT/US2020/019114 filed on Feb. 20, 2020 (Applicant—Duke University) (6 pages).

International Preliminary Report on Patentability mailed Mar. 12, 2021 for PCT/US2020/019114 filed on Feb. 20, 2020 (Applicant—Duke University) (44 pages).

Written Opinion mailed Jul. 1, 2020 for PCT/US2020/019114 filed on Feb. 20, 2020 (Applicant—Duke University) (12 pages).

Bao Y, et al. (1997) Isolation and nucleotide sequence of human liver glycogen debranching enzyme mRNA: identification of multiple tissue-specific isoforms. Gene. 197(1-2):389-398.

Mauro VP, et al. (2014) A critical analysis of codon optimization in human therapeutics. Trends Mol Med. 20(11):604-13.

Kishnani PS, et al. (2010) Glycogen storage disease type III diagnosis and management guidelines. ACMG. Genet Med. 12(7):446-463.

Aguti SA., et al. (2018) The progress of AAV-mediated gene therapy in neuromuscular disorders. Expert Opin Biol Ther. 18(6):681-693.

Akman HO, et al. (2015) A novel mouse model that recapitulates adult-onset glycogenosis type 4. Hum Mol Genet. 24(23):6801-6810.

Asokan A, et al. (2012) The AAV vector toolkit: poised at the clinical crossroads. Mol Ther. 20(4):699-708.

Balkaya M, et al. (2013) Assessing post-stroke behavior in mouse models of focal ischemia. J Cereb Blood Flow Metab. 33(3):330-338.

Ban HR, et al. (2009) Living Donor Liver Transplantation in a Korean Child with Glycogen Storage Disease Type IV and a GBE1 Mutation. Gut Liver. 2009;3(1):60-63.

Bao Y, et al. (1996) Hepatic and neuromuscular forms of glycogen storage disease type IV caused by mutations in the same glycogen-branching enzyme gene. J Clin Invest. 97(4):941-948.

Brooks ED, et al. (2016) Natural Progression of Canine Glycogen Storage Disease Type IIIa. Comp Med. 66(1):41-51.

Bruno C, et al. (2004) Clinical and genetic heterogeneity of branching enzyme deficiency (glycogenosis type IV). Neurology. 63(6):1053-1058.

Chaplan SR, et al. (1994) Quantitative assessment of tactile allodynia in the rat paw. J Neurosci Methods. 53(1):55-63.

Davis MK, et al. (2008) Liver transplantation in children with glycogen storage disease: controversies and evaluation of the risk/benefit of this procedure. Pediatr Transplant. 12(2):137-45.

Demo E, et al. (2007) Glycogen storage disease type III-hepatocellular carcinoma a long-term complication? J Hepatol. 46(3):492-8.

Dixon WJ (1980) Efficient analysis of experimental observations. Annu Rev Pharmacol Toxicol. 20:441-462.

Franco LM, et al. (2005) Evasion of immune responses to introduced human acid alpha-glucosidase by liver-restricted expression in glycogen storage disease type II. Mol Ther. 12(5):876-884.

Gao GP, et al. (2002) Novel adeno-associated viruses from rhesus monkeys as vectors for human gene therapy. Proc Natl Acad Sci USA. 99(18):11854-11859.

Guggino WB, et al. (2017) Adeno-Associated Virus (AAV) gene therapy for cystic fibrosis: current barriers and recent developments. Expert Opin Biol Ther. 17(10):1265-1273.

Gupta S, et al. (2018) Association of immune response with efficacy and safety outcomes in adults with phenylketonuria administered pegvaliase in phase 3 clinical trials. EBioMedicine. 37:366-373.

Harding CO, et al. (2018) Pegvaliase for the treatment of phenylketonuria: A pivotal, double-blind randomized discontinuation Phase 3 clinical trial. Mol Genet Metab. 124(1):20-26.

Heck DH, et al. (2008) Analysis of cerebellar function in Ube3a-deficient mice reveals novel genotype-specific behaviors. Hum Mol Genet. 17(14):2181-2189.

Hermens WT, et al. (1999) Purification of recombinant adeno-associated virus by iodixanol gradient ultracentrifugation allows rapid and reproducible preparation of vector stocks for gene transfer in the nervous system. Hum Gene Ther. 10(11):1885-1891.

Inagaki K, et al. (2006) Robust systemic transduction with AAV9 vectors in mice: efficient global cardiac gene transfer superior to that of AAV8. Mol Ther. 14(1):45-53.

Keeler AM, et al. (2017) Gene Therapy: Progress and Future Directions. Clin Transl Sci. 10(4):242-248.

Kumlien J, et al. (1988) Urinary excretion of a glucose-containing tetrasaccharide. A parameter for increased degradation of glycogen. Clin Chim Acta. 176(1):39-48.

Klein CJ. DNMT1-Related Disorder. Feb. 16, 2012 [updated Jan. 31, 2019]. In: Adam MP, Ardinger HH, Pagon RA, Wallace SE, Bean LJH, Mirzaa G, Amemiya A, editors. GeneReviews® [Internet]. Seattle (WA): University of Washington, Seattle; 1993-2021.

Knab AM, et al. (2009) Repeatability of exercise behaviors in mice. Physiol Behav. 98(4):433-440.

Labrune P, et al. (1991) Cardiomyopathy in glycogen-storage disease type III: clinical and echographic study of 18 patients. Pediatr Cardiol. 12(3):161-163.

Labrune P, et al. (1997) Hepatocellular adenomas in glycogen storage disease type I and III: a series of 43 patients and review of the literature. J Pediatr Gastroenterol Nutr. 24(3):276-279.

Lee PJ, et al. (1997) Comparison of the functional significance of left ventricular hypertrophy in hypertrophic cardiomyopathy and glycogenosis type III. Am J Cardiol. 79(6):834-838.

Leger M, et al. (2013) Object recognition test in mice. Nat Protoc. 8(12):2531-2537.

Lim JA, et al. (2019) Intravenous Injection of an AAV-PHP.B Vector Encoding Human Acid α-Glucosidase Rescues Both Muscle and CNS Defects in Murine Pompe Disease. Mol. Ther. 12:233-245.

Lim JA, et al. (2020) A Novel Gene Therapy Approach for GSD III Using an AAV Vector Encoding a Bacterial Glycogen Debranching Enzyme. Mol. Ther.—Meth. & Clin. Dev. 18:240-249.

Lock M, et al. (2010) Rapid, simple, and versatile manufacturing of recombinant adeno-associated viral vectors at scale. Human Gene Therapy. 21(10):1259-1271.

Lossos A, et al. (1998) Adult polyglucosan body disease in Ashkenazi Jewish patients carrying the Tyr329Ser mutation in the glycogen-branching enzyme gene. Ann Neurol. 44(6):867-872.

Luong TN, et al. (2011) Assessment of motor balance and coordination in mice using the balance beam. J Vis Exp. (49):2376.

Lynch CM, et al. (2005) High-resolution light microscopy (HRLM) and digital analysis of Pompe disease pathology. J. Histochem. Cystochem. 53(1):63-73.

Manwaring V, et al. (2012) Urine analysis of glucose tetrasaccharide by HPLC; a useful marker for the investigation of patients with Pompe and other glycogen storage diseases. J Inherit Metab Dis. 35(2):311-316.

Miniarikova J, et al. (2017) AAV5-miHTT gene therapy demonstrates suppression of mutant huntingtin aggregation and neuronal dysfunction in a rat model of Huntington's disease. Gene Ther. 24(10):630-639.

Mochel F, et al. (2012) Adult polyglucosan body disease: Natural History and Key Magnetic Resonance Imaging Findings. Ann Neurol. 72(3):433-441.

Mogahed EA, et al. (2015) Skeletal and cardiac muscle involvement in children with glycogen storage disease type III. Eur J Pediatr. 174(11):1545-1548.

Moses SW, et al. (1986) Neuromuscular involvement in glycogen storage disease type III. Acta Paediatr Scand. 75(2):289-296.

Moses SW, et al. (2002) The variable presentations of glycogen storage disease type IV: a review of clinical, enzymatic and molecular studies. Curr Mol Med. 2(2):177-188.

Olson LJ, et al. (1984) Cardiac involvement in glycogen storage disease III: morphologic and biochemical characterization with endomyocardial biopsy. Am J Cardiol. 53(7):980-981.

(56) References Cited

OTHER PUBLICATIONS

Pompe Disease Diagnostic Working G, et al. (2008) Methods for a prompt and reliable laboratory diagnosis of Pompe disease: report from an international consensus meeting. Mol Genet Metab. 93(3):275-281.

Ramachandran PS, et al. (2017) Evaluation of Dose and Safety of AAV7m8 and AAV8BP2 in the Non-Human Primate Retina. Hum Gene Ther. 28(2):154-167.

Ruzo A, et al. (2012) Correction of pathological accumulation of glycosaminoglycans in central nervous system and peripheral tissues of MPSIIIA mice through systemic AAV9 gene transfer. Hum Gene Ther. 23(12):1237-1246.

Samaranch L, et al. (2012) Adeno-associated virus serotype 9 transduction in the central nervous system of nonhuman primates. Hum Gene Ther. 23(4):382-389.

Scharr KL, et al. (2010) Functional assessments in the rodent stroke model. Exp Transl Stroke Med. 2(1):13.

Selby R, et al. (1993). Liver transplantation for type I and type IV glycogen storage disease. Eur J Pediatr. 152 Suppl 1 (Suppl 1):S71-76.

Sentner CP, et al. (2016) Glycogen storage disease type III: diagnosis, genotype, management, clinical course and outcome. J Inherit Metab Dis. 39(5):697-704.

\* cited by examiner

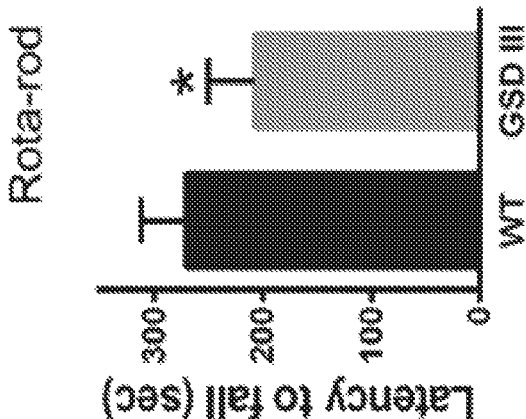
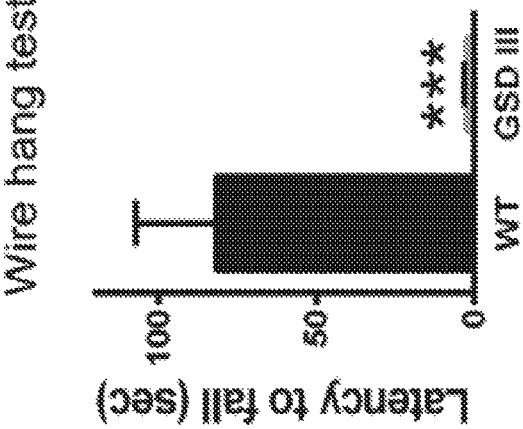
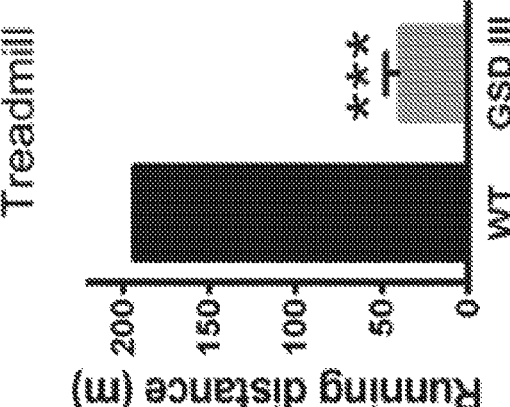
FIG. 4

FIG. 22

```
MVSIRRSFEAYVDDMNIITVLIPAEQKEIMTPPERLETEITDFPLAVREEYSLEAKYKYVCVSDHPVTFGKIHCVRASSG
HKTDLQIGAVIRTAAFDDEFYDGELGAVYTADHTVFKVWAPAATSAAVKLSHPNKSGRTFQMTRLEKGVYAVTVTGDLH
GYEYLFCICNNSEWMETVDQYAKAVTVNGEKGVVLRPDQMKWTAPLKPFSHPVDAVIYETHLRDFSIHENSGMINKGKYL
ALTETDTQTANGSSSGLAYVKELGVTHVELLPVNDFAGVDEEKPLDAYNWGYNPLHFFAPEGSYASNPHDPQTRKTELKQ
MINTLHQHGLRVILDVVFNHVYKRENSPFEKTVPGYFFRHDECGMPSNGTGVGNDIASERRMARKFIADCVVYWLEEYNV
DGFRFDLLGILDIDTVLYMKEKATKAKPGILLFEGEGWDLATPLPHEQKAALANAPRMPGIGFFNDMFRDAVKGNTFHLKA
TGEALGNGESAQAVMHGIAGSSGWKALAPIVPEPSQSINYVESHDNHTEWDKMSFALPQENDSRKRSRQRLAAAIILLAQ
GVPFIHSGQEFFRTKQGVENSYQSSDSINQLDWDRRETFKEDVHYIRRLISLRKAHPAFRLRSAADIQRHLECLTLKEHL
IAYRLYDLDEVDEWKDIIVIHHASPDSVEWRLPNDIPYRLLCDPSGFQEDPTEIKKTVAVNGIGTVILYLASDLKSFA
```

(SEQ ID NO:01)

FIG. 23

```
ATGGTCAGCATCCGCCGCAGCTTCGAAGCGTATGTCGATGACATGAATATCATTACTGTTCTGATTCCTGCTGAACAAAAGGAAATCA
TGACACCGCCGTTTCGGCTTGAGACAGAAATAACAGATTTTCCTCTGGCTGTCAGGGAGGAATACTCCCTTGAAGCAAAATACAAGTA
CGTCTGCGTATCCGACCATCCTGTGACATTTGGAAAAATCCATTGCGTCAGAGCATCCAGCGGCCACAAAACGGATCTCCAAATTGGC
GCGGTCATCCGGACGGCAGCGTTTGATGACGAATTTTATTATGACGGAGAGCTGGGCGCCGTTTATACCGCGGATCATACCGTATTTA
AAGTATGGGCGCCTGCTGCAACCTCAGCTGCTGTCAAGCTTTCACACCCCAATAAAAGCGGGCGCACATTCCAAATGACTCGCTTGGA
AAAAGGCGTCTATGCCGTTACGGTCACAGGTGACCTTCACGGATATGAGTATTTGTTTTGCATCTGCAACAATTCAGAATGGATGGAA
ACAGTTGACCAGTATGCCAAGGCTGTGACTGTAAATGGAGAGAAGGGCGTCGTCTTGCGCCCCGGATCAAATGAAATGGACTGCTCCTC
TTAAACCATTCTCACACCCTGTGGATGCCGTCATCTATGAGACGCATCTTCGCGACTTCTCCATCCATGAAAACAGCGGCATGATAAA
CAAGGGAAAATACTTAGCGCTGACGGAAACTGATACACAAACCGCAAATGGCAGTTCTTCGGGATTAGCGTATGTAAAAGAGCTTGGT
GTGACACATGTGGAGCTTCTGCCGGTGAATGATTTTGCCGGAGTTGATGAAGAGAAGCCGCTTGATGCATACAATTGGGGATATAACC
CGCTTCATTTCTTTGCCCCGGAGGGAAGCTATGCCTCAAATCCTCATGATCCTCAAACGAGAAAAACAGAGCTGAAACAAATGATCAA
TACCCTGCATCAGCACGGTCTGCGAGTCATTCTGGATGTTGTTTTTAACCATGTGTATAAGAGGGAGAATTCCCCCTTTGAAAAGACA
GTGCCCGGTTATTTTTTCCGGCACGACGAATGTGGGATGCCATCAAACGGCACCGGCGTTGGCAATGATATTGCATCAGAAAGAAGGA
TGGCAAGAAAATTCATTGCGGATTGCGTGGTCTATTGGCTTGAAGAATACAATGTTGACGGCTTCCGCTTTGATCTCCTCGGGATTTT
AGATATTGACACCGTGCTTTATATGAAAGAGAAAGCAACTAAGGCAAAGCCCGGAATCCTGCTTTTTGGAGAAGGGTGGGACCTGGCT
ACACCGCTGCCGCATGAACAGAAAGCTGCTTTGGCGAACGCGCCAAGAATGCCGGGCATCGGCTTTTTTAATGATATGTTTCGTGACG
CTGTAAAAGGGAACACCTTTCACCTTAAGGCAACAGGGTTTGCGCTCGGCAACGGTGAATCAGCACAAGCTGTGATGCATGGAATTGC
CGGGTCTTCCGGATGGAAGGCATTAGCACCGATTGTTCCGGAACCAAGCCAGTCCATCAATTATGTCGAATCACACGACAATCACACC
TTTTGGGATAAAATGAGCTTTGCGCTTCCTCAAGAAAATGACAGCCGAAAGCGAAGCAGGCAAAGGCTTGCAGCCGCGATTATTTGC
TTGCCCAAGGGGTGCCGTTTATTCACAGCGGCCAGGAATTTTTCCGGACGAAGCAGGGAGTGGAAAACAGCTATCAATCCAGTGACAG
CATCAACCAGCTCGACTGGGATCGCCGTGAAACATTCAAAGAAGATGTTCACTATATCCGCAGGCTGATCTCGCTGAGAAAAGCGCAT
CCTGCATTCCGTCTTAGGTCCGCTGCAGACATCCAGCGCCATCTTGAATGCTTGACGCTAAAAGAACACCTTATCGCATACAGGCTTT
ATGATCTTGACGAGGTTGACGAATGGAAAGATATCATTGTTATCCATCACGCGAGTCCAGACTCCGTCGAGTGGAGGCTGCCAAACGA
CATACCTTATCGGCTTTTATGTGATCCATCAGGATTTCAGGAAGACCCAACAGAAATCAAGAAAACGGTTGCAGTAAACGGCATCGGA
ACGGTTATCTTATATTTAGCATCAGATCTTAAGAGTTTTGCTTGA
```

(SEQ ID NO:02)

FIG. 24

```
ATGGTGAGCATCCGGAGATCCTTCGAGGCCTACGTGGACGATGATGAACATCATCACCGTGCTGATCCGAGCGCAGGAAGGAGATCATGACACCC
CTTTCCGGCTCGGAGAGACCGAGATCACAGACTTTCCCCTGGCCGTGAGAGGAGTAGCCTGGAGGCCAAGTACAGTACGTGTGCGTGAGCGATCA
CCCTGTGACCTTTGGCAAGATCCCACTGCGTGCGGGGCAAGCTCCGGACGTGTACACCGCCGTGTACCTGGGCAGCCAGCATCCGCCGCAGTGA
GATGAGTTTTACTATGACGGAGAGCTGGGAGCCGTGTACACCGCCGTGTACCTGGGCAGCCAGCATCCGCCGCAGTGA
AGCTGAGCGACCCCAACAAGTCCGGCAGGACCTTTCAGATGACACGCCTGGAGAAGGGCGTGTACGCCGTGACCGTGACAGGCGATCTGCACGGCTA
CGAGTATCTGTTCTGCATCTGTAACAATTCTGAGTGGATGGAGACCGTGGATCAGTATGCCAAGGCCGTGACAGTGAATGGAGAGGGAGTGGTG
CTTGAGGCCAGAACCAGATGAAGTGGACCGCACCCCTGAAGCCTTTCAGCACCCTGTGACGCCGTGATCTACGAACAGCCAACGGCTCTAGCTCCGGCCTGGCCTA
TCCACGAGACAGCGGCATGATCAATAAGGGCAAGTACCCTGGCCCTGAATGACTTTGCCGCGGTGAATGACTTTGCCAGCAACCCACAGACCAACCCCAGAACGGCTCTAGCTGCCTACAACTGGGGC
TGTGAAGGAGCTGGGAGTGACCCACGTGGAGCTGCGCTCCGAGGCTCTTATGCCCAGCAACCCACACGACCCCCAGACCAACCGCGAGACCAGGGATGATCAATA
CACTGCACCAGCACGGCCTGAGAGTGACCTGGCATGCCATCTAACCGCGGTGGGCAATGATGATATCGCCGAGGAGGGCATGGCCGGAGTTCATCGCC
TTTCTTTCGGCACGAGCAGTGCCGACGAGTGCTTCAGATTTGCATCTCGCTGGCCATCCTGGACCGTATAACGTGGACGAGTATAAACGTGGACGAGTATAAACCGTCTGCTTCTACATGAAGG
GACTGCCGTGGTGTACTGGCTGGAGGAGTATAAACGTGGACGAGTATAAACGTGGCCAACCCACTGCCACACCCACTGCCAACCCACTGCCACACGAGAGCCGCCCTGCAAA
AGAAGGCCACAAAGCCAGCCAGCATCCTGCTGTTCCGGAGAGGGATGGACCTGCCAACCCACTGCCACACCTTCCACCTGAAGGCCCACAGGCTTTGCACTG
CGCACCTAGGATGCCAGGCATCGGCTTCTTTAACGACATGTTTCGGCATGCCGTGAAGGGCAATACCTTCCACCTGAAGGCCCACAGGCTTTGCACTG
GGAAATGGAGAGTCCGCCCAGCCGTGATCCACGGAATCGCACGGATCTAGCGGATGGAGGCCCTGGCCTGAGCCAAGCCAGTCCA
TCAACTACGTGGAGTCCACGACAATCACACCTTCTGGGATAAGATGTCTTTTGCCCTGCCTCCAGGAGAATGATTCTAGGAAGAGAAGCAGGCAGCG
CCTGGCAGCAGCAATCATCCTGCTGGCCAGGGCGTGCCATTCATCCACGAGGCGTGCCATTCATCCACGAGGGCCAGGAGTTCTTTCGGACCAAGCAGGGCGTGGAGAACTCCTAC
CAGTCCTCTGATTCTATCAATCAGCTGGACTGGAGATCGCCGCGAGATCCCGCAGACATCCAGAGAGGCACCTGAGTGCCTGACCCTGAGGAGGCACCTGATCGCCTACAGACTGTATGA
CACACCCAGCCTTTCGGCTGAGATCCGTGAGATGTTTCGGCTGAGATCCGGAGTGCCCAGAGGCACCTGAGTGCCTGACCCTGATCGCCTACAGACTGTATGA
CCTGGATGAGGTGGACGAGTGGAAGGATATATCATCGTGACTCGTGGAGTGGCGGCGTGCCGCTCCCCTGACTCTGTGGAGTGGCGGCGTGCCGCCAACGATATCCCTTACAGA
CTGCCTGTGCGACCCCTCCGGCTTCCAGGAGGATCCTACCGAGGATCCTACCGAGGATCAAGAGACGAGTGCCGCCGCACCGTGATCGTGAATGGCCATCGGCACCGTGATCCTGTATCTGGCCT
CCGACCTGAAGTCTTTTGCCTGA
```

(SEQ ID NO:03)

FIG. 25

>sp|P15067|GLGX_ECOLI Glycogen debranching enzyme
OS=Escherichia coli (strain K12) OX=83333 GN=glgX PE=1 SV=3
MTQLAIGKPAPLGAHYDGQGVNFTLFSAHAERVELCVFDANGQEHRYDLPGHSGDIWHGY
LPDARPGLRYGYRVHGPWQPAEGHRFNPAKLLIDPCARQIDGEFKDNPLLHAGHNEPDYR
DNAAIAPKCVVVVDHYDWEDDAPPRTPWGSTIIYEAHVKGLTYLHPEIPVEIRGTYKALG
HPVMINYLKQLGITALELLPVAQFASEPRLQRMGLSNYWGYNPVAMFALHPAYACSPETA
LDEFRDAIKALHKAGIEVILDIVLNHSAELDLDGPLFSLRGIDNRSYYWIREDGDYHNWT
GCGNTLNLSHPAVVDYASACLRYWVETCHVDGFRFDLAAVMGRTPEFRQDAPLFTAIQNC
PVLSQVKLIAEPWDIAPGGYQVGNFPPLFAEWNDHFRDAARRFWLHYDLPLGAFAGRFAA
SSDVFKRNGRLPSAAINLVTAHDGFTLRDCVCFNHKHNEANGEENRDGTNNNYSNNHGKE
GLGGSLDLVERRRDSIHALLTTLLLSQGTPMLLAGDEHGHSQHGNNNAYCQDNQLTWLDW
SQASSGLTAFTAALIHLRKRIPALVENRWWEEGDGNVRWLNRYAQPLSTDEWQNGPKQLQ
ILLSDRFLIAINATLEVTEIVLPAGEWHAIPPFAGEDNPVITAVWQGPAHGLCVFQR (SEQ ID NO:04)

FIG. 26

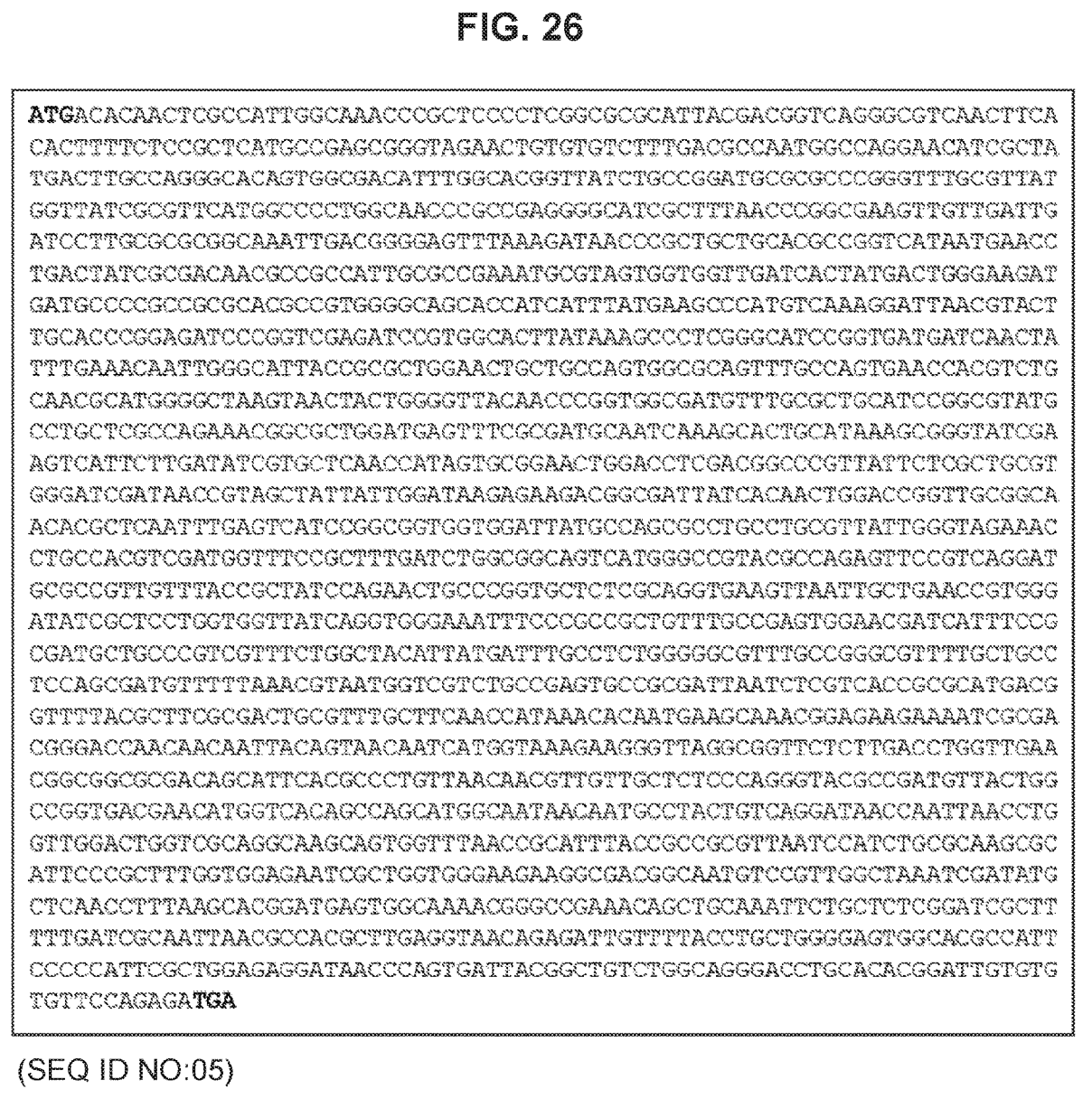

```
ATGACACAACTCGCCATTGGCAAACCCGCTCCCCTCGGCGCGCATTACGACGGTCAGGGCGTCAACTTCA
CACTTTTCTCCGCTCATGCCGAGCGGGTAGAACTGTGTGTCTTTGACGCCAATGGCCAGGAACATCGCTA
TGACTTGCCAGGGCACAGTGGCGACATTTGGCACGGTTATCTGCCGGATGCGCGCCCGGGTTTGCGTTAT
GGTTATCGCGTTCATGGCCCCTGGCAACCCGCCGAGGGGCATCGCTTTAACCCGGCGAAGTTGTTGATTG
ATCCTTGCGCGGGCAAATTGACGGGGAGTTTAAAGATAACCCGCTGCTGCACGCCGGTCATAATGAACC
TGACTATCGCGACAACGCCGCCATTGCGCCGAAATGCGTAGTGGTGGTTGATCACTATGACTGGGAAGAT
GATGCCCCGCCGCGCACGCCGTGGGGCAGCACCATCATTTATGAAGCCCATGTCAAAGGATTAACGTACT
TGCACCCGGAGATCCCGGTCGAGATCCGTGGCACTTATAAAGCCCTCGGGCATCCGGTGATGATCAACTA
TTTGAAACAATTGGGCATTACCGCGCTGGAACTGCTGCCAGTGGCGCAGTTTGCCAGTGAACCACGTCTG
CAACGCATGGGGCTAAGTAACTACTGGGGTTACAACCCGGTGGCGATGTTTGCGCTGCATCCGGCGTATG
CCTGCTCGCCAGAAACGGCGCTGGATGAGTTTCGCGATGCAATCAAAGCACTGCATAAAGCGGGTATCGA
AGTCATTCTTGATATCGTGCTCAACCATAGTGCGGAACTGGACCTCGACGGCCCGTTATTCTCGCTGCGT
GGGATCGATAACCGTAGCTATTATTGGATAAGAGAAGACGGCGATTATCACAACTGGACCGGTTGCGGCA
ACACGCTCAATTTGAGTCATCCGGCGGTGGTGGATTATGCCAGCGCCTGCCTGCGTTATTGGGTAGAAAC
CTGCCACGTCGATGGTTTCCGCTTTGATCTGGCGGCAGTCATGGGCCGTACGCCAGAGTTCCGTCAGGAT
GCGCCGTTGTTTACCGCTATCCAGAACTGCCCGGTGCTCTCGCAGGTGAAGTTAATTGCTGAACCGTGGG
ATATCGCTCCTGGTGGTTATCAGGTGGAAAATTTCCCGCCGCTGTTTGCCGAGTGGAACGATCATTTCCG
CGATGCTGCCCGTCGTTTCTGGCTACATTATGATTTGCCTCTGGGGGCGTTTGCCGGGCGTTTTGCTGCC
TCCAGCGATGTTTTTAAACGTAATGGTCGTCTGCCGAGTGCCGCGATTAATCTCGTCACCGCGCATGACG
GTTTTACGCTTCGCGACTGCGTTTGCTTCAACCATAAACACAATGAAGCAAACGGAGAAGAAATCGCGA
CGGGACCAACAACAATTACAGTAACAATCATGGTAAAGAAGGGTTAGGCGGTTCTCTTGACCTGGTTGAA
CGGCGGCGCGACAGCATTCACGCCCTGTTAACAACGTTGTTGCTCTCCCAGGGTACGCCGATGTTACTGG
CCGGTGACGAACATGGTCACAGCCAGCATGGCAATAACAATGCCTACTGTCAGGATAACCAATTAACCTG
GTTGGACTGGTCGCAGGCAAGCAGTGGTTTAACCGCATTTACCGCCGCGTTAATCCATCTGCGCAAGCGC
ATTCCCGCTTTGGTGGAGAATCGCTGGTGGGAAGAAGGCGACGGCAATGTCCGTTGGCTAAATCGATATG
CTCAACCTTTAAGCACGGATGAGTGGCAAAACGGGCCGAAACAGCTGCAAATTCTGCTCTCGGATCGCTT
TTTGATCGCAATTAACGCCACGCTTGAGGTAACAGAGATTGTTTTACCTGCTGGGGAGTGGCACGCCATT
CCCCCATTCGCTGGAGAGGATAACCCAGTGATTACGGCTGTCTGGCAGGGACCTGCACACGGATTGTGTG
TGTTCCAGAGATGA
```

(SEQ ID NO:05)

FIG. 27

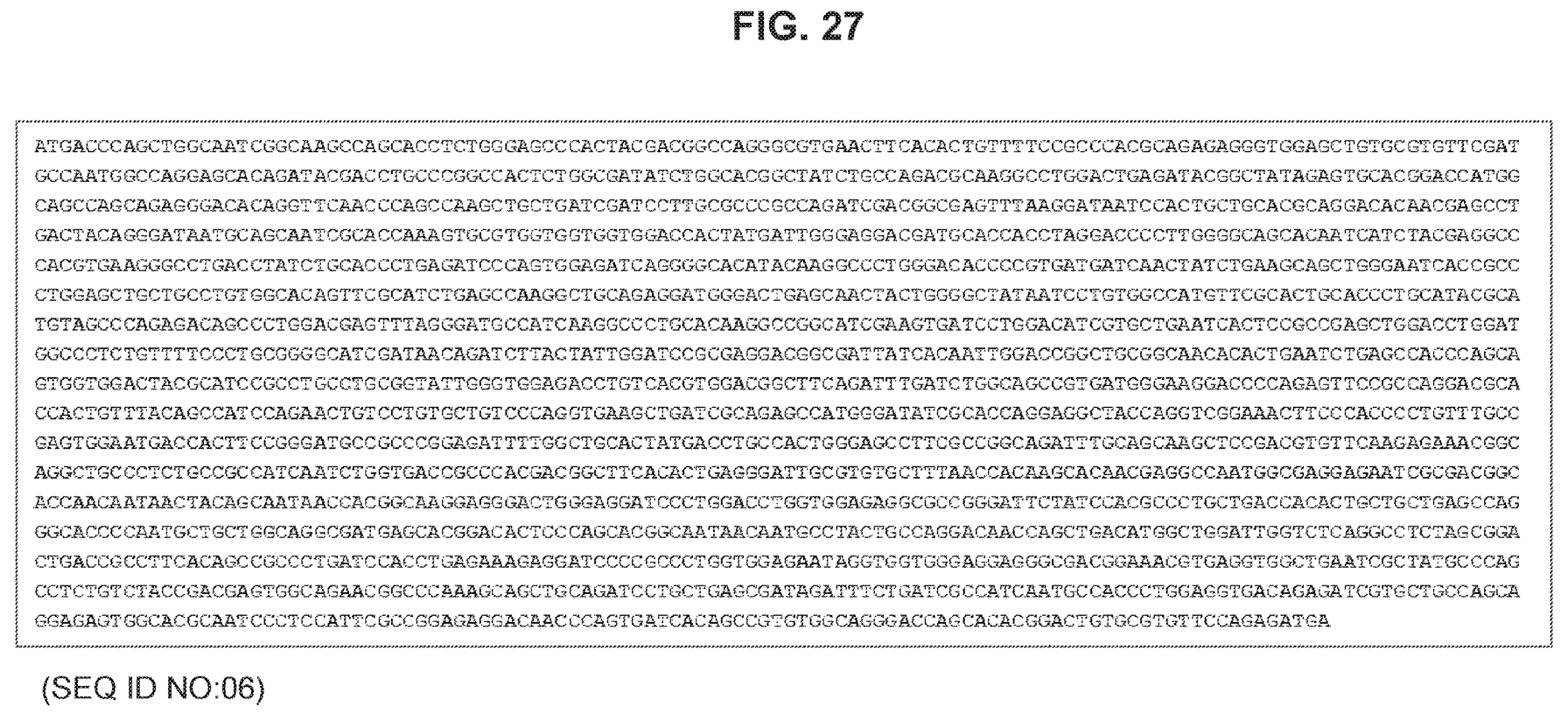

```
ATGACCCAGAGCTGGCAATCGGCAAGCCAGCACCTCTGGGAGCCCACTACGACGGCCAGGGCGGTGAACTTCACACTGTTTCCGCCCACGCAGCAGAGGGTGGAGCTGTGCGTGTTCGAT
GCCAATGGCCAGGAGCACAGATACGACGACCTGCCCGGCCACTCTGGCGATATCTGGCAGACGCAAGGCCTGAGACTGAGATACGGCTATAGAGTGCACGGACCACGAGCCT
CAGCCAGCAGAGGGACACAGGTTCAACCCAGCCAAGCTGCTGATCGATCCGATCCTTGCGCGCCCAGATCGACGGCGAGTTAAGGATAATCCACTGCTGCACCGCAGGACAACAATCATCTACGAGGCC
GACTACAGAGGGATAATGCACAATCGGCACCAAAGTGCGTGGTGGTGGACGATGCACATACAAGGCCCTGGGACACCCCGTGATGATCAACTAACTATCTGAAGCAGCTGGGAATCACCGCC
CACGTGAAGGGCCTGACCTATCTGCGACCCTGCCACCAGTTCGCATCTGAGCCAAGGCTGCAGAGGATGGGACTGCAGAGGAGGCAACTACTGGGGCTATAATCCTGTGGGCCATGTTCGCCACCTGCATACGGCA
CTGGAGCTGCTGCCTGTGCGACAGTTCGCATCTGAGCCAAGGCTGCAGAGGATGGGACTGCAGAGGAGGCAACTACTGGGGCTATAATCCTGTGGGCCATGTTCGCCACCTGCATACGGCA
TGTAGCCCAGAGACAGCCCCTGGACGAGTTTAGGGATGCCATCAAGGGCCCTGCACAAGGCCGGCATCGAGTGCATCGAGTGCATCGGCAGCGCA
GGCCCTCTGTTTCCCTGCGGGCATCCGGCCTGCCTGCGGCTATTGGGACCTGTCACCGTCGGGTATCGCAGGCGGCTTCAGATTGATCTGGCAGCGGCCGTGATCGCAGGCCGTGATGGCAGGACCCCAGGACGCA
GTGGTGGACTACGGCATCCGGCCTGCCTGCGGCTATTGGGACCTGTCACCGTCGGGTATCGCAGGCGGCTTCAGATTGATCTGGCAGCGGCCGTGATCGCAGGCCGTGATGGCAGGACCCCAGGACGCA
CCCACTGTTTACAGGCCATCCGAGTGTCCTGTGCTGTCCCAGTGAAGGTGAAGCTGATCGCAGAGCCATGGCCATGGATATCGGCAGGGCTTCCCACCCCTGTTTGCC
GAGTGGAATGACCACTCCGGGATGCCGGCCCATCAATCTGTGACCGGCTTCACACTGAGGGATTTGGCTGCCACTATGCCTGCGTGTGCTTTAACCACAAGCACCTCCGACGTGTTCAAGAGAATCGGCGACGGC
AGGCTGCCCTCTGCCGGCCATCAATCTGTGACCGGCAAGGAGGGACTGGAGGATCCCTGGACCTGGTGGAGAGGCGCGCCCTGCTGACCGCCCTGCTGACCCGCCTGCTGCAGGCCTCTAGCGGA
ACCAACAATAACTACAGCAATAACCACGGCAAGGAGGACACTCCCAGGACACTCCCCAGGACAACCAGCTGACCATGGCTGGATGGTGCTGGAATGGCTGGAATCGCTATGCCCAG
GGCGACCCCAATGCCTGCTGGCAGCGGATGAGCACTGGGACACTCCCCAGGACAACCAGCTGACCATGGCTGGATGGTGCTGGAATGGCTGGAATCGCTATGCCCAG
CTGACGGCCTTCACACGAGCCGGCCGCCCTGATCCCCCTGAGCAGGATCCCCGCCCTGGTGAGCCAGATGGTGGGAGGAATAGGTGGTGGCTGGAATCGGCTGAATCGGCTATGCCCAG
CCTCTGTCTACCGGACGAGTGGCACGCAATCCCATTCGGCCGGGAGCACTACAGCCCAGTGATCAACCCAGTGGCCAGGGACCACCAGCCACGACCACCAGCCACGACCCAGGACCACCAGCCACGACCGTGTGGCGTGTTCCAGTGAGCCAGCA
GGAGAGTGGCACGCAATCCCATTCGGCCGGGAGCACTACAGCCCAGTGATCAACCCAGTGGCCAGGGACCACCAGCCACGACCGTGTGGCGTGTTCCAGAGATGA
```

(SEQ ID NO:06)

FIG. 28

MKCPKILAALLGCAVLAGVPAMPAHAAINSMSLGASYDAQQANITFRVYSSQATRIVLYLYSAGYGVQESATYTLSPAGSGVWAVTVPVSSIKAAG
ITGAVYYGYRAWGPNWPYASNWGKGSQAGFVSDVDANGDRFNPNKLLLDPYAQEVSQDPLNPSNQNGNVFASGASYRTTDSGIYAPKGVVLV
PSTQSTGTKPTRAQKDDVIYEVHVRGFTEQDTSIPAQYRGTYYGAGLKASYLASLGVTAVEFLPVQETQNDANDVVPNSDANQNYWGYMTENY
FSPDRRYAYNKAAGGPTAEFQAMVQAFHNAGIKVVYMDVVYNHTAEGGTWTSSDPTTATIYSWRGLDNATYYELTSGNQYFYDNTGIGANFNTY
NTVAQNLIVDSLAYWANTMGVDGFRFDLASVLGNSCLNGAYTASAPNCPNGGYNFDAADSNVAINRILREFTVRPAAGGSGLDLFAEPWAIGG
NSYQLGGFPQGWSEWNGLFRDSLRQAQNELGSMTIYVTQDANDFSGSSNLFQSSGRSPWNSINFIDVHDGMTLKDVYSCNGANNSQAWPY
GPSDGGTSTNYSWDQGMSAGTGAAVDQRRAARTGMAFEMLSAGTPLMQGGDEYLRTLQCNINNAYNLDSSANWLTYSWTTDQSNFYTFAQ
RLIAFRKAHPALRPSSWYSGSQLTWYQPSGAVADSNYWNNTSNYAIAYAINGPSLGDSNSIYVAYNGWSSSVTFTLPAPPSGTQWYRVTDTCDW
NDGASTFVAPGSETLIGGAGTTYGQCGQSLLLISK (SEQ ID NO:07)

FIG. 29A

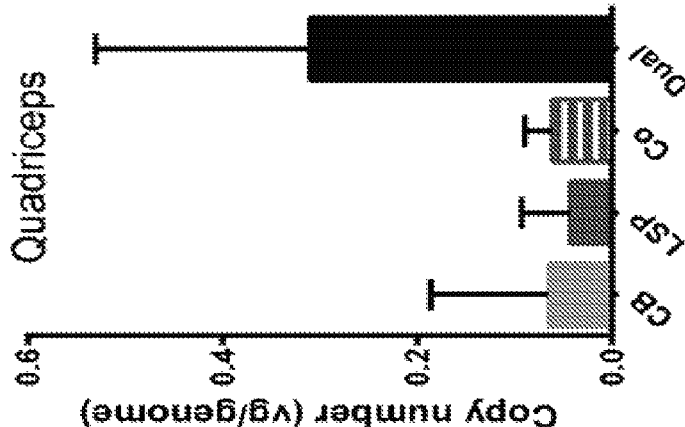
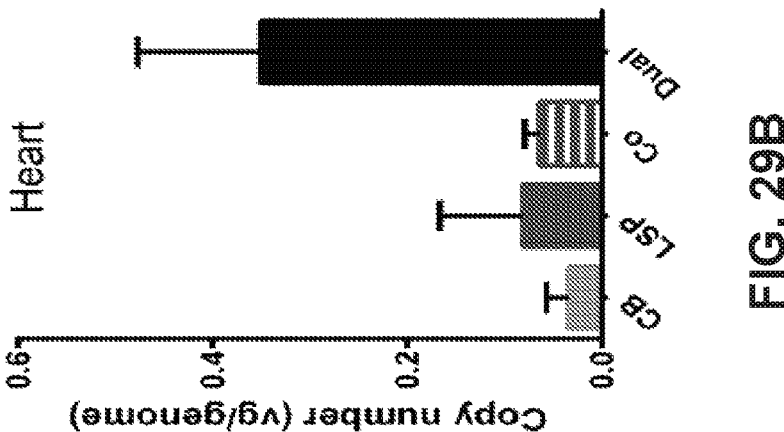
FIG. 29B
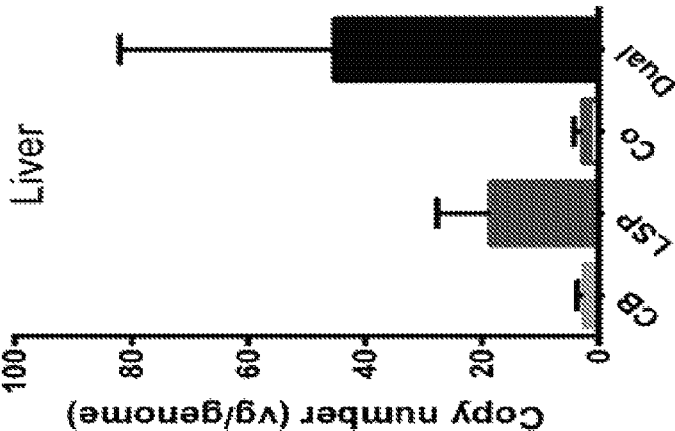

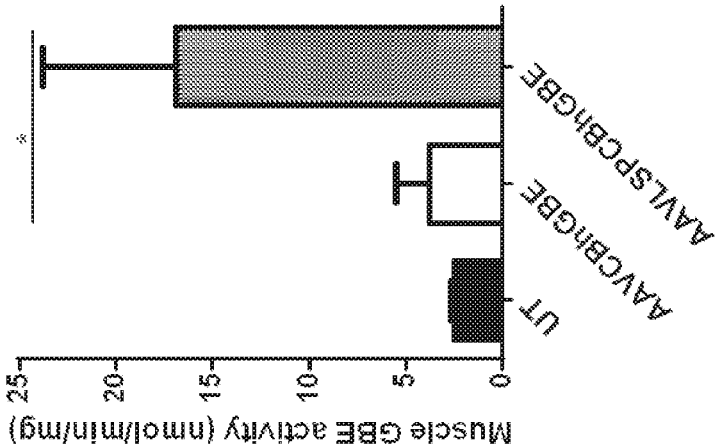
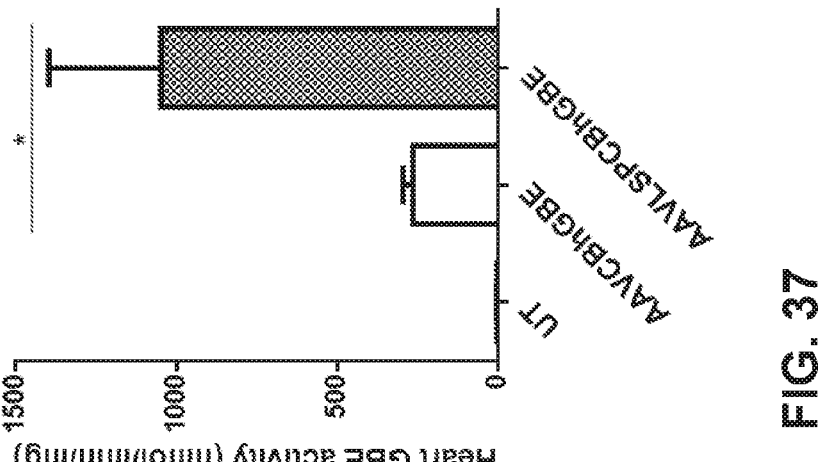
FIG. 37
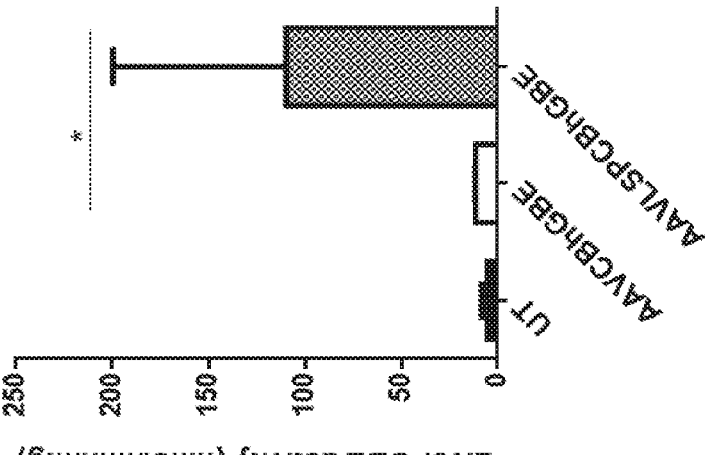

SEQUENCE LISTING

<160> NUMBER OF SEQ ID NOS: 38

<210> SEQ ID NO 1
<211> LENGTH: 718

```
<212> TYPE: PRT
<213> ORGANISM: Bacillus subtilis

<400> SEQUENCE: 1

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Ile Thr Asp Phe Pro Leu Ala Val Arg
        35                  40                  45

Glu Glu Tyr Ser Leu Glu Ala Lys Tyr Lys Tyr Val Cys Val Ser Asp
    50                  55                  60

His Pro Val Thr Phe Gly Lys Ile His Cys Val Arg Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Thr Ser Ala Ala
        115                 120                 125

Val Lys Leu Ser His Pro Asn Lys Ser Gly Arg Thr Phe Gln Met Thr
    130                 135                 140

Arg Leu Glu Lys Gly Val Tyr Ala Val Thr Val Thr Gly Asp Leu His
145                 150                 155                 160

Gly Tyr Glu Tyr Leu Phe Cys Ile Cys Asn Asn Ser Glu Trp Met Glu
                165                 170                 175

Thr Val Asp Gln Tyr Ala Lys Ala Val Thr Val Asn Gly Glu Lys Gly
            180                 185                 190

Val Val Leu Arg Pro Asp Gln Met Lys Trp Thr Ala Pro Leu Lys Pro
        195                 200                 205

Phe Ser His Pro Val Asp Ala Val Ile Tyr Glu Thr His Leu Arg Asp
    210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Val Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285

Asn Trp Gly Tyr Asn Pro Leu His Phe Phe Ala Pro Glu Gly Ser Tyr
    290                 295                 300

Ala Ser Asn Pro His Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr Lys Arg Glu Asn Ser Pro Phe Glu Lys Thr
            340                 345                 350

Val Pro Gly Tyr Phe Phe Arg His Asp Glu Cys Gly Met Pro Ser Asn
        355                 360                 365

Gly Thr Gly Val Gly Asn Asp Ile Ala Ser Glu Arg Arg Met Ala Arg
    370                 375                 380

Lys Phe Ile Ala Asp Cys Val Val Tyr Trp Leu Glu Glu Tyr Asn Val
385                 390                 395                 400
```

-continued

```
Asp Gly Phe Arg Phe Asp Leu Leu Gly Ile Leu Asp Ile Asp Thr Val
            405             410             415

Leu Tyr Met Lys Glu Lys Ala Thr Lys Ala Lys Pro Gly Ile Leu Leu
            420             425             430

Phe Gly Glu Gly Trp Asp Leu Ala Thr Pro Leu Pro His Glu Gln Lys
            435             440             445

Ala Ala Leu Ala Asn Ala Pro Arg Met Pro Gly Ile Gly Phe Phe Asn
            450             455             460

Asp Met Phe Arg Asp Ala Val Lys Gly Asn Thr Phe His Leu Lys Ala
465             470             475             480

Thr Gly Phe Ala Leu Gly Asn Gly Glu Ser Ala Gln Ala Val Met His
            485             490             495

Gly Ile Ala Gly Ser Ser Gly Trp Lys Ala Leu Ala Pro Ile Val Pro
            500             505             510

Glu Pro Ser Gln Ser Ile Asn Tyr Val Glu Ser His Asp Asn His Thr
            515             520             525

Phe Trp Asp Lys Met Ser Phe Ala Leu Pro Gln Glu Asn Asp Ser Arg
            530             535             540

Lys Arg Ser Arg Gln Arg Leu Ala Ala Ala Ile Ile Leu Leu Ala Gln
545             550             555             560

Gly Val Pro Phe Ile His Ser Gly Gln Glu Phe Phe Arg Thr Lys Gln
            565             570             575

Gly Val Glu Asn Ser Tyr Gln Ser Ser Asp Ser Ile Asn Gln Leu Asp
            580             585             590

Trp Asp Arg Arg Glu Thr Phe Lys Glu Asp Val His Tyr Ile Arg Arg
            595             600             605

Leu Ile Ser Leu Arg Lys Ala His Pro Ala Phe Arg Leu Arg Ser Ala
            610             615             620

Ala Asp Ile Gln Arg His Leu Glu Cys Leu Thr Leu Lys Glu His Leu
625             630             635             640

Ile Ala Tyr Arg Leu Tyr Asp Leu Asp Glu Val Asp Glu Trp Lys Asp
            645             650             655

Ile Ile Val Ile His His Ala Ser Pro Asp Ser Val Glu Trp Arg Leu
            660             665             670

Pro Asn Asp Ile Pro Tyr Arg Leu Leu Cys Asp Pro Ser Gly Phe Gln
            675             680             685

Glu Asp Pro Thr Glu Ile Lys Lys Thr Val Ala Val Asn Gly Ile Gly
            690             695             700

Thr Val Ile Leu Tyr Leu Ala Ser Asp Leu Lys Ser Phe Ala
705             710             715
```

```
<210> SEQ ID NO 2
<211> LENGTH: 2157
<212> TYPE: DNA
<213> ORGANISM: Bacillus subtilis

<400> SEQUENCE: 2
atggtcagca tccgccgcag cttcgaagcg tatgtcgatg acatgaatat cattactgtt      60
ctgattcctg ctgaacaaaa ggaaatcatg acaccgccgt ttcggcttga dacagaaata     120
acagattttc tctggctgt cagggaggaa tactcccttg aagcaaaata caagtacgtc      180
tgcgtatccg accatcctgt gacatttgga aaaatccatt gcgtcagagc atccagcggc     240
cacaaaacgg atctccaaat tggcgcggtc atccggacgg cagcgtttga tgacgaattt     300
```

```
tattatgacg gagagctggg cgccgtttat accgcggatc ataccgtatt taaagtatgg        360
gcgcctgctg caacctcagc tgctgtcaag ctttcacacc ccaataaaag cgggcgcaca        420
ttccaaatga ctcgcttgga aaaaggcgtc tatgccgtta cggtcacagg tgaccttcac        480
ggatatgagt atttgttttg catctgcaac aattcagaat ggatggaaac agttgaccag        540
tatgccaagg ctgtgactgt aaatggagag aagggcgtcg tcttgcgccc ggatcaaatg        600
aaatggactg ctcctcttaa accattctca caccctgtgg atgccgtcat ctatgagacg        660
catcttcgcg acttctccat ccatgaaaac agcggcatga taaacaaggg aaaatactta        720
gcgctgacgg aaactgatac acaaaccgca aatggcagtt cttcgggatt agcgtatgta        780
aaagagcttg gtgtgacaca tgtggagctt ctgccggtga atgattttgc cggagttgat        840
gaagagaagc cgcttgatgc atacaattgg ggatataacc cgcttcattt ctttgccccg        900
gagggaagct atgcctcaaa tcctcatgat cctcaaacga gaaaaacaga gctgaaacaa        960
atgatcaata ccctgcatca gcacggtctg cgagtcattc tggatgttgt ttttaaccat       1020
gtgtataaga gggagaattc cccctttgaa aagacagtgc ccggttattt tttccggcac       1080
gacgaatgtg ggatgccatc aaacggcacc ggcgttggca atgatattgc atcagaaaga       1140
aggatggcaa gaaaattcat tgcggattgc gtggtctatt ggcttgaaga atacaatgtt       1200
gacggcttcc gctttgatct cctcgggatt ttagatattg acaccgtgct ttatatgaaa       1260
gagaaagcaa ctaaggcaaa gccccggaatc ctgctttttg gagaagggtg ggacctggct       1320
acaccgctgc cgcatgaaca gaaagctgct ttggcgaacg cgccaagaat gccgggcatc       1380
ggctttttta atgatatgtt tcgtgacgct gtaaaaggga acacctttca ccttaaggca       1440
acagggtttg cgctcggcaa cggtgaatca gcacaagctg tgatgcatgg aattgccggg       1500
tcttccggat ggaaggcatt agcaccgatt gttccggaac caagccagtc catcaattat       1560
gtcgaatcac acgacaatca caccttttgg gataaaatga gctttgcgct tcctcaagaa       1620
aatgacagcc gaaagcgaag caggcaaagg cttcagccg cgattatttt gcttgcccaa       1680
ggggtgccgt ttattcacag cggccaggaa ttttttccgga cgaagcaggg agtggaaaac       1740
agctatcaat ccagtgacag catcaaccag ctcgactggg atcgccgtga aacattcaaa       1800
gaagatgttc actatatccg caggctgatc tcgctgagaa aagcgcatcc tgcattccgt       1860
cttaggtccg ctgcagacat ccagcgccat cttgaatgct tgacgctaaa agaacacctt       1920
atcgcataca ggctttatga tcttgacgag gttgacgaat ggaaagatat cattgttatc       1980
catcacgcga gtccagactc cgtcgagtgg aggctgccaa acgacatacc ttatcggctt       2040
ttatgtgatc catcaggatt tcaggaagac ccaacagaaa tcaagaaaac ggttgcagta       2100
aacggcatcg gaacggttat cttatattta gcatcagatc ttaagagttt tgcttga          2157
```

<210> SEQ ID NO 3
<211> LENGTH: 2157
<212> TYPE: DNA
<213> ORGANISM: Artificial Sequence
<220> FEATURE:
<223> OTHER INFORMATION: codon optimized pullulanase sequence derived
     from B. subtilis strain 168

<400> SEQUENCE: 3

```
atggtgagca tccggagatc cttcgaggcc tacgtggacg atatgaacat catcaccgtg         60
ctgatcccag ccgagcagaa ggagatcatg acacccccctt tccggctgga gaccgagatc        120
acagactttc ccctggccgt gagagaggag tatagcctgg aggccaagta caagtacgtg        180
```

-continued

```
tgcgtgagcg atcaccctgt gacctttggc aagatccact gcgtgcgggc aagctccgga    240
cacaagaccg acctgcagat cggagccgtg atcaggacag cagccttcga cgatgagttt    300
tactatgacg gagagctggg agccgtgtac accgcagatc acacagtgtt caaggtctgg    360
gcaccagcag ccacatccgc cgcagtgaag ctgagccacc ccaacaagtc cggcaggacc    420
tttcagatga cacgcctgga gaagggcgtg tacgccgtga ccgtgacagg cgatctgcac    480
ggctacgagt atctgttctg catctgtaac aattctgagt ggatggagac cgtggatcag    540
tatgccaagg ccgtgacagt gaatggagag aagggagtgg tgctgaggcc agaccagatg    600
aagtggaccg cacccctgaa gcctttcagc caccctgtgg acgccgtgat ctacgagaca    660
cacctgcgcg attttttctat ccacgagaac agcggcatga tcaataaggg caagtacctg    720
gccctgaccg agacagacac ccagacagcc aacggctcta gctccggcct ggcctatgtg    780
aaggagctgg gagtgaccca cgtggagctg ctgcctgtga atgactttgc cggcgtggat    840
gaggagaagc cactggatgc ctacaactgg ggctataatc cactgcactt ctttgccccc    900
gagggctctt atgccagcaa cccacacgac ccccagacca ggaagacaga gctgaagcag    960
atgatcaata cactgcacca gcacggcctg agagtgatcc tggatgtggt gttcaaccac   1020
gtgtacaagc gcgagaatag ccctttttgag aagaccgtgc caggctattt cttttcggcac   1080 gacgagtgcg gcatgccatc taacggcaca ggcgtgggca atgatatcgc cagcgagagg   1140
cgcatggccc ggaagttcat cgccgactgc gtggtgtact ggctggagga gtataacgtg   1200
gacggcttca gatttgatct gctgggcatc ctggacatcg ataccgtgct gtacatgaag   1260
gagaaggcca caaaggccaa gccaggcatc ctgctgttcg agagggatg ggacctggca   1320 accccactgc cacacgagca gaaggccgcc ctggcaaacg cacctaggat gccaggcatc   1380
ggcttcttta cgacatgtt tcgcgatgcc gtgaagggca ataccttcca cctgaaggcc   1440
acaggctttg cactgggaaa tggagagtcc gcccaggccg tgatgcacgg aatcgcagga   1500
tctagcggat ggaaggccct ggcaccaatc gtgcctgagc caagccagtc catcaactac   1560
gtggagtccc acgacaatca caccttctgg ataagatgt cttttgcccct gcctcaggag   1620 aatgattcta ggaagagaag caggcagcgc ctggcagcag caatcatcct gctggcccag   1680
ggcgtgccat tcatccacag cggccaggag ttctttcgga ccaagcaggg cgtggagaac   1740
tcctaccagt cctctgattc tatcaatcag ctggactggg atcggagaga gacattcaag   1800
gaggacgtgc actatatcag gcgcctgatc agcctgagaa aggcacaccc agcctttcgg   1860
ctgagatccg ccgcagacat ccagaggcac ctggagtgcc tgaccctgaa ggagcacctg   1920
atcgcctaca gactgtatga cctggatgag gtggacgagt ggaaggatat catcgtgatc   1980
caccacgcct cccctgactc tgtggagtgg cggctgccca cgatatccc ttacagactg   2040 ctgtgcgacc cctccggctt ccaggaggat cctaccgaga tcaagaagac agtggccgtg   2100
aatggcatcg gcaccgtgat cctgtatctg gcctccgacc tgaagtcttt tgcctga      2157
```

<210> SEQ ID NO 4
<211> LENGTH: 657
<212> TYPE: PRT
<213> ORGANISM: Escherichia coli

<400> SEQUENCE: 4

```
Met Thr Gln Leu Ala Ile Gly Lys Pro Ala Pro Leu Gly Ala His Tyr
1               5                   10                  15

Asp Gly Gln Gly Val Asn Phe Thr Leu Phe Ser Ala His Ala Glu Arg
            20                  25                  30
```

-continued

```
Val Glu Leu Cys Val Phe Asp Ala Asn Gly Gln Glu His Arg Tyr Asp
    35              40              45

Leu Pro Gly His Ser Gly Asp Ile Trp His Gly Tyr Leu Pro Asp Ala
    50              55              60

Arg Pro Gly Leu Arg Tyr Gly Tyr Arg Val His Gly Pro Trp Gln Pro
65              70              75              80

Ala Glu Gly His Arg Phe Asn Pro Ala Lys Leu Leu Ile Asp Pro Cys
                85              90              95

Ala Arg Gln Ile Asp Gly Glu Phe Lys Asp Asn Pro Leu Leu His Ala
                100             105             110

Gly His Asn Glu Pro Asp Tyr Arg Asp Asn Ala Ala Ile Ala Pro Lys
                115             120             125

Cys Val Val Val Asp His Tyr Asp Trp Glu Asp Asp Ala Pro Pro
    130             135             140

Arg Thr Pro Trp Gly Ser Thr Ile Ile Tyr Glu Ala His Val Lys Gly
145             150             155             160

Leu Thr Tyr Leu His Pro Glu Ile Pro Val Glu Ile Arg Gly Thr Tyr
                165             170             175

Lys Ala Leu Gly His Pro Val Met Ile Asn Tyr Leu Lys Gln Leu Gly
                180             185             190

Ile Thr Ala Leu Glu Leu Leu Pro Val Ala Gln Phe Ala Ser Glu Pro
                195             200             205

Arg Leu Gln Arg Met Gly Leu Ser Asn Tyr Trp Gly Tyr Asn Pro Val
    210             215             220

Ala Met Phe Ala Leu His Pro Ala Tyr Ala Cys Ser Pro Glu Thr Ala
225             230             235             240

Leu Asp Glu Phe Arg Asp Ala Ile Lys Ala Leu His Lys Ala Gly Ile
                245             250             255

Glu Val Ile Leu Asp Ile Val Leu Asn His Ser Ala Glu Leu Asp Leu
                260             265             270

Asp Gly Pro Leu Phe Ser Leu Arg Gly Ile Asp Asn Arg Ser Tyr Tyr
                275             280             285

Trp Ile Arg Glu Asp Gly Asp Tyr His Asn Trp Thr Gly Cys Gly Asn
    290             295             300

Thr Leu Asn Leu Ser His Pro Ala Val Val Asp Tyr Ala Ser Ala Cys
305             310             315             320

Leu Arg Tyr Trp Val Glu Thr Cys His Val Asp Gly Phe Arg Phe Asp
                325             330             335

Leu Ala Ala Val Met Gly Arg Thr Pro Glu Phe Arg Gln Asp Ala Pro
                340             345             350

Leu Phe Thr Ala Ile Gln Asn Cys Pro Val Leu Ser Gln Val Lys Leu
                355             360             365

Ile Ala Glu Pro Trp Asp Ile Ala Pro Gly Gly Tyr Gln Val Gly Asn
    370             375             380

Phe Pro Pro Leu Phe Ala Glu Trp Asn Asp His Phe Arg Asp Ala Ala
385             390             395             400

Arg Arg Phe Trp Leu His Tyr Asp Leu Pro Leu Gly Ala Phe Ala Gly
                405             410             415

Arg Phe Ala Ala Ser Ser Asp Val Phe Lys Arg Asn Gly Arg Leu Pro
                420             425             430

Ser Ala Ala Ile Asn Leu Val Thr Ala His Asp Gly Phe Thr Leu Arg
                435             440             445
```

```
Asp Cys Val Cys Phe Asn His Lys His Asn Glu Ala Asn Gly Glu Glu
    450                 455                 460

Asn Arg Asp Gly Thr Asn Asn Asn Tyr Ser Asn Asn His Gly Lys Glu
465                 470                 475                 480

Gly Leu Gly Gly Ser Leu Asp Leu Val Glu Arg Arg Arg Asp Ser Ile
                485                 490                 495

His Ala Leu Leu Thr Thr Leu Leu Leu Ser Gln Gly Thr Pro Met Leu
            500                 505                 510

Leu Ala Gly Asp Glu His Gly His Ser Gln His Gly Asn Asn Asn Ala
            515                 520                 525

Tyr Cys Gln Asp Asn Gln Leu Thr Trp Leu Asp Trp Ser Gln Ala Ser
    530                 535                 540

Ser Gly Leu Thr Ala Phe Thr Ala Ala Leu Ile His Leu Arg Lys Arg
545                 550                 555                 560

Ile Pro Ala Leu Val Glu Asn Arg Trp Trp Glu Glu Gly Asp Gly Asn
                565                 570                 575

Val Arg Trp Leu Asn Arg Tyr Ala Gln Pro Leu Ser Thr Asp Glu Trp
                580                 585                 590

Gln Asn Gly Pro Lys Gln Leu Gln Ile Leu Leu Ser Asp Arg Phe Leu
            595                 600                 605

Ile Ala Ile Asn Ala Thr Leu Glu Val Thr Glu Ile Val Leu Pro Ala
    610                 615                 620

Gly Glu Trp His Ala Ile Pro Pro Phe Ala Gly Glu Asp Asn Pro Val
625                 630                 635                 640

Ile Thr Ala Val Trp Gln Gly Pro Ala His Gly Leu Cys Val Phe Gln
                645                 650                 655

Arg
```

<210> SEQ ID NO 5
<211> LENGTH: 1974
<212> TYPE: DNA
<213> ORGANISM: Escherichia coli

<400> SEQUENCE: 5

```
atgacacaac tcgccattgg caaacccgct cccctcggcg cgcattacga cggtcagggc      60
gtcaacttca cactttttctc cgctcatgcc gagcgggtag aactgtgtgt ctttgacgcc     120
aatggccagg aacatcgcta tgacttgcca gggcacagtg gcgacatttg cacggttat     180 ctgccggatg cgcgcccggg tttgcgttat ggttatcgcg ttcatggccc ctggcaaccc     240
gccgaggggc atcgctttaa cccggcgaag ttgttgattg atccttgcgc gcggcaaatt     300
gacggggagt ttaaagataa cccgctgctg cacgccggtc ataatgaacc tgactatcgc     360
gacaacgccg ccattgcgcc gaaatgcgta gtggtggttg atcactatga ctgggaagat     420
gatgccccgc cgcgcacgcc gtggggcagc accatcattt atgaagccca tgtcaaagga     480
ttaacgtact gcacccggga tcccggtc gagatccgtg cacttataa agccctcggg     540 catccggtga tgatcaacta tttgaaacaa ttgggcatta ccgcgctgga actgctgcca     600
gtggcgcagt tgccagtga accacgtctg caacgcatgg ggctaagtaa ctactggggt     660
tacaacccgg tggcgatgtt tgcgctgcat ccggcgtatg cctgctcgcc agaaacggcg     720
ctggatgagt ttcgcgatgc aatcaaagca ctgcataaag cgggtatcga agtcattctt     780
gatatcgtgc tcaaccatag tgcggaactg gacctcgacg gccgttatt ctcgctgcgt     840 gggatcgata accgtagcta ttattggata agagaagacg gcgattatca caactggacc     900
```

```
ggttgcggca acacgctcaa tttgagtcat ccggcggtgg tggattatgc cagcgcctgc      960
ctgcgttatt gggtagaaac ctgccacgtc gatggtttcc gctttgatct ggcggcagtc     1020
atgggccgta cgccagagtt ccgtcaggat gcgccgttgt ttaccgctat ccagaactgc     1080
ccggtgctct cgcaggtgaa gttaattgct gaaccgtggg atatcgctcc tggtggttat     1140
caggtgggaa atttcccgcc gctgtttgcc gagtggaacg atcatttccg cgatgctgcc     1200
cgtcgtttct ggctacatta tgatttgcct ctgggggcgt ttgccgggcg ttttgctgcc     1260
tccagcgatg ttttttaaacg taatggtcgt ctgccgagtg ccgcgattaa tctcgtcacc     1320
gcgcatgacg gttttacgct tcgcgactgc gtttgcttca accataaaca caatgaagca     1380
aacggagaag aaaatcgcga cgggaccaac aacaattaca gtaacaatca tggtaaagaa     1440
gggttaggcg gttctcttga cctggttgaa cggcggcgcg acagcattca cgccctgtta     1500
acaacgttgt tgctctccca gggtacgccg atgttactgg ccggtgacga acatggtcac     1560
agccagcatg gcaataacaa tgcctactgt caggataacc aattaacctg gttggactgg     1620
tcgcaggcaa gcagtggttt aaccgcattt accgccgcgt taatccatct gcgcaagcgc     1680
attcccgctt tggtggagaa tcgctggtgg gaagaaggcg acggcaatgt ccgttggcta     1740
aatcgatatg ctcaaccttt aagcacggat gagtggcaaa acgggccgaa acagctgcaa     1800
attctgctct cggatcgctt tttgatcgca attaacgcca cgcttgaggt aacagagatt     1860
gttttacctg ctgggggagtg gcacgccatt cccccattcg ctggagagga taacccagtg     1920
attacggctg tctggcaggg acctgcacac ggattgtgtg tgttccagag atga          1974
```

```
<210> SEQ ID NO 6
<211> LENGTH: 1974
<212> TYPE: DNA
<213> ORGANISM: Artificial Sequence
<220> FEATURE:
<223> OTHER INFORMATION: codon optimized glgX sequence derived from E.
      coli strain K-12

<400> SEQUENCE: 6
atgacccagc tggcaatcgg caagccagca cctctgggag cccactacga cggccagggc       60
gtgaacttca cactgttttc cgcccacgca gagagggtgg agctgtgcgt gttcgatgcc      120
aatggccagg agcacagata cgacctgccc ggccactctg gcgatatctg cacggctat      180 ctgccagacg caaggcctgg actgagatac ggctatagag tgcacggacc atggcagcca      240
gcagagggac acaggttcaa cccagccaag ctgctgatcg atccttgcgc ccgccagatc      300
gacggcgagt ttaaggataa tccactgctg cacgcaggac acaacgagcc tgactacagg      360
gataatgcag caatcgcacc aaagtgcgtg gtggtggtgg accactatga ttgggaggac      420
gatgcaccac ctaggacccc ttggggcagc acaatcatct acgaggccca cgtgaagggc      480
ctgacctatc tgcaccctga tcccagtg agatcaggg gcacatacaa ggccctggga      540
caccccgtga tgatcaacta tctgaagcag ctggaatca ccgccctgga gctgctgcct      600
gtggcacagt tcgcatctga gccaaggctg cagaggatgg gactgagcaa ctactggggc      660
tataatcctg tggccatgtt cgcactgcac cctgcatacg catgtagccc agagacagcc      720
ctggacgagt ttagggatgc catcaaggcc ctgcacaagg ccggcatcga agtgatcctg      780
gacatcgtgc tgaatcactc cgccgagctg gacctggatg ccctctgtt ttccctgcgg      840 ggcatcgata acagatctta ctattggatc cgcgaggacg cgattatca caattggacc      900 ggctgcggca acacactgaa tctgagccac ccagcagtgg tggactacgc atccgcctgc      960
```

```
ctgcggtatt gggtggagac ctgtcacgtg gacggcttca gatttgatct ggcagccgtg    1020
atgggaagga ccccagagtt ccgccaggac gcaccactgt ttacagccat ccagaactgt    1080
cctgtgctgt cccaggtgaa gctgatcgca gagccatggg atatcgcacc aggaggctac    1140
caggtcggaa acttcccacc cctgtttgcc gagtggaatg accacttccg ggatgccgcc    1200
cggagatttt ggctgcacta tgacctgcca ctgggagcct tcgccggcag atttgcagca    1260
agctccgacg tgttcaagag aaacggcagg ctgccctctg ccgccatcaa tctggtgacc    1320
gcccacgacg gcttcacact gagggattgc gtgtgcttta accacaagca caacgaggcc    1380
aatggcgagg agaatcgcga cggcaccaac aataactaca gcaataacca cggcaaggag    1440
ggactgggag atccctgga cctggtggag aggcgccggg attctatcca cgccctgctg    1500
accacactgc tgctgagcca gggcacccca atgctgctgg caggcgatga gcacggacac    1560
tcccagcacg gcaataacaa tgcctactgc caggacaacc agctgacatg gctggattgg    1620
tctcaggcct ctagcggact gaccgccttc acagccgccc tgatccacct gagaaagagg    1680
atccccgccc tggtggagaa taggtggtgg gaggagggcg acggaaacgt gaggtggctg    1740
aatcgctatg cccagcctct gtctaccgac gagtggcaga acggcccaaa gcagctgcag    1800
atcctgctga gcgatagatt tctgatcgcc atcaatgcca ccctggaggt gacagagatc    1860
gtgctgccag caggagagtg gcacgcaatc cctccattcg ccggagagga caacccagtg    1920
atcacagccg tgtggcaggg accagcacac ggactgtgcg tgttccagag atga          1974
```

<210> SEQ ID NO 7
<211> LENGTH: 776
<212> TYPE: PRT
<213> ORGANISM: Pseudomonas amyloderamosa

<400> SEQUENCE: 7

```
Met Lys Cys Pro Lys Ile Leu Ala Ala Leu Leu Gly Cys Ala Val Leu
1               5                   10                  15

Ala Gly Val Pro Ala Met Pro Ala His Ala Ala Ile Asn Ser Met Ser
            20                  25                  30

Leu Gly Ala Ser Tyr Asp Ala Gln Gln Ala Asn Ile Thr Phe Arg Val
        35                  40                  45

Tyr Ser Ser Gln Ala Thr Arg Ile Val Leu Tyr Leu Tyr Ser Ala Gly
    50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ser Ile Lys Ala Ala Gly
                85                  90                  95

Ile Thr Gly Ala Val Tyr Tyr Gly Tyr Arg Ala Trp Gly Pro Asn Trp
            100                 105                 110

Pro Tyr Ala Ser Asn Trp Gly Lys Gly Ser Gln Ala Gly Phe Val Ser
        115                 120                 125

Asp Val Asp Ala Asn Gly Asp Arg Phe Asn Pro Asn Lys Leu Leu Leu
    130                 135                 140

Asp Pro Tyr Ala Gln Glu Val Ser Gln Asp Pro Leu Asn Pro Ser Asn
145                 150                 155                 160

Gln Asn Gly Asn Val Phe Ala Ser Gly Ala Ser Tyr Arg Thr Thr Asp
                165                 170                 175

Ser Gly Ile Tyr Ala Pro Lys Gly Val Val Leu Val Pro Ser Thr Gln
            180                 185                 190

Ser Thr Gly Thr Lys Pro Thr Arg Ala Gln Lys Asp Asp Val Ile Tyr
```

-continued

```
                195                 200                 205

Glu Val His Val Arg Gly Phe Thr Glu Gln Asp Thr Ser Ile Pro Ala
    210                 215                 220

Gln Tyr Arg Gly Thr Tyr Tyr Gly Ala Gly Leu Lys Ala Ser Tyr Leu
225                 230                 235                 240

Ala Ser Leu Gly Val Thr Ala Val Glu Phe Leu Pro Val Gln Glu Thr
                245                 250                 255

Gln Asn Asp Ala Asn Asp Val Val Pro Asn Ser Asp Ala Asn Gln Asn
                260                 265                 270

Tyr Trp Gly Tyr Met Thr Glu Asn Tyr Phe Ser Pro Asp Arg Arg Tyr
                275                 280                 285

Ala Tyr Asn Lys Ala Ala Gly Gly Pro Thr Ala Glu Phe Gln Ala Met
    290                 295                 300

Val Gln Ala Phe His Asn Ala Gly Ile Lys Val Tyr Met Asp Val Val
305                 310                 315                 320

Tyr Asn His Thr Ala Glu Gly Gly Thr Trp Thr Ser Ser Asp Pro Thr
                325                 330                 335

Thr Ala Thr Ile Tyr Ser Trp Arg Gly Leu Asp Asn Ala Thr Tyr Tyr
                340                 345                 350

Glu Leu Thr Ser Gly Asn Gln Tyr Phe Tyr Asp Asn Thr Gly Ile Gly
                355                 360                 365

Ala Asn Phe Asn Thr Tyr Asn Thr Val Ala Gln Asn Leu Ile Val Asp
    370                 375                 380

Ser Leu Ala Tyr Trp Ala Asn Thr Met Gly Val Asp Gly Phe Arg Phe
385                 390                 395                 400

Asp Leu Ala Ser Val Leu Gly Asn Ser Cys Leu Asn Gly Ala Tyr Thr
                405                 410                 415

Ala Ser Ala Pro Asn Cys Pro Asn Gly Gly Tyr Asn Phe Asp Ala Ala
                420                 425                 430

Asp Ser Asn Val Ala Ile Asn Arg Ile Leu Arg Glu Phe Thr Val Arg
                435                 440                 445

Pro Ala Ala Gly Gly Ser Gly Leu Asp Leu Phe Ala Glu Pro Trp Ala
    450                 455                 460

Ile Gly Gly Asn Ser Tyr Gln Leu Gly Gly Phe Pro Gln Gly Trp Ser
465                 470                 475                 480

Glu Trp Asn Gly Leu Phe Arg Asp Ser Leu Arg Gln Ala Gln Asn Glu
                485                 490                 495

Leu Gly Ser Met Thr Ile Tyr Val Thr Gln Asp Ala Asn Asp Phe Ser
                500                 505                 510

Gly Ser Ser Asn Leu Phe Gln Ser Ser Gly Arg Ser Pro Trp Asn Ser
                515                 520                 525

Ile Asn Phe Ile Asp Val His Asp Gly Met Thr Leu Lys Asp Val Tyr
    530                 535                 540

Ser Cys Asn Gly Ala Asn Asn Ser Gln Ala Trp Pro Tyr Gly Pro Ser
545                 550                 555                 560

Asp Gly Gly Thr Ser Thr Asn Tyr Ser Trp Asp Gln Gly Met Ser Ala
                565                 570                 575

Gly Thr Gly Ala Ala Val Asp Gln Arg Arg Ala Ala Arg Thr Gly Met
                580                 585                 590

Ala Phe Glu Met Leu Ser Ala Gly Thr Pro Leu Met Gln Gly Gly Asp
    595                 600                 605

Glu Tyr Leu Arg Thr Leu Gln Cys Asn Asn Asn Ala Tyr Asn Leu Asp
    610                 615                 620
```

```
Ser Ser Ala Asn Trp Leu Thr Tyr Ser Trp Thr Thr Asp Gln Ser Asn
625             630             635             640

Phe Tyr Thr Phe Ala Gln Arg Leu Ile Ala Phe Arg Lys Ala His Pro
            645             650             655

Ala Leu Arg Pro Ser Ser Trp Tyr Ser Gly Ser Gln Leu Thr Trp Tyr
            660             665             670

Gln Pro Ser Gly Ala Val Ala Asp Ser Asn Tyr Trp Asn Asn Thr Ser
            675             680             685

Asn Tyr Ala Ile Ala Tyr Ala Ile Asn Gly Pro Ser Leu Gly Asp Ser
            690             695             700

Asn Ser Ile Tyr Val Ala Tyr Asn Gly Trp Ser Ser Val Thr Phe
705             710             715             720

Thr Leu Pro Ala Pro Pro Ser Gly Thr Gln Trp Tyr Arg Val Thr Asp
            725             730             735

Thr Cys Asp Trp Asn Asp Gly Ala Ser Thr Phe Val Ala Pro Gly Ser
            740             745             750

Glu Thr Leu Ile Gly Gly Ala Gly Thr Thr Tyr Gly Gln Cys Gly Gln
            755             760             765

Ser Leu Leu Leu Leu Ile Ser Lys
            770             775
```

<210> SEQ ID NO 8
<211> LENGTH: 2157
<212> TYPE: DNA
<213> ORGANISM: Artificial Sequence
<220> FEATURE:
<223> OTHER INFORMATION: Codon optimized polynucleotide coding sequence
      #2 for expressing Pullulanase

<400> SEQUENCE: 8

```
atggttagca tcaggcgatc ctttgaagcc tacgtggatg acatgaatat catcaccgtg      60
ctcataccgg ccgaacaaaa ggagattatg acacctcctt ccgactcga aaccgagata     120 acagactttc tctcgctgt tcgagaggaa tatagtttgg aagctaagta taagtacgtt     180
tgtgtaagcg atcatccggt tactttcgga aagatacatt gcgtaagagc ttcttctgga     240
cacaagaccg atcttcaaat aggtgccgta atacgcacgg cagcgttcga cgatgaattt     300
tattacgacg gtgaacttgg cgccgtatac actgccgacc atactgtttt taaagtttgg     360
gccccggctg caacttctgc ggctgttaaa ctttctcatc ccaataagtc aggacgaacc     420
ttccagatga ccagattgga gaaaggtgtg tacgcagtga ctgtcacggg ggatctccac     480
ggttatgaat acctgttctg catttgcaat aattctgaat ggatggaaac tgtcgatcaa     540
tacgccaagg ctgtgacagt caacggggaa aagggtgtgg ttctgcgccc ggatcaaatg     600
aagtggacag ctcctcttaa accattctca caccctgtgg acgcggtaat ttacgagacg     660
catctccgag atttcagtat tcacgagaat agtggtatga ttaataaggg gaagtacctg     720
gctttgacgg aaacagatac gcaaactgcc aacggatcaa gcagcggtct ggcatacgtc     780
aaggaactgg gcgtaacaca tgttgaactc ctccctgtca cgacttcgc tggtgttgac     840 gaggaaaagc ccttggacgc ttacaattgg ggatataatc cattgcattt ctttgccccc     900
gagggcagct acgcgagcaa ccctcatgat ccacagaccc gaaagactga gctgaaacag     960
atgattaaca cgctgcacca gcatggattg cgagtcatat ggacgtggt attcaaccat    1020 gtctataaac gcgagaacag tccctttgag aagacagtcc caggttactt cttcagacac    1080
gatgagtgtg gcatgcccag caacgggacc ggtgtcggta atgatatcgc gtccgaacgc    1140
```

```
cggatggccc ggaaatttat cgccgattgt gtagtttact ggcttgagga atataatgta    1200
gacgggtttc ggttcgattt gctcggtata ttggatattg acaccgttct ctatatgaag    1260
gagaaagcga cgaaggctaa gccgggcata ctcctgttcg gtgaaggttg ggatctggcg    1320
accccgctcc cgcacgagca aaaagcagct cttgctaacg caccgaggat gccgggaata    1380 ggattttttca atgacatgtt ccgcgatgcc gtgaaaggaa atacattcca ccttaaagcc    1440
acaggtttcg cactgggcaa cggtgagtcc gcccaagctg tcatgcacgg gattgcaggt    1500
tcatccgggt ggaaggccct tgcacctatt gtaccagagc cttctcaatc cattaattac    1560
gtcgaatcac atgataacca cacgttctgg gataaaatgt cattcgccct gccacaggaa    1620
aacgactcta ggaaacggtc ccgacaacgg ctggccgcag ctattatctt gcttgcacaa    1680
ggggtgccct ttatccattc cgggcaagag ttttttagaa ccaaacaagg agtcgagaac    1740
agctaccagt catcagactc catcaaccag ttggactggg ataggagaga gacgttcaaa    1800
gaggatgtgc attacatcag acggctcata tcactccgaa aggcacaccc ggcatttcgc    1860
ctcaggtctg ctgcggacat acagcgccat ttggagtgtc tcaccttgaa ggagcatctc    1920
attgcgtata ggttgtacga cttggacgag gtggatgagt ggaaggatat cattgttatt    1980
catcatgcgt ctcccgactc cgtcgagtgg cgattgccga acgacatacc ataccgattg    2040
ctgtgcgacc catcaggttt ccaggaggac ccaactgaaa tcaaaaaaac cgtggctgtc    2100
aatggtattg gtaccgttat actttacctc gcttcagatc tgaagtcttt cgcctga      2157
```

<210> SEQ ID NO 9
<211> LENGTH: 2157
<212> TYPE: DNA
<213> ORGANISM: Artificial Sequence
<220> FEATURE:
<223> OTHER INFORMATION: Codon optimized polynucleotide coding sequence
      #3 for expressing Pullulanase

<400> SEQUENCE: 9

```
atggtctcca ttaggcgaag cttcgaggct tatgtagacg atatgaacat tattactgtc     60
cttataccag cagaacagaa agaaattatg actccgccgt tccgattgga gacagagatt    120
acggactttc ctttggccgt tcgggaagag tattctcttg aggccaaata taaatatgtg    180
tgcgttagtg atcatccagt aacgtttggc aaaatccact cgtccgggc tctagtgga    240 cataagacgg accttcagat aggggctgtc atccggacag ctgcattcga tgatgagttt    300
tactatgatg gggagctcgg agcggtatat acagccgatc atactgtatt taaagtttgg    360
gcacctgctg ccacctccgc ggcggttaag ctttcccatc cgaataaatc cggccgcact    420
tttcagatga ctcgacttga aaagggggtt tacgccgtga cggtgaccgg agatttgcac    480
gggtacgagt atcttttctg catatgtaat aactcagaat ggatggaaac tgtagaccag    540
tatgccaagg cggttacggt gaacggggaa aagggggttg ttctgcggcc ggatcaaatg    600
aaatggacgg caccccttgaa gccctttct catccagtcg acgctgtcat atacgagacg    660
cacctgagag acttttcaat ccacgaaaat agtggtatga ttaataaagg caaatatctt    720
gcacttacag agaccgatac acagaccgca aacggatcta gttctggtt ggcgtacgtc    780 aaagagctgg gagttactca tgtagaattg ctccctgtta acgacttcgc aggtgtagat    840
gaggaaaagc ctctggacgc atataactgg ggatacaatc ctctccattt tttcgcacca    900
gaagggtcat atgccagcaa tccccatgac ccgcaaacga aaagactgaa acttaagcag    960 atgataaaata ctctgcacca acacggtctt cgcgttattc tcgatgttgt cttcaaccat    1020
```

-continued

```
gtttacaagc gcgagaattc ccctttcgaa aaaacggtac ctgggtactt ttttcggcat      1080
gacgaatgcg gtatgcctag caacggaaca ggagttggga acgacattgc aagcgaacgg      1140
cgaatggcga gaaagtttat tgccgattgt gtagtctact ggttggagga gtataacgtt      1200
gatggtttcc gattcgacct gttgggtata ttggatatcg ataccgtgtt gtacatgaaa      1260
gaaaaagcaa caaaagccaa acctgggatt ttgctgtttg gtgaaggttg ggacttggcc      1320
acgccgctcc cgcacgagca gaaggccgct ctcgcgaatg caccgcgcat gccaggaatc      1380
gggtttttta acgacatgtt cagggacgct gtgaaaggaa acacgtttca tcttaaggct      1440
acggggttcg ctcttgggaa cggcgagagc gcacaggcag tcatgcacgg tatagctggt      1500
agttcaggtt ggaaggcgct cgcaccaatc gtgcctgagc cgtcccagag cattaattat      1560
gtcgaatccc acgataatca caccttttgg gataaaatgt cctttgcctt gccacaggag      1620
aacgattcta gaaagcggtc acgccagcgg cttgctgctg caattatctt gttggcccag      1680
ggtgtcccgt tcatccacag tggccaggag ttcttcagaa caaaacaagg agtggagaac      1740
agctaccaaa gctcagactc tataaatcag ttggactggg acaggcgcga aacatttaaa      1800
gaagatgtgc actacattag gcgactgatt tcactccgca aagcgcaccc tgcattccga      1860
cttagatccg ccgctgacat acaaagacat ctggaatgcc tcactctcaa ggaacatctg      1920
atagcttata ggttgtacga cttggacgag gtcgacgaat ggaaagacat tatcgttata      1980
catcatgcgt ctcctgatag cgtcgagtgg agattgccaa acgatattcc atatcggctt      2040
ctttgcgacc cctctggctt tcaggaggac ccgaccgaga taaagaagac tgtggcggtt      2100
aacggtattg gtacggtaat tttgtacttg gcgtctgatt tgaaatcttt cgcgtga      2157
```

<210> SEQ ID NO 10
<211> LENGTH: 2157
<212> TYPE: DNA
<213> ORGANISM: Artificial Sequence
<220> FEATURE:
<223> OTHER INFORMATION: Codon optimized polynucleotide coding sequence
        #4 for expressing Pullulanase <400> SEQUENCE: 10

```
atggtaagta ttcggagatc tttttgaggct tacgttgatg atatgaacat tattacagtt        60
ctcattccgg cggagcaaaa ggagataatg accccaccat ttagacttga gactgagata       120
actgactttc ctcttgcagt tagggaagaa tatagtctgg aggcaaagta taaatacgta       180
tgcgtcagtg accaccctgt aacatttggt aaaatacact gtgtaagagc gtctagcgga       240
cataaaactg accttcagat tggcgccgtt atacggacag cagcattcga tgacgagttt       300
tattacgacg gggaacttgg ggcagtttac actgcagatc atacggtgtt taaagtttgg       360
gcgccagctg ctacctctgc agcagtaaaa ttgagtcacc ctaataaatc aggtaggacg       420
ttccagatga ctagactcga aaagggggtt tacgcagtca cggtaacggg tgatttgcac       480
ggctacgaat accttttttg catttgcaac aacagtgagt ggatggaaac cgttgaccaa       540
tatgccaagg ctgtgacggt caatggggaa aaaggtgtcg tgttgcggcc tgatcaaatg       600
aagtggacag caccctcaa gccatttagt catcccgttg acgctgtaat atacgaaacg       660
cacttgcgcg acttctcaat tcacgaaaac tccggaatga taaacaaagg taaatacctt       720
gcacttactg aaacggatac ccagacggcg aacggaagta gtagcgggct cgcctacgtc       780
aaagaattgg gggttacaca cgttgaactc ctgcctgtta atgacttcgc cggcgtcgac       840
gaagagaagc cccttgatgc atataattgg gggtataacc ccctgcattt ctttgcccct       900
```

```
gagggatcat atgcaagtaa tccgcatgat ccacagactc gaaaaacaga gctcaaacaa      960
atgattaaca cgcttcacca gcatggtctt agggtgatcc ttgacgtggt ttttaaccat     1020
gtgtataagc gagagaactc ccctttcgaa aagactgtcc ccggatattt ctttcgccat     1080
gatgagtgcg gtatgcctag caatgggact ggggtcggta atgatatcgc cagcgaaagg     1140
cgaatggcta gaaaatttat agcggactgc gtagtatact ggctcgagga atataacgtt     1200
gacggatttc gcttcgattt gttgggaatc cttgacatag acactgtact ttatatgaag     1260
gaaaaggcta caaaagcaaa gcccggaata ttgctctttg gcgaggggtg ggatcttgcg     1320
acgcccctcc cccacgaaca gaaagccgct ctcgcaaacg ctccccgaat gcctggcatt     1380 ggattttca atgatatgtt ccgagacgcc gtaaagggca acaccttcca tctgaaagcc     1440
actggatttg ccctcggtaa cggagaatcc gctcaagctg tcatgcacgg tattgcaggc     1500
agcagcgggt ggaaggcctt ggcccccata gtgccggaac cctcacagtc aatcaactat     1560
gtggaaagtc atgataacca tacttttttgg gacaagatgt catttgcatt gccgcaagag     1620
aacgactcca ggaagcggag ccggcaaagg ttggcggccg cgatcatcct gttggctcag     1680
ggagtgccct tcatccattc cggtcaggag ttctttcgga ccaaacaggg ggttgaaaac     1740
tcctaccaat catctgattc cataaatcaa ctcgactggg atagacgaga aaccttcaaa     1800
gaggacgtcc actatataag gagactgata tctttgcgaa aggcgcatcc tgcttttcgg     1860
ctccggagcg ctgcggacat ccagagacat ctcgagtgtc tgacccttaa ggagcatttg     1920
attgcctatc gactgtatga cttggatgag gtcgacgaat ggaaggatat catagttatt     1980
catcacgcct ctccagacag tgttgaatgg cgactgccta acgacatccc ctacaggctg     2040
ctctgcgacc cgtccggttt tcaggaagac ccgacagaaa ttaaaaagac cgtggccgtg     2100
aatggaattg ggacagtcat cctctacctg gcatcagatc tcaagtcttt tgcctga       2157
```

```
<210> SEQ ID NO 11
<211> LENGTH: 2157
<212> TYPE: DNA
<213> ORGANISM: Artificial Sequence
<220> FEATURE:
<223> OTHER INFORMATION: Codon optimized polynucleotide coding sequence
      #5 for expressing Pullulanase

<400> SEQUENCE: 11
```

```
atggtatcta tccggaggtc atttgaggcc tacgttgacg atatgaacat tattacagtt      60
ctgataccgg ctgaacagaa agaaattatg acaccacctt tccgactgga gactgaaata     120
accgacttcc ccctggcggt gagagaagag tacagcctgg aggctaagta caagtatgta     180
tgtgtaagcg atcatccagt gacctttggc aagatccatt gtgttcgagc ttcatccggg     240
cacaagaccg atctccagat tggcgccgtc atccgaacgg cggcgttcga cgatgagttc     300
tattacgacg gggaactggg ggcagtttac accgctgatc atactgtctt taaggtctgg     360 gccccgcgg ctacctctgc cgcagttaag ctttcacacc cgaacaagag cgggagaaca     420
tttcaaatga cgaggttgga aagggcgtc tatgcagtca cggtcactgg agatctccac     480
ggctatgaat acctcttttg catatgtaat aacagtgagt ggatggagac agtagaccag     540
tacgcgaaag ccgttacagt caacggggag aaaggagtgg tactgcgccc cgaccagatg     600
aaatggaccg cacccccttaa gcccttcagc caccctgttg acgcggtgat ctatgagacc     660
caccttagag attttagcat acatgaaaac agcggcatga ttaataaagg taagtacctt     720
gccctgaccg agacagacac tcagacggcg aacggaagct cctcaggtct cgcatatgtg     780
```

```
aaggaactcg gcgtgaccca tgtcgagctc ctccctgtta acgatttcgc aggggtcgac      840
gaggaaaaac cgttggatgc gtacaattgg ggctacaacc cccttcattt tttcgctccc      900
gaaggaagtt atgcaagcaa tccacacgat ccccaaacaa ggaaaactga actcaagcag      960
atgattaata cactgcatca acacgggctg agagttatcc tggatgtggt tttttaaccat     1020 gtttacaaga gagaaaacag ccccttcgag aaaactgttc cgggttactt ttttcggcat     1080
gacgagtgtg gcatgccttc aaacggaact ggtgtgggta atgatatagc ttccgagcga     1140
cgaatggcca ggaagtttat agctgactgt gtcgtgtact ggctcgagga gtataatgtt     1200
gatggttttc gattcgattt gctgggcatc cttgacatcg atacggtcct ctatatgaaa     1260
gaaaaggcga cgaaggcgaa acctggaatt ctcttgtttg gtgagggttg ggaccttgca     1320
acgccgctgc cccatgaaca aaaggcagcc cttgcgaatg cgcccaggat gccggggatt     1380
ggtttcttta atgatatgtt tcgggatgcc gtgaagggga acacgtttca ccttaaggct     1440
acgggatttg ccttgggaaa tggtgaatca gcacaggcag tgatgcatgg cattgccggc     1500
agctccggtt ggaaagcact ggcgccgatt gtgcctgaac cctcacaatc tattaattac     1560
gtagaatcac atgacaatca cactttctgg gacaaaatga gcttcgcatt gccccaggag     1620
aacgatagca ggaaaaggtc acgccagagg ctcgcagcag cgatcatttt gcttgcccag     1680
ggcgttccat ttatacattc aggacaagag ttcttccgga cgaaacaggg tgtcgagaat     1740
tcctatcaga gtagtgatag tataaatcaa ctggattggg accgccgaga gacattcaag     1800
gaagacgtac actacatcag acgccttatc tctctgcgca aggcacaccc agcatttcga     1860
ttgagatcag cggccgacat ccagagacac ctggagtgtc tgacactgaa agaacatttg     1920
atagcctatc gcctctatga tcttgacgag gtcgatgagt ggaaagatat tatcgtcata     1980
catcatgcat cacccgacag cgttgaatgg cggcttccga acgacattcc ttatcggctg     2040
ttgtgcgatc cgagtgggtt ccaggaagat ccaacggaga taaaaaaaac agtggcagtc     2100
aatggcatcg gtacggtcat tctctacctg gcttcagatc tcaagtcatt tgcgtga       2157
```

```
<210> SEQ ID NO 12
<211> LENGTH: 2157
<212> TYPE: DNA
<213> ORGANISM: Artificial Sequence
<220> FEATURE:
<223> OTHER INFORMATION: Codon optimized polynucleotide coding sequence
      #6 for expressing Pullulanase

<400> SEQUENCE: 12
```

```
atggtgagta tccgcaggag ctttgaagct tatgtagatg acatgaacat tattaccgtt       60
ctcatccctg cagaacaaaa ggaaataatg acgcctccct ttcgccttga cacagaaatt      120
acagactttc ctctggcagt gcgagaagag tattctctgg aggctaaata taagtacgta      180
tgcgtgagcg accaccctgt tacgttcggc aaaatacatt gtgtgcgcgc ttcctctggc      240
cataagacag atctccagat cggtgctgta attagaaccg ccgccttcga cgacgaattt      300
tattacgatg gagagcttgg ggctgtgtat actgctgatc acaccgtgtt taaagtgtgg      360
gccccggcag caactagtgc ggcagtcaaa ctctcacacc caaacaaatc tggtagaact      420
tttcaaatga ctaggctgga aaaggtgtg tacgcagtca ctgttaccgg agatttgcat      480
ggttacgaat acctgttttg tatctgcaac aatagtgagt ggatggagac cgtagaccaa      540
tacgccaaag ctgttactgt caatggcgaa aaggggggtcg ttcttcggcc ggatcagatg      600
aagtggacag ctccattgaa gcccttcagc caccctgttg acgccgttat ctatgaaaca      660
```

-continued

```
cacctgcgag acttcagtat tcatgaaaat tctggaatga taaacaaggg gaagtatctt    720
gctctcactg aaactgatac ccagactgcc aacggcagta gtagcggcct cgcctacgta    780
aaggagctcg gagttactca tgttgaactt cttccggtaa atgatttcgc aggtgttgat    840
gaagagaagc cattggacgc atataattgg ggttataacc cgcttcactt tttcgctccc    900
gaagggtctt atgcctctaa cccccatgat ccacagacac gcaagactga gcttaaacag    960
atgattaata cactgcacca acatggtctt agggtgattt tggatgtggt atttaaccac   1020
gtatacaaac gagaaaactc ccctttgag aaaaccgttc ccggttactt tttccggcat   1080
gatgagtgcg gcatgcctag taatggtacc ggggttggaa atgacattgc gtcagaacga   1140
cgaatggccc gcaagttcat tgctgattgt gtcgtatatt ggctcgaaga gtataacgtc   1200
gacgggtttc gctttgactt gcttggtatc ctcgatattg ataccgtcct ctacatgaag   1260
gaaaaagcga caaaagcaaa accgggaata ctcctcttcg gcgagggctg ggacctggcg   1320
acaccattgc ctcacgagca gaaggctgcg ctcgcgaatg cgccacgcat gcctggtata   1380 gggttttta acgatatgtt tagggacgcg gtaaaaggca acacgttcca tctcaaggct   1440
acaggattcg cactcgggaa tggagaatca gctcaggctg tcatgcatgg cattgcaggc   1500
tcatccggtt ggaaagcttt ggcaccgatt gtacctgagc catctcagtc tatcaattac   1560
gtggagtcac atgataatca cacgttttgg gataagatga gttttgccct cccgcaagag   1620
aatgactctc gaaaaagaag tcgacaaaga ctggccgcgg ctataattct cctcgcgcag   1680
ggcgttccgt ttatacactc tggacaagaa tttttttagga ctaagcaagg ggtagaaaat   1740
agttatcagt ctagcgattc tattaaccag ttggactggg acagaaggga gacgttcaaa   1800
gaagatgtgc actacatacg aaggcttata agcttgcgca aggctcaccc agcttttaga   1860
cttcgatccg cagcggatat tcaacggcac ttggaatgtc ttacgctgaa ggaacacctc   1920
atagcctata gactgtatga cttggacgaa gttgacgagt ggaaagatat tattgtgata   1980
caccatgcgt cacctgacag tgtagagtgg agattgccta acgacattcc ctaccgcctg   2040
ctctgtgatc cctctgggtt ccaagaggac ccgaccgaaa tcaagaaaac agtagcagtt   2100
aacggaatcg gtactgtaat actttatctc gcttccgatc tgaagtcctt cgcatga      2157
```

<210> SEQ ID NO 13
<211> LENGTH: 2157
<212> TYPE: DNA
<213> ORGANISM: Artificial Sequence
<220> FEATURE:
<223> OTHER INFORMATION: Codon optimized polynucleotide coding sequence
      #7 for expressing Pullulanase

<400> SEQUENCE: 13

```
atggtatcca taaggagaag cttcgaagct tatgtggatg atatgaatat aataaccgta     60
ctgattcccg cggaacaaaa agaaataatg acgccgccct tcaggttgga gacggaaata    120
acggatttcc cgttggcagt acgagaggaa tatagcctgg aggcgaaata taaatatgta    180
tgcgtgagcg accatcccgt gacatttggc aaaatacatt gcgtaagggc ttcctccgga    240
cataagactg accttcaaat aggtgcagtc atacgaacgg ccgcatttga tgatgagttt    300
tattatgacg gcgagttggg cgcggtctat actgctgacc ataccgtgtt taaagtctgg    360
gctcctgcgg ctacatcagc cgcggtcaag ctctcccacc caaataagag tgggcgaaca    420
ttccaaatga cgcgcctcga gaagggtgtt tacgcggtta cggtcaccgg gatttgcat    480 gggtacgaat acctgttctg catatgtaac aacagtgagt ggatggaaac ggtggatcaa    540
```

-continued

```
tacgcgaaag cggtgactgt taacggagaa aagggcgtag tccttagacc cgaccaaatg    600
aagtggactg cacctctgaa accattctca cacccagtgg atgctgttat ttatgaaact    660
catcttaggg actttagcat ccatgagaac tccggaatga tcaataaggg aaagtacctg    720
gcacttacgg aaaccgatac ccagacggcc aatggatcta gttcagggct cgcttatgtc    780
aaggagttgg gtgtcacgca cgtagagctt ctccccgtca atgactttgc gggggtggac    840
gaggaaaaac cccttgatgc gtacaactgg ggctacaacc ccctgcattt cttcgccccc    900
gagggcagtt acgcgtctaa tccacatgac ccacaaacac gaaagaccga gctcaagcag    960
atgataaaca cacttcacca gcacgggctc agggtaattc ttgatgtagt gtttaaccac   1020
gtgtacaaga gggagaactc accttttgaa aagaccgtac cgggatattt ttttagacat   1080
gacgaatgcg gaatgccgtc caacggaaca ggcgttggca atgacatagc tagcgagcgg   1140
cggatggcac gaaagttcat agcagattgt gtcgtttact ggcttgagga gtacaacgtg   1200
gacggattta ggtttgacct tctcggaatt ctggatattg atacggttct ttacatgaaa   1260
gagaaagcga caaaggctaa gccaggtata ttgctctttg gtgaaggatg ggaccttgca   1320
acaccactgc cccatgaaca gaaagcagcc ctcgccaatg cgccccggat gcctggcatt   1380
ggcttcttca atgatatgtt tcgggacgca gtaaagggca cacctttca ccttaaagcc   1440 acaggatttg cactcgggaa tggtgaaagc gcgcaggccg ttatgcacgg cattgccggt   1500
agttctggtt ggaaggccct tgctccaatt gtgcctgaac cgagccaatc tataaactac   1560
gtcgagagtc acgataacca cacttttttgg gataaaatga gtttcgcgtt gccgcaggag   1620
aatgacagca ggaaacggag taggcagcgc cttgccgcag caattatatt gttggcccaa   1680
ggtgtgcctt ttatacactc agggcaagag ttctttcgaa ctaaacaagg tgtcgagaac   1740
tcttaccagt cctccgattc catcaaccag ctggattggg accgccgcga gacttttaaa   1800
gaagacgttc actacatcag gagacttatt agtctccgca aagctcatcc agcgttcagg   1860
cttcggtccg ccgctgacat ccaacgacac cttgagtgtc tcacactcaa ggagcatctg   1920
atcgcttacc gcttgtatga cttggatgaa gtagacgagt ggaaagacat aatcgtaatc   1980
caccatgcct caccagattc tgtcgagtgg aggctcccca cgatattcc ctatcgcttg   2040 ctgtgcgatc cgagcggttt ccaagaggac ccaaccgaaa taaaaaaac cgttgcggta   2100 aacggtatcg ggactgttat actttacctg gctagcgatc tgaaatcttt tgcctga     2157
```

```
<210> SEQ ID NO 14
<211> LENGTH: 2157
<212> TYPE: DNA
<213> ORGANISM: Artificial Sequence
<220> FEATURE:
<223> OTHER INFORMATION: Codon optimized polynucleotide coding sequence
      #8 for expressing Pullulanase

<400> SEQUENCE: 14
```

```
atggtgtcca taaggcggag cttcgaggct tacgtagacg atatgaatat tattactgtt     60
ttgatccccg ccgaacaaaa agagattatg actcccccct ttagattgga gacagagatc    120
acggatttcc cattggcggt acgggaggag tactctttgg aagcaaagta taagtatgtc    180
tgtgtaagtg atcatccggt tactttcggc aagatccact gcgttagagc gtcatccggt    240
cacaaaaccg acctgcagat tggagcggtg attagaacag cggctttcga tgacgaattt    300
tactacgacg gtgagctcgg cgctgtgtac acagccgacc acacagtatt taaagtatgg    360
gctcccgcag ctacaagcgc agcagtaaag ctctcccatc caaataaaag tggcagaacg    420
```

```
tttcagatga ctcgactcga gaagggagtc tacgccgtta ccgtcacggg ggatctccac    480
gggtatgagt atctgttttg catttgcaac aactctgaat ggatggaaac ggtggatcag    540
tacgctaagg cagtgaccgt taatggcgaa aagggcgttg tgctgagacc cgatcagatg    600
aaatggacgg cccctcttaa accattctct catcctgtgg acgccgtcat ttatgaaacg    660
cacttgagag atttcagtat acacgaaaat agtggaatga taaacaaggg aaagtacctg    720
gcacttaccg aaactgatac gcagaccgca aatggaagtt catctggact cgcctatgtc    780
aaagagcttg gtgttactca tgttgagttg ctgcctgtca cgacttcgc tggagtagac    840 gaggaaaagc tcttgacgc atataactgg ggttacaacc cgctgcactt cttcgccccc    900
gaaggatcct acgctagcaa tcctcacgac ccgcaaaccc gcaagacaga actcaaacag    960
atgataaaca cccttcatca gcatggcctt agagtgattc ttgacgttgt cttcaatcat   1020
gtttacaaac gagagaatag tcctttcgaa aaaactgtcc cgggatattt ctttcggcac   1080
gatgagtgcg gaatgccgtc aaacggaacg ggcgttggga cgatatagc ttccgagcga   1140 agaatggccc ggaagttcat tgctgattgc gtcgtctatt ggctggagga atacaatgtg   1200
gacgggtttc gctttgacct gctcggaatt ttggatatag acacagtact gtatatgaaa   1260
gagaaggcga ccaaggcgaa acccggcatt cttctttcg gtgaagggtg ggaccttgcc   1320 acaccctgc cccatgaaca aaaggccgcc ctggctaacg cccccagaat gccgggaata   1380 ggcttttca atgatatgtt ccgagatgcg gtaaaaggta atacatttca ccttaaggca   1440
acagggttcg cgctcgggaa tggcgaatca gcgcaggccg tgatgcacgg tatcgctggt   1500
tcttcaggat ggaaggctct cgctccgatc gtaccggagc cgtctcagtc aattaattac   1560
gtggagagtc acgataatca tacttttgg gataagatgt ctttcgcact cccccaggaa   1620
aacgactccc gaaaaagatc aaggcaacgg ttggcagctg ctataatctt gctcgcccaa   1680
ggtgttccat ttatccattc tggtcaagaa ttctttcgaa cgaagcaggg tgtggagaat   1740
agctaccagt cctccgactc aatcaatcaa cttgattggg atagaaggga aacttttaag   1800
gaagatgttc attacatccg ccggctgata tctttgagaa aggcacaccc agctttccgc   1860
ctgaggagcg cggcggacat acagcgccat ttggagtgcc tgacactcaa agagcacctc   1920
attgcctata gactctacga tttggacgaa gtagacgagt ggaaggacat tatagtaata   1980
caccatgcgt ctcccgacag cgtagaatgg cgcctcccta acgacatacc ttatcggctc   2040
ctctgcgacc ccagtggatt tcaagaggat ccgaccgaga tcaagaaaac agtcgcggta   2100
aacggtatag gtacggtcat actgtatctc gcctcagact tgaagagctt tgcgtga     2157
```

<210> SEQ ID NO 15
<211> LENGTH: 2157
<212> TYPE: DNA
<213> ORGANISM: Artificial Sequence
<220> FEATURE:
<223> OTHER INFORMATION: Codon optimized polynucleotide coding sequence
      #9 for expressing Pullulanase

<400> SEQUENCE: 15

```
atggtaagca tccgccgatc attcgaggct tacgtggacg acatgaacat tattaccgtt      60
ctcatccctg ctgagcaaaa ggaaatcatg acgccaccct tccgccttga gacagaaata     120
acagattttc ccctggcggt gagagaggag tactccctgg aagccaaata caaatacgtg     180
tgtgttagcg accatccagt aacgttcggg aagatccatt gcgtgcgggc atcctccggc     240
cacaaaacgg atcttcagat tggagccgtg attcggacag ctgcgtttga tgatgagttt     300
```

```
tactacgatg gagaactggg ggcagtatat acggccgacc atacggtatt taaggtgtgg      360 gccctgcag ctacatcagc ggctgtcaaa cttagccatc caaacaagtc cgggcgaacg       420
tttcaaatga ctagactgga gaaagggtg tatgctgtca ccgttactgg ggaccttcac       480
ggatacgagt acttgttttg catatgtaat aattccgagt ggatggagac cgtagaccag      540
tatgctaaag ctgtaactgt taatggtgaa aagggtgttg ttctccggcc agaccaaatg      600
aaatggaccg cgccactcaa accctttct catccagtgg atgcagtgat ttatgagacc       660
cacttgcgag atttctcaat acatgaaaac tctggtatga tcaacaaggg caaatatttg      720
gcactcacgg agaccgatac gcaaaccgct aatgggagta gtagtggcct cgcctacgta      780
aaagagctcg gggtaacgca tgtagagctc cttccagtca atgactttgc aggggtagat      840
gaagaaaaac ctctggatgc gtacaactgg ggctacaatc cacttcactt cttcgctcct      900
gagggttctt atgcaagcaa cccgcacgac cctcaaacac ggaaaactga acttaaacaa      960
atgattaata cactccatca gcatggtctg cgcgtcatct tggatgtggt cttcaatcac     1020
gtttataaac gagaaaacag tccgtttgag aaaaccgttc ctggatattt tttcaggcat     1080
gatgaatgcg gcatgccctc taatggtacg ggagttggta acgacatagc tagtgaaaga     1140
cgaatggcgc gcaaattcat agcagactgc gtggtctatt ggctggagga atataacgtt     1200
gatggcttca gatttgacct gctcggcatt ctcgacattg acacggttct ttacatgaag     1260
gagaaagcaa cgaaagccaa accgggaatc cttttgttcg gcgagggttg ggatcttgct     1320 accccctttgc cacatgagca aaaggctgct ctggcaaacg ctcctagaat gcctggaata     1380
ggcttcttta atgatatgtt tagggacgcc gtcaagggga acacgtttca cctgaaagca     1440
acaggatttg cgctgggaaa cggcgaaagc gctcaagctg taatgcatgg gatagcgggc     1500
tcctccggat ggaaagccct ggcgcctatt gtacccgagc cgtcacaaag tatcaattac     1560
gtggaatctc atgataatca tacttttttgg gacaagatgt cattcgcgct gcctcaagag     1620
aacgactctc ggaagagatc tcggcagcgc cttgcagccg caatcattct tttggctcag     1680
ggagtcccct tcatccatag tgggcaagaa tttttcagaa ctaagcaagg cgtggaaaat     1740
tcctaccaaa gctccgattc cataaatcaa ctggactggg atcgccgaga gaccttcaaa     1800
gaggatgttc actacattcg gaggttgatc tctttgagaa aagcccaccc ggccttcagg     1860
ctgaggagtg ccgcagacat tcaaagacac ctcgaatgtc ttactctcaa ggagcatctt     1920
attgcgtacc ggctgtacga cttggacgag gtggacgagt ggaaagatat aattgttata     1980
catcatgctt ccccggatag tgtcgagtgg cgcttgccca acgatatccc ctacagactc     2040
ttgtgtgacc caagcggctt tcaagaggat ccaacggaaa tcaaaaaaac tgtagcagtc     2100
aacggcattg gtacggttat cctttacctc gcgtccgacc tcaagagctt tgcgtga       2157
```

```
<210> SEQ ID NO 16
<211> LENGTH: 2157
<212> TYPE: DNA
<213> ORGANISM: Artificial Sequence
<220> FEATURE:
<223> OTHER INFORMATION: Codon optimized polynucleotide coding sequence
      #10 for expressing Pullulanase

<400> SEQUENCE: 16
atggttagca ttaggcggag cttcgaggct tatgtagatg atatgaatat cataaccgtt       60
ctcatccctg cagagcaaaa agaaataatg acacctccct ttaggcttga aacggaaatc      120
acggatttcc cccttgcggt ccgcgaagaa tactccttgg aagccaaata caagtacgtc      180
```

-continued

```
tgtgtctctg accaccctgt aacgtttggt aaaattcact gcgtacgcgc gagctcagga      240
cataagacgg accttcagat aggggcagtt attcggacag ctgcttttga cgacgagttt      300
tattacgacg gtgaattggg cgcagtttac actgccgatc acactgtttt caaggtgtgg      360
gcacctgctg ccacatctgc cgcggttaag ttgtctcacc ctaacaagag cggccggaca      420
tttcagatga cccgactcga aaaggggta tacgcagtga ccgtaactgg tgatttgcac       480
gggtacgaat accttttctg catttgtaac aattccgaat ggatggagac agtggaccag      540
tatgcaaagg cagtgacggt caacggagaa aagggcgttg tgttgcgccc tgatcagatg      600
aagtggacgg cccctcttaa acctttagt cacccagtag atgcagtgat atacgagacg        660
catctgagag acttctctat acatgagaat tcaggtatga ttaataaggg taagtacctg      720
gcccttaccg agacagatac ccaaactgca aatggctcct ctagtggcct ggcatatgta      780
aaggaactgg gagtgacccca tgtcgaactc ctcccagtaa atgattttgc gggggttgat     840
gaggaaaagc cacttgatgc atacaattgg ggttacaacc cactgcactt ttttgctcct      900
gaagggtcct acgctagcaa ccctcatgat cctcaaacca ggaagacaga attgaaacaa       960
atgattaata ccctccacca gcacggtttg agagtgatcc tcgatgttgt ctttaaccat     1020
gtgtacaaac gggagaacag tcccttcgaa aagacagtcc cggggtactt tttccgccac     1080
gatgaatgtg gcatgccctc caatggaact ggtgtaggca atgacattgc gtctgaaaga     1140
aggatggcca ggaagtttat agctgattgt gtagtctact ggttggagga atacaatgtg     1200
gacggttttc ggtttgatct gctcgggatc ctggacatcg atactgtatt gtacatgaag     1260
gagaaagcta ctaaagcaaa accgggcatc ttgttgtttg gtgaaggatg ggatcttgca     1320
acgcctcttc ctcatgaaca gaaagcagcg ttggcaaacg caccaaggat gccggggata     1380
ggtttcttca atgatatgtt ccgggatgcc gtcaaaggaa acacattcca cctgaaggcc     1440
acaggcttcg ctctcggcaa cggcgagtca gcgcaagccg taatgcatgg catcgcaggc     1500
tcctcagggt ggaaagcact ggcgcctatt gtgcctgaac catctcaaag cataaactac     1560
gtcgagtccc acgacaacca tacttttgg gataaaatga gctttgcgct cccacaagaa       1620
aacgacagtc ggaaacggag caggcagcga ctcgctgccg ctattatact cttggctcag     1680
ggggttccct ttatacacag cgggcaagaa ttctttagaa ccaagcaggg agtagaaaat     1740
tcttatcaga gttccgactc aatcaaccaa ctcgattggg ataggcggga aacatttaag     1800
gaggacgtcc attacataag gagacttatt tctctcagaa aagcacatcc tgctttcagg     1860
ttgcgatccg ccgccgatat tcaacgccat ctcgagtgcc tcacactgaa ggaacacctc     1920
atcgcatacc gactctacga tttggatgag gtggatgagt ggaaagacat aatcgtcata     1980
caccatgcta gcccggattc cgtagagtgg cggttgccga atgacatccc ataccgactg     2040
ctttgtgatc cttcaggttt ccaagaagac cccaccgaga ttaagaaaac agtggccgtt     2100
aatggtattg aacggtcat tctgtacctc gcatctgacc tgaaatcatt cgcgtga       2157
```

<210> SEQ ID NO 17
<211> LENGTH: 1974
<212> TYPE: DNA
<213> ORGANISM: Artificial Sequence
<220> FEATURE:
<223> OTHER INFORMATION: Codon optimized polynucleotide coding sequence
     (#2) for expressing the bacterial limit dextrin alpha-1,6-
     glucohydrolase (GlgX)

<400> SEQUENCE: 17

-continued

```
atgacccagt tggcaatagg aaagcccgca ccacttggcg cacattatga tggtcagggt          60
gttaatttca ctcttttttc cgctcatgcg gagagggtag aactctgtgt cttcgacgca         120
aatggccaag aacatagata tgacttgccg ggacactcag gcgacatttg gcatgggtac         180
ttgcccgatg ctcggcctgg cctcaggtat ggatatcgcg tacacggacc gtggcaaccg         240
gcagaagggc atcggttcaa tccagcaaaa ctcctcatag acccgtgcgc aaggcagatt         300
gatggagagt tcaaagataa cccgcttttg catgcgggcc ataacgaacc tgactatcgg         360
gataacgcgg caatcgcgcc gaaatgtgta gtagttgttg accattacga ttgggaagat         420
gatgcaccac cgcgaacacc ttggggtagc accattattt atgaagcaca tgtcaaaggt         480
cttacgtacc tgcatccgga gattcccgtg gaaataagag gaacgtacaa agccttgggt         540 cacccccgtaa tgataaacta ccttaaacag ttgggaataa ccgcattgga attgctgccc         600
gtggcgcaat ttgccagcga gccgcgattg caacggatgg gtctcagtaa ttactggggg         660
tataatccgg tagctatgtt cgcccttcac cctgcttatg catgttctcc agagactgca         720
ttggacgaat tccgcgacgc aataaaagca cttcacaagg ctggaattga ggttattttg         780
gacattgtgt tgaaccactc tgccgagctt gacttggatg ggccgctgtt ttcactgagg         840
ggtatcgaca acaggagcta ctattggatc cgggaagatg gcgactacca caactggaca         900
ggatgtggga atactctgaa tctctctcac ccggctgtcg tggattatgc cagcgcttgc         960
ctgcgatatt gggtcgagac gtgtcacgtt gatgggttcc gatttgactt ggctgcagtg        1020
atggggagaa cgccagagtt ccgacaggat gccccccttt tcaccgctat tcaaaattgc        1080
cccgtactga gtcaggtgaa gctcatcgct gagccgtggg acatagcacc gggcggatac        1140
caagtgggaa attttccgcc gttgtttgct gaatggaatg accatttccg ggacgcagct        1200
cgccgatttt ggttgcacta tgatctccct ttgggggctt tcgctggccg ctttgctgct        1260
tcttcagatg ttttcaaaag aaacggacgg ctgccatccg ccgcaataaa cctcgtaaca        1320
gcccacgacg gatttacact tcgggactgt gtttgtttta accataagca caatgaagca        1380
aacggggagg aaaaccgaga cggcactaac aataactata gtaacaacca cggcaaagag        1440
ggcttgggtg gaagtctgga tctggtggag cggcggcgcg actccattca tgctctgctt        1500
accactcttt tgctgtccca gggtaccca atgctcctgg ctggggatga acatggccac        1560
tcccagcatg gcaataacaa tgcatattgt caggacaatc agcttacttg gctcgactgg        1620
agccaagcgt catcaggcct cacagcattt accgctgccc ttattcactt gcgcaaacgc        1680
attcctgctt tggtcgaaaa ccgatggtgg gaagagggag atggcaatgt gaggtggttg        1740
aatcggtacg cccagccgct tagcactgat gagtggcaga atggcccgaa gcagctccag        1800
atactccttt cagatcgctt tttgatagcg atcaacgcca cacttgaggt gaccgagatt        1860
gttctccctg caggggaatg gcacgcaatc cctccgttcg caggtgagga taaccccgtt        1920
ataacagctg tttggcaagg ccccgcccat gggctgtgcg tattccaacg atga            1974
```

<210> SEQ ID NO 18
<211> LENGTH: 1974
<212> TYPE: DNA
<213> ORGANISM: Artificial Sequence
<220> FEATURE:
<223> OTHER INFORMATION: Codon optimized polynucleotide coding sequence
     (#3) for expressing the bacterial limit dextrin alpha-1,6-
     glucohydrolase (GlgX)

<400> SEQUENCE: 18

```
atgacccaac ttgcgatcgg caagccggca ccgctggggg cacactacga cggccaggt           60
```

```
gttaacttca cgctgttctc agcacatgca gaacgcgtag agctctgtgt attcgacgct        120
aatggacaag agcacaggta tgatctgcct gggcactccg gagacatctg gcatggttat        180
ttgccagacg ctcgccccgg actcaggtac gggtaccgag tgcacggacc atggcaacca        240
gccgaaggac accgctttaa cccagccaag ctgctgattg acccgtgcgc gaggcaaatc        300
gacggagaat ttaaagataa ccctcttctt cacgcaggac acaatgaacc cgactatcga        360
gataatgctg cgattgcacc aaagtgcgtc gtcgtcgtcg accattatga ctgggaagac        420
gatgcgccac cccgaacacc atgggggagc acgataatat atgaggctca cgttaagggc        480
ctgacgtact tgcatccgga gatacctgta gaaatcaggg ggacctacaa ggcccttggt        540
catcccgtta tgattaacta tttgaagcag cttggaatta ctgcccttga acttctcccc        600
gtggcgcaat ttgcatcaga accccggctg cagcgaatgg gactgagtaa ctactgggga        660
tacaatccag tggccatgtt tgcactccac cctgcttatg cgtgtagccc cgaaacagca        720
ttggacgagt tcagggatgc aatcaaggcc ttgcataaag ccgggattga ggtaatactc        780
gacatagttc tgaatcatag cgcggaactg gatctcgatg gaccacttttt ttcacttaga        840 gggattgaca accgctcata ttattggatc agagaggatg gcgattatca taattggaca        900
gggtgtggaa acacactcaa tctctcccat ccggctgtgg tagattatgc atccgcttgc        960
ctccggtatt gggtagaaac atgtcatgtg gacgggttcc ggttcgatct ggcggccgtc       1020
atgggcagga cacctgaatt cagacaggac gccccttttgt tcaccgccat acagaactgt       1080
ccggtcttgt cccaagtgaa gttgattgcg gaaccatggg acattgcccc tggggggctac      1140 caggtcggaa attttccgcc cctcttcgct gagtggaatg accacttccg ggatgcagcc       1200
cgccgctttt ggttgcacta cgatttgccg ttgggcgcct tcgctgggcg ctttgctgcg       1260
agctcagacg tatttaaaag aaatgggcga ttgcctagtc cggcaattaa tctggtgact       1320
gcacacgatg gatttacgct tagggactgt gtttgttttta atcacaagca taatgaagcg       1380
aacggggaag aaaacaggga cggaactaat aataattatt caaacaatca tggtaaggaa       1440
ggtttggggg gttcccttga tcttgttgaa agacgaaggg actccatcca cgcccttctc       1500
actactcttc tgcttagtca aggtacgcct atgttgctcg ccggcgatga acacggacac       1560
tcccagcatg gcaataacaa cgcatactgc caggataatc agctgacctg gctcgattgg       1620
tcccaggcct cctccggatt gaccgccttt accgctgcgt tgatacacct tcgcaaacga       1680
attcccgcat tggtggagaa taggtggtgg gaagagggcg acggcaacgt gaggtggctc       1740
aacaggtatg ctcaaccgct ttccaccgat gagtggcaaa acgggcccaa acagctccaa       1800
attctgctga cgaccgatt cttgattgca atcaatgcga ccctcgaggt caccgaaatc        1860
gtcttgcccg ctggtgagtg gcacgctata ccgccatttg cgggtgagga caatcccgta       1920
ataacagcgg tctggcaggg accagcacac ggtctctgtg tgttccaacg atga            1974
```

<210> SEQ ID NO 19
<211> LENGTH: 1974
<212> TYPE: DNA
<213> ORGANISM: Artificial Sequence
<220> FEATURE:
<223> OTHER INFORMATION: Codon optimized polynucleotide coding sequence
     (#4) for expressing the bacterial limit dextrin alpha-1,6-
     glucohydrolase (GlgX)

<400> SEQUENCE: 19

```
atgacgcagc tcgcaatagg aaagccagca ccccttggag cccattatga tggtcagggc         60
```

```
gttaatttca cactgttttc tgcccatgca gaacgggtcg aattgtgtgt atttgacgct    120
aatggtcaag agcatcgcta tgacctcccg ggacacagtg gggacatttg gcatggctat    180
ctgcctgacg cgcgcccagg gctccggtac gggtaccgag ttcacggtcc ctggcaacca    240
gccgaggggc ataggtttaa tccggcaaag ctgctcattg acccctgcgc tcgccagata    300
gacggagaat ttaaggacaa cccccctgctc cacgctggtc ataatgaacc agactatcga    360
gacaatgcgg ccattgctcc gaaatgtgta gtcgttgttg atcactatga ctgggaagac    420
gacgctccac ctagaactcc ttgggggtcc acgatcatct acgaagctca tgttaagggt    480
ctcacttatc tgcacccaga aatacccgtg gaaatacgcg gaacttataa ggcactgggt    540
catcccgtaa tgatcaacta cctgaagcag cttggtatca cggcgcttga actcctccca    600
gttgcacaat ttgcaagtga gccacgactc cagagaatgg ggctttccaa ttactgggt    660 tacaatccag tggccatgtt tgcactccat ccagcgtacg cttgctcccc tgagacggct    720
cttgatgagt ttagagatgc tataaaggca ctgcataagg ctggaataga agtcatcttg    780
gacatagtgc tcaatcacag tgccgagttg gatctggacg ggccgctctt tagcctgcgg    840
gggatagata tcggagtta ctattggatt agggaggacg gcgattacca taattggacg    900
ggttgcggaa atacgctgaa cttgtctcac cctgcggtcg tagactacgc ctccgcatgt    960
cttagatact gggtcgaaac gtgccatgta gatggtttca ggttcgactt ggcggcggtt   1020
atggggagga cgcccgagtt tcggcaagat gcgcccctgt ttacggcgat ccagaactgc   1080
cccgtactgt cacaggttaa actgatcgcg gaaccctggg acattgcccc aggcggttat   1140
caggttggaa acttcccacc actgttcgca gagtggaatg atcactttcg cgatgcagca   1200
cggcggttct ggcttcatta tgatttgccg ctgggcgctt tcgccgggcg gtttgcagca   1260
agttcagatg tatttaagcg caatggtcgc ctcccctccg ctgctattaa cctcgtgaca   1320
gcgcatgatg gattcacgct tagagactgt gtgtgtttca accataaaca taacgaggct   1380
aacggtgagg aaaacagaga tggtacgaat aacaactata gcaataacca cggaaaggaa   1440
ggactcggag gttccttgga tctcgttgaa cgcagacgag attccatcca tgcactgctg   1500
accacgctgt tgttgagcca aggtacacct atgctccttg ctggcgatga gcacgggcat   1560
tcccaacacg aaacaacaa cgcctattgt caagacaacc agcttacatg gttggactgg   1620
tcacaggcgt ccagtggact gacagcattt actgctgccc tcatacattt gcgcaaacgc   1680
ataccggccc ttgttgagaa ccgctggtgg gaggaaggcg acggtaacgt tcgatggttg   1740
aatcgctacg cgcagcctct cagtacagac gaatggcaga acggaccgaa acagttgcag   1800
attttgctta gcgatcgctt cttgattgcg ataaatgcca cccttgaggt caccgaaatc   1860
gtactgcctg ctggggaatg gcatgccata cctccattcg ccggcgagga taaccctgtg   1920
atcactgctg tctggcaggg cccggcacat ggactttgcg tctttcagag atga   1974
```

```
<210> SEQ ID NO 20
<211> LENGTH: 1974
<212> TYPE: DNA
<213> ORGANISM: Artificial Sequence
<220> FEATURE:
<223> OTHER INFORMATION: Codon optimized polynucleotide coding sequence
      (#5) for expressing the bacterial limit dextrin alpha-1,6-
      glucohydrolase (GlgX)

<400> SEQUENCE: 20
atgacacaat ggcgattgg aaaaccggca ccccttggtg ctcattatga cggccagggt     60
gtgaatttca ccctgttttc tgcccacgca gaaagggtgg agctttgcgt ctttgacgcg    120
```

```
aacgggcagg aacatcggta cgatttgccg ggtcattcag gagatatctg gcatgggtac      180
cttcctgatg ctcgaccagg tcttcggtat gggtatagag ttcatgggcc gtggcagcca      240
gctgaagggc accgctttaa tccagctaaa ctgctcatcg atccgtgtgc gcgccaaata      300
gatggagagt tcaaggataa tcccctcctg cacgcggggc ataatgagcc ggactataga      360
gacaacgctg cgattgctcc gaagtgtgtg gttgtggtcg accactatga ctgggaggat      420
gatgctcccc ctcggacacc atggggctca acgattatct atgaagctca cgtcaaaggg      480
ctgacgtatc tccaccccga gatcccggta gaaattagag ggacctataa agccctcggc      540
catccagtga tgatcaacta tttgaaacaa cttggtataa ctgcgctgga acttctgcct      600
gtagcacagt tcgcgtctga accacgcctt cagagaatgg ggctttccaa ttattgggga      660
tacaatccag tcgcgatgtt tgctcttcac cccgcctatg cctgcagccc tgaaaccgca      720
ctcgacgaat ttagagatgc gataaaagct ctccacaaag cgggcataga ggtaattctt      780
gatatcgtac tcaatcacag cgccgagctt gatcttgatg ggccgctgtt tagtctgcga      840
ggcatagata accgaagtta ctactggatc agagaagacg gagattacca caactggacg      900
ggttgtggga atactctcaa tctgagtcat cccgccgtag tcgattacgc ttccgcatgt      960
cttcgatatt gggttgagac atgccatgtt gatggattca ggttcgacct ggcggcagtc     1020
atgggcagga cccccgagtt tagacaagat gcaccccttt ttacggccat acagaactgc     1080
ccggtcctct cccaggttaa actcatcgcc gagccatggg acattgcacc aggtggctat     1140
caagtcggaa actttccacc actcttcgcc gaatggaatg accatttccg agatgcagct     1200
agaaggtttt ggctccacta cgatctgcct ctcggtgcct ttgcaggacg attcgctgcg     1260
agctctgatg tgtttaagag aaacgggagg cttccgtccg cagctatcaa tcttgtaacg     1320
gcccacgacg gctttactct tcgagattgc gtctgtttca atcacaaaca caatgaggct     1380
aatggagaag aaaaccggga tggaacaaac aataactact caaataacca cggtaaggaa     1440
ggcctcggag ggagccttga cctcgtcgaa cgaagacgcg acagtataca cgctttgctg     1500
accactttgt tgctcagcca aggtacccct atgttgctgg ctggagatga acacggtcac     1560
agccagcacg gaaacaataa tgcgtattgt caagacaacc agcttacatg gcttgactgg     1620
tctcaagcta gttctggact gacagcgttc acggcggctc tgatccattt gagaaagcgc     1680
attccagcgc tggttgagaa ccgctggtgg aagagggtga tggcaacgt aaggtggctt     1740 aacaggtatg cacaaccgtt gagtaccgat gaatggcaaa atggaccgaa acagctccag     1800
atactcttga gtgaccgctt cttgatcgca ataaacgcta ccctcgaggt taccgagatt     1860
gttttgccag caggagagtg gcacgcaatc ccaccgtttg caggcgaaga taacccagtg     1920
ataacggcag tctggcaggg accagcccac ggcttgtgtg tatttcagcg ctga          1974
```

```
<210> SEQ ID NO 21
<211> LENGTH: 1974
<212> TYPE: DNA
<213> ORGANISM: Artificial Sequence
<220> FEATURE:
<223> OTHER INFORMATION: Codon optimized polynucleotide coding sequence
      (#6) for expressing the bacterial limit dextrin alpha-1,6-
      glucohydrolase (GlgX)

<400> SEQUENCE: 21
atgacacaac tggcaatcgg taaaccagca ccactcggcg ctcactacga tggccaggggt       60 gttaatttca cgttgttttc tgcccatgcg gagcgggtgg aactgtgtgt atttgacgcg      120
```

-continued

```
aatggacaag agcataggta tgacctcccg ggacattccg gtgacatctg gcatggatac      180
ttgccagatg caaggcccgg actcaggtat ggctaccgag tccacggccc ttggcagcct      240
gcggagggtc atcggtttaa ccctgcaaaa ctcctgatcg accCctgtgc acgacaaatt      300
gacggagaat tcaaagacaa tccgttgctt catgcggggc acaacgagcc ggattacagg      360
gataatgcgg ctattgcccc gaaatgcgtg gttgtcgtcg accactatga ctgggaggac      420
gacgctccac caagaacacc ttgggggtca accataattt atgaagccca cgttaaaggg      480
ctgacctatt tgcaccctga aattccggta gaaatccgag gtacctataa ggccctcggc      540
catccggtaa tgatcaatta tcttaaacag ctgggtatta cagccctgga actgctccca      600
gtagcccagt ttgcgagtga accacggctg caaaggatgg gtctttctaa ctactggggg      660
tataatccag ttgcgatgtt tgctcttcat ccggcttatg catgctcacc tgagactgcc      720
ctggacgagt tccgggatgc aataaaagca ctgcataaag cgggcattga ggttatactt      780
gacattgtat tgaaccactc cgctgaactg gatcttgatg gacctctctt cagcctgcga      840
ggaatagata accgctccta ttactggata agggaagacg gtgactatca caattggacc      900
gggtgcggca acactctcaa tctctcccat cccgccgttg tggattacgc ttcagcgtgc      960
ttgagatatt gggtagagac ttgtcacgta gacggcttcc gattcgatct tgcagctgtc     1020 atggacgaa ccccagagtt cagacaggat gctcctctgt ttactgcaat tcaaaactgc     1080
ccagtgctgt ctcaggtgaa gttgatagca gagccgtggg acatagcccc cggagggtat     1140
caagttggga actttccgcc cctgttcgcg gagtggaacg atcatttcag ggacgccgca     1200
agacgcttct ggttgcacta cgatctgcct ctcggcgctt ttgcaggtcg gtttgcggct     1260
agtagtgacg tattcaagcg caacggacgg cttccgtctg ccgcaatcaa ccttgtaacc     1320
gcacacgacg gcttcacatt gcgggactgc gtatgtttca atcataagca taacgaggcc     1380
aatggtgagg aaaaccggga tggaaccaac aataactata gtaataatca tggtaaagaa     1440
ggtctgggtg gatcactcga cttggtcgag cgccgacggg attccataca tgcattgctt     1500
actaccctcc tcctctccca aggaaccca atgttgcttg ctggagatga gcacggtcac     1560
agccaacatg ggaataataa tgcttattgt caggataacc aactcacgtg gttggattgg     1620
agtcaagcaa gttcaggcct gaccgctttt acggcagcgt tgatacatct gcgcaaacgc     1680
attcctgcgc tcgttgaaaa cagatggtgg gaagaaggcg acggcaacgt cagatggttg     1740
aatcgatatg cgcaacctct gtcaacggat gaatggcaaa acggtcctaa gcagctccag     1800
atactgctga gtgataggtt cctcattgca atcaacgcga ccctggaagt cacggaaatc     1860
gttttgcccg ctggtgaatg gcacgctata ccgccttttg cgggtgagga taaccccgtt     1920
atcactgccg tgtggcaggg accagcgcac ggcctgtgtg tgttccaacg atga          1974
```

<210> SEQ ID NO 22
<211> LENGTH: 1974
<212> TYPE: DNA
<213> ORGANISM: Artificial Sequence
<220> FEATURE:
<223> OTHER INFORMATION: Codon optimized polynucleotide coding sequence
       (#7) for expressing the bacterial limit dextrin alpha-1,6-
       glucohydrolase (GlgX)

<400> SEQUENCE: 22

```
atgactcagc ttgccatcgg gaaacccgcc ccgcttggag ctcattacga tggtcaaggc       60
gtaaatttca cactcttctc agcacatgcg gaacgagtcg aactctgtgt atttgatgca      120
aacgggcaag aacatcgcta cgatcttcca ggtcactccg gggacatctg gcatggatac      180
```

```
ctccccgacg ctaggccggg acttagatac gggtaccgag tgcatggacc ctggcagcca      240
gcggaggggc atcgatttaa tccagctaag ttgcttatcg atccctgcgc taggcagata      300
gacggcgaat ttaaagataa tcccctttttg catgctgggc ataacgagcc tgactatcgc     360
gacaatgctg cgattgcgcc gaagtgcgta gtagtagtcg accactatga ttgggaggac      420
gatgcaccgc cgaggacccc ttggggagt actatcatat atgaagcaca tgttaaaggt       480
cttacatatc ttcatcccga gatccctgtc gaaatccgag ggacttataa agcattgggg      540
catcctgtta tgatcaatta cttgaaacaa cttggcatca ccgccttgga actgctgccc      600
gtggcccagt tcgcctccga gccccgactg caaaggatgg gactctctaa ttattggggc      660
tataaccccg ttgctatgtt cgcgttgcac ccggcatacg catgttctcc tgagaccgcg      720
ctcgatgaat ttcgagatgc cataaaaagct cttcacaagg ccggaattga agtcatactc     780
gacattgttc ttaaccactc agctgaactt gacttggatg ggccgctttt ttctttgcgc      840
gggattgata acagaagtta ctactggata cgggaagacg gtgattatca caattggacg      900
ggttgtggta ataccctcaa tctttcccac ccggctgttg tggattatgc atctgcgtgc      960
cttaggtact gggtcgagac ctgtcatgta gatggctttc gatttgatct cgcggcggtt     1020
atggggagaa cgcccgagtt ccggcaggat gctccacttt tcaccgcaat acagaattgt     1080
cctgtacttt cccaagttaa acttatcgcg gagccatggg acatagctcc tggagggtac     1140
caggttggaa attttccgcc cttgtttgcc gaatggaacg accacttccg cgatgccgct     1200
cggaggttct ggctccatta cgatctccca ctgggagctt tcgcaggtcg ctttgcagcg     1260
tctagcgacg tgtttaagag aaatgggcgg ttgccatccg ctgcgataaa ccttgttacc     1320
gcgcacgacg gctttactct gagagactgt gtttgtttca accataagca caacgaggct     1380
aatggagagg aaaaccgcga cggtacaaat aacaattact ctaataacca tggcaaggag     1440
ggtctgggcg gcagtcttga cctggtcgaa cgaagacggg actctattca tgctctgctc     1500
acaacccttt tgctcagtca ggggacacct atgctgctgg ccggagatga gcacggccac     1560
tcccagcatg gtaataacaa cgcttactgc caggacaacc aacttacgtg gttggattgg     1620
tctcaagcaa gtagtggtct tactgcattt acagcagctc ttatccactt gcgaaaaaga     1680
atacccgctc tggtggagaa ccggtggtgg gaggaaggag acggaaacgt ccggtggctg     1740
aaccgctatg ctcaaccact tagcactgac gagtggcaaa atggcccaaa gcagcttcaa     1800
atactcctca gcgatcgatt cctgattgca ataaatgcca ctcttgaggt caccgagatt     1860
gtccttcccg caggagaatg gcatgccata ccccgtttg ctggagaaga caatccagta     1920
attacggctg tatggcaggg acctgcacac ggcctgtgcg tcttccaaag gtga          1974
```

<210> SEQ ID NO 23
<211> LENGTH: 1974
<212> TYPE: DNA
<213> ORGANISM: Artificial Sequence
<220> FEATURE:
<223> OTHER INFORMATION: Codon optimized polynucleotide coding sequence
       (#8) for expressing the bacterial limit dextrin alpha-1,6-
       glucohydrolase (GlgX)

<400> SEQUENCE: 23

```
atgactcagc ttgcgattgg gaaacctgct ccgttgggcg ctcattacga tggacaaggc       60
gtcaacttta ctttgtttag cgctcatgca gagagagtag agctgtgcgt gttcgatgcg      120
aatggacaag agcacaggta tgacctcccg ggccactcag gggacatatg gcatggctac      180
```

-continued

```
ctccccgacg cgagaccggg tttgaggtat ggttaccgcg ttcacggtcc gtggcagccc      240
gcggaaggcc atcggttcaa tcccgccaag ctcctcatcg acccatgtgc ccgacagatt      300
gacggcgagt ttaaagataa tccgctcctc catgcgggtc ataatgaacc ggactaccga      360
gacaatgctg cgatcgcacc taagtgcgtc gttgtagtag accattatga ttgggaagat      420
gacgcaccac cacggactcc ttgggggagc acgataatat acgaggcaca tgtgaaagga      480
ctcacctatc tgcatccgga gattcccgta gaaattcggg gcacttataa ggcgctcggg      540
caccccgtta tgattaatta cctcaagcag ctggggataa ctgcactcga attgcttcca      600
gttgcccaat ttgccagcga gcctcgactt caacgaatgg gcctgagcaa ctattggggt      660
tataatcctg tggcaatgtt tgcgttgcac ccggcatatg cgtgcagccc cgaaacggct      720
ttggatgagt tccgggacgc aataaaaggc cttcataagg ccgggataga agtaatcctt      780
gacattgtac ttaatcatag tgcggaactg gacttggatg gccctctgtt cagcttgcgg      840
gggatcgaca acaggagcta ctattggatc cgggaggatg gcgactacca taattggact      900
ggatgtggta acacactgaa tctgagtcat cctgcagtgg ttgactacgc cagtgcatgt      960
ttgagatatt gggttgaaac ctgtcatgtg gacggtttta gattcgatct cgccgcagta     1020
atgggacgaa caccggaatt ccgacaagac gccccgcttt ttacggccat acagaattgt     1080
cccgtgctct ctcaggttaa actgattgct gaaccgtggg atatagcccc cggagggtat     1140
caagtcggca atttccctcc gctgttcgcc gaatggaacg atcattttag agacgccgct     1200
agaagattct ggttgcacta tgacttgccg cttggagctt cgccggtcg atttgctgcc      1260 tcatcagatg tcttcaagcg caacgggcga ctgccgtccg ctgcaattaa tttggtgacc     1320
gcgcacgatg gattcacact tagggattgc gtatgtttta accataagca caacgaggct     1380
aatggcgaag aaaatagaga cggcacaaat aataactact ccaacaacca cgggaaggaa     1440
ggactcggtg ggagtttgga tctcgttgag cggcgacgcg attctattca tgcgcttctg     1500
acaactcttc ttctctcaca ggggacgcca atgctccttg ccggtgacga gcacggtcat     1560
agccaacatg gcaacaataa tgcatattgt caggacaatc aattgacgtg gcttgactgg     1620
tctcaggcaa gcagtggcct gactgcgttc acagcagccc ttatccatct tcgaaaaagg     1680
atcccagcgc tggtggagaa tcgatggtgg aagagggtg acgggaatgt gcgctggctg      1740
aatagatatg ctcagccgct gagcacggat gaatggcaga acggaccgaa gcagcttcaa     1800
attctgctgt cagatcgatt tttgatcgcc attaacgcaa cactcgaggt gacagaaatc     1860
gtattgcccg ctggagagtg gcatgccata ccaccatttg ctggtgaaga taatccggtc     1920
atcactgcgg tatggcaagg tccggcacac ggtctgtgtg tttttcaacg atga          1974
```

```
<210> SEQ ID NO 24
<211> LENGTH: 1974
<212> TYPE: DNA
<213> ORGANISM: Artificial Sequence
<220> FEATURE:
<223> OTHER INFORMATION: Codon optimized polynucleotide coding sequence
      (#9) for expressing the bacterial limit dextrin alpha-1,6-
      glucohydrolase (GlgX)

<400> SEQUENCE: 24
atgacgcagt tggcaatagg taaaccagct ccgcttggag cgcattacga cgggcagggt       60
gtgaatttca cgctgttttc cgcccatgca gaacgcgtag aactgtgcgt gtttgacgca      120
aatggacagg aacatagata cgacctgccg ggtcactctg cgatatatg cacggatat       180 ctcccagacg cgaggcccgg tctccggtac ggttaccggg ttcatggtcc gtggcagccc      240
```

-continued

```
gcagaaggcc atcgctttaa cccagctaag ttgcttatcg acccttgcgc cagacaaata    300
gacggtgaat tcaaggataa tccgctcttg catgcaggac acaacgagcc agattaccgc    360
gacaacgcgg ccattgcccc caagtgcgtt gttgtagttg accattatga ctgggaagac    420 gatgccctc cacgcacgcc atgggcagc actattatct atgaagccca cgttaaaggt    480
ctcacttatt tgcatcccga gatcccagtt gagatacgag gtacgtataa agctctcggg    540
caccctgtaa tgatcaacta tttgaaacaa ttgggaatta ctgcgctgga gcttttgcca    600
gttgcacagt cgcgagtga accccgattg cagcgcatgg gtttgagcaa ttattggggt    660
tacaaccctg tagccatgtt cgctctgcat ccagcgtatg cgtgtagtcc cgagaccgct    720
ctcgatgaat ttagggatgc cattaaggca ctccataagg caggcatcga ggtcattctg    780
gatattgtac tcaaccatag cgctgaattg gacctcgatg gcccattgtt ttcattgagg    840
gggatagaca ataggagtta ctattggata cgcgaagacg gcgattatca taactggacg    900
gggtgtggga acacactgaa cctcagccat cctgctgttg tggattatgc ttccgcgtgc    960
ctgaggtatt gggtagagac ctgccacgtt gatggatttc gctttgatct ggcagccgtg   1020
atgggccgca cccctgagtt ccgacaggat gcaccactct ttactgctat ccaaaattgc   1080
ccggttctgt ctcaagtgaa actgattgcg gaaccatggg atatcgcccc aggaggttat   1140
caggtcggca actttcctcc gctcttcgcc gagtggaacg accacttccg agacgctgcc   1200
cgcagattct ggctgcacta cgatctccca cttggtgcgt ttgcggggcg ctttgcagct   1260
tcctccgatg tcttcaagcg gaatgggaga ctgcctagtg cagcgatcaa tctcgtgacg   1320
gcgcacgacg ggttcacact tagagactgc gtctgcttta atcataagca caatgaggcc   1380
aatggggaag agaaccggga cggcacgaac aataactatt caaataacca cggaaaggaa   1440
ggactcgggg gctcactgga tcttgtagaa aggcgacgag attccatcca cgcgctgttg   1500
acaactctgc ttttgagcca gggtacacca atgttgttgg caggggacga acatggacac   1560
agtcagcacg gaaacaataa tgcgtactgc caggacaacc aactcacgtg gcttgattgg   1620
tcacaagcat cctccgggct cacagctttc acagcagcac tgatacacct gcgaaaacga   1680
attccagcac ttgttgaaaa ccgatggtgg gaggaggggc atggaaacgt tagatggctc   1740
aataggtacg ctcagccttt gtccacggac gaatggcaga atggccccaa gcaattgcag   1800
attctcctgt ctgataggtt ccttatagca attaacgcga ccctcgaggt gacagaaatc   1860
gtcctgcccg cgggagaatg gcacgcaatc ccgccgttcg caggtgagga caacccagta   1920
ataacggctg tgtggcaagg accggctcat ggcctttgtg ttttccagag gtga         1974
```

<210> SEQ ID NO 25
<211> LENGTH: 1974
<212> TYPE: DNA
<213> ORGANISM: Artificial Sequence
<220> FEATURE:
<223> OTHER INFORMATION: Codon optimized polynucleotide coding sequence
      (#10) for expressing the bacterial limit dextrin alpha-1,6-
      glucohydrolase (GlgX)

<400> SEQUENCE: 25

```
atgacacaac ttgctattgg caagccggca ccactcggtg cccattatga cggccagggc     60
gtaaacttca cactcttctc cgcacacgct gaaagagttg aattgtgcgt ctttgacgcc    120
aatggccagg agcaccgata tgatctcccg ggacactccg gtgatatctg cacggatat    180 ctccctgatg caagaccagg gctgcggtac ggctaccgcg tgcacgggcc ttggcagcca    240
```

-continued

```
gcagaaggac atcgattcaa tccggccaaa ctgctgattg atccgtgcgc tcggcagatt      300
gacggggagt tcaaagacaa cccctcctg catgctggcc ataacgaacc cgactatcgc      360
gataatgccg cgatcgcccc gaagtgcgta gtggtagttg accactatga ctgggaagat      420
gatgcaccac cgcgaactcc gtggggcagc acaattatat atgaagcaca tgtcaaaggt      480
ctgacatatt tgcatccgga aatacctgtc gaaatacggg gcacttacaa ggcccttgga      540
caccctgtaa tgattaatta cctgaaacaa ctcggtatca cggcattgga gctgctgccc      600
gtggcccagt ttgcttctga gccacgattg caacggatgg ggttgagtaa ctactggggt      660
tataaccccg ttgccatgtt tgcactccat cccgcgtatg cgtgcagtcc ggagacggcc      720
cttgacgagt tccgagatgc aataaaggcg ctccataagg ccggaataga ggttattctt      780
gatattgtcc ttaaccattc tgctgagttg gatctggacg gtcccctgtt cagtcttaga      840
ggtatagaca atcggtctta ttattggatt cgagaggatg gcgactacca caattggacc      900
ggatgcggaa acacgctcaa cctcagccac ccagccgtag tcgattatgc ctcagcttgc      960
cttcgatatt gggtagagac atgccacgtt gatgggttcc gctttgattt ggcggcagtg     1020
atggggcgga ctccggaatt taggcaggat gctccactgt ttacagcaat tcaaaattgc     1080
cccgtacttt cccaggtgaa actgattgcc gagccctggg acatagcccc cggcgggtac     1140
caagtgggca atttccctcc tttgttcgcc gagtggaacg accacttccg cgacgctgcg     1200
cgcaggtttt ggctccacta tgacttgccc ctcggagcct tcgcaggtcg cttcgcggca     1260
agtagcgatg tcttcaagcg caatggtcgc ttgccctcag cggctattaa tctcgtgacc     1320
gcacacgacg gctttacttt gcgagattgc gtttgcttca atcacaaaca caacgaagcc     1380
aacggcgagg agaatagggga tggaacgaat aacaactact caaacaatca cggtaaagag     1440
ggtcttgggg ggagcctgga tcttgttgaa agacggcggg acagtattca cgccctcttg     1500
acgacccttc ttcttagcca gggaactcct atgctcttgg ctggcgatga acacggtcac     1560
tctcaacatg gcaataataa tgcgtattgt caggacaacc aactcacgtg gcttgattgg     1620
agtcaggctt cctctgggct tacggcgttc acggcggccc tgatccacct ccgcaagaga     1680
atccctgctc ttgtagagaa ccgctggtgg gaagaagggg atggaaatgt tcggtggctg     1740
aacagatacg cacaaccact gtctacggac gagtggcaaa atggtccaaa gcagctccag     1800
attctgcttt ctgataggtt cctcattgcc attaatgcca cgcttgaggt gacggagatc     1860
gtcttgccgg cgggtgagtg gcatgcgata ccgcccttcg caggggaaga caatccggtt     1920
attactgcgg tttggcaagg ccccgcacat gggctctgcg tgtttcagag gtga          1974
```

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26

```
gccactggat gcctacaact                                                   20
```

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27

-continued

```
cgtgctggtg cagtgtattg                                                 20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
agagggaaat cgtgcgtgac                                                 20

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
caatagtgat gacctggccg t                                               21

<210> SEQ ID NO 30
<211> LENGTH: 1265
<212> TYPE: DNA
<213> ORGANISM: Artificial Sequence
<220> FEATURE:
<223> OTHER INFORMATION: LSP-CB dual promoter

<400> SEQUENCE: 30
gagttaattt ttaaaaagca gtcaaaagtc caagtggccc ttgcgagcat ttactctctc      60
tgtttgctct ggttaataat ctcaggagca caaaattcct tactagtcct agaagttaat     120
ttttaaaaag cagtcaaaag tccaagtcca agtggccctt gcgagcattt actctctctg     180
tttgctctgg ttaataatct caggagcaca aacattcctt actagttcta gagcggccgc     240
cagtgtgctg gaattcggct tttttagggc tggaagctac ctttgacatc atctcctctg     300
cgaatgcatg tataatttct acagaaccta ttagaaagga tcacccagcc tctgcttttg     360
tacaactttc ccttaaaaaa ctgccaatcc cactgctgtt tggcccaata gtgagaactt     420
tttctgctgc ctcttggtgc tttttgcctat ggcccctatt ctgctgctga agacactctt     480
gccagcatgg acttaaaccc ctccagctct gacaatcctc tttctctttt gtttacatg      540 aagggtctgg cagccaaagc aatcactcaa agttcaaacc ttatcatttt ttgctttgtt     600
cctcttggcc ttggttttgt acatcagctt tgaaaatacc atcccagggt taatgctggg     660
gttaatttat aactgagagt gctctagttt tgcaatacag gacatgctat aaaaatggct     720
taaggttccg cgttacataa cttacggtaa atggcccgcc tggctgaccg cccaacgacc     780
cccgcccatt gacgtcaata atgacgtatg ttcccatagt aacgccaata gggactttcc     840
attgacgtca atgggtggag tatttacggt aaactgccca cttggcagta catcaagtgt     900
atcatatgcc aagtacgccc cctattgacg tcaatgacgg taaatggccc gcctggcatt     960
atgcccagta catgacctta tgggactttc ctacttggca gtacatctac gtattagtca    1020
tcgctattac catgcatggt cgaggtgagc cccacgttct gcttcactct ccccatctcc    1080
cccccctccc cacccccaat tttgtattta tttatttttt aattattttg tgcagcgagg    1140
ggcggggcgg ggcgaggcgg agaggtgcgg cggcagccaa tcagagcggc gcgctccgaa    1200
agtttccttt tatggcgagg cggcggcggc ggcggcccta taaaaagcga agcgcgcggc    1260
```

-continued

```
gggcg                                                                        1265

<210> SEQ ID NO 31
<211> LENGTH: 724
<212> TYPE: DNA
<213> ORGANISM: Artificial Sequence
<220> FEATURE:
<223> OTHER INFORMATION: LSP promoter

<400> SEQUENCE: 31
gagttaattt ttaaaaagca gtcaaaagtc caagtggccc ttgcgagcat ttactctctc       60
tgtttgctct ggttaataat ctcaggagca caaaattcct tactagtcct agaagttaat      120
ttttaaaaag cagtcaaaag tccaagtcca agtggcccct gcgagcattt actctctctg      180
tttgctctgg ttaataatct caggagcaca aacattcctt actagttcta gagcggccgc      240
cagtgtgctg gaattcggct tttttagggc tggaagctac ctttgacatc atctcctctg      300
cgaatgcatg tataatttct acagaaccta ttagaaagga tcacccagcc tctgcttttg      360
tacaactttc ccttaaaaaa ctgccaatcc cactgctgtt tggcccaata gtgagaactt      420
tttctgctgc ctcttggtgc ttttgcctat ggcccctatt ctgctgctga agacactctt      480
gccagcatgg acttaaaccc ctccagctct gacaatcctc tttctctttt gttttacatg      540
aagggtctgg cagccaaagc aatcactcaa agttcaaacc ttatcatttt ttgctttgtt      600
cctcttggcc ttggttttgt acatcagctt tgaaaatacc atcccagggt taatgctggg      660
gttaatttat aactgagagt gctctagttt tgcaatacag gacatgctat aaaaatggct      720
taag                                                                     724

<210> SEQ ID NO 32
<211> LENGTH: 541
<212> TYPE: DNA
<213> ORGANISM: Artificial Sequence
<220> FEATURE:
<223> OTHER INFORMATION: CB promoter

<400> SEQUENCE: 32
gttccgcgtt acataactta cggtaaatgg cccgcctggc tgaccgccca acgacccccg       60
cccattgacg tcaataatga cgtatgttcc catagtaacg ccaatadgga ctttccattg      120
acgtcaatgg gtggagtatt tacggtaaac tgcccacttg gcagtacatc aagtgtatca      180
tatgccaagt acgccccota ttgacgtcaa tgacggtaaa tggcccgcct ggcattatgc      240
ccagtacatg accttatggg actttcctac ttggcagtac atctacgtat tagtcatcgc      300
tattaccatg catggtcgag gtgagcccca cgttctgctt cactctcccc atctccccc       360 cctccccacc cccaattttg tatttatttta tttttaatt attttgtgca gcgagggggcg      420 gggcggggcg aggcggagag gtgcggcggc agccaatcag agcggcgcgc tccgaaagtt      480
tccttttatg gcgaggcggc ggcggcggcg gccctataaa aagcgaagcg cgcggcgggc      540
g                                                                        541

<210> SEQ ID NO 33
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 33 cccccttaaga gctgcatgtc taagctagac cc                                      32
```

-continued

```
<210> SEQ ID NO 34
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 34
cggggtaccc gctggctggc tcctgagt                                          28

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
agttctagag cggccgccag                                                   20

<210> SEQ ID NO 36
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 36
ccccttaagc catttttata gcatgtcctg tattgcaaaa cta                         43

<210> SEQ ID NO 37
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 37
ccccttaagg ttccgcgtta cataacttac ggtaaat                                37

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 38
gtcgacggta ccgcgcag                                                     18
```

COMPOSITIONS COMPRISING MICROBIAL POLYPEPTIDES FOR DEGRADING GLYCOGEN AND METHODS FOR THE TREATMENT OF GLYCOGEN STORAGE DISEASES

CROSS REFERENCE TO RELATED APPLICATIONS

This application is a national phase application of International Application No. PCT/US2020/019114 filed Feb. 20, 2020, which claims priority to U.S. Provisional Patent Application Ser. No. 62/807,790, filed Feb. 20, 2019, and U.S. Provisional Patent Application Ser. No. 62/823,894, filed Mar. 26, 2019, the contents of each of which are hereby incorporated by reference in their entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file is 87 kilobytes in size, and titled 19-331-WO_SequenceListing_ST25.txt.

BACKGROUND OF THE DISCLOSURE

Field

The present disclosure provides compositions comprising isolated nucleic acid molecules comprising nucleic acid sequences encoding microbial polypeptides, vectors comprising a tissue-specific promoter or an immunotolerant dual promoter system, and gene therapy methods of using the isolated nucleic acid molecules for treating glycogen storage diseases (GSDs) or other inherited diseases in a subject.

Technical Background

The present disclosure relates to gene therapy methods of treating a human genetic disease with a viral or non-viral vector expressing a therapeutic enzyme derived from bacteria or other microorganisms. Specifically, this disclosure relates to a method of treating a patient suffering from glycogen storage disease type III (GSD III) with an adeno-associated virus (AAV) vector expressing a bacterial glycogen debranching enzyme. This disclosure further relates to a method of using a tissue-specific promoter or an immunotolerant dual promoter system approach as one way to prevent bacterial enzyme induced immune responses towards gene therapy. This disclosure further relates to a method of using an immunotolerant dual promoter system to prevent a therapeutic transgene product induced immune responses towards gene therapy for a human inherited disorder.

Glycogen is a multi-branched polysaccharide consisting of $\alpha$-1,4-linked glucose subunits with $\alpha$-1,6-linked glucose at the branching points that serves as a form of energy storage in humans, animals, yeasts, and bacteria. Glycogen debranching enzyme (GDE) and glycogen phosphorylase are the two major enzymes responsible for glycogen breakdown. In mammals and yeast, GDE is a single polypeptide with two distinct enzyme activities: 4-$\alpha$-D-glycosyltransferase (EC 2.4.1.25) and amylo-$\alpha$-1,6-glucosidase (EC 3.2.1.33). Glycogen phosphorylase initiates the glycogen degradation process by continually cleaving $\alpha$-1,4-glycosidic bonds to remove glucose units from the non-reducing ends of external chains until it reaches four residues from a branching point. At this stage, GDE transfers three glucose residues from the one of the four-residue branches to a nearby branch and then cleaves the $\alpha$-1,6-glycosidic bond to release the remaining single glucose residue from the branching point, which forms a new linear chain to repeat the process. In contrast, GDE in bacteria and other microorganisms has only a single $\alpha$-1,6-glycosidic bond hydrolyzing activity for glycogen and amylopectin, which include Pullulanase (E.C. 3.2.1.41), limit dextrin alpha-1,6-hydrolase (GlgX) (E.C. 3.2.1.-), and Isoamylase (E.C. 3.2.1.68).

Mutations in the human AGL gene cause a genetic deficiency of GDE in GSD III, resulting in the accumulation of abnormally structured glycogen with short outer branches (called limit dextrin) in multiple tissues. Most patients (~85%) have both muscle and liver involvement (type IIIa) while others have disease limited primarily to the liver (type IIIb). The peripheral nervous system can also be affected by mutations in the human AGL gene. Liver symptoms including hepatomegaly, elevated aminotransferases, and hypoglycemia normally appear in infancy and childhood; progressive liver cirrhosis and hepatic failure can occur with age; hepatic adenomas and hepatocellular carcinoma have also been reported in some cases (Labrune, P., et al. (1997) *J Pediatr Gastroenterol Nutr,* 24(3):276-9, Demo, E. et al. (2007) *J Hepatol,* 46(3):492-8; Kishnani, P. et al. (2010) *Genet Med,* 12(7):446-63). In addition to liver disease progression, progressive myopathy and cardiomyopathy are a major cause of morbidity in adults. Muscle weakness is present during childhood and becomes more prominent in the third or fourth decade of life; some patients can become wheel chair bound due to severe impairment of skeletal muscle function. Ventricular hypertrophy is a frequent finding in GSD III. Sudden deaths caused by cardiac arrhythmias or cardiac failure have been reported (Olson, L. J., et al. (1984) *Am J Cardiol,* 53(7):980-81, Moses, S. W., et al. (1986) *Acta Paediatr Scand,* 75(2):289-96; Labrune, P. et al. (1991) *Pediatr Cardiol,* 12(3):161-3; Lee, P. J. et al. (1997) *Am J Cardiol,* 79(6):834-8, Mogahed, E. A. et al. (2015) *Eur J Pediatr,* 174(11):1545-8).

To date, there is no cure for GSD III. Treatment strategies have relied on symptomatic and dietary management to control blood glucose levels. Dietary interventions, such as controlling hypoglycemia with frequent meals high in complex carbohydrates and cornstarch supplements and a high-protein diet for patients with myopathy, do little to alter the long-term course and morbidity of the disease (Kishnani, P. S. et al. (2010) *Genet Med,* 12(7):446-63, Sentner, C. P et al. (2016) *J Inherit Metab Dis,* 39(5):697-704). There are a few case reports of improvement of cardiomyopathy on a high protein diet. The long term natural history of GSD III is evolving, and it is being recognized that long term complications are occurring, likely due to accumulation of limit dextrin in liver and muscle.

Gene therapy to replace the defective gene with a normal human gene would be an ideal treatment approach for patients with single-gene disorders like GSD III. In the past decade, AAV vectors have emerged as a promising tool for in vivo gene delivery. However, the small carrying capacity (<4.7 kb) of an AAV vector makes it impossible to deliver a gene expression cassette containing the large coding sequence for a human protein like human GDE.

Furthermore, elicitation of immune responses towards transgene products is a major concern in gene therapy. In particular, transgene-induced cytotoxic T lymphocyte (CTL) responses can result in the elimination of transgene-expressing cells after gene transfer and the loss of efficacy of gene therapy. It has been reported that tissue-restricted gene therapy using a tissue-specific promoter can prevent trans-gene-induced immune responses, but this gene therapy approach corrects disease only in that tissue but not in other tissues.

Thus, there is a need for gene therapy treatments for inherited diseases caused by a large defective gene, such as GSD III. Described herein are compositions and methods for a novel gene therapy approach that address this need by using: (1) a smaller microbial enzyme to replace the large human GDE to overcome the limitation of the small carrying capacity of a viral vector, and optionally (2) a single or a tandem tissue-specific promoter or an immunotolerant dual promoter system as one possible way to prevent transgene-induced immune responses against the therapeutic enzyme and thereby to enhance the long-term efficacy of gene therapy. This approach can be complemented with other treatment strategies such as the use of small molecule drugs, RNA interference (RNAi) polynucleotides and other approaches to inhibit glycogen synthase, the use of immune modulation approaches to prevent or reduce host immunity to gene therapy, or dietary approaches to address the under-lying pathophysiologic issues due to GDE deficiency.

SUMMARY OF THE DISCLOSURE

The present disclosure provides compositions comprising nucleic acids encoding a microbial polypeptide for degrad-ing glycogen and gene therapy methods for treating glyco-gen storage disease in a subject.

One aspect of the disclosure provides an isolated nucleic acid molecule comprising a nucleic acid sequence encoding a microbial polypeptide for degrading glycogen, wherein the nucleic acid sequence is codon-optimized for expression in a mammalian cell. In some embodiments, the encoded microbial polypeptide has debranching enzyme activity that can cleave the α-1,6-glycosidic bonds in glycogen and/or limit dextrin or can cleave both the α-1,6-glycosidic bonds and α-1,4-glycosidic bonds in glycogen and/or limit dextrin.

In some embodiments of the disclosure, the encoded microbial polypeptide is a glycogen debranching enzyme (GDE) from bacteria or another microorganism. In other embodiments of the disclosure, the encoded microbial poly-peptide is a type II Pullulanase or a pullulan hydrolase type III from bacteria or other microorganism, or a type I Pul-lulanase from *Bacillus subtilis* or a limit dextrin alpha-1,6-glucohydrolase (GIg X) from *Escherichia coli* or an iso-amylase from *Pseudomonas amyloderamosa*.

In some embodiments of the disclosure, the encoded microbial polypeptide has an amino acid sequence set forth in SEQ ID NO:01 or SEQ ID NO:04 or SEQ ID NO:07, or has at least 50%, 90%, or 90-99% sequence identity to the amino acid sequence set forth in SEQ ID NO:01 or SEQ ID NO:04 or SEQ ID NO:07.

In some embodiments of the disclosure, the nucleic acid sequence comprises a sequence as set forth in SEQ ID NOs:03 and 08-16, or SEQ ID NOs:06 and 17-25, or has at least 50% sequence identity to the nucleic acid sequence as set forth in SEQ ID NOs:03 and 08-16, or SEQ ID NOs:06 and 17-25.

In some embodiments of the disclosure, the encoded microbial polypeptide is from bacteria, algae, protozoa, or viruses.

In some embodiments of the disclosure, the nucleic acid sequence has a coding sequence that is less than about 4.0 kilobases.

Another aspect of the disclosure provides a vector com-prising an isolated nucleic acid molecule comprising a nucleic acid sequence encoding a microbial polypeptide for degrading glycogen, wherein the nucleic acid sequence is codon-optimized for expression in a mammalian cell.

In some embodiments of the disclosure, the vector is a viral vector or non-viral vector. In some embodiments, the viral vector can include, but not limited to, an adenovirus vector, an AAV vector, a herpes simplex virus vector, a retrovirus vector, a lentivirus vector, and alphavirus vector, a flavivirus vector, a rhabdovirus vector, a measles virus vector, a Newcastle disease viral vector, a poxvirus vector, or a picornavirus vector. In other embodiments, the non-viral vector can include, but is not limited to, a polymer based vector, a peptide based vector, a lipid nanoparticle, a solid lipid nanoparticle, or a cationic lipid based vector.

In some embodiments of the disclosure, the vector com-prises a ubiquitous promoter operably linked to the nucleic acid molecule that can drive the expression of the microbial polypeptide in any tissues. In other embodiments, the ubiq-uitous promoter is a CMV enhancer/chicken β-actin pro-moter.

In some embodiments of the disclosure, the vector com-prises a tissue-specific promoter operably linked to the nucleic acid molecule. In other embodiments, the tissue-specific promoter is a liver-specific promoter, a muscle-specific promoter, a neuron-specific promoter, or a combi-nation of any of the two or more thereof. In yet other embodiments, the vector comprises a liver-specific promoter that is an α1-microglobulin/bikunin enhancer/thyroid hor-mone-binding globulin promoter. In yet other embodiments, the vector comprises an immunotolerant dual promoter consisting of a liver-specific promoter and a ubiquitous promoter.

In some embodiments of the disclosure, the vector com-prises a gene expression cassette comprising one or more promoters, the isolated nucleic acid molecule comprising a nucleic acid sequence encoding a microbial polypeptide, and a polyadenylation sequence. In other embodiments, the gene expression cassette contains a nucleotide sequence having about 4.5 kb or less.

Yet another aspect of the disclosure provides a pharma-ceutical formulation comprising a vector comprising an isolated nucleic acid molecule comprising a nucleic acid sequence encoding a microbial polypeptide for degrading glycogen, wherein the nucleic acid sequence is codon-optimized for expression in a mammalian cell in a pharma-ceutically acceptable carrier.

Yet another aspect of the disclosure proves a method of treating a deficiency of a polypeptide for degrading glyco-gen in a subject, comprising administering to the subject a therapeutically effective amount of a vector comprising an isolated nucleic acid molecule comprising a nucleic acid sequence encoding a microbial polypeptide for degrading glycogen, wherein the nucleic acid sequence is codon-optimized for expression in a mammalian cell.

In some embodiment of the above method, the microbial polypeptide is a type I Pullulanase, or a limit dextrin alpha-1,6-glucohydrolase (GIg X) or an isoamylase from bacteria or other microorganisms. In other embodiments of the above method, the microbial polypeptide is capable of cleaving α-1,6-glycosidic bonds in glycogen and/or limit dextrin or is capable of cleaving both α-1,6-glycosidic bonds and α-1,4-glycosidic bonds.

In some embodiments of the above method, the deficiency of a polypeptide for degrading glycogen is GSD III, GSD I, GSD II, GSD IV, GSD V, GSD VI, GSD VII, GSD IX, GSD X, GSD XII, GSD XIII, GSD XIV, Danon disease, Lafora disease, PRKAG2 (protein kinase gamma 2 subunit) deficiency, or other condition where there is cytoplasmic accumulation of glycogen. In other embodiments, the deficiency of a polypeptide for degrading glycogen is GSD III.

In some embodiments of the above method, the microbial polypeptide is a type Pullulanase or a pullulan hydrolase type III from bacteria or other microorganisms.

In some embodiments of the above method, the vector is administered via intravenous, intraarterial, intramuscular, intraperitoneal, intrathecal, intraventricular, or in utero administration.

In some embodiments of the above method, the subject is a human subject.

In some embodiments of the above method, the vector is delivered to areas of the body including but not limited to the liver, heart, skeletal muscle, smooth muscle, kidney, and the central and peripheral nervous systems in the subject.

In other embodiments, the method further comprises administering to the subject a therapeutically effective amount of an immunosuppressive agent and/or a glycogen synthase inhibitor.

Yet another aspect of the present disclosure provides, a method of treating a deficiency of a polypeptide for degrading glycogen in a subject, comprising administering to the subject an isolated nucleic acid molecule comprising a nucleic acid sequence encoding a microbial polypeptide for degrading glycogen.

In some embodiments of the above method, the nucleic acid sequence is codon-optimized for expression in human or mammalian cells.

In some embodiments of the above method, the encoded microbial polypeptide is a type I Pullulanase or a limit dextrin alpha-1,6-glucohydrolase (GIg X) or an isoamylase from bacteria or another microorganism, or a type Pullulanase or a pullulan hydrolase type III from bacteria or other microorganisms.

In some embodiments of the above method, the encoded microbial polypeptide is capable of cleaving α-1,6-glycosidic bonds or is capable of cleaving both α-1,6-glycosidic bonds and α-1,4-glycosidic bonds.

In some embodiments of the above method, the encoded microbial polypeptide has an amino acid sequence set forth in SEQ ID NO:01 or SEQ ID NO:04 or SEQ ID NO:07, or has at least 50%, 90%, or 90-99% sequence identity to the amino acid sequence set forth in SEQ ID NO:01 or SEQ ID NO:04 or SEQ ID NO:07.

In some embodiments of the above method, the nucleic acid sequence comprises a sequence as set forth in SEQ ID NOs:03 and 08-16, or SEQ ID NOs:06 and 17-25, or has at least 50% sequence identity to the nucleic acid sequence as set forth in SEQ ID NOs:03 and 08-16, or SEQ ID NOs:6 and 17-25.

In some embodiments of the above method, the deficiency of a polypeptide for degrading glycogen is GSD III, GSD I, GSD II, GSD IV, GSD V, GSD VI, GSD VII, GSD IX, GSD X, GSD XII, GSD XIII, GSD XIV, Danon disease, Lafora disease, PRKAG2 (protein kinase gamma 2 subunit) deficiency, or other condition where there is cytoplasmic accumulation of glycogen. In other embodiments of the above method, the deficiency of a polypeptide for degrading glycogen is GSD III.

In some embodiments of the above method, the isolated nucleic acid molecule is administered intravenously, intramuscularly, intrathecally, intraventricularly, intraarterially, intraperitoneally, or directly into utero.

In some embodiments of the above method, the subject is a human subject.

In some embodiments of the above method, the isolated nucleic acid molecule is delivered to areas of the body including but not limited to the liver, heart, skeletal and smooth muscle, kidney, and/or the central and peripheral nervous systems in the subject.

In some embodiments of the above method, the isolated nucleic acid molecule is present in a vector, which can be a viral vector or non-viral vector. In some embodiments of the above method, the viral vector is selected from the group consisting of an adenovirus vector, an AAV vector, a herpes simplex virus vector, a retrovirus vector, a lentivirus vector, and alphavirus vector, a flavivirus vector, a rhabdovirus vector, a measles virus vector, a Newcastle disease virus vector, a poxvirus vector, or a picornavirus vector.

In some embodiments of the above method, the vector comprises a ubiquitous promoter. In other embodiment so the above method, the ubiquitous promoter is a CMV enhancer/chicken β-actin promoter.

In some embodiments of the above-method, the vector comprises a tissue-specific promoter. In some embodiments of the above method, the tissue-specific promoter is a liver-specific promoter, a muscle-specific promoter, a neuron-specific promoter, or a combination of any of the two or more thereof. In other embodiments of the above method, the vector comprises a liver-specific promoter that is the α1-microglobulin/bikunin enhancer/thyroid hormone-binding globulin promoter. In other embodiments of the above method, the vector comprises an immunotolerant dual promoter consisting of a liver-specific promoter and a ubiquitous promoter.

In some embodiments, the above method further comprises administering to the subject a therapeutically effective amount of an immunosuppressive agent and/or a glycogen synthase inhibitor.

In other embodiments, the above method comprises the isolated nucleic acid molecule is present in a first vector and in a second vector, wherein the first vector and second vector are administered simultaneously or wherein the second vector is administered after the first vector. In some embodiments, the second vector is administered in the minutes, hours, days, weeks, or months after the first vector is administered. In some embodiments, the first vector is selected an AAV-LSP-Pull vector or an AAV-CB-Pull vector and wherein the second vector is an AAV-LSP-Pull vector or an AAV-CB-Pull vector.

Yet another aspect of the present disclosure provides a vector comprising an isolated nucleic acid molecule comprising a nucleic acid sequence encoding a microbial polypeptide having fewer than about 4.0 kilobases, wherein a counterpart human nucleic acid sequence has a coding sequence that is greater than about 4.0 kilobases, and wherein the nucleic acid sequence is codon-optimized for expression in a human cell.

Yet another aspect of the present disclosure provides a vector comprising a gene expression cassette comprising an isolated nucleic acid molecule comprising a nucleic acid sequence encoding a therapeutic protein under the control of an immunotolerant dual promoter consisting of a liver-specific promoter and a ubiquitous promoter. In some embodiments, the immunotolerant dual promoter comprises an α1-microglobulin/bikunin enhancer/thyroid hormone-binding globulin promoter and a CMV enhancer/beta-actin (CE) promoter. In some embodiments, the immunotolerant dual promoter has the nucleic acid sequence as set forth in SEQ ID NO:30, or has at least 50% sequence identity to the nucleic acid sequence set forth in SEQ ID NO:30.

In some embodiments, the therapeutic protein can be a variety of therapeutic proteins/enzymes and polypeptides that are used to treat a number of diseases, including microbial polypeptides for degrading glycogen and non-microbial proteins to treat human genetic diseases that affect multiple tissues.

Yet another aspect of the present disclosure provides a method of treating a deficiency of a polypeptide for degrading glycogen in a subject, comprising administering to the subject an a vector comprising a gene expression cassette comprising an isolated nucleic acid molecule comprising a nucleic acid sequence encoding a polypeptide for degrading glycogen under the control of an immunotolerant dual promoter consisting of a liver-specific promoter and a ubiquitous promoter Additional features and advantages are described herein, and will be apparent from the Drawings, Detailed Description, and the Claims.

BRIEF DESCRIPTION OF THE DRAWINGS

The accompanying drawings are included to provide a further understanding of the methods and compositions of the disclosure, and are incorporated in and constitute a part of this specification. The drawings illustrate one or more embodiment(s) of the disclosure, and together with the description serve to explain the principles and operation of the disclosure.

FIG. 4 illustrates impaired muscle function of GSD IIIa mice compared with wild-type (WT) mice assessed by Treadmill, Wire-hang, and Rota-rod tests at 6 months of age. Data shown as Mean±SD and analyzed with equal variance, unpaired, two-tailed Student's t test. n=5 each group. * indicates p<0.05; *** indicates p<0.001.

FIG. 5A shows pullulanase activity. FIG. 5B shows glycogen content. UT, untreated GSD IIIa mice; AAV-CB-Pull or AAV-LSP-Pull, AAV-treated GSD IIIa mice; WT, age-matched wild-type control mice. Data shown as mean±SD and analyzed with one-way ANOVA. n=5 for each GSD III group; n=4 for WT. **** indicates p<0.0001 vs UT.

FIG. 7A shows the ratios of liver to body weight. FIG. 7B shows liver enzyme ALT activities in plasma. UT, untreated GSD IIIa mice; AAV-CB-Pull or AAV-LSP-Pull, AAV-treated GSD IIIa mice; WT, wild-type mice. Data shown as Mean±SD. n=5 for each GSD III group; n=4 for WT. *, p<0.05; ****, p<0.0001 vs UT.

FIG. 10A shows the ratios of liver to body weight. FIG. 10B shows plasma alanine aminotransferase (ALT) activities. UT, untreated GSD IIIa mice; AAV-CB-Pull or AAV-LSP-Pull, AAV-treated GSD IIIa mice; WT, wild-type mice. Data shown as Mean±SD. n=5 for each GSD III group; n=4 for WT. *, p<0.05; ****, p<0.0001 vs UT.

FIG. 12A shows detection of Pullulanase expression in liver by Western blot with an anti-HA antibody. FIG. 12B is a graph showing glycogen content in the liver biopsies was measured. Data shown are mean±SD. Student's t-test. ***p<0.001.

FIG. 13A is radiographic images of a GSD IIIa dog showing reduced liver size after two weeks of treatment. The shape of the abdomen (dot lines) showed unusual curvatures before treatment due to hepatomegaly. However, the shape had less curvature after two weeks of treatment. FIG. 13B is a graph of the liver size during the pre-treatment and post-treatment periods. The length of the right liver lobe in dorsoventral radiographs was normalized with the length of the T11 bone. The normalized liver size was significantly reduced after two weeks of treatment. The graph represents the mean±SD of n=2 GSD IIIa dogs. Student's t-test. **p<0.01.

FIG. 14A shows pullulanase activity. FIG. 14B shows glycogen content. UT, untreated GSD III mice (n=7); AAV-CB-Pull, AAV-treated GSD IIIa mice (n=8). Data shown as mean±SD and analyzed with one-way ANOVA. n.s., no significant difference; ****, p<0.0001 vs UT.

FIG. 16A shows plasma alanine aminotransferase (ALT) activity. FIG. 16B shows plasma creatine kinase (CK) activity. FIG. 16C shows urinary Glc4 concentration. UT, untreated GSD IIIa mice (n=7); AAV-CB-Pull, AAV-treated GSD IIIa mice (n=8). Data shown as mean SD. *, p<0.05 vs UT.

FIG. 17A is a graph showing pullulanase activities in the liver, heart and quadriceps two weeks following AAV injection. FIG. 17B is a graph showing glycogen content in the liver, heart, at quadriceps two weeks following AAV injection. UT, untreated GSD IIIa mice (n=9); AAV, AAV9-MHCK7-Pull treated GSD IIIa mice (n=5). Data shown as mean±SD. Student's test. p<0.01, **p<0.0001.

FIG. 18A is a graph showing the maximum running of mice treated with AAV-MHCK7-Pull (AAV) and untreated (UT) mice as evaluated by a treadmill test to assess exercise intolerance. FIG. 18B is a graph showing the time to latency of mice treated with AAV-MHCK7-Pull (AAV) and untreated (UT) mice as evaluated by a wire-hand test to assess limb muscle strength.

FIG. 19A is a schematic that shows the constructs of AAV vector containing the 2.2 kb codon-optimized Pullulanase cDNA under the control of the ubiquitous CMV enhancer/chicken β-actin promoter (CB) and the α1-microglobulin/bikunin enhancer/thyroid hormone-binding globulin liver specific promoter (LSP). ITR: inverted terminal repeats; polyA: human growth hormone polyadenylation signal sequence. FIG. 19B is a schematic that shows an experimental flow chart of AAV treatments in GSD IIIa mice. Fifteen mice were injected with AAV9-CB-Pull at two weeks of age at a dose of $1 \times 10^{13}$ vg/kg. Eight mice were sacrificed after 10 weeks of treatment (3-month-old, gray arrow) for sample collection; the remaining seven mice received a second AAV injection with AAV8-LSP-Pull at the same dose. Tissues and plasma were analyzed after another 10 weeks (5-month-old, black arrow). Behavioral tests were performed at ages 2, 2.5, 3, 4, and 5 months old (open arrows). FIG. 19C is a graph showing the AAV genome copy numbers of AAV9-CB-Pull (CB) treated mice at 3 months of age and after subsequent treatment with AAV8-LSP-Pull 10 weeks later (CB+LSP). AAV genome copy numbers were evaluated by real-time-PCR using primers for Pullulanase. The graph represents the mean±SD. n=5 for each group. vg/genome: vector genome copies per nucleus (genome). FIG. 19D is a Western blot analysis using an anti-HA antibody confirmed the expression of Pullulanase in tissues of the AAV treated GSD IIIa mice. Pullulanase was undetectable in any tissues of the untreated (UT) mice. Pullulanase was not detectable in the liver of the CB treated mice but was highly expressed in the liver of CB+LSP treated mice. The heart showed a high level and skeletal muscle showed a low level (but detectable) of Pullulanase in both CB and CB+LSP treated mice. β-Actin was used as a loading control. FIG. 19E is a graph showing pullulanase activity in the liver, heart, and skeletal muscle in mice treated with AAV9-CB-Pull alone (CB) and with an additional treatment with AAV8-LSP-Pull 10 weeks later (CB+LSP) as compared to untreated (UT) mice using the Pullulanase activity kit (Megazyme). Consistent with the western blot results, the enzyme activity was not detectable in the CB treated liver but drastically increased in the CB+LSP treated liver. The enzyme activity was significantly elevated in the heart and skeletal muscle of both CB and CB+LSP treated mice compared to the UT mice. The graph represents the mean±SD. n=5 for UT, n=8 for CB, and n=7 for CB+LSP; Student's test. *p<0.05, *p<0.001, and **p<0.0001.

FIG. 20A is a graph showing glycogen contents in the liver, heart, and skeletal muscle of mice treated with AAV9-CB-Pull alone (CB) or with an additional treatment with AAV8-LSP-Pull (CB+LSP). Consistent with the enzyme activity results, there is no difference in liver glycogen content between the UT and CB treated GSD IIIa mice at 3 months of age, but glycogen level was reduced significantly in the CB+LSP treated liver at 5 months of age. Glycogen content was profoundly decreased in the heart and skeletal muscle of both CB and CB+LSP treated mice. The graph represents the mean±SD. n=5 for UT, n=8 for CB, and n=7 for CB+LSP; Student's test. *p<0.001 and **p<0.0001. FIG. 20B is histology images of wild type, untreated (UT), and mice treated with AAV9-CB-Pull alone (CB) or with a subsequent treatment with AAV8-LSP-Pull (CB+LSP). PAS staining was used for histological detection of glycogen accumulation in tissues. Untreated GSD IIIa mice showed intense PAS-positive glycogen accumulation (dark staining) in the liver, heart, and skeletal muscle. CB treatment had no effect on liver glycogen accumulation; in contrast, CB+LSP treatment markedly reduced glycogen accumulation in the liver. Glycogen buildup was profoundly cleared in the heart and skeletal muscle by both CB and CB+LSP treatments. At least 3 mice were examined in each group, and representative images are shown. Scale bar=50 μm. FIG. 20C is histology images of wild type (WT), untreated (UT), and mice treated with AAV9-CB-Pull (CB). Glycogen level was assessed by PAS staining in tissues of WT mice and UT and CB treated GSD IIIa mice at 3 months of age. Untreated GSD IIIa mice showed massive glycogen staining in the skeletal muscles (gastrocnemius, soleus, diaphragm, and tongue) and smooth muscle (bladder) and a mild but significant amount of glycogen accumulation in some regions of the brain (cerebellum) and spinal cord. CB treatment markedly reduced glycogen accumulation in all the skeletal muscles but had no effect on the smooth muscle, brain, and spinal cord. At least 3 mice were examined in each group, and representative images are shown. Scale bar=50 μm. FIG. 20D is histology images showing trichrome staining, which is used for detection of liver fibrosis. The blue staining (arrows) indicates the presence of fibrotic tissues in the liver of UT and CB treated GSD IIIa mice. CB+LSP treatment successfully reversed liver fibrosis. At least 3 mice were examined in each group, and representative images are shown. Scale bar=50 μm.

FIG. 21A is a graph showing liver to body weight (%). The ratio of liver to body weight was measured to determine hepatomegaly. The ratio did not change by the CB alone treatment. However, the liver size was significantly reduced by the combination CB+LSP treatment. The dotted line represents the level of liver to body weight ratio in WT mice (4.5±0.2%, n=6). The graph represents the mean±SD. n=7 for UT (3 mo) and CB+LSP, n=8 for CB, and n=5 for UT (5 mo). Each dot/triangle represents an individual mouse. Student's test. *p<0.05. FIG. 21B is a graph showing activity of alanine aminotransferase (ALT). The activity of alanine aminotransferase (ALT) was measured in the plasma from UT and AAV treated GSD IIIa mice to evaluate liver function. The ALT level was slightly reduced (p=0.09) in the CB treated mice compared to UT. The ALT level was remarkably increased in UT mice from age 3 to 5 months. CB+LSP treatment significantly reduced plasma ALT activity compared with UT mice. The graph represents the mean±SD. n=7 for UT (3 mo) and CB+LSP, n=8 for CB, and n=5 for UT (5 mo). Each dot/triangle represents an individual mouse. The dotted line represents the ALT level in WT mice (98.1±33.24 U/L, n=4). Student's test. *p<0.05 and ****p<0.0001. FIG. 21C is a graph showing the Glc4 urinary concentrations. The concentrations of urinary Glc4 were assessed in the UT and AAV-CB-Pull (CB) treated GSD IIIa mice. The CB treated mice showed a significant decrease in the level of urinary Glc4 compared to the UT mice. The urinary creatinine level was used for normalization. The graph represents the mean±SD. n=6 for UT and n=8 for CB. Each dot represents an individual mouse. The dotted line represents the WT level (4.4±1.7 mmol/mol of creatinine, n=7). Student's test. *p<0.05. FIG. 21D is graphs showing the results of the behavioral tests in untreated (UT) and AAV treated mice. Treadmill test was used for evaluating exercise intolerance in UT and AAV treated GSD IIIa mice. The graph represents the maximum running distance. The running distance gradually declined in the UT mice with time (UT, dots). However, the running distance was steady in the AAV treated mice (AAV, squares). Wire hang test was used to assess limb muscle strength. The time of latency to fall was measured and the maximum time from three independent trials was used for comparison. The hanging time was also progressively decreased in UT mice with age (UT, dots), but AAV treatments significantly improved the hanging time (AAV, squares). Rota-rod test was used to measure muscle strength, motor coordination, and balance. The mice were tested during three sessions using the accelerating Rota-rod protocol (4.0-40 rpm), and the latency to fall was recorded. AAV treated mice also showed significant improvement in Rota-rod performance compared to the UT mice. The data represents the mean±SD. n=7 for both groups. Student's test. *p<0.05, p<0.01, *p<0.001, ****p<0.0001.

FIG. 22 shows the protein sequence of pullulanase derived from *Bacillus subtilis* strain 168 (718 amino acids). Gene: amyX. UniProtKB #C0SPA0; NCBI Database #NP_390871.2 (SEQ ID NO:01).

FIG. 23 shows the cDNA sequence of pullulanase derived from *Bacillus subtilis* strain 168 (2157 bp). Gene: amyX. NCBI Reference #NC_000964.3 (SEQ ID NO:02).

FIG. 24 shows the codon optimized coding sequence for expressing pullulanase derived from *Bacillus subtilis* strain 168 in human cells (SEQ ID NO:03).

FIG. 25 shows the protein sequence of the bacterial limit dextrin alpha-1,6-glucohydrolase (GlgX) derived from *E. coli* strain K-12 (657 amino acids). Gene: glgX. UniProt #P15067. NCBI Database #NP_417889.1 (SEQ ID NO:04).

FIG. 26 shows the cDNA sequence of the limit dextrin alpha-1,6-glucohydrolase (GlgX) derived from *E. coli* strain K-12 (1974 bp). NCBI Reference #NP_417889.1 (SEQ ID NO:05).

FIG. 27 shows the codon optimized coding sequence for expressing the bacterial limit dextrin alpha-1,6-glucohydrolase (GlgX) derived from *Escherichia coli* strain K-12 in human cells (SEQ ID NO:06).

FIG. 28 shows the protein sequence of isoamylase derived from *Pseudomonas amyloderamosa* SB-15 (776 amino acids). Uniprot #P10342.3 (SEQ ID NO:07).

FIG. 29A-FIG. 29B show AAV treatment groups and AAV vector bio-distribution. FIG. 29A is a schematic that shows the constructs of indicated AAV vectors and the treatment groups with these AAV vectors. FIG. 29B is graphs showing the AAV copy numbers in the liver, heart, and quadriceps of GSD IIIa mice ten weeks after AAV treatment. CB, AAV9-CB-Pull injection; LSP, AAV9-LSP-Pull injection; Co, AAV9-CB-Pull+AAV9-LSP-Pull co-injection; Dual, AAV9-LSP-CB-Pull injection. Data shown as mean±SD. n=5 for each group.

FIG. 30A is a graph of pullulanase activities in liver, heart, and skeletal of GSD IIIa mice ten weeks after AAV treatment. FIG. 30B is a graph of glycogen contents in tissues in FIG. 30A. UT, untreated GSD IIIa mice; CB, AAV9-CB-Pull injection; LSP, AAV9-LSP-Pull injection; Co, AAV9-CB-Pull and AAV9-LSP-Pull co-injection; Dual, AAV9-LSP-CB-Pull injection. Data shown as mean±SD. n=5 for each group. Student's test. *p<0.05,p<0.01, *p<0.001, and ****p<0.0001 vs UT.

FIG. 32A is a graph of the ratio of liver to body weight, which was measured to determine liver size. FIG. 32B is a graph showing the activity of alanine aminotransferase (ALT) in plasma, which were measured ten weeks after treatment to evaluate liver damage. FIG. 32C is a graph showing the activity of aspartate aminotransferase (AST) in plasma, which were measured ten weeks after treatment to evaluate liver damage. Data shown as mean±SD. n=5 for each group. Student's test. *p<0.05, p<0.01, and *p<0.001 vs UT. FIG. 32D is trichrome staining of liver sections for the detection of liver fibrosis. Stained fibrotic tissues is observed in livers of UT, CB-treated, and Co-treated mice but invisible in livers of LSP-treated and LSP-CB (Dual)-treated mice. Scale bar=50 μm. The images represent at least three mice in each group.

FIG. 36A is a Western blot showing expression of hGBE from the two plasmids. Twenty µg total protein was loaded per lane. FIG. 36B is a graph of GBE activity in cell lysates. UT, untreated HEK293 cells.

FIG. 37 is graphs that show expression of hGBE in the liver, heart, and muscle of adult Gbe1$^{ys/ys}$ mice. Liver, heart and muscle (quadriceps) tissues were collected 2 weeks after AAV injection and GBE activities were measured in tissue lysates. N=3 mice for each group; *p<0.01.

DETAILED DESCRIPTION OF THE DISCLOSURE

Figures 1A, 1B:
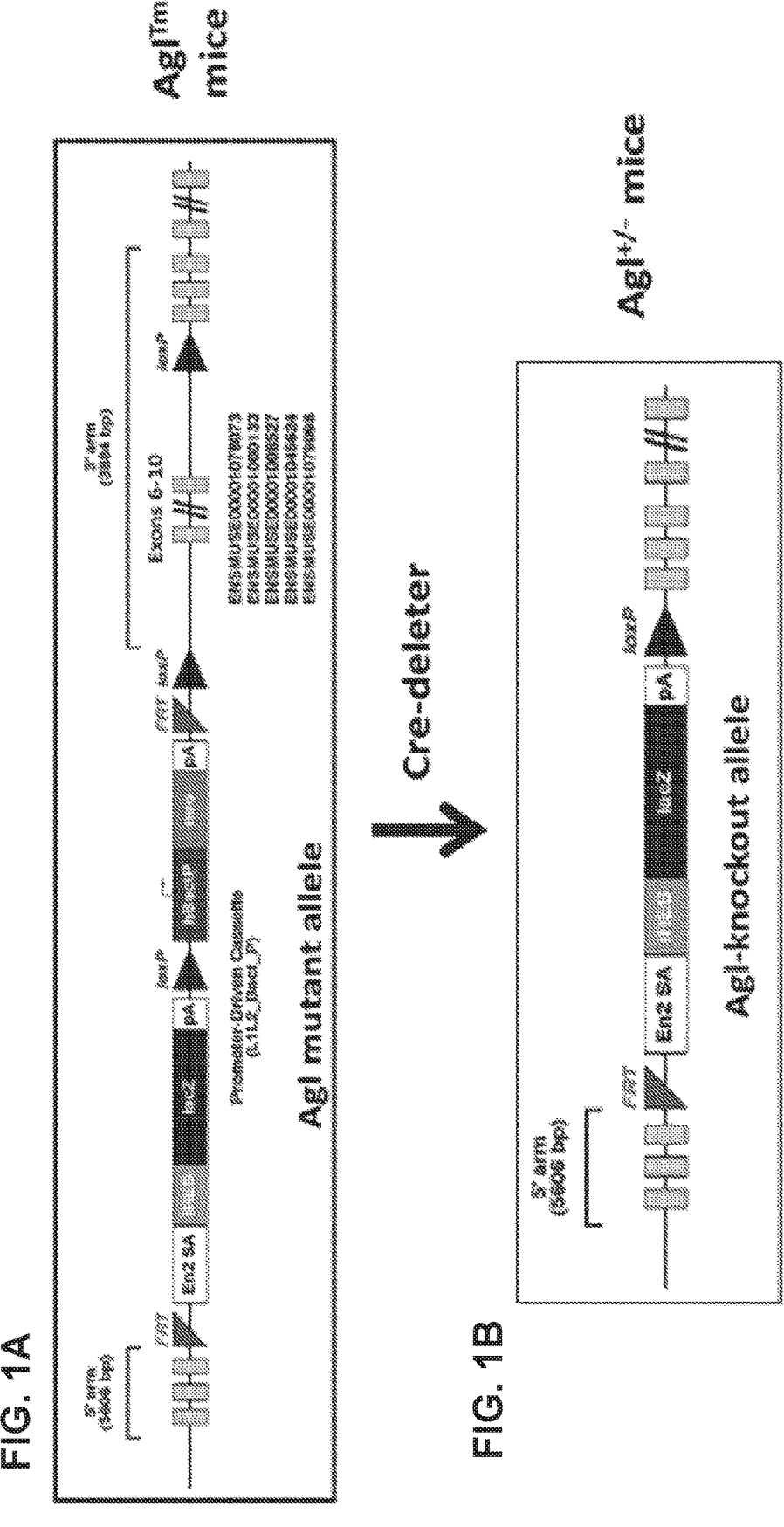
FIG. 1A illustrates the generation of heterozygous Agl$^{+/-}$ mice by crossing the Ag$^{Tm1a}$ mice with CMV-Cre mice to delete exons 6-10 in the Agl gene.
FIG. 1B illustrates that homozygous Agl$^{-/-}$ mice were used as breeders to produce Agl knockout (Agl-KO, Agl$^{-/-}$, or GSD IIIa) mice.

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "about" in association with a numerical value means that the numerical value can vary plus or minus by 5% or less of the numerical value.

The embodiments illustratively described herein suitably can be practiced in the absence of any element or elements, limitation or limitations that are not specifically disclosed herein. Thus, for example, in each instance herein any of the terms "comprising," "consisting essentially of," and "consisting of" can be replaced with either of the other two terms, while retaining their ordinary meanings.

As used herein, the term "contacting" includes the physical contact of at least one substance to another substance.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results. Alternatively stated, a "therapeutically effective" amount is an amount that will provide some alleviation, mitigation or decrease in at least one clinical symptom in the subject. For example, in the case of a deficiency of a polypeptide for degrading glycogen, an amount that provides some alleviation, mitigation or decrease in at least one clinical symptom of a deficiency of a polypeptide for degrading glycogen (e.g., reduced glycogen stores in liver, skeletal, cardiac muscles, nervous system, prevented hepatic fibrosis and cirrhosis, improved muscle strength and function, improved motor development or attainment of motor developmental milestones, prevention of cardiac arrhythmias and cardiac failure, prevention of neuropathy and the like). Those skilled in the art will appreciate that the therapeutic effects need not be complete or curative, as long as some benefit is provided to the subject.

A "reduction in glycogen stores" in a tissue is intended to indicate about a 2%, 5%, 10%, 15%, 20%, 25%, 35%, 40%, 50%, 60%, 75%, 85%, 90%, 95%, or more reduction in total glycogen in a particular tissue, unless otherwise indicated.

As used herein, the terms "express" or "expression" of a nucleic acid coding sequence, in particular a coding sequence for a microbial polypeptide for degrading glycogen, it is meant that the sequence is transcribed, and optionally, translated. Generally, however, according to the present disclosure, the term "express" or "expression" is intended to refer to transcription and translation of the coding sequence resulting in production of the encoded polypeptide.

By "enhanced" or "enhancement" with respect to nucleic acid expression or polypeptide production, it is meant an increase and/or prolongation of steady-state levels of the indicated nucleic acid or polypeptide, e.g., by at least about 2%, 5%, 10%, 15%, 20%, 25%, 40%, 50%, 60%, 75%, 2-fold, 2.5-fold, 3-fold, 5-fold, 10-fold, 15-fold, 20-fold, 30-fold, 50-fold, 100-fold or more.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The subject can be a human patient that is at risk for, or suffering from, a GSD, in particular GSD III or any other conditions where there is an abnormal accumulation of glycogen (both in terms of quality and quantity). The subject can also be a human patient that is at risk for, or suffering from, a disease caused by a deficiency of a protein or enzyme in the body caused by a large defective gene (e.g., a gene having greater than about 5 kilobases). The human patient can be of any age (e.g., an infant, child, or adult). The human patient can also be an infant that has an underdeveloped immune system. The human patient can also be a fetus in utero.

"Recombinant" is used herein to refer to new combinations of genetic material as a result of genetic engineering. For instance, a recombinant organism (e.g., bacteria) can be an organism that contains different genetic material from either of its parents as a result of genetic modification, recombinant DNA can be a form of artificial DNA, a recombinant protein or enzyme can be an artificially produced and purified form of the protein or enzyme, and a recombinant virus can be a virus formed by recombining genetic material.

As used herein, the term "disease" refers to any condition that is abnormal, such as a disorder or a structure or function that affects part or all of a subject.

Gene Therapy Using Microbial Glycogen Debranching Enzyme (GDE)

The inventors have discovered a gene therapy method of treating a glycogen storage disease by administering a vector containing a coding sequence codon optimized for expressing a therapeutic microbial GDE in human cells to patients suffering from the disease. These vectors can further comprise a tissue-specific promoter (e.g., a liver-specific promoter, a muscle-specific promoter, a neuron-specific promoter, or a combination of any of the two or more thereof) or an immunotolerant dual promoter consisting of a liver-specific promoter and a ubiquitous promoter to reduce the risk of an immune response to the microbial protein.

As described in more detail below, the present disclosure provides improved polypeptides having glycogen degrading enzymatic activity to treat GSDs, which are autosomal recessive disorders or X-linked disorders. The problem underlying GSDs is that the subject has an absence or deficiency in an enzyme that is responsible for making or breaking down glycogen in the body. The enzyme deficiency in GSDs causes either abnormal concentrations of glycogen or abnormally formed glycogen or both in the affected tissues. Depending on the type of GSD, the subject can have an enzyme deficiency in all parts of the body, or only in some parts of the body (e.g., liver, muscle, heart tissues, or nervous system).

Notably, the data described herein indicate that gene therapy with vectors expressing a microbial GDE can be successfully used to treat GSDs and the cellular immune responses induced by the microbial polypeptides can be overcome by using a tissue-specific promoter or an immunotolerant dual promoter.

Furthermore, the present disclosure provides for successful transduction of vectors carrying a therapeutic bacterial GDE or other therapeutic proteins that are capable of being packaged in a vector, without eliciting any immune responses against the therapeutic protein.

GSDs include, but are not limited to, GSD III, GSD II or Pompe Disease, GSD I, GSD IV, GSD V, GSD VI, GSD VII, GSD IX, GSD XI, GSD XII, GSD XIII, GSD XIV, Danon disease, Lafora disease, or PRKAG2 (protein kinase gamma 2 subunit) deficiency. Glycogen storage diseases can also include any other condition where there is cytoplasmic accumulation of glycogen.

The gene therapy methods described herein can offer several advantages over enzyme replacement therapy (ERT). ERT involves treating a patient with an intravenous infusion of a solution containing the enzyme that is deficient in the patient, whereas gene therapy involves delivering a gene (e.g., cDNA) encoding the deficient enzyme into the affected cells of a patient via a delivery vector where the gene can then express a functioning enzyme in the patient. Unlike ERT or small molecule therapy, gene therapy can provide equal or better outcomes while requiring typically only a single administration, which further reduces the risk of an immune response. Furthermore, ERT/small molecule therapy could be used in combination with gene therapy at a lower dose. Finally, gene therapy provides a cost savings to the patient and the convenience of fewer administrations.

Unlike its human counterpart, bacterial GDE does not have glycosyltransferase activity, but has only amylo-α-1, 6-glucosidase activity, and can directly hydrolyze α-1,6-glycosidic bonds at the branching points in limit dextrin to release maltotetraose (4-glucose) molecules, thus performing a similar function as human GDE.

GDEs can be found in many species and strains of bacteria. GDEs can differ in sequence, but they have the same amylo-α-1,6-glucosidase hydrolyzing activity.

A GDE can be derived from any microorganism. As used herein, the term "microorganism" refers to an organism that can only be seen through a microscope. A microorganism can include bacteria, protozoa, algae, fungi (e.g., yeast), and viruses.

Examples of GDE, can include, but are not limited to, pullulanase (EC 3.2.1.41) (e.g., type I pullulanase, type II pullulanase (amylopullalanase), type III pullulan hydrolase), limit dextrin alpha-1,6-hydrolase (GlgX) (E.C.3.2.1.-) encoded by the gene glgX, and isoamylase (EC 3.2.1.68).

Pullanase (EC 3.2.1.41) enzymes can be found in a variety of microbial species, including, but not limited to, *Anaerobranca gottschalkii, Anoxybacillus* sp., *Anoxybacillus* sp. SK3-4, *Aureobasidium pullulans, Avena sativa, Bacillus acidopullulyticus, Bacillus cereus, Bacillus cereus* FDTA 13, *Bacillus circulans, Bacillus deramificans, Bacillus subtilis, Bacillus subtilis* strain 168, thermophilic *Bacillus* sp. AN-7, *Bacteroides* thetaiotaomicron, *Beta vulgaris, Desulfurococcus mucosus, Exiguobacterium acetylicum, Exiguobacterium acetylicum* YH5, *Exiguobacterium* sp., *Exiguobacterium* sp. Sh3, *Fervidobacterium pennivorans, Fervidobacterium pennivorans* Ven5, *Geobacillus stearothermophilus, Geobacillus thermoleovorans, Geobacillus thermoleovorans* US105, *Halorubrum* sp. Ha25, *Hordeum vulgare, Klebsiella aerogenes, Klebsiella oxytoca, Klebsiella planticola, Klebsiella pneumonia, Klebsiella pneumoniae* U N F5023, *Laceyella sacchari, Lactococcus lactis, Lactococcus lactis* BB500, *Micrococcus* sp., *Nostoc punctiforme, Oryctolagus cuniculus, Oryza sativa, Paenibacillus macerans, Pullulanibacillus naganoensis, Pyrococcus furiosus, Pyrococcus woesei, Raoultella planticola, Rhodothermus marinus, Saccharomyces cerevisiae, Spinacia oleracea, Streptococcus pyogenes, Streptococcus* sp., *Sulfolobus acidocaldarius, Sulfolobus acidocaldarius* DSM 639, *Thermoanaerobacter acetoethylicus, Thermoanaerobacter brockii* subsp. Finnii, *Thermoanaerobacter ethanolicus, Thermoanaerobacter thermohydrosulfuricus, Thermoanaerobacterium saccharolyticum, Thermoanaerobacterium saccharolyticum* NTOU1, *Thermoanaerobacterium thermosaccharolyticum, Thermoanaerobium sp., Thermococcus kodakarensis, Thermococcus litoralis, Thermococcus litoralis* DSM 5473, *Thermococcus siculi, Thermococcus siculi* HJ21, *Thermotoga neapolitana, Thermus aquaticus, Thermus caldophilus, Thermus thermophiles*, and *Thermus thermophilus* HB8/ATCC 27634/DSM 579. In some embodiments, pullanase is derived from *Bacillus subtilis, Bacillus subtilis* strain 168.

Limit dextrin alpha-1,6-hydrolase (GlgX) (E.C.3.2.1.-) enzymes can be found in a variety of microbial species, including, but not limited to *Corynebacterium glutamicum, Corynebacterium glutamicum* ATCC 13032, *Escherichia coli, Escherichia coli* BW25113, *Escherichia coli* K-12, *Rhizobium tropici, Rhizobium tropici* PRF 81, Synechococcus elongates, and Synechococcus *elongatus* PCC 6803. In some embodiments, limit dextrin alpha-1,6-hydrolase is derived from *Escherichia coli* K-12.

Isoamylase (EC 3.2.1.68) enzymes can be found in a variety of microbial species, including, but not limited to *Amaranthus hybridus* subsp. *cruentus, Arthrobacter* sp., *Arthrobacter* sp. Q36, *Bacillus* sp., *Chlamydomonas reinhardtii, Chlamydomonas reinhardtii* 330, *Cytophaga* sp., *Dickeya chrysanthemi, Dickeya chrysanthemi* PY35, *Flavobacterium* sp., *Lipomyces kononenkoae, Musa acuminate, Myroides odoratus, Pseudomonas amyloderamosa, Pseudomonas amyloderamosa* JD210, *Pseudomonas amyloderamosa* MI-414, *Pseudomonas amyloderamosa* SB-15, *Pseudomonas amyloderamosa* SMP1, *Pseudomonas amyloderamosa* WU-5315, *Pseudomonas amyloderamosa* WU7211-2, and *Pseudomonas* sp. In other embodiments, the isoamylase can be derived from *Pseudomonas amyloderamosa* SB-15.

The gene therapy methods described herein can be applied to any protein or enzyme from a microbial species that is smaller (e.g., contains fewer nucleobases) than its human counterpart protein or enzyme such that it is more suited for packaging in vectors that have the capacity to carry only smaller genes.

Furthermore, the gene therapy compositions and methods described herein that utilize a microbial polypeptide for degrading glycogen can be used to treat not only GSDs, but also other disorders caused by a large defective gene.

Isolated Nucleic Acids

The present disclosure provides, in part, an isolated nucleic acid molecule, comprising a nucleic acid sequence encoding a microbial polypeptide for degrading glycogen, wherein the nucleic acid is codon-optimized for expression in a mammalian or a human cell.

As used herein, the term "isolated" nucleic acid molecule (e.g., an isolated DNA, isolated cDNA, or an isolated vector genome) means a nucleic acid molecule separated or substantially free from at least some of the other components of the naturally occurring organism or virus, for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

The term "nucleotide" refers to sequences with conventional nucleotide bases, sugar residues and internucleotide phosphate linkages, but also to those that contain modifications of any or all of these moieties. The term "nucleotide" as used herein includes those moieties that contain not only the natively found purine and pyrimidine bases adenine (A), guanine (G), thymine (T), cytosine (C), and uracil (U), but also modified or analogous forms thereof.

Polynucleotides include RNA and DNA sequences of more than one nucleotide in a single chain. Modified RNA or modified DNA, as used herein, refers to a nucleic acid molecule in which one or more of the components of the nucleic acid, namely sugars, bases, and phosphate moieties, are different from that which occurs in nature.

The term "nucleic acid" or "nucleic acid molecule" refers to any of deoxyribonucleic acid (DNA), ribonucleic acid (RNA), oligonucleotides, fragments generated, for example, by a polymerase chain reaction (PCR) or by in vitro translation, and fragments generated by any one or more of ligation, scission, endonuclease action, or exonuclease action. Nucleic acid molecules can be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination thereof. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, morpholino, or the like. Nucleic acid molecules can be either single stranded or double stranded.

The term "microbial polypeptide" refers to a polypeptide that is from a microorganism species (e.g., a bacterial species).

In some embodiments, the microbial polypeptide is a therapeutic glycogen debranching enzyme (GDE) from bacteria or another microorganism. In other embodiments, the microbial polypeptide has debranching enzyme activity that can cleave the α-1,6-glycosidic bonds in glycogen and/or limit dextrin (e.g., type I pullulanase, limit dextrin alpha-1, 6-hydrolase (GlgX), isoamylase, and derivatives thereof). In other embodiments, the microbial polypeptide can cleave both the α-1,6-glycosidic bonds and α-1,4-glycosidic bonds in glycogen (e.g., type II pullulanase or type III pullulan hydrolase, and derivatives thereof).

In some embodiments, the microbial polypeptide has an amino acid sequence as set forth in SEQ ID NO:01 or SEQ ID NO:04 or SEQ ID NO:07, or has at least 60%, 70%, 80%, 85%, 86%, 87%, 88%, 89%, 90%, 91%, 92%, 93%, 94%, 95%, 96%, 97%, 98%, or 99% sequence identity to the amino acid sequence set forth in SEQ ID NO:01 or SEQ ID NO:04 or SEQ ID NO:07. In other embodiments, the microbial polypeptide has at least 50% sequence identity to the amino acid sequence set forth in SEQ ID NO:01 or SEQ ID NO:04 or SEQ ID NO:07.

In some embodiments, the nucleic acid sequence has a sequence as set forth in SEQ ID NO:03, SEQ ID NO:06, or SEQ ID NOS:08-25, or has at least 50%, 60%, 70%, 80%, 85%, 86%, 87%, 88%, 89%, 90%, 91%, 92%, 93%, 94%, 95%, 96%, 97%, 98%, or 99% sequence identity to the nucleic acid sequence set forth in SEQ ID NO:03, SEQ ID NO:06, or SEQ ID NOS:08-25.

The term "sequence identity" refers to the number of identical or similar nucleotide bases on a comparison between a test and reference oligonucleotide or nucleotide sequence. Sequence identity can be determined by sequence alignment of nucleic acid to identify regions of similarity or identity. As described herein, sequence identity is generally determined by alignment to identify identical residues. Matches, mismatches, and gaps can be identified between compared sequences. Alternatively, sequence identity can be determined without taking into account gaps as the number of identical positions/length of the total aligned sequence× 100. In one non-limiting embodiment, the term "at least 90% sequence identity to" refers to percent identities from 90 to 100%, relative to the reference nucleotide sequence. Identity at a level of 90% or more is indicative of the fact that, assuming for exemplary purposes a test and reference oligonucleotide length of 100 nucleotides are compared, no more than 10% (i.e., 10 out of 100) of the nucleotides in the test oligonucleotide differ from those of the reference oligonucleotide. Differences are defined as nucleic acid substitutions, insertions, or deletions.

The term "codon optimized" relates to the alteration of codons in nucleic acid molecules to reflect the typical codon usage of the host organism (e.g., mammals such as humans) without altering the polypeptide encoded by the DNA, to improve expression. Many methods and software tools for codon optimization have been reported previously. See, for example, genomes.urv.es/OPTIMIZER/; Puigbo et al., *Nucleic Acids Res.* (2007) (Web Server issue): W126-W131; Chin et al. (2014) *Bioinformatics,* 30(15):2210-2; Fuglsang, (2003) *Protein Expr. Purif.,* 31(2):247-9; Narum et al., (2001) *Infect. Immun.,* 69(12):7250-7253, Outchkourov et al., (2002) *Protein Expr. Purif,* 24(1):18-24, Feng et al., (200) *Biochemistry,* 39(50):15399-15409, Humphreys et al., (2000) *Protein Expr. Purif,* 20(2):252-64.

Table 1 below provides exemplary codon optimization for gene expression in humans.

| Triplet | Amino acid | Fraction | Frequency/ Thousand | Number |
|---|---|---|---|---|
| TTT | F | 0.45 | 16.9 | 336562 |
| TTC | F | 0.55 | 20.4 | 406571 |
| TTA | L | 0.07 | 7.2 | 143715 |
| TTG | L | 0.13 | 12.6 | 249879 |
| TAT | Y | 0.43 | 12.0 | 239268 |
| TAC | Y | 0.57 | 15.6 | 310695 |
| TAA | * | 0.28 | 0.7 | 14322 |
| TAG | * | 0.20 | 0.5 | 10915 |
| CTT | L | 0.13 | 12.8 | 253795 |
| CTC | L | 0.20 | 19.4 | 386182 |
| CTA | L | 0.07 | 6.9 | 138154 |
| CTG | L | 0.41 | 40.3 | 800774 |
| CAT | H | 0.41 | 10.4 | 207826 |
| CAC | H | 0.59 | 14.9 | 297048 |
| CAA | Q | 0.25 | 11.8 | 234785 |
| CAG | Q | 0.75 | 34.6 | 688316 |
| ATT | I | 0.36 | 15.7 | 313225 |
| ATC | I | 0.48 | 21.4 | 426570 |
| ATA | I | 0.16 | 7.1 | 140652 |
| ATG | M | 1.00 | 22.3 | 443795 |
| AAT | N | 0.46 | 16.7 | 331714 |
| AAC | N | 0.54 | 19.5 | 387148 |
| AAA | K | 0.42 | 24.0 | 476554 |
| AAG | K | 0.58 | 32.9 | 654280 |
| GTT | V | 0.18 | 10.9 | 216818 |
| GTC | V | 0.24 | 14.6 | 290874 |

-continued

| Triplet | Amino acid | Fraction | Frequency/ Thousand | Number |
|---|---|---|---|---|
| GTA | V | 0.11 | 7.0 | 139156 |
| GTG | V | 0.47 | 28.9 | 575438 |
| GAT | D | 0.46 | 22.3 | 443369 |
| GAC | D | 0.54 | 26.0 | 517579 |
| GAA | E | 0.42 | 29.0 | 577846 |
| GAG | E | 0.58 | 40.8 | 810842 |
| TCT | S | 0.18 | 14.6 | 291040 |
| TCC | S | 0.22 | 17.4 | 346943 |
| TCA | S | 0.15 | 11.7 | 233110 |
| TCG | S | 0.06 | 4.5 | 89429 |
| TGT | C | 0.45 | 9.9 | 197293 |
| TGC | C | 0.55 | 12.2 | 243685 |
| TGA | * | 0.52 | 1.3 | 25383 |
| TGG | W | 1.00 | 12.8 | 255512 |
| CCT | P | 0.28 | 17.3 | 343793 |
| CCC | P | 0.33 | 20.0 | 397790 |
| CCA | P | 0.27 | 16.7 | 331944 |
| CCG | P | 0.11 | 7.0 | 139414 |
| CGT | R | 0.08 | 4.7 | 93458 |
| CGC | R | 0.19 | 10.9 | 217130 |
| CGA | R | 0.11 | 6.3 | 126113 |
| CGG | R | 0.21 | 11.9 | 235938 |
| ACT | T | 0.24 | 12.8 | 255582 |
| ACC | T | 0.36 | 19.2 | 382050 |
| ACA | T | 0.28 | 14.8 | 294223 |
| ACG | T | 0.12 | 6.2 | 123533 |
| AGT | S | 0.15 | 11.9 | 237404 |
| AGC | S | 0.24 | 19.4 | 385113 |
| AGA | R | 0.20 | 11.5 | 228151 |
| AGG | R | 0.20 | 11.4 | 227281 |
| GCT | A | 0.26 | 18.6 | 370873 |
| GCC | A | 0.40 | 28.5 | 567930 |
| GCA | A | 0.23 | 16.0 | 317338 |
| GCG | A | 0.11 | 7.6 | 150708 |
| GGT | G | 0.16 | 10.8 | 215544 |
| GGC | G | 0.34 | 22.8 | 453917 |
| GGA | G | 0.25 | 16.3 | 325243 |
| GGG | G | 0.25 | 16.4 | 326879 |

In some embodiments, the nucleic acid sequence encoding a microbial polypeptide has a coding sequence that is less than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, or 5.5 kilobases (kb).

TABLE 2

Potential sequences related to this disclosure.

| | |
|---|---|
| Protein sequence of pullulanase [*Bacillus subtilis* subsp. *subtilis* str. 168] NCBI Reference Sequence: NP_390871.2 Uniprot # NP15067 | MVSIRRSFEAYVDDMNIITVLIPAEQKEIMTPPFRLETEITDFPLAVREEYSL EAKYKYVCVSDHPVTFGKIHCVRASSGHKTDLQIGAVIRTAAFDDEFYYDGEL GAVYTADHTVFKVWAPAATSAAVKLSHPNKSGRTFQMTRLEKGVYAVTVTGDL HGYEYLFCICNNSEWMETVDQYAKAVTVNGEKGVVLRPDQMKWTAPLKPFSHP VDAVIYETHLRDFSIHENSGMINKGKYLALTETDTQTANGSSSGLAYVKELGV THVELLPVNDFAGVDEEKPLDAYNWGYNPLHFFAPEGSYASNPHDPQTRKTEL KQMINTLHQHGLRVILDVVFNHVYKRENSPFEKTVPGYFFRHDECGMPSNGTG VGNDIASERRMARKFIADCVVYWLEEYNVDGFRFDLLGILDIDTVLYMKEKAT KAKPGILLFGEGWDLATPLPHEQKAALANAPRMPGIGFFNDMFRDAVKGNTFH LKATGFALGNGESAQAVMHGIAGSSGWKALAPIVPEPSQSINYVESHDNHTFW DKMSFALPQENDSRKRSRQRLAAAIILLAQGVPFIHSGQEFFRTKQGVENSYQ SSDSINQLDWDRRETFKEDVHYIRRLISLRKAHPAFRLRSAADIQRHLECLTL KEHLIAYRLYDLDEVDEWKDIIVIHHASPDSVEWRLPNDIPYRLLCDPSGFQE DPTEIKKTVAVNGIGTVILYLASDLKSFA (SEQ ID NO: 01) |
| cDNA sequence of pullulanase derived from *B. subtilis* strain 168 (2157 bp) amyX pullulanase [*Bacillus subtilis* subsp. *subtilis* str. 168] | ATGGTCAGCATCCGCCGCAGCTTCGAAGCGTATGTCGATGACATGAATATCAT TACTGTTCTGATTCCTGCTGAACAAAAGGAAATCATGACACCGCCGTTTCGGC TTGAGACAGAAATAACAGATTTTCCTCTGGCTGTCAGGGAGGAATACTCCCTT GAAGCAAAATACAAGTACGTCTGCGTATCCGACCATCCTGTGACATTTGGAAA AATCCATTGCGTCAGAGCATCCAGCGGCCACAAAACGGATCTCCAAATTGGCG CGGTCATCCGGACAGGCAGCGTTTGATGACGAATTTTATTATGACGGAGAGCTG |

TABLE 2-continued

Potential sequences related to this disclosure.

| | |
|---|---|
| Gene ID: 937292<br>Sequence: NC_000964.3<br>(3061651 . . . 3063807,<br>complement) | GGCGCCGTTTATACCGCGGATCATACCGTATTTAAAGTATGGGCGCCTGCTGC<br>AACCTCAGCTGCTGTCAAGCTTTCACACCCCAATAAAAGCGGGCGCACATTCC<br>AAATGACTCGCTTGGAAAAAGGCGTCTATGCCGTTACGGTCACAGGTGACCTT<br>CACGGATATGAGTATTTGTTTTGCATCTGCAACAATTCAGAATGGATGGAAAC<br>AGTTGACCAGTATGCCAAGGCTGTGACTGTAAATGGAGAGAAGGGCGTCGTCT<br>TGCGCCCGGATCAAATGAAATGGACTGCTCCTCTTAAACCATTCTCACACCCT<br>GTGGATGCCGTCATCTATGAGACGCATCTTCGCGACTTCTCCATCCATGAAAA<br>CAGCGGCATGATAAACAAGGGAAAATACTTAGCGCTGACGGAAACTGATACAC<br>AAACCGCAAATGGCAGTTCTTCGGGATTAGCGTATGTAAAAGAGCTTGGTGTG<br>ACACATGTGGAGCTTCTGCCGGTGAATGATTTTGCCGGAGTTGATGAAGAGAA<br>GCCGCTTGATGCATACAATTGGGGATATAACCCGCTTCATTTCTTTGCCCCGG<br>AGGGAAGCTATGCCTCAAATCCTCATGATCCTCAAACGAGAAAAACAGAGCTG<br>AAACAAATGATCAATACCCTGCATCAGCACGGTCTGCGAGTCATTCTGGATGT<br>TGTTTTTAACCATGTGTATAAGAGGGAGAATTCCCCCTTTGAAAAGACAGTGC<br>CCGGTTATTTTTTCCGGCACGACGAATGTGGGATGCCATCAAACGGCACCGGC<br>GTTGGCAATGATATTGCATCAGAAAGAAGGATGGCAAGAAAATTCATTGCGGA<br>TTGCGTGGTCTATTGGCTTGAAGAATACAATGTTGACGGCTTCCGCTTTGATC<br>TCCTCGGGATTTTAGATATTGACACCGTGCTTTATATGAAAGAGAAAGCAACT<br>AAGGCAAAGCCCGGAATCCTGCTTTTTGGAGAAGGGTGGGACCTGGCTACACC<br>GCTGCCGCATGAACAGAAAGCTGCTTTGGCGAACGCGCCAAGAATGCCGGGCA<br>TCGGCTTTTTTAATGATATGTTTCGTGACGCTGTAAAAGGGAACACCTTTCAC<br>CTTAAGGCAACAGGGTTTGCGCTCGGCAACGGTGAATCAGCACAAGCTGTGAT<br>GCATGGAATTGCCGGGTCTTCCGGATGGAAGGCATTAGCACCGATTGTTCCGG<br>AACCAAGCCAGTCCATCAATTATGTCGAATCACACGACAATCACACCTTTTGG<br>GATAAAATGAGCTTTGCGCTTCCTCAAGAAAATGACAGCCGAAAGCGAAGCAG<br>GCAAAGGCTTGCAGCCGCGATTATTTTGCTTGCCCAAGGGGTGCCGTTTATTC<br>ACAGCGGCCAGGAATTTTTCCGGACGAAGCAGGGAGTGGAAAACAGCTATCAA<br>TCCAGTGACAGCATCAACCAGCTCGACTGGGATCGCCGTGAAACATTCAAAGA<br>AGATGTTCACTATATCCGCAGGCTGATCTCGCTGAGAAAAGCGCATCCTGCAT<br>TCCGTCTTAGGTCCGCTGCAGACATCCAGCGCCATCTTGAATGCTTGACGCTA<br>AAAGAACACCTTATCGCATACAGGCTTTATGATCTTGACGAGGTTGACGAATG<br>GAAAGATATCATTGTTATCCATCACGCGAGTCCAGACTCCGTCGAGTGGAGGC<br>TGCCAAACGACATACCTTATCGGCTTTTATGTGATCCATCAGGATTTCAGGAA<br>GACCCAACAGAAATCAAGAAAACGGTTGCAGTAAACGGCATCGGAACGGTTAT<br>CTTATATTTAGCATCAGATCTTAAGAGTTTTGCTTGA (SEQ ID NO: 02) |
| Codon optimized<br>polynucleotide coding<br>sequence #1 for expressing<br>pullulanase derived from<br>*Bacillus subtilis* strain<br>168 in human cells. | ATGGTGAGCATCCGGAGATCCTTCGAGGCCTACGTGGACGATATGAACATCAT<br>CACCGTGCTGATCCCAGCCGAGCAGAAGGAGATCATGACACCCCTTTCCGGC<br>TGGAGACCGAGATCACAGACTTTCCCCTGGCCGTGAGAGAGGAGTATAGCCTG<br>GAGGCCAAGTACAAGTACGTGTGCGTGAGCGATCACCCTGTGACCTTTGGCAA<br>GATCCACTGCGTGCGGGCAAGCTCCGGACACAAGACCGACCTGCAGATCGGAG<br>CCGTGATCAGGACAGCAGCCTTCGACGATGAGTTTTACTATGACGGAGAGCTG<br>GGAGCCGTGTACACCGCAGATCACACAGTGTTCAAGGTCTGGGCACCAGCAGC<br>CACATCCGCCGCAGTGAAGCTGAGCCACCCCAACAAGTCCGGCAGGACCTTTC<br>AGATGACACGCCTGGAGAAGGGCGTGTACGCCGTGACCGTGACAGGCGATCTG<br>CACGGCTACGAGTATCTGTTCTGCATCTGTAACAATTCTGAGTGGATGGAGAC<br>CGTGGATCAGTATGCCAAGGCCGTGACAGTGAATGGAGAGAAGGGAGTGGTGC<br>TGAGGCCAGACCAGATGAAGTGGACCGCACCCCTGAAGCCTTTCAGCCACCCT<br>GTGGACGCCGTGATCTACGAGACACACCTGCGCGATTTTTCTATCCACGAGAA<br>CAGCGGCATGATCAATAAGGGCAAGTACCTGGCCCTGACCGAGACAGACACCC<br>AGACAGCCAACGGCTCTAGCTCCGGCCTGGCCTATGTGAAGGAGCTGGGAGTG<br>ACCCACGTGGAGCTGCTGCCTGTGAATGACTTTGCCGGCGTGGATGAGGAGAA<br>GCCACTGGATGCCTACAACTGGGGCTATAATCCACTGCACTTCTTTGCCCCCG<br>AGGGCTCTTATGCCAGCAACCCACACGACCCCCAGACCAGGAAGACAGAGCTG<br>AAGCAGATGATCAATACACTGCACCAGCACGGCCTGAGAGTGATCCTGGATGT<br>GGTGTTCAACCACGTGTACAAGCGCGAGAATAGCCCTTTTGAGAAGACCGTGC<br>CAGGCTATTTCTTTCGGCACGACGAGTGCGGCATGCCCATCTAACGGCACAGGC<br>GTGGGCAATGATATCGCCAGCGAGAGGCGCATGGCCCGGAAGTTCATCGCCGA<br>CTGCGTGGTGTACTGGCTGGAGGAGTATAACGTGGACGGCTTCAGATTTGATC<br>TGCTGGGCATCCTGGACATCGATACCGTGCTGTACATGAAGGAGAAGGCCACA<br>AAGGCCAAGCCCAGGCATCCTGCTGTTCGGAGAGGGATGGGACCTGGCAACCCC<br>ACTGCCACACGAGCAGAAGGCCGCCCTGGCAAACGCACCTAGGATGCCAGGCA<br>TCGGCTTCTTTAACGACATGTTTCGCGATGCCGTGAAGGGCAATACCTTCCAC<br>CTGAAGGCCACAGGCTTTGCACTGGGAAATGGAGAGTCCGCCCAGGCCGTGAT<br>GCACGGAATCGCCAGGATCTAGCGGATGGAAGGCCCTGGCACCAATCGTGCCTG<br>AGCCAAGCCAGTCCATCAACTACGTGGAGTCCCACGACAATCACACCTTCTGG<br>GATAAGATGTCTTTTGCCCTGCCTCAGGAGAATGATTCTAGGAAGAGAAGCAG<br>GCAGCGCCTGGCAGCAGCAATCATCCTGCTGGCCCAGGGCGTGCCATTCATCC<br>ACAGCGGCCAGGAGTTCTTTCGGACCAAGCAGGGCGTGGAGAACTCCTACCAG<br>TCCTCTGATTCTATCAATCAGCTGGACTGGGATCGGAGAGAGACATTCAAGGA<br>GGACGTGCACTATATCAGGCGCCTGATCAGCCTGAGAAAGGCACACCCAGCCT<br>TTCGGCTGAGATCCGCCGCAGACATCCAGAGGCACCTGGAGTGCCTGACCCTG<br>AAGGAGCACCTGATCGCCTACAGACTGTATGACCTGGATGAGGTGGACGAGTG<br>GAAGGATATCATCGTGATCCACCACGCCTCCCCTGACTCTGTGGAGTGGCGGC<br>TGCCCAACGATATCCCTTACGACTGCGTGTGCGACCCCTCCGGCTTCCAGGAG<br>GATCCTACCGAGATCAAGAAGACAGTGGCCGTGAATGGCATCGGCACCGTGAT<br>CCTGTATCTGGCCTCCGACCTGAAGTCTTTTGCCTGA (SEQ ID NO: 03) |

Potential sequences related to this disclosure.

| | |
|---|---|
| Codon optimized polynucleotide coding sequence #2 for expressing Pullulanase derived from *Bacillus subtilis* strain 168 in human cells | ATG GTT AGC ATC AGG CGA TCC TTT GAA GCC TAC GTG GAT GAC ATG AAT ATC ATC ACC GTG CTC ATA CCG GCC GAA CAA AAG GAG ATT ATG ACA CCT CCT TTC CGA CTC GAA ACC GAG ATA ACA GAC TTT CCT CTC GCT GTT CGA GAG GAA TAT AGT TTG GAA GCT AAG TAT AAG TAC GTT TGT GTA AGC GAT CAT CCG GTT ACT TTC GGA AAG ATA CAT TGC GTA AGA GCT TCT TCT GGA CAC AAG ACC GAT CTT CAA ATA GGT GCC GTA ATA CGC ACG GCA GCG TTC GAC GAT GAA TTT TAT TAC GAC GGT GAA CTT GGC GCC GTA TAC ACT GCC GAC CAT ACT GTT TTT AAA GTT TGG GCC CCG GCT GCA ACT TCT GCG GCT GTT AAA CTT TCT CAT CCC AAT AAG TCA GGA CGA ACC TTC CAG ATG ACC AGA TTG GAG AAA GGT GTG TAC GCA GTG ACT GTC ACG GGG GAT CTC CAC GGT TAT GAA TAC CTG TTC TGC ATT TGC AAT AAT TCT GAA TGG ATG GAA ACT GTC GAT CAA TAC GCC AAG GCT GTG ACA GTC AAC GGG GAA AAG GGT GTG GTT CTG CGC CCG GAT CAA ATG AAG TGG ACA GCT CCT CTT AAA CCA TTC TCA CAC CCT GTG GAC GCG GTA ATT TAC GAG ACG CAT CTC CGA GAT TTC AGT ATT CAC GAG AAT AGT GGT ATG ATT AAT AAG GGG AAG TAC CTG GCT TTG ACG GAA ACA GAT ACG CAA ACT GCC AAC GGA TCA AGC AGC GGT CTG GCA TAC GTC AAG GAA CTG GGC GTA ACA CAT GTT GAA CTC CTC CCT GTC AAC GAC TTC GCT GGT GTT GAC GAG GAA AAG CCC TTG GAC GCT TAC AAT TGG GGA TAT AAT CCA TTG CAT TTC TTT GCC CCC GAG GGC AGC TAC GCG AGC AAC CCT CAT GAT CCA CAG ACC CGA AAG ACT GAG CTG AAA CAG ATG ATT AAC ACG CTG CAC CAG CAT GGA TTG CGA GTC ATA TTG GAC GTG GTA TTC AAC CAT GTC TAT AAA CGC GAG AAC AGT CCC TTT GAG AAG ACA GTC CCA GGT TAC TTC TTC AGA CAC GAT GAG TGT GGC ATG CCC AGC AAC GGG ACC GGT GTC GGT AAT GAT ATC GCG TCC GAA CGC CGG ATG GCC CGG AAA TTT ATC GCC GAT TGT GTA GTT TAC TGG CTT GAG GAA TAT AAT GTA GAC GGG TTT CGG TTC GAT TTG CTC GGT ATA TTG GAT ATT GAC ACC GTT CTC TAT ATG AAG GAG AAA GCG ACG AAG GCT AAG CCG GGC ATA CTC CTG TTC GGT GAA GGT TGG GAT CTG GCG ACC CCG CTC CCG CAC GAG CAA AAA GCA GCT CTT GCT AAC GCA CCG AGG ATG CCG GGA ATA GGA TTT TTC AAT GAC ATG TTC CGC GAT GCC GTG AAA GGA AAT ACA TTC CAC CTT AAA GCC ACA GGT TTC GCA CTG GGC AAC GGT GAG TCC GCC CAA GCT GTC ATG CAC GGG ATT GCA GGT TCA TCC GGG TGG AAG GCC CTT GCA CCT ATT GTA CCA GAG CCT TCT CAA TCC ATT AAT TAC GTC GAA TCA CAT GAT AAC CAC ACG TTC TGG GAT AAA ATG TCA TTC GCC CTG CCA CAG GAA AAC GAC TCT AGG AAA CGG TCC CGA CAA CGG CTG GCC GCA GCT ATT ATC TTG CTT GCA CAA GGG GTG CCC TTT ATC CAT TCC GGG CAA GAG TTT TTT AGA ACC AAA CAA GGA GTC GAG AAC AGC TAC CAG TCA TCA GAC TCC ATC AAC CAG TTG GAC TGG GAT AGG AGA GAG ACG TTC AAA GAG GAT GTG CAT TAC ATC AGA CGG CTC ATA TCA CTC CGA AAG GCA CAC CCG GCA TTT CGC CTC AGG TCT GCT GCG GAC ATA CAG CGC CAT TTG GAG TGT CTC ACC TTG AAG GAG CAT CTC ATT GCG TAT AGG TTG TAC GAC TTG GAC GAG GTG GAT GAG TGG AAG GAT ATC ATT GTT ATT CAT CAT GCG TCT CCC GAC TCC GTC GAG TGG CGA TTG CCG AAC GAC ATA CCA TAC CGA TTG CTG TGC GAC CCA TCA GGT TTC CAG GAG GAC CCA ACT GAA ATC AAA AAA ACC GTG GCT GTC AAT GGT ATT GGT ACC GTT ATA CTT TAC CTC GCT TCA GAT CTG AAG TCT TTC GCC TGA (SEQ ID NO: 08) |
| Codon optimized polynucleotide coding sequence #3 for expressing Pullulanase derived from *Bacillus subtilis* strain 168 in human cells | ATG GTC TCC ATT AGG CGA AGC TTC GAG GCT TAT GTA GAC GAT ATG AAC ATT ATT ACT GTC CTT ATA CCA GCA GAA CAG AAA GAA ATT ATG ACT CCG CCG TTC CGA TTG GAG ACA GAG ATT ACG GAC TTT CCT TTG GCC GTT CGG GAA GAG TAT TCT CTT GAG GCC AAA TAT AAA TAT GTG TGC GTT AGT GAT CAT CCA GTA ACG TTT GGC AAA ATC CAC TGC GTC CGG GCC TCT AGT GGA CAT AAG ACG GAC CTT CAG ATA GGG GCT GTC ATC CGG ACA GCT GCA TTC GAT GAT GAG TTT TAC TAT GAT GGG GAG CTC GGA GCG GTA TAT ACA GCC GAT CAT ACT GTA TTT AAA GTT TGG GCA CCT GCT GCC ACC TCC GCG GCG GTT AAG CTT TCC CAT CCG AAT AAA TCC GGC CGC ACT TTT CAG ATG ACT CGA CTT GAA AAA GGG GTT TAC GCC GTG ACG GTG ACC GGA GAT TTG CAC GGG TAC GAG TAT CTT TTC TGC ATA TGT AAT AAC TCA GAA TGG ATG GAA ACT GTA GAC CAG TAT GCC AAG GCG GTT ACG GTG AAC GGG GAA AAG GGG GTT GTT CTG CGG CCG GAT CAA ATG AAA TGG ACG GCA CCG TTG AAG CCC TTT TCT CAT CCA GTC GAC GCT GTC ATA TAC GAG ACG CAC CTG AGA GAC TTT TCA ATC CAC GAA AAT AGT GGT ATG ATT AAT AAA GGC AAA TAT CTT GCA CTT ACA GAG ACC GAT ACA CAG ACC GCA AAC GGA TCT AGT TCT GGG TTG GCG TAC GTC AAA GAG CTG GGA GTT ACT CAT GTA GAA TTG CTC CCT GTT |

TABLE 2-continued

Potential sequences related to this disclosure.

```
                            AAC GAC TTC GCA GGT GTA GAT GAG GAA AAG CCT CTG GAC
                            GCA TAT AAC TGG GGA TAC AAT CCT CTC CAT TTT TTC GCA
                            CCA GAA GGG TCA TAT GCC AGC AAT CCC CAT GAC CCG CAA
                            ACG AGA AAG ACT GAA CTT AAG CAG ATG ATA AAT ACT CTG
                            CAC CAA CAC GGT CTT CGC GTT ATT CTC GAT GTT GTC TTC
                            AAC CAT GTT TAC AAG CGC GAG AAT TCC CCT TTC GAA AAA
                            ACG GTA CCT GGG TAC TTT TTT CGG CAT GAC GAA TGC GGT
                            ATG CCT AGC AAC GGA ACA GGA GTT GGG AAC GAC ATT GCA
                            AGC GAA CGG CGA ATG GCG AGA AAG TTT ATT GCC GAT TGT
                            GTA GTC TAC TGG TTG GAG GAG TAT AAC GTT GAT GGT TTC
                            CGA TTC GAC CTG TTG GGT ATA TTG GAT ATC GAT ACC GTG
                            TTG TAC ATG AAA GAA AAA GCA ACA AAA GCC AAA CCT GGG
                            ATT TTG CTG TTT GGT GAA GGT TGG GAC TTG GCC ACG CCG
                            CTC CCG CAC GAG CAG AAG GCC GCT CTC GCG AAT GCA CCG
                            CGC ATG CCA GGA ATC GGG TTT TTT AAC GAC ATG TTC AGG
                            GAC GCT GTG AAA GGA AAC ACG TTT CAT CTT AAG GCT ACG
                            GGG TTC GCT CTT GGG AAC GGC GAG AGC GCA CAG GCA GTC
                            ATG CAC GGT ATA GCT GGT AGT TCA GGT TGG AAG GCG CTC
                            GCA CCA ATC GTG CCT GAG CCG TCC CAG AGC ATT AAT TAT
                            GTC GAA TCC CAC GAT AAT CAC ACC TTT TGG GAT AAA ATG
                            TCC TTT GCC TTG CCA CAG GAG AAC GAT TCT AGA AAG CGG
                            TCA CGC CAG CGG CTT GCT GCT GCA ATT ATC TTG TTG GCC
                            CAG GGT GTC CCG TTC ATC CAC AGT GGC CAG GAG TTC TTC
                            AGA ACA AAA CAA GGA GTG GAG AAC AGC TAC CAA AGC TCA
                            GAC TCT ATA AAT CAG TTG GAC TGG GAC AGG CGC GAA ACA
                            TTT AAA GAA GAT GTG CAC TAC ATT AGG CGA CTG ATT TCA
                            CTC CGC AAA GCG CAC CCT GCA TTC CGA CTT AGA TCC GCC
                            GCT GAC ATA CAA AGA CAT CTG GAA TGC CTC ACT CTC AAG
                            GAA CAT CTG ATA GCT TAT AGG TTG TAC GAC TTG GAC GAG
                            GTC GAC GAA TGG AAA GAC ATT ATC GTT ATA CAT CAT GCG
                            TCT CCT GAT AGC GTC GAG TGG AGA TTG CCA AAC GAT ATT
                            CCA TAT CGG CTT CTT TGC GAC CCC TCT GGC TTT CAG GAG
                            GAC CCG ACC GAG ATA AAG AAG ACT GTG GCG GTT AAC GGT
                            ATT GGT ACG GTA ATT TTG TAC TTG GCG TCT GAT TTG AAA
                            TCT TTC GCG TGA (SEQ ID NO: 09)

Codon optimized          ATG GTA AGT ATT CGG AGA TCT TTT GAG GCT TAC GTT GAT
polynucleotide coding    GAT ATG AAC ATT ATT ACA GTT CTC ATT CCG GCG GAG CAA
sequence #4 for expressing   AAG GAG ATA ATG ACC CCA CCA TTT AGA CTT GAG ACT GAG
Pullulanase derived from     ATA ACT GAC TTT CCT CTT GCA GTT AGG GAA GAA TAT AGT
Bacillus subtilis strain     CTG GAG GCA AAG TAT AAA TAC GTA TGC GTC AGT GAC CAC
168 in human cells           CCT GTA ACA TTT GGT AAA ATA CAC TGT GTA AGA GCG TCT
                            AGC GGA CAT AAA ACT GAC CTT CAG ATT GGC GCC GTT ATA
                            CGG ACA GCA GCA TTC GAT GAC GAG TTT TAT TAC GAC GGG
                            GAA CTT GGG GCA GTT TAC ACT GCA GAT CAT ACG GTG TTT
                            AAA GTT TGG GCG CCA GCT GCT ACC TCT GCA GCA GTA AAA
                            TTG AGT CAC CCT AAT AAA TCA GGT AGG ACG TTC CAG ATG
                            ACT AGA CTC GAA AAG GGG GTT TAC GCA GTC ACG GTA ACG
                            GGT GAT TTG CAC GGC TAC GAA TAC CTT TTT TGC ATT TGC
                            AAC AAC AGT GAG TGG ATG GAA ACC GTT GAC CAA TAT GCC
                            AAG GCT GTG ACG GTC AAT GGG GAA AAA GGT GTC GTG TTG
                            CGG CCT GAT CAA ATG AAG TGG ACA GCA CCC CTC AAG CCA
                            TTT AGT CAT CCC GTT GAC GCT GTA ATA TAC GAA ACG CAC
                            TTG CGC GAC TTC TCA ATT CAC GAA AAC TCC GGA ATG ATA
                            AAC AAA GGT AAA TAC CTT GCA CTT ACT GAA ACG GAT ACC
                            CAG ACG GCG AAC GGA AGT AGT AGC GGG CTC GCC TAC GTC
                            AAA GAA TTG GGG GTT ACA CAC GTT GAA CTC CTG CCT GTT
                            AAT GAC TTC GCC GGC GTC GAC GAA GAG AAG CCC CTT GAT
                            GCA TAT AAT TGG GGG TAT AAC CCC CTG CAT TTC TTT GCC
                            CCT GAG GGA TCA TAT GCA AGT AAT CCG CAT GAT CCA CAG
                            ACT CGA AAA ACA GAG CTC AAA CAA ATG ATT AAC ACG CTT
                            CAC CAG CAT GGT CTT AGG GTG ATC CTT GAC GTG GTT TTT
                            AAC CAT GTG TAT AAG CGA GAG AAC TCC CCT TTC GAA AAG
                            ACT GTC CCC GGA TAT TTC TTT CGC CAT GAT GAG TGC GGT
                            ATG CCT AGC AAT GGG ACT GGG GTC GGT AAT GAT ATC GCC
                            AGC GAA AGG CGA ATG GCT AGA AAA TTT ATA GCG GAC TGC
                            GTA GTA TAC TGG CTC GAG GAA TAT AAC GTT GAC GGA TTT
                            CGC TTC GAT TTG TTG GGA ATC CTT GAC ATA GAC ACT GTA
                            CTT TAT ATG AAG GAA AAG GCT ACA AAA GCA AAG CCC GGA
                            ATA TTG CTC TTT GGC GAG GGG TGG GAT CTT GCG ACG CCC
                            CTC CCC CAC GAA CAG AAA GCC GCT CTC GCA AAC GCT CCC
                            CGA ATG CCT GGC ATT GGA TTT TTC AAT GAT ATG TTC CGA
                            GAC GCC GTA AAG GGC AAC ACC TTC CAT CTG AAA GCC ACT
                            GGA TTT GCC CTC GGT AAC GGA GAA TCC GCT CAA GCT GTC
                            ATG CAC GGT ATT GCA GGC AGC AGC GGG TGG AAG GCC TTG
                            GCC CCC ATA GTG CCG GAA CCC TCA CAG TCA ATC AAC TAT
                            GTG GAA AGT CAT GAT AAC CAT ACT TTT TGG GAC AAG ATG
                            TCA TTT GCA TTG CCG CAA GAG AAC GAC TCC AGG AAG CGG
```

TABLE 2-continued

Potential sequences related to this disclosure.

|  |  |
|---|---|
|  | AGC CGG CAA AGG TTG GCG GCC GCG ATC ATC CTG TTG GCT |
|  | CAG GGA GTG CCC TTC ATC CAT TCC GGT CAG GAG TTC TTT |
|  | CGG ACC AAA CAG GGG GTT GAA AAC TCC TAC CAA TCA TCT |
|  | GAT TCC ATA AAT CAA CTC GAC TGG GAT AGA CGA GAA ACC |
|  | TTC AAA GAG GAC GTC CAC TAT ATA AGG AGA CTG ATA TCT |
|  | TTG CGA AAG GCG CAT CCT GCT TTT CGG CTC CGG AGC GCT |
|  | GCG GAC ATC CAG AGA CAT CTC GAG TGT CTG ACC CTT AAG |
|  | GAG CAT TTG ATT GCC TAT CGA CTG TAT GAC TTG GAT GAG |
|  | GTC GAC GAA TGG AAG GAT ATC ATA GTT ATT CAT CAC GCC |
|  | TCT CCA GAC AGT GTT GAA TGG CGA CTG CCT AAC GAC ATC |
|  | CCC TAC AGG CTG CTC TGC GAC CCG TCC GGT TTT CAG GAA |
|  | GAC CCG ACA GAA ATT AAA AAG ACC GTG GCC GTG AAT GGA |
|  | ATT GGG ACA GTC ATC CTC TAC CTG GCA TCA GAT CTC AAG |
|  | TCT TTT GCC TGA (SEQ ID NO: 10) |

| Codon optimized | ATG GTA TCT ATC CGG AGG TCA TTT GAG GCC TAC GTT GAC |
|---|---|
| polynucleotide coding | GAT ATG AAC ATT ATT ACA GTT CTG ATA CCG GCT GAA CAG |
| sequence #5 for expressing | AAA GAA ATT ATG ACA CCA CCT TTC CGA CTG GAG ACT GAA |
| Pullulanase derived from | ATA ACC GAC TTC CCC CTG GCG GTG AGA GAA GAG TAC AGC |
| *Bacillus subtilis* strain | CTG GAG GCT AAG TAC AAG TAT GTA TGT GTA AGC GAT CAT |
| 168 in human cells | CCA GTG ACC TTT GGC AAG ATC CAT TGT GTT CGA GCT TCA |
|  | TCC GGG CAC AAG ACC GAT CTC CAG ATT GGC GCC GTC ATC |
|  | CGA ACG GCG GCG TTC GAC GAT GAG TTC TAT TAC GAC GGG |
|  | GAA CTG GGG GCA GTT TAC ACC GCT GAT CAT ACT GTC TTT |
|  | AAG GTC TGG GCC CCC GCG GCT ACC TCT GCC GCA GTT AAG |
|  | CTT TCA CAC CCG AAC AAG AGC GGG AGA ACA TTT CAA ATG |
|  | ACG AGG TTG GAG AAG GGC GTC TAT GCA GTC ACG GTC ACT |
|  | GGA GAT CTC CAC GGC TAT GAA TAC CTC TTT TGC ATA TGT |
|  | AAT AAC AGT GAG TGG ATG GAG ACA GTA GAC CAG TAC GCG |
|  | AAA GCC GTT ACA GTC AAC GGG GAG AAA GGA GTG GTA CTG |
|  | CGC CCC GAC CAG ATG AAA TGG ACC GCA CCC CTT AAG CCC |
|  | TTC AGC CAC CCT GTT GAC GCG GTG ATC TAT GAG ACC CAC |
|  | CTT AGA GAT TTT AGC ATA CAT GAA AAC AGC GGC ATG ATT |
|  | AAT AAA GGT AAG TAC CTT GCC CTG ACC GAG ACA GAC ACT |
|  | CAG ACG GCG AAC GGA AGC TCC TCA GGT CTC GCA TAT GTG |
|  | AAG GAA CTC GGC GTG ACC CAT GTC GAG CTC CTC CCT GTT |
|  | AAC GAT TTC GCA GGG GTC GAC GAG GAA AAA CCG TTG GAT |
|  | GCG TAC AAT TGG GGC TAC AAC CCC CTT CAT TTT TTC GCT |
|  | CCC GAA GGA AGT TAT GCA AGC AAT CCA CAC GAT CCC CAA |
|  | ACA AGG AAA ACT GAA CTC AAG CAG ATG ATT AAT ACA CTG |
|  | CAT CAA CAC GGG CTG AGA GTT ATC CTG GAT GTG GTT TTT |
|  | AAC CAT GTT TAC AAG AGA GAA AAC AGC CCC TTC GAG AAA |
|  | ACT GTT CCG GGT TAC TTT TTT CGG CAT GAC GAG TGT GGC |
|  | ATG CCT TCA AAC GGA ACT GGT GTG GGT AAT GAT ATA GCT |
|  | TCC GAG CGA CGA ATG GCC AGG AAG TTT ATA GCT GAC TGT |
|  | GTC GTG TAC TGG CTC GAG GAG TAT AAT GTT GAT GGT TTT |
|  | CGA TTC GAT TTG CTG GGC ATC CTT GAC ATC GAT ACG GTC |
|  | CTC TAT ATG AAA GAA AAG GCG ACG AAG GCG AAA CCT GGA |
|  | ATT CTC TTG TTT GGT GAG GGT TGG GAC CTT GCA ACG CCG |
|  | CTG CCC CAT GAA CAA AAG GCA GCC CTT GCG AAT GCG CCC |
|  | AGG ATG CCG GGG ATT GGT TTC TTT AAT GAT ATG TTT CGG |
|  | GAT GCC GTG AAG GGG AAC ACG TTT CAC CTT AAG GCT ACG |
|  | GGA TTT GCC TTG GGA AAT GGT GAA TCA GCA CAG GCA GTG |
|  | ATG CAT GGC ATT GCC GGC AGC TCC GGT TGG AAA GCA CTG |
|  | GCG CCG ATT GTG CCT GAA CCC TCA CAA TCT ATT AAT TAC |
|  | GTA GAA TCA CAT GAC AAT CAC ACT TTC TGG GAC AAA ATG |
|  | AGC TTC GCA TTG CCC CAG GAG AAC GAT AGC AGG AAA AGG |
|  | TCA CGC CAG AGG CTC GCA GCA GCG ATC ATT TTG CTT GCC |
|  | CAG GGC GTT CCA TTT ATA CAT TCA GGA CAA GAG TTC TTC |
|  | CGG ACG AAA CAG GGT GTC GAG AAT TCC TAT CAG AGT AGT |
|  | GAT AGT ATA AAT CAA CTG GAT TGG GAC CGC CGA GAG ACA |
|  | TTC AAG GAA GAC GTA CAC TAC ATC AGA CGC CTT ATC TCT |
|  | CTG CGC AAG GCA CAC CCA GCA TTT CGA TTG AGA TCA GCG |
|  | GCC GAC ATC CAG AGA CAC CTG GAG TGT CTG ACA CTG AAA |
|  | GAA CAT TTG ATA GCC TAT CGC CTC TAT GAT CTT GAC GAG |
|  | GTC GAT GAG TGG AAA GAT ATT ATC GTC ATA CAT CAT GCA |
|  | TCA CCC GAC AGC GTT GAA TGG CGG CTT CCG AAC GAC ATT |
|  | CCT TAT CGG CTG TTG TGC GAT CCG AGT GGG TTC CAG GAA |
|  | GAT CCA ACG GAG ATA AAA AAA ACA GTG GCA GTC AAT GGC |
|  | ATC GGT ACG GTC ATT CTC TAC CTG GCT TCA GAT CTC AAG |
|  | TCA TTT GCG TGA (SEQ ID NO: 11) |

| Codon optimized | ATG GTG AGT ATC CGC AGG AGC TTT GAA GCT TAT GTA GAT |
|---|---|
| polynucleotide coding | GAC ATG AAC ATT ATT ACC GTT CTC ATC CCT GCA GAA CAA |
| sequence #6 for expressing | AAG GAA ATA ATG ACG CCT CCC TTT CGC CTT GAG ACA GAA |
| Pullulanase derived from | ATT ACA GAC TTT CCT CTG GCA GTG CGA GAA GAG TAT TCT |
| *Bacillus subtilis* strain | CTG GAG GCT AAA TAT AAG TAC GTA TGC GTG AGC GAC CAC |
| 168 in human cells | CCT GTT ACG TTC GGC AAA ATA CAT TGT GTG CGC GCT TCC |

TABLE 2-continued

Potential sequences related to this disclosure.

```
                          TCT GGC CAT AAG ACA GAT CTC CAG ATC GGT GCT GTA ATT
                          AGA ACC GCC GCC TTC GAC GAC GAA TTT TAT TAC GAT GGA
                          GAG CTT GGG GCT GTG TAT ACT GCT GAT CAC ACC GTG TTT
                          AAA GTG TGG GCC CCG GCA GCA ACT AGT GCG GCA GTC AAA
                          CTC TCA CAC CCA AAC AAA TCT GGT AGA ACT TTT CAA ATG
                          ACT AGG CTG GAG AAA GGT GTG TAC GCA GTC ACT GTT ACC
                          GGA GAT TTG CAT GGT TAC GAA TAC CTG TTT TGT ATC TGC
                          AAC AAT AGT GAG TGG ATG GAG ACC GTA GAC CAA TAC GCC
                          AAA GCT GTT ACT GTC AAT GGC GAA AAG GGG GTC GTT CTT
                          CGG CCG GAT CAG ATG AAG TGG ACA GCT CCA TTG AAG CCC
                          TTC AGC CAC CCT GTT GAC GCC GTT ATC TAT GAA ACA CAC
                          CTG CGA GAC TTC AGT ATT CAT GAA AAT TCT GGA ATG ATA
                          AAC AAG GGG AAG TAT CTT GCT CTC ACT GAA ACT GAT ACC
                          CAG ACT GCC AAC GGC AGT AGT AGC GGC CTC GCC TAC GTA
                          AAG GAG CTC GGA GTT ACT CAT GTT GAA CTT CTT CCG GTA
                          AAT GAT TTC GCA GGT GTT GAT GAA GAG AAG CCA TTG GAC
                          GCA TAT AAT TGG GGT TAT AAC CCG CTT CAC TTT TTC GCT
                          CCC GAA GGG TCT TAT GCC TCT AAC CCC CAT GAT CCA CAG
                          ACA CGC AAG ACT GAG CTT AAA CAG ATG ATT AAT ACA CTG
                          CAC CAA CAT GGT CTT AGG GTG ATT TTG GAT GTG GTA TTT
                          AAC CAC GTA TAC AAA CGA GAA AAC TCC CCT TTT GAG AAA
                          ACC GTT CCC GGT TAC TTT TTC CGG CAT GAT GAG TGC GGC
                          ATG CCT AGT AAT GGT ACC GGG GTT GGA AAT GAC ATT GCG
                          TCA GAA CGA CGA ATG GCC CGC AAG TTC ATT GCT GAT TGT
                          GTC GTA TAT TGG CTC GAA GAG TAT AAC GTC GAC GGG TTT
                          CGC TTT GAC TTG CTT GGT ATC CTC GAT ATT GAT ACC GTC
                          CTC TAC ATG AAG GAA AAA GCG ACA AAA GCA AAA CCG GGA
                          ATA CTC CTC TTC GGC GAG GGC TGG GAC CTG GCG ACA CCA
                          TTG CCT CAC GAG CAG AAG GCT GCG CTC GCG AAT GCG CCA
                          CGC ATG CCT GGT ATA GGG TTT TTT AAC GAT ATG TTT AGG
                          GAC GCG GTA AAA GGC AAC ACG TTC CAT CTC AAG GCT ACA
                          GGA TTC GCA CTC GGG AAT GGA GAA TCA GCT CAG GCT GTC
                          ATG CAT GGC ATT GCA GGC TCA TCC GGT TGG AAA GCT TTG
                          GCA CCG ATT GTA CCT GAG CCA TCT CAG TCT ATC AAT TAC
                          GTG GAG TCA CAT GAT AAT CAC ACG TTT TGG GAT AAG ATG
                          AGT TTT GCC CTC CCG CAA GAG AAT GAC TCT CGA AAA AGA
                          AGT CGA CAA AGA CTG GCC GCG GCT ATA ATT CTC CTC GCG
                          CAG GGC GTT CCG TTT ATA CAC TCT GGA CAA GAA TTT TTT
                          AGG ACT AAG CAA GGG GTA GAA AAT AGT TAT CAG TCT AGC
                          GAT TCT ATT AAC CAG TTG GAC TGG GAC AGA AGG GAG ACG
                          TTC AAA GAA GAT GTG CAC TAC ATA CGA AGG CTT ATA AGC
                          TTG CGC AAG GCT CAC CCA GCT TTT AGA CTT CGA TCC GCA
                          GCG GAT ATT CAA CGG CAC TTG GAA TGT CTT ACG CTG AAG
                          GAA CAC CTC ATA GCC TAT AGA CTG TAT GAC TTG GAC GAA
                          GTT GAC GAG TGG AAA GAT ATT ATT GTG ATA CAC CAT GCG
                          TCA CCT GAC AGT GTA GAG TGG AGA TTG CCT AAC GAC ATT
                          CCC TAC CGC CTG CTC TGT GAT CCC TCT GGG TTC CAA GAG
                          GAC CCG ACC GAA ATC AAG AAA ACA GTA GCA GTT AAC GGA
                          ATC GGT ACT GTA ATA CTT TAT CTC GCT TCC GAT CTG AAG
                          TCC TTC GCA TGA (SEQ ID NO: 12)
```

Codon optimized                 ATG GTA TCC ATA AGG AGA AGC TTC GAA GCT TAT GTG GAT
polynucleotide coding           GAT ATG AAT ATA ATA ACC GTA CTG ATT CCC GCG GAA CAA
sequence #7 for expressing      AAA GAA ATA ATG ACG CCG CCC TTC AGG TTG GAG ACG GAA
Pullulanase derived from        ATA ACG GAT TTC CCG TTG GCA GTA CGA GAG GAA TAT AGC
*Bacillus subtilis* strain      CTG GAG GCG AAA TAT AAA TAT GTA TGC GTG AGC GAC CAT
168 in human cells              CCC GTG ACA TTT GGC AAA ATA CAT TGC GTA AGG GCT TCC
                                TCC GGA CAT AAG ACT GAC CTT CAA ATA GGT GCA GTC ATA
                                CGA ACG GCC GCA TTT GAT GAT GAG TTT TAT TAT GAC GGC
                                GAG TTG GGC GCG GTC TAT ACT GCT GAC CAT ACC GTG TTT
                                AAA GTC TGG GCT CCT GCG GCT ACA TCA GCC GCG GTC AAG
                                CTC TCC CAC CCA AAT AAG AGT GGG CGA ACA TTC CAA ATG
                                ACG CGC CTC GAG AAG GGT GTT TAC GCG GTT ACG GTC ACC
                                GGG GAT TTG CAT GGG TAC GAA TAC CTG TTC TGC ATA TGT
                                AAC AAC AGT GAG TGG ATG GAA ACG GTG GAT CAA TAC GCG
                                AAA GCG GTG ACT GTT AAC GGA GAA AAG GGC GTA GTC CTT
                                AGA CCC GAC CAA ATG AAG TGG ACT GCA CCT CTG AAA CCA
                                TTC TCA CAC CCA GTG GAT GCT GTT ATT TAT GAA ACT CAT
                                CTT AGG GAC TTT AGC ATC CAT GAG AAC TCC GGA ATG ATC
                                AAT AAG GGA AAG TAC CTG GCA CTT ACG GAA ACC GAT ACC
                                CAG ACG GCC AAT GGA TCT AGT TCA GGG CTC GCT TAT GTC
                                AAG GAG TTG GGT GTC ACG CAC GTA GAG CTT CTC CCC GTC
                                AAT GAC TTT GCG GGG GTG GAC GAG GAA AAA CCC CTT GAT
                                GCG TAC AAC TGG GGC TAC AAC CCC CTG CAT TTC TTC GCC
                                CCC GAG GGC AGT TAC GCG TCT AAT CCA CAT GAC CCA CAA
                                ACA CGA AAG ACC GAG CTC AAG CAG ATG ATA AAC ACA CTT
                                CAC CAG CAC GGG CTC AGG GTA ATT CTT GAT GTA GTG TTT
                                AAC CAC GTG TAC AAG AGG GAG AAC TCA CCT TTT GAA AAG TABLE 2-continued Potential sequences related to this disclosure.

```
                              ACC GTA CCG GGA TAT TTT TTT AGA CAT GAC GAA TGC GGA
                              ATG CCG TCC AAC GGA ACA GGC GTT GGC AAT GAC ATA GCT
                              AGC GAG CGG CGG ATG GCA CGA AAG TTC ATA GCA GAT TGT
                              GTC GTT TAC TGG CTT GAG GAG TAC AAC GTG GAC GGA TTT
                              AGG TTT GAC CTT CTC GGA ATT CTG GAT ATT GAT ACG GTT
                              CTT TAC ATG AAA GAG AAA GCG ACA AAG GCT AAG CCA GGT
                              ATA TTG CTC TTT GGT GAA GGA TGG GAC CTT GCA ACA CCA
                              CTG CCC CAT GAA CAG AAA GCA GCC CTC GCC AAT GCG CCC
                              CGG ATG CCT GGC ATT GGC TTC TTC AAT GAT ATG TTT CGG
                              GAC GCA GTA AAG GGC AAC ACC TTT CAC CTT AAA GCC ACA
                              GGA TTT GCA CTC GGG AAT GGT GAA AGC GCG CAG GCC GTT
                              ATG CAC GGC ATT GCC GGT AGT TCT GGT TGG AAG GCC CTT
                              GCT CCA ATT GTG CCT GAA CCG AGC CAA TCT ATA AAC TAC
                              GTC GAG AGT CAC GAT AAC CAC ACT TTT TGG GAT AAA ATG
                              AGT TTC GCG TTG CCG CAG GAG AAT GAC AGC AGG AAA CGG
                              AGT AGG CAG CGC CTT GCC GCA GCA ATT ATA TTG TTG GCC
                              CAA GGT GTG CCT TTT ATA CAC TCA GGG CAA GAG TTC TTT
                              CGA ACT AAA CAA GGT GTC GAG AAC TCT TAC CAG TCC TCC
                              GAT TCC ATC AAC CAG CTG GAT TGG GAC CGC CGC GAG ACT
                              TTT AAA GAA GAC GTT CAC TAC ATC AGG AGA CTT ATT AGT
                              CTC CGC AAA GCT CAT CCA GCG TTC AGG CTT CGG TCC GCC
                              GCT GAC ATC CAA CGA CAC CTT GAG TGT CTC ACA CTC AAG
                              GAG CAT CTG ATC GCT TAC CGC TTG TAT GAC TTG GAT GAA
                              GTA GAC GAG TGG AAA GAC ATA ATC GTA ATC CAC CAT GCC
                              TCA CCA GAT TCT GTC GAG TGG AGG CTC CCC AAC GAT ATT
                              CCC TAT CGC TTG CTG TGC GAT CCG AGC GGT TTC CAA GAG
                              GAC CCA ACC GAA ATA AAA AAA ACC GTT GCG GTA AAC GGT
                              ATC GGG ACT GTT ATA CTT TAC CTG GCT AGC GAT CTG AAA
                              TCT TTT GCC TGA (SEQ ID NO: 13)

Codon optimized              ATG GTG TCC ATA AGG CGG AGC TTC GAG GCT TAC GTA GAC
polynucleotide coding        GAT ATG AAT ATT ATT ACT GTT TTG ATC CCC GCC GAA CAA
sequence #8 for expressing   AAA GAG ATT ATG ACT CCC CCC TTT AGA TTG GAG ACA GAG
Pullulanase derived from     ATC ACG GAT TTC CCA TTG GCG GTA CGG GAG GAG TAC TCT
Bacillus subtilis strain     TTG GAA GCA AAG TAT AAG TAT GTC TGT GTA AGT GAT CAT
168 in human cells           CCG GTT ACT TTC GGC AAG ATC CAC TGC GTT AGA GCG TCA
                              TCC GGT CAC AAA ACC GAC CTG CAG ATT GGA GCG GTG ATT
                              AGA ACA GCG GCT TTC GAT GAC GAA TTT TAC TAC GAC GGT
                              GAG CTC GGC GCT GTG TAC ACA GCC GAC CAC ACA GTA TTT
                              AAA GTA TGG GCT CCC GCA GCT ACA AGC GCA GCA GTA AAG
                              CTC TCC CAT CCA AAT AAA AGT GGC AGA ACG TTT CAG ATG
                              ACT CGA CTC GAG AAG GGA GTC TAC GCC GTT ACC GTC ACG
                              GGG GAT CTC CAC GGG TAT GAG TAT CTG TTT TGC ATT TGC
                              AAC AAC TCT GAA TGG ATG GAA ACG GTG GAT CAG TAC GCT
                              AAG GCA GTG ACC GTT AAT GGC GAA AAG GGC GTT GTG CTG
                              AGA CCC GAT CAG ATG AAA TGG ACG GCC CCT CTT AAA CCA
                              TTC TCT CAT CCT GTG GAC GCC GTC ATT TAT GAA ACG CAC
                              TTG AGA GAT TTC AGT ATA CAC GAA AAT AGT GGA ATG ATA
                              AAC AAG GGA AAG TAC CTG GCA CTT ACC GAA ACT GAT ACG
                              CAG ACC GCA AAT GGA AGT TCA TCT GGA CTC GCC TAT GTC
                              AAA GAG CTT GGT GTT ACT CAT GTT GAG TTG CTG CCT GTC
                              AAC GAC TTC GCT GGA GTA GAC GAG GAA AAG CCT CTT GAC
                              GCA TAT AAC TGG GGT TAC AAC CCG CTG CAC TTC TTC GCC
                              CCC GAA GGA TCC TAC GCT AGC AAT CCT CAC GAC CCG CAA
                              ACC CGC AAG ACA GAA CTC AAA CAG ATG ATA AAC ACC CTT
                              CAT CAG CAT GGC CTT AGA GTG ATT CTT GAC GTT GTC TTC
                              AAT CAT GTT TAC AAA CGA GAG AAT AGT CCT TTC GAA AAA
                              ACT GTC CCG GGA TAT TTC TTT CGG CAC GAT GAG TGC GGA
                              ATG CCG TCA AAC GGA ACG GGC GTT GGG AAC GAT ATA GCT
                              TCC GAG CGA AGA ATG GCC CGG AAG TTC ATT GCT GAT TGC
                              GTC GTC TAT TGG CTG GAG GAA TAC AAT GTG GAC GGG TTT
                              CGC TTT GAC CTG CTC GGA ATT TTG GAT ATA GAC ACA GTA
                              CTG TAT ATG AAA GAG AAG GCG ACC AAG GCG AAA CCC GGC
                              ATT CTT CTT TTC GGT GAA GGG TGG GAC CTT GCC ACA CCC
                              CTG CCC CAT GAA CAA AAG GCC GCC CTG GCT AAC GCC CCC
                              AGA ATG CCG GGA ATA GGC TTT TTC AAT GAT ATG TTC CGA
                              GAT GCG GTA AAA GGT AAT ACA TTT CAC CTT AAG GCA ACA
                              GGG TTC GCG CTC GGG AAT GGC GAA TCA GCG CAG GCC GTG
                              ATG CAC GGT ATC GCT GGT TCT TCA GGA TGG AAG GCT CTC
                              GCT CCG ATC GTA CCG GAG CCG TCT CAG TCA ATT AAT TAC
                              GTG GAG AGT CAC GAT AAT CAT ACT TTT TGG GAT AAG ATG
                              TCT TTC GCA CTC CCC CAG GAA AAC GAC TCC CGA AAA AGA
                              TCA AGG CAA CGG TTG GCA GCT GCT ATA ATC TTG CTC GCC
                              CAA GGT GTT CCA TTT ATC CAT TCT GGT CAA GAA TTC TTT
                              CGA ACG AAG CAG GGT GTG GAG AAT AGC TAC CAG TCC TCC
                              GAC TCA ATC AAT CAA CTT GAT TGG GAT AGA AGG GAA ACT
                              TTT AAG GAA GAT GTT CAT TAC ATC CGC CGG CTG ATA TCT
                              TTG AGA AAG GCA CAC CCA GCT TTC CGC CTG AGG AGC GCG
```

TABLE 2-continued

| Potential sequences related to this disclosure. |
| --- |

```
                              GCG GAC ATA CAG CGC CAT TTG GAG TGC CTG ACA CTC AAA
                              GAG CAC CTC ATT GCC TAT AGA CTC TAC GAT TTG GAC GAA
                              GTA GAC GAG TGG AAG GAC ATT ATA GTA ATA CAC CAT GCG
                              TCT CCC GAC AGC GTA GAA TGG CGC CTC CCT AAC GAC ATA
                              CCT TAT CGG CTC CTC TGC GAC CCC AGT GGA TTT CAA GAG
                              GAT CCG ACC GAG ATC AAG AAA ACA GTC GCG GTA AAC GGT
                              ATA GGT ACG GTC ATA CTG TAT CTC GCC TCA GAC TTG AAG
                              AGC TTT GCG TGA (SEQ ID NO: 14)
```

| | |
| --- | --- |
| Codon optimized<br>polynucleotide coding<br>sequence #9 for expressing<br>Pullulanase derived from<br>*Bacillus subtilis* strain<br>168 in human cells | ```
ATG GTA AGC ATC CGC CGA TCA TTC GAG GCT TAC GTG GAC
GAC ATG AAC ATT ATT ACC GTT CTC ATC CCT GCT GAG CAA
AAG GAA ATC ATG ACG CCA CCC TTC CGC CTT GAG ACA GAA
ATA ACA GAT TTT CCC CTG GCG GTG AGA GAG GAG TAC TCC
CTG GAA GCC AAA TAC AAA TAC GTG TGT GTT AGC GAC CAT
CCA GTA ACG TTC GGG AAG ATC CAT TGC GTG CGG GCA TCC
TCC GGC CAC AAA ACG GAT CTT CAG ATT GGA GCC GTG ATT
CGG ACA GCT GCG TTT GAT GAT GAG TTT TAC TAC GAT GGA
GAA CTG GGG GCA GTA TAT ACG GCC GAC CAT ACG GTA TTT
AAG GTG TGG GCC CCT GCA GCT ACA TCA GCG GCT GTC AAA
CTT AGC CAT CCA AAC AAG TCC GGG CGA ACG TTT CAA ATG
ACT AGA CTG GAG AAA GGG GTG TAT GCT GTC ACC GTT ACT
GGG GAC CTT CAC GGA TAC GAG TAC TTG TTT TGC ATA TGT
AAT AAT TCC GAG TGG ATG GAG ACC GTA GAC CAG TAT GCT
AAA GCT GTA ACT GTT AAT GGT GAA AAG GGT GTT GTT CTC
CGG CCA GAC CAA ATG AAA TGG ACC GCG CCA CTC AAA CCC
TTT TCT CAT CCA GTG GAT GCA GTG ATT TAT GAG ACC CAC
TTG CGA GAT TTC TCA ATA CAT GAA AAC TCT GGT ATG ATC
AAC AAG GGC AAA TAT TTG GCA CTC ACG GAG ACC GAT ACG
CAA ACC GCT AAT GGG AGT AGT AGT GGC CTC GCC TAC GTA
AAA GAG CTC GGG GTA ACG CAT GTA GAG CTC CTT CCA GTC
AAT GAC TTT GCA GGG GTA GAT GAA GAA AAA CCT CTG GAT
GCG TAC AAC TGG GGC TAC AAT CCA CTT CAC TTC TTC GCT
CCT GAG GGT TCT TAT GCA AGC AAC CCG CAC GAC CCT CAA
ACA CGG AAA ACT GAA CTT AAA CAA ATG ATT AAT ACA CTC
CAT CAG CAT GGT CTG CGC GTC ATC TTG GAT GTG GTC TTC
AAT CAC GTT TAT AAA CGA GAA AAC AGT CCG TTT GAG AAA
ACC GTT CCT GGA TAT TTT TTC AGG CAT GAT GAA TGC GGC
ATG CCC TCT AAT GGT ACG GGA GTT GGT AAC GAC ATA GCT
AGT GAA AGA CGA ATG GCG CGC AAA TTC ATA GCA GAC TGC
GTG GTC TAT TGG CTG GAG GAA TAT AAC GTT GAT GGC TTC
AGA TTT GAC CTG CTC GGC ATT CTC GAC ATT GAC ACG GTT
CTT TAC ATG AAG GAG AAA GCA ACG AAA GCC AAA CCG GGA
ATC CTT TTG TTC GGC GAG GGT TGG GAT CTT GCT ACC CCT
TTG CCA CAT GAG CAA AAG GCT GCT CTG GCA AAC GCT CCT
AGA ATG CCT GGA ATA GGC TTC TTT AAT GAT ATG TTT AGG
GAC GCC GTC AAG GGG AAC ACG TTT CAC CTG AAA GCA ACA
GGA TTT GCG CTG GGA AAC GGC GAA AGC GCT CAA GCT GTA
ATG CAT GGA ATA GCG GGC TCC TCC GGA TGG AAA GCC CTG
GCG CCT ATT GTA CCC GAG CCG TCA CAA AGT ATC AAT TAC
GTG GAA TCT CAT GAT AAT CAT ACT TTT TGG GAC AAG ATG
TCA TTC GCG CTG CCT CAA GAG AAC GAC TCT CGG AAG AGA
TCT CGG CAG CGC CTT GCA GCC GCA ATC ATT CTT TTG GCT
CAG GGA GTC CCC TTC ATC CAT AGT GGG CAA GAA TTT TTC
AGA ACT AAG CAA GGC GTG GAA AAT TCC TAC CAA AGC TCC
GAT TCC ATA AAT CAA CTG GAC TGG GAT CGC CGA GAG ACC
TTC AAA GAG GAT GTT CAC TAC ATT CGG AGG TTG ATC TCT
TTG AGA AAA GCC CAC CCG GCC TTC AGG CTG AGG AGT GCC
GCA GAC ATT CAA AGA CAC CTC GAA TGT CTT ACT CTC AAG
GAG CAT CTT ATT GCG TAC CGG CTG TAC GAC TTG GAC GAG
GTG GAC GAG TGG AAA GAT ATA ATT GTT ATA CAT CAT GCT
TCC CCG GAT AGT GTC GAG TGG CGC TTG CCC AAC GAT ATC
CCC TAC AGA CTC TTG TGT GAC CCA AGC GGC TTT CAA GAG
GAT CCA ACG GAA ATC AAA AAA ACT GTA GCA GTC AAC GGC
ATT GGT ACG GTT ATC CTT TAC CTC GCG TCC GAC CTC AAG
AGC TTT GCG TGA (SEQ ID NO: 15)
``` |
| Codon optimized<br>polynucleotide coding<br>sequence #10 for expressing<br>Pullulanase derived from<br>*Bacillus subtilis* strain<br>168 in human cells | ```
ATG GTT AGC ATT AGG CGG AGC TTC GAG GCT TAT GTA GAT
GAT ATG AAT ATC ATA ACC GTT CTC ATC CCT GCA GAG CAA
AAA GAA ATA ATG ACA CCT CCC TTT AGG CTT GAA ACG GAA
ATC ACG GAT TTC CCC CTT GCG GTC CGC GAA GAA TAC TCC
TTG GAA GCC AAA TAC AAG TAC GTC TGT GTC TCT GAC CAC
CCT GTA ACG TTT GGT AAA ATT CAC TGC GTA CGC GCG AGC
TCA GGA CAT AAG ACG GAC CTT CAG ATA GGG GCA GTT ATT
CGG ACA GCT GCT TTT GAC GAC GAG TTT TAT TAC GAC GGT
GAA TTG GGC GCA GTT TAC ACT GCC GAT CAC ACT GTT TTC
AAG GTG TGG GCA CCT GCT GCC ACA TCT GCC GCG GTT AAG
TTG TCT CAC CCT AAC AAG AGC GGC CGG ACA TTT CAG ATG
ACC CGA CTC GAA AAG GGG GTA TAC GCA GTG ACC GTA ACT
``` |

TABLE 2-continued

Potential sequences related to this disclosure.

|  |  |
|---|---|
|  | GGT GAT TTG CAC GGG TAC GAA TAC CTT TTC TGC ATT TGT |
|  | AAC AAT TCC GAA TGG ATG GAG ACA GTG GAC CAG TAT GCA |
|  | AAG GCA GTG ACG GTC AAC GGA GAA AAG GGC GTT GTG TTG |
|  | CGC CCT GAT CAG ATG AAG TGG ACG GCC CCT CTT AAA CCT |
|  | TTT AGT CAC CCA GTA GAT GCA GTG ATA TAC GAG ACG CAT |
|  | CTG AGA GAC TTC TCT ATA CAT GAG AAT TCA GGT ATG ATT |
|  | AAT AAG GGT AAG TAC CTG GCC CTT ACC GAG ACA GAT ACC |
|  | CAA ACT GCA AAT GGC TCC TCT AGT GGC CTG GCA TAT GTA |
|  | AAG GAA CTG GGA GTG ACC CAT GTC GAA CTC CTC CCA GTA |
|  | AAT GAT TTT GCG GGG GTT GAT GAG GAA AAG CCA CTT GAT |
|  | GCA TAC AAT TGG GGT TAC AAC CCA CTG CAC TTT TTT GCT |
|  | CCT GAA GGG TCC TAC GCT AGC AAC CCT CAT GAT CCT CAA |
|  | ACC AGG AAG ACA GAA TTG AAA CAA ATG ATT AAT ACC CTC |
|  | CAC CAG CAC GGT TTG AGA GTG ATC CTC GAT GTT GTC TTT |
|  | AAC CAT GTG TAC AAA CGG GAG AAC AGT CCC TTC GAA AAG |
|  | ACA GTC CCG GGG TAC TTT TTC CGC CAC GAT GAA TGT GGC |
|  | ATG CCC TCC AAT GGA ACT GGT GTA GGC AAT GAC ATT GCG |
|  | TCT GAA AGA AGG ATG GCC AGG AAG TTT ATA GCT GAT TGT |
|  | GTA GTC TAC TGG TTG GAG GAA TAC AAT GTG GAC GGT TTT |
|  | CGG TTT GAT CTG CTC GGG ATC CTG GAC ATC GAT ACT GTA |
|  | TTG TAC ATG AAG GAG AAA GCT ACT AAA GCA AAA CCG GGC |
|  | ATC TTG TTG TTT GGT GAA GGA TGG GAT CTT GCA ACG CCT |
|  | CTT CCT CAT GAA CAG AAA GCA GCG TTG GCA AAC GCA CCA |
|  | AGG ATG CCG GGG ATA GGT TTC TTC AAT GAT ATG TTC CGG |
|  | GAT GCC GTC AAA GGA AAC ACA TTC CAC CTG AAG GCC ACA |
|  | GGC TTC GCT CTC GGC AAC GGC GAG TCA GCG CAA GCC GTA |
|  | ATG CAT GGC ATC GCA GGC TCC TCA GGG TGG AAA GCA CTG |
|  | GCG CCT ATT GTG CCT GAA CCA TCT CAA AGC ATA AAC TAC |
|  | GTC GAG TCC CAC GAC AAC CAT ACT TTT TGG GAT AAA ATG |
|  | AGC TTT GCG CTC CCA CAA GAA AAC GAC AGT CGG AAA CGG |
|  | AGC AGG CAG CGA CTC GCT GCC GCT ATT ATA CTC TTG GCT |
|  | CAG GGG GTT CCC TTT ATA CAC AGC GGG CAA GAA TTC TTT |
|  | AGA ACC AAG CAG GGA GTA GAA AAT TCT TAT CAG AGT TCC |
|  | GAC TCA ATC AAC CAA CTC GAT TGG GAT AGG CGG GAA ACA |
|  | TTT AAG GAG GAC GTC CAT TAC ATA AGG AGA CTT ATT TCT |
|  | CTC AGA AAA GCA CAT CCT GCT TTC AGG TTG CGA TCC GCC |
|  | GCC GAT ATT CAA CGC CAT CTC GAG TGC CTC ACA CTG AAG |
|  | GAA CAC CTC ATC GCA TAC CGA CTC TAC GAT TTG GAT GAG |
|  | GTG GAT GAG TGG AAA GAC ATA ATC GTC ATA CAC CAT GCT |
|  | AGC CCG GAT TCC GTA GAG TGG CGG TTG CCG AAT GAC ATC |
|  | CCA TAC CGA CTG CTT TGT GAT CCT TCA GGT TTC CAA GAA |
|  | GAC CCC ACC GAG ATT AAG AAA ACA GTG GCC GTT AAT GGT |
|  | ATT GGA ACG GTC ATT CTG TAC CTC GCA TCT GAC CTG AAA |
|  | TCA TTC GCG TGA (SEQ ID NO: 16) |
| Protein sequence of limit dextrin alpha-1,6-glucohydrolase (GlgX) [*Escherichia coli* str. K-12 substr. MG1655] NCBI Reference Sequence: NP_417889.1 Uniprot # P15067 | MTQLAIGKPAPLGAHYDGQGVNFTLFSAHAERVELCVFDANGQEHRYDLPGHS GDIWHGYLPDARPGLRYGYRVHGPWQPAEGHRFNPAKLLIDPCARQIDGEFKD NPLLHAGHNEPDYRDNAAIAPKCVVVVDHYDWEDDAPPRTPWGSTIIYEAHVK GLTYLHPEIPVEIRGTYKALGHPVMINYLKQLGITALELLPVAQFASEPRLQR MGLSNYWGYNPVAMFALHPAYACSPETALDEFRDAIKALHKAGIEVILDIVLN HSAELDLDGPLFSLRGIDNRSYYWIREDGDYHNWTGCGNTLNLSHPAVVDYAS ACLRYWVETCHVDGFRFDLAAVMGRTPEFRQDAPLFTAIQNCPVLSQVKLIAE PWDIAPGGYQVGNFPPLFAEWNDHFRDAARRFWLHYDLPLGAFAGRFAASSDV FKRNGRLPSAAINLVTAHDGFTLRDCVCFNHKHNEANGEENRDGTNNNYSNNH GKEGLGGSLDLVERRRDSIHALLTTLLLSQGTPMLLAGDEHGHSQHGNNNAYC QDNQLTWLDWSQASSGLTAFTAALIHLRKRIPALVENRWWEEGDGNVRWLNRY AQPLSTDEWQNGPKQLQILLSDRFLIAINATLEVTEIVLPAGEWHAIPPFAGE DNPVITAVWQGPAHGLCVFQR (SEQ ID NO: 04) |
| cDNA sequence of limit dextrin alpha-1,6-glucohydrolase (GlgX) [*Escherichia coli* str. K-12 substr. MG1655] Gene ID: 947941 | ATGACACAACTCGCCATTGGCAAACCCGCTCCCCTCGGCGCGCATTACGACGG TCAGGGCGTCAACTTCACACTTTTCTCCGCTCATGCCGAGCGGGTAGAACTGT GTGTCTTTGACGCCAATGGCCAGGAACATCGCTATGACTTGCCAGGGCACAGT GGCGACATTTGGCACGGTTATCTGCCGGATGCGCGCCCGGGTTTGCGTTATGG TTATCGCGTTCATGGCCCCTGGCAACCCGCCGAGGGGCATCGCTTTAACCCGG CGAAGTTGTTGATTGATCCTTGCGCGCGGCAAATTGACGGGGAGTTTAAAGAT AACCCGCTGCTGCACGCCGGTCATAATGAACCTGACTATCGCGACAACGCCGC CATTGCGCCGAAATGCGTAGTGGTGGTTGATCACTATGACTGGGAAGATGATG CCCCGCCGCGCACGCCGTGGGGCAGCACCATCATTTATGAAGCCCATGTCAAA GGATTAACGTACTTGCACCCGGAGATCCCGGTCGAGATCCGTGGCACTTATAA AGCCCTCGGGCATCCGGTGATGATCAACTATTTGAAACAATTGGGCATTACCG CGCTGGAACTGCTGCCAGTGGCGCAGTTTGCCAGTGAACCACGTCTGCAACGC ATGGGGCTAAGTAACTACTGGGGTTACAACCCGGTGGCGATGTTTGCGCTGCA TCCGGCGTATGCCTGCTCGCCAGAAACGGCGCTGGATGAGTTTCGCGATGCAA TCAAAGCACTGCATAAAGCGGGTATCGAAGTCATTCTTGATATCGTGCTCAAC CATAGTGCGGAACTGGACCTCGACGGCCCGTTATTCTCGCTGCGTGGGATCGA TAACCGTAGCTATTATTGGATAAGAGAAGACGGCGATTATCACAACTGGACCG GTTGCGGCAACACGCTCAATTTGAGTCATCCGGCGGTGGTGGATTATGCCAGC GCCTGCCTGCGTTATTGGGTAGAAACCTGCCACGTCGATGGTTTCCGCTTTGA |

TABLE 2-continued

Potential sequences related to this disclosure.

| | |
|---|---|
| | TCTGGCGGCAGTCATGGGCCGTACGCCAGAGTTCCGTCAGGATGCGCCGTTGT<br>TTACCGCTATCCAGAACTGCCCGGTGCTCTCGCAGGTGAAGTTAATTGCTGAA<br>CCGTGGGATATCGCTCCTGGTGGTTATCAGGTGGGAAATTTCCCGCCGCTGTT<br>TGCCGAGTGGAACGATCATTTCCGCGATGCTGCCCGTCGTTTCTGGCTACATT<br>ATGATTTGCCTCTGGGGGCGTTTGCCGGGCGTTTTGCTGCCTCCAGCGATGTT<br>TTTAAACGTAATGGTCGTCTGCCGAGTGCCGCGATTAATCTCGTCACCGCGCA<br>TGACGGTTTTACGCTTCGCGACTGCGTTTGCTTCAACCATAAACACAATGAAG<br>CAAACGGAGAAGAAATCGCGACGGGACCAACAACAATTACAGTAACAATCAT<br>GGTAAAGAAGGGTTAGGCGGTTCTCTTGACCTGGTTGAACGGCGGCGCGACAG<br>CATTCACGCCCTGTTAACAACGTTGTTGCTCTCCCAGGGTACGCCGATGTTAC<br>TGGCCGGTGACGAACATGGTCACAGCCAGCATGGCAATAACAATGCCTACTGT<br>CAGGATAACCAATTAACCTGGTTGGACTGGTCGCAGGCAAGCAGTGGTTTAAC<br>CGCATTTACCGCCGCGTTAATCCATCTGCGCAAGCGCATTCCCGCTTTGGTGG<br>AGAATCGCTGGTGGGAAGAAGGCGACGGCAATGTCCGTTGGCTAAATCGATAT<br>GCTCAACCTTTAAGCACGGATGAGTGGCAAAACGGGCCGAAACAGCTGCAAAT<br>TCTGCTCTCGGATCGCTTTTTGATCGCAATTAACGCCACGCTTGAGGTAACAG<br>AGATTGTTTTACCTGCTGGGGAGTGGCACGCCATTCCCCCATTCGCTGGAGAG<br>GATAACCCAGTGATTACGGCTGTCTGGCAGGGACCTGCACACGGATTGTGTGT<br>GTTCCAGAGATGA (SEQ ID NO: 05) |
| Codon optimized<br>polynucleotide coding<br>sequence (#1) for expressing<br>the bacterial limit dextrin<br>alpha-1 ,6-glucohydrolase<br>(GlgX) derived from<br>*Escherichia coli* strain K-12<br>in mammalian cells | ATGACCCAGCTGGCAATCGGCAAGCCAGCACCTCTGGGAGCCCACTACGACGG<br>CCAGGGCGTGAACTTCACACTGTTTTCCGCCCACGCAGAGAGGGTGGAGCTGT<br>GCGTGTTCGATGCCAATGGCCAGGAGCACAGATACGACCTGCCCGGCCACTCT<br>GGCGATATCTGGCACGGCTATCTGCCAGACGCAAGGCCTGGACTGAGATACGG<br>CTATAGAGTGCACGGACCATGGCAGCCAGCAGAGGGACACAGGTTCAACCCAG<br>CCAAGCTGCTGATCGATCCTTGCGCCCGCCAGATCGACGGCGAGTTTAAGGAT<br>AATCCACTGCTGCACGCAGGACACAACGAGCCTGACTACAGGGATAATGCAGC<br>AATCGCACCAAAGTGCGTGGTGGTGGTGGACCACTATGATTGGGAGGACGATG<br>CACCACCTAGGACCCCTTGGGGCAGCACAATCATCTACGAGGCCCACGTGAAG<br>GGCCTGACCTATCTGCACCCTGAGATCCCAGTGGAGATCAGGGGCACATACAA<br>GGCCCTGGGACACCCCGTGATGATCAACTATCTGAAGCAGCTGGGAATCACCG<br>CCCTGGAGCTGCTGCCTGTGGCACAGTTCGCATCTGAGCCAAGGCTGCAGAGG<br>ATGGGACTGAGCAACTACTGGGGCTATAATCCTGTGGCCATGTTCGCACTGCA<br>CCCTGCATACGCATGTAGCCCAGAGACAGCCCTGGACGAGTTTAGGGATGCCA<br>TCAAGGCCCTGCACAAGGCCGGCATCGAAGTGATCCTGGACATCGTGCTGAAT<br>CACTCCGCCGAGCTGGACCTGGATGGCCCTCTGTTTTCCCTGCGGGGCATCGA<br>TAACAGATCTTACTATTGGATCCGCGAGGACGGCGATTATCACAATTGGACCG<br>GCTGCGGCAACACACTGAATCTGAGCCACCCAGCAGTGGTGGACTACGCATCC<br>GCCTGCCTGCGGTATTGGGTGGAGACCTGTCACGTGGACGGCTTCAGATTTGA<br>TCTGGCAGCCGTGATGGGAAGGACCCCAGAGTTCCGCCAGGACGCCACCACTGT<br>TTACAGCCATCCAGAACTGTCCTGTGCTGTCCCAGGTGAAGCTGATCGCAGAG<br>CCATGGGATATCGCACCAGGAGGCTACCAGGTCGGAAACTTCCCACCCCTGTT<br>TGCCGAGTGGAATGACCACTTCCGGGATGCCGCCCGGAGATTTTGGCTGCACT<br>ATGACCTGCCACTGGGAGCCTTCGCCGGCAGATTTGCAGCAAGCTCCGACGTG<br>TTCAAGAGAAACGGCAGGCTGCCCTCTGCCGCCATCAATCTGGTGACCGCCCA<br>CGACGGCTTCACACTGAGGGATTGCGTGTGCTTTAACCACAAGCACAACGAGG<br>CCAATGGCGAGGAGAATCGCGACGGCACCAACAATAACTACAGCAATAACCAC<br>GGCAAGGAGGGACTGGGAGGGATCCCTGGACCTGGTGGAGAGGCGCCGGGATTC<br>TATCCACGCCCTGCTGACCACACTGCTGCTGAGCCAGGGCACCCCAATGCTGC<br>TGGCAGGCGATGAGCACGGACACTCCCAGCACGGCAATAACAATGCCTACTGC<br>CAGGACAACCAGCTGACATGGCTGGATTGGTCTCAGGCCTCTAGCGGACTGAC<br>CGCCTTCACAGCCGCCCTGATCCACCTGAGAAAGAGGATCCCCGCCCTGGTGG<br>AGAATAGGTGGTGGGAGGAGGGCGACGGAAACGTGAGGTGGCTGAATCGCTAT<br>GCCCAGCCTCTGTCTACCGACGAGTGGCAGAACGGCCCAAAGCAGCTGCAGAT<br>CCTGCTGAGCGATAGATTTCTGATCGCCATCAATGCCACCCTGGAGGTGACAG<br>AGATCGTGCTGCCAGCAGGAGAGTGGCACGCAATCCCTCCATTCGCCGGAGAG<br>GACAACCCAGTGATCACAGCCGTGTGGCAGGGACCAGCACACGGACTGTGCGT<br>GTTCCAGAGATGA (SEQ ID NO: 06) |
| Codon optimized<br>polynucleotide coding<br>sequence (#2) for expressing<br>the bacterial limit dextrin<br>alpha-1,6-glucohydrolase<br>(GlgX) derived from<br>*Escherichia coli* strain K-12<br>in mammalian cells | ATG ACC CAG TTG GCA ATA GGA AAG CCC GCA CCA CTT GGC<br>GCA CAT TAT GAT GGT CAG GGT GTT AAT TTC ACT CTT TTT<br>TCC GCT CAT GCG GAG AGG GTA GAA CTC TGT GTC TTC GAC<br>GCA AAT GGC CAA GAA CAT AGA TAT GAC TTG CCG GGA CAC<br>TCA GGC GAC ATT TGG CAT GGG TAC TTG CCC GAT GCT CGG<br>CCT GGC CTC AGG TAT GGA TAT CGC GTA CAC GGA CCG TGG<br>CAA CCG GCA GAA GGG CAT CGG TTC AAT CCA GCA AAA CTC<br>CTC ATA GAC CCG TGC GCA AGG CAG ATT GAT GGA GAG TTC<br>AAA GAT AAC CCG CTT TTG CAT GCG GGC CAT AAC GAA CCT<br>GAC TAT CGG GAT AAC GCG GCA ATC GCG CCG AAA TGT GTA<br>GTA GTT GTT GAC CAT TAC GAT TGG GAA GAT GAT GCA CCA<br>CCG CGA ACA CCT TGG GGT AGC ACC ATT ATT TAT GAA GCA<br>CAT GTC AAA GGT CTT ACG TAC CTG CAT CCG GAG ATT CCC<br>GTG GAA ATA AGA GGA ACG TAC AAA GCC TTG GGT CAC CCC<br>GTA ATG ATA AAC TAC CTT AAA CAG TTG GGA ATA ACC GCA<br>TTG GAA TTG CTG CCC GTG GCG CAA TTT GCC AGC GAG CCG<br>CGA TTG CAA CGG ATG GGT CTC AGT AAT TAC TGG GGG TAT<br>AAT CCG GTA GCT ATG TTC GCC CTT CAC CCT GCT TAT GCA<br>TGT TCT CCA GAG ACT GCA TTG GAC GAA TTC CGC GAC GCA |

TABLE 2-continued

Potential sequences related to this disclosure.

|  |  |
|---|---|
|  | ATA AAA GCA CTT CAC AAG GCT GGA ATT GAG GTT ATT TTG<br>GAC ATT GTG TTG AAC CAC TCT GCC GAG CTT GAC TTG GAT<br>GGG CCG CTG TTT TCA CTG AGG GGT ATC GAC AAC AGG AGC<br>TAC TAT TGG ATC CGG GAA GAT GGC GAC TAC CAC AAC TGG<br>ACA GGA TGT GGG AAT ACT CTG AAT CTC TCT CAC CCG GCT<br>GTC GTG GAT TAT GCC AGC GCT TGC CTG CGA TAT TGG GTC<br>GAG ACG TGT CAC GTT GAT GGG TTC CGA TTT GAC TTG GCT<br>GCA GTG ATG GGG AGA ACG CCA GAG TTC CGA CAG GAT GCC<br>CCC CTT TTC ACC GCT ATT CAA AAT TGC CCC GTA CTG AGT<br>CAG GTG AAG CTC ATC GCT GAG CCG TGG GAC ATA GCA CCG<br>GGC GGA TAC CAA GTG GGA AAT TTT CCG CCG TTG TTT GCT<br>GAA TGG AAT GAC CAT TTC CGG GAC GCA GCT CGC CGA TTT<br>TGG TTG CAC TAT GAT CTC CCT TTG GGG GCT TTC GCT GGC<br>CGC TTT GCT GCT TCT TCA GAT GTT TTC AAA AGA AAC GGA<br>CGG CTG CCA TCC GCC GCA ATA AAC CTC GTA ACA GCC CAC<br>GAC GGA TTT ACA CTT CGG GAC TGT GTT TGT TTT AAC CAT<br>AAG CAC AAT GAA GCA AAC GGG GAG GAA AAC CGA GAC GGC<br>ACT AAC AAT AAC TAT AGT AAC AAC CAC GGC AAA GAG GGC<br>TTG GGT GGA AGT CTG GAT CTG GTG GAG CGG CGG CGC GAC<br>TCC ATT CAT GCT CTG CTT ACC ACT CTT TTG CTG TCC CAG<br>GGT ACC CCA ATG CTC CTG GCT GGG GAT GAA CAT GGC CAC<br>TCC CAG CAT GGC AAT AAC AAT GCA TAT TGT CAG GAC AAT<br>CAG CTT ACT TGG CTC GAC TGG AGC CAA GCG TCA TCA GGC<br>CTC ACA GCA TTT ACC GCT GCC CTT ATT CAC TTG CGC AAA<br>CGC ATT CCT GCT TTG GTC GAA AAC CGA TGG TGG GAA GAG<br>GGA GAT GGC AAT GTG AGG TGG TTG AAT CGG TAC GCC CAG<br>CCG CTT AGC ACT GAT GAG TGG CAG AAT GGC CCG AAG CAG<br>CTC CAG ATA CTC CTT TCA GAT CGC TTT TTG ATA GCG ATC<br>AAC GCC ACA CTT GAG GTG ACC GAG ATT GTT CTC CCT GCA<br>GGG GAA TGG CAC GCA ATC CCT CCG TTC GCA GGT GAG GAT<br>AAC CCC GTT ATA ACA GCT GTT TGG CAA GGC CCC GCC CAT<br>GGG CTG TGC GTA TTC CAA CGA TGA (SEQ ID NO: 17) |
| Codon optimized<br>polynucleotide coding<br>sequence (#3) for expressing<br>the bacterial limit dextrin<br>alpha-1,6-glucohydrolase<br>(GlgX) derived from<br>*Escherichia coli* strain K-12<br>in mammalian cells | ATG ACC CAA CTT GCG ATC GGC AAG CCG GCA CCG CTG GGG<br>GCA CAC TAC GAC GGC CAG GGT GTT AAC TTC ACG CTG TTC<br>TCA GCA CAT GCA GAA CGC GTA GAG CTC TGT GTA TTC GAC<br>GCT AAT GGA CAA GAG CAC AGG TAT GAT CTG CCT GGG CAC<br>TCC GGA GAC ATC TGG CAT GGT TAT TTG CCA GAC GCT CGC<br>CCC GGA CTC AGG TAC GGG TAC CGA GTG CAC GGA CCA TGG<br>CAA CCA GCC GAA GGA CAC CGC TTT AAC CCA GCC AAG CTG<br>CTG ATT GAC CCG TGC GCG AGG CAA ATC GAC GGA GAA TTT<br>AAA GAT AAC CCT CTT CTT CAC GCA GGA CAC AAT GAA CCC<br>GAC TAT CGA GAT AAT GCT GCG ATT GCA CCA AAG TGC GTC<br>GTC GTC GTC GAC CAT TAT GAC TGG GAA GAC GAT GCG CCA<br>CCC CGA ACA CCA TGG GGG AGC ACG ATA ATA TAT GAG GCT<br>CAC GTT AAG GGC CTG ACG TAC TTG CAT CCG GAG ATA CCT<br>GTA GAA ATC AGG GGG ACC TAC AAG GCC CTT GGT CAT CCC<br>GTT ATG ATT AAC TAT TTG AAG CAG CTT GGA ATT ACT GCC<br>CTT GAA CTT CTC CCC GTG GCG CAA TTT GCA TCA GAA CCC<br>CGG CTG CAG CGA ATG GGA CTG AGT AAC TAC TGG GGA TAC<br>AAT CCA GTG GCC ATG TTT GCA CTC CAC CCT GCT TAT GCG<br>TGT AGC CCC GAA ACA GCA TTG GAC GAG TTC AGG GAT GCA<br>ATC AAG GCC TTG CAT AAA GCC GGG ATT GAG GTA ATA CTC<br>GAC ATA GTT CTG AAT CAT AGC GCG GAA CTG GAT CTC GAT<br>GGA CCA CTT TTT TCA CTT AGA GGG ATT GAC AAC CGC TCA<br>TAT TAT TGG ATC AGA GAG GAT GGC GAT TAT CAT AAT TGG<br>ACA GGG TGT GGA AAC ACA CTC AAT CTC TCC CAT CCG GCT<br>GTG GTA GAT TAT GCA TCC GCT TGC CTC CGG TAT TGG GTA<br>GAA ACA TGT CAT GTG GAC GGG TTC CGG TTC GAT CTG GCG<br>GCC GTC ATG GGC AGG ACA CCT GAA TTC AGA CAG GAC GCC<br>CCT TTG TTC ACC GCC ATA CAG AAC TGT CCG GTC TTG TCC<br>CAA GTG AAG TTG ATT GCG GAA CCA TGG GAC ATT GCC CCT<br>GGG GGC TAC CAG GTC GGA AAT TTT CCG CCC CTC TTC GCT<br>GAG TGG AAT GAC CAC TTC CGG GAT GCA GCC CGC CGC TTT<br>TGG TTG CAC TAC GAT TTG CCG TTG GGC GCC TTC GCT GGG<br>CGC TTT GCT GCG AGC TCA GAC GTA TTT AAA AGA AAT GGG<br>CGA TTG CCT AGT GCG GCA ATT AAT CTG GTG ACT GCA CAC<br>GAT GGA TTT ACG CTT AGG GAC TGT GTT TGT TTT AAT CAC<br>AAG CAT AAT GAA GCG AAC GGG GAA GAA AAC ACG GAC GGA<br>ACT AAT AAT AAT TAT TCA AAC AAT CAT GGT AAG GAA GGT<br>TTG GGG GGT TCC CTT GAT CTT GTT GAA AGA CGA AGG GAC<br>TCC ATC CAC GCC CTT CTC ACT ACT CTT CTG CTT AGT CAA<br>GGT ACG CCT ATG TTG CTC GCC GGC GAT GAA CAC GGA CAC<br>TCC CAG CAT GGC AAT AAC AAC GCA TAC TGC CAG GAT AAT<br>CAG CTG ACC TGG CTC GAT TGG TCC CAG GCC TCC TCC GGA<br>TTG ACC GCC TTT ACC GCT GCG TTG ATA CAC CTT CGC AAA<br>CGA ATT CCC GCA TTG GTG GAG AAT AGG TGG TGG GAA GAG<br>GGC GAC GGC AAC GTG AGG TGG CTC AAC AGG TAT GCT CAA |

TABLE 2-continued

Potential sequences related to this disclosure.

|  |  |
|---|---|
|  | CCG CTT TCC ACC GAT GAG TGG CAA AAC GGG CCC AAA CAG |
|  | CTC CAA ATT CTG CTG AGC GAC CGA TTC TTG ATT GCA ATC |
|  | AAT GCG ACC CTC GAG GTC ACC GAA ATC GTC TTG CCC GCT |
|  | GGT GAG TGG CAC GCT ATA CCG CCA TTT GCG GGT GAG GAC |
|  | AAT CCC GTA ATA ACA GCG GTC TGG CAG GGA CCA GCA CAC |
|  | GGT CTC TGT GTG TTC CAA CGA TGA (SEQ ID NO: 18) |
| Codon optimized polynucleotide coding sequence (#4) fore xpressing the bacterial limit dextrin alpha-1,6-glucohydrolase (GlgX) derived from *Escherichia coli* strain K-12 in mammalian cells | ATG ACG CAG CTC GCA ATA GGA AAG CCA GCA CCC CTT GGA |
|  | GCC CAT TAT GAT GGT CAG GGC GTT AAT TTC ACA CTG TTT |
|  | TCT GCC CAT GCA GAA CGG GTC GAA TTG TGT GTA TTT GAC |
|  | GCT AAT GGT CAA GAG CAT CGC TAT GAC CTC CCG GGA CAC |
|  | AGT GGG GAC ATT TGG CAT GGC TAT CTG CCT GAC GCG CGC |
|  | CCA GGG CTC CGG TAC GGG TAC CGA GTT CAC GGT CCC TGG |
|  | CAA CCA GCC GAG GGG CAT AGG TTT AAT CCG GCA AAG CTG |
|  | CTC ATT GAC CCC TGC GCT CGC CAG ATA GAC GGA GAA TTT |
|  | AAG GAC AAC CCC CTG CTC CAC GCT GGT CAT AAT GAA CCA |
|  | GAC TAT CGA GAC AAT GCG GCC ATT GCT CCG AAA TGT GTA |
|  | GTC GTT GTT GAT CAC TAT GAC TGG GAA GAC GAC GCT CCA |
|  | CCT AGA ACT CCT TGG GGG TCC ACG ATC ATC TAC GAA GCT |
|  | CAT GTT AAG GGT CTC ACT TAT CTG CAC CCA GAA ATA CCC |
|  | GTG GAA ATA CGC GGA ACT TAT AAG GCA CTG GGT CAT CCC |
|  | GTA ATG ATC AAC TAC CTG AAG CAG CTT GGT ATC ACG GCG |
|  | CTT GAA CTC CTC CCA GTT GCA CAA TTT GCA AGT GAG CCA |
|  | CGA CTC CAG AGA ATG GGG CTT TCC AAT TAC TGG GGT TAC |
|  | AAT CCA GTG GCC ATG TTT GCA CTC CAT CCA GCG TAC GCT |
|  | TGC TCC CCT GAG ACG GCT CTT GAT GAG TTT AGA GAT GCT |
|  | ATA AAG GCA CTG CAT AAG GCT GGA ATA GAA GTC ATC TTG |
|  | GAC ATA GTG CTC AAT CAC AGT GCC GAG TTG GAT CTG GAC |
|  | GGG CCG CTC TTT AGC CTG CGG GGG ATA GAT AAT CGG AGT |
|  | TAC TAT TGG ATT AGG GAG GAC GGC GAT TAC CAT AAT TGG |
|  | ACG GGT TGC GGA AAT ACG CTG AAC TTG TCT CAC CCT GCG |
|  | GTC GTA GAC TAC GCC TCC GCA TGT CTT AGA TAC TGG GTC |
|  | GAA ACG TGC CAT GTA GAT GGT TTC AGG TTC GAC TTG GCG |
|  | GCG GTT ATG GGG AGG ACG CCC GAG TTT CGG CAA GAT GCG |
|  | CCC CTG TTT ACG GCG ATC CAG AAC TGC CCC GTA CTG TCA |
|  | CAG GTT AAA CTG ATC GCG GAA CCC TGG GAC ATT GCC CCA |
|  | GGC GGT TAT CAG GTT GGA AAC TTC CCA CCA CTG TTC GCA |
|  | GAG TGG AAT GAT CAC TTT CGC GAT GCA GCA CGG CGG TTC |
|  | TGG CTT CAT TAT GAT TTG CCG CTG GGC GCT TTC GCC GGG |
|  | CGG TTT GCA GCA AGT TCA GAT GTA TTT AAG GAC GAC AAT GGT |
|  | CGC CTC CCC TCC GCT GCT ATT AAC CTC GTG ACA GCG CAT |
|  | GAT GGA TTC ACG CTT AGA GAC TGT GTG TGT TTC AAC CAT |
|  | AAA CAT AAC GAG GCT AAC GGT GAG GAA AAC AGA GAT GGT |
|  | ACG AAT AAC AAC TAT AGC AAT AAC CAC GGA AAG AAG GGA |
|  | CTC GGA GGT TCC TTG GAT CTC GTT GAA CGC AGA CGA GAT |
|  | TCC ATC CAT GCA CTG CTG ACC ACG CTG TTG TTG AGC CAA |
|  | GGT ACA CCT ATG CTC CTT GCT GGC GAT GAG CAC GGG CAT |
|  | TCC CAA CAC GGA AAC AAC AAC GCC TAT TGT CAA GAC AAC |
|  | CAG CTT ACA TGG TTG GAC TGG TCA CAG GCG TCC AGT GGA |
|  | CTG ACA GCA TTT ACT GCT GCC CTC ATA CAT TTG CGC AAA |
|  | CGC ATA CCG GCC CTT GTT GAG AAC CGC TGG TGG GAG GAA |
|  | GGC GAC GGT AAC GTT CGA TGG TTG AAT CGC TAC GCG CAG |
|  | CCT CTC AGT ACA GAC GAA TGG CAG AAC GGA CCG AAA CAG |
|  | TTG CAG ATT TTG CTT AGC GAT CGC TTC TTG ATT GCG ATA |
|  | AAT GCC ACC CTT GAG GTC ACC GAA ATC GTA CTG CCT GCT |
|  | GGG GAA TGG CAT GCC ATA CCT CCA TTC GCC GGC GAG GAT |
|  | AAC CCT GTG ATC ACT GCT GTC TGG CAG GGC CCG GCA CAT |
|  | GGA CTT TGC GTC TTT CAG AGA TGA (SEQ ID NO: 19) |
| Codon optimized polynucleotide coding sequence (#5) for expressing the bacterial limit dextrin alpha-1,6-glucohydrolase (GlgX) derived from *Escherichia coli* strain K-12 in mammalian cells | ATG ACA CAA TTG GCG ATT GGA AAA CCG GCA CCC CTT GGT |
|  | GCT CAT TAT GAC GGC CAG GGT GTG AAT TTC ACC CTG TTT |
|  | TCT GCC CAC GCA GAA AGG GTG GAG CTT TGC GTC TTT GAC |
|  | GCG AAC GGG CAG GAA CAT CGG TAC GAT TTG CCG GGT CAT |
|  | TCA GGA GAT ATC TGG CAT GGG TAC CTT CCT GAT GCT CGA |
|  | CCA GGT CTT GGA TAT GGG TAT AGA GTT CAT GGG CCG TGG |
|  | CAG CCA GCT GAA GGG CAC CGC TTT AAT CCA GCT AAA CTG |
|  | CTC ATC GAT CCG TGT GCG CGC CAA ATA GAT GGA GAG TTC |
|  | AAG GAT AAT CCC CTC CTG CAC GCG GGG CAT AAT GAG CCG |
|  | GAC TAT AGA GAC AAC GCT GCG ATT GCT CCG AAG TGT GTG |
|  | GTT GTG GTC GAC CAC TAT GAC TGG GAG GAT GAT GCT CCC |
|  | CCT CGG ACA CCA TGG GGC TCA ACG ATT ATC TAT GAA GCT |
|  | CAC GTC AAA GGG CTG ACG TAT CTC CAC CCC GAG ATC CCG |
|  | GTA GAA ATT AGA GGG ACC TAT AAA GCC CTC GGC CAT CCA |
|  | GTG ATG ATC AAC TAT TTG AAA CAA CTT GGT ATA ACT GCG |
|  | CTG GAA CTT CTG CCT GTA GCA CAG TTC GCG TCT GAA CCA |
|  | CGC CTT CAG AGA ATG GGG CTT TCC AAT TAT TGG GGA TAC |
|  | AAT CCA GTC GCG ATG TTT GCT CTT CAC CCC GCC TAT GCC |
|  | TGC AGC CCT GAA ACC GCA CTC GAC GAA TTT AGA GAT GCG |

TABLE 2-continued

Potential sequences related to this disclosure.

|  |  |
|---|---|
|  | ATA AAA GCT CTC CAC AAA GCG GGC ATA GAG GTA ATT CTT |
|  | GAT ATC GTA CTC AAT CAC AGC GCC GAG CTT GAT CTT GAT |
|  | GGG CCG CTG TTT AGT CTG CGA GGC ATA GAT AAC CGA AGT |
|  | TAC TAC TGG ATC AGA GAA GAC GGA GAT TAC CAC AAC TGG |
|  | ACG GGT TGT GGG AAT ACT CTC AAT CTG AGT CAT CCC GCC |
|  | GTA GTC GAT TAC GCT TCC GCA TGT CTT CGA TAT TGG GTT |
|  | GAG ACA TGC CAT GTT GAT GGA TTC AGG TTC GAC CTG GCG |
|  | GCA GTC ATG GGC AGG ACC CCC GAG TTT AGA CAA GAT GCA |
|  | CCC CTT TTT ACG GCC ATA CAG AAC TGC CCG GTC CTC TCC |
|  | CAG GTT AAA CTC ATC GCC GAG CCA TGG GAC ATT GCA CCA |
|  | GGT GGC TAT CAA GTC GGA AAC TTT CCA CCA CTC TTC GCC |
|  | GAA TGG AAT GAC CAT TTC CGA GAT GCA GCT AGA AGG TTT |
|  | TGG CTC CAC TAC GAT CTG CCT CTC GGT GCC TTT GCA GGA |
|  | CGA TTC GCT GCG AGC TCT GAT GTG TTT AAG AGA AAC GGG |
|  | AGG CTT CCG TCC GCA GCT ATC AAT CTT GTA ACG GCC CAC |
|  | GAC GGC TTT ACT CTT CGA GAT TGC GTC TGT TTC AAT CAC |
|  | AAA CAC AAT GAG GCT AAT GGA GAA GAA AAC CGG GAT GGA |
|  | ACA AAC AAT AAC TAC TCA AAT AAC CAC GGT AAG GAA GGC |
|  | CTC GGA GGG AGC CTT GAC CTC GTC GAA CGA AGA CGC GAC |
|  | AGT ATA CAC GCT TTG CTG ACC ACT TTG TTG CTC AGC CAA |
|  | GGT ACC CCT ATG TTG CTG GCT GGA GAT GAA CAC GGT CAC |
|  | AGC CAG CAC GGA AAC AAT AAT GCG TAT TGT CAA GAC AAC |
|  | CAG CTT ACA TGG CTT GAC TGG TCT CAA GCT AGT TCT GGA |
|  | CTG ACA GCG TTC ACG GCG GCT CTG ATC CAT TTG AGA AAG |
|  | CGC ATT CCA GCG CTG GTT GAG AAC CGC TGG TGG GAA GAG |
|  | GGT GAT GGC AAC GTA AGG TGG CTT AAC AGG TAT GCA CAA |
|  | CCG TTG AGT ACC GAT GAA TGG CAA AAT GGA CCG AAA CAG |
|  | CTC CAG ATA CTC TTG AGT GAC CGC TTC TTG ATC GCA ATA |
|  | AAC GCT ACC CTC GAG GTT ACC GAG ATT GTT TTG CCA GCA |
|  | GGA GAG TGG CAC GCA ATC CCA CCG TTT GCA GGC GAA GAT |
|  | AAC CCA GTG ATA ACG GCA GTC TGG CAG GGA CCA GCC CAC |
|  | GGC TTG TGT GTA TTT CAG CGC TGA (SEQ ID NO: 20) |
| Codon optimized polynucleotide coding sequence (#6) for expressing the bacterial limit dextrin alpha-1,6-glucohydrolase (GlgX) derived from *Escherichia coli* strain K-12 in mammalian cells | ATG ACA CAA CTG GCA ATC GGT AAA CCA GCA CCA CTC GGC |
|  | GCT CAC TAC GAT GGC CAG GGT GTT AAT TTC ACG TTG TTT |
|  | TCT GCC CAT GCG GAG CGG GTG GAA CTG TGT GTA TTT GAC |
|  | GCG AAT GGA CAA GAG CAT AGG TAT GAC CTC CCG GGA CAT |
|  | TCC GGT GAC ATC TGG CAT GGA TAC TTG CCA GAT GCA AGG |
|  | CCC GGA CTC AGG TAT GGC TAC CGA GTC CAC GGC CCT TGG |
|  | CAG CCT GCG GAG GGT CAT CGG TTT AAC GCT GCA AAA CTC |
|  | CTG ATC GAC CCC TGT GCA CGA CAA ATT GAC GGA GAA TTC |
|  | AAA GAC AAT CCG TTG CTT CAT GCG GGG CAC AAC GAG CCG |
|  | GAT TAC AGG GAT AAT GCG GCT ATT GCC CCG AAA TGC GTG |
|  | GTT GTC GTC GAC CAC TAT GAC TGG GAG GAC GAC GCT CCA |
|  | CCA AGA ACA CCT TGG GGG TCA ACC ATA ATT TAT GAA GCC |
|  | CAC GTT AAA GGG CTG ACC TAT TTG CAC CCT GAA ATT CCG |
|  | GTA GAA ATC CGA GGT ACC TAT AAG GCC CTC GGC CAT CCG |
|  | GTA ATG ATC AAT TAT CTT AAA CAG CTG GGT ATT ACA GCC |
|  | CTG GAA CTG CTC CCA GTA GCC CAG TTT GCG AGT GAA CCA |
|  | CGG CTG CAA AGG ATG GGT CTT TCT AAC TAC TGG GGG TAT |
|  | AAT CCA GTT GCG ATG TTT GCT CTT CAT CCG GCT TAT GCA |
|  | TGC TCA CCT GAG ACT GCC CTG GAC GAG TTC CGG GAT GCA |
|  | ATA AAA GCA CTG CAT AAA GCG GGC ATT GAG GTT ATA CTT |
|  | GAC ATT GTA TTG AAC CAC TCC GCT GAA CTG GAT CTT GAT |
|  | GGA CCT CTC TTC AGC CTG CGA GGA ATA GAT AAC CGC TCC |
|  | TAT TAC TGG ATA AGG GAA GAC GGT GAC TAT CAC AAT TGG |
|  | ACC GGG TGC GGC AAC ACT CTC AAT CTC TCC CAT CCC GCC |
|  | GTT GTG GAT TAC GCT TCA GCG TGC TTG AGA TAT TGG GTA |
|  | GAG ACT TGT CAC GTA GAC GGC TTC CGA TTC GAT CTT GCA |
|  | GCT GTC ATG GGA CGA ACC CCA GAG TTC AGA CAG GAT GCT |
|  | CCT CTG TTT ACT GCA ATT CAA AAC TGC CCA GTG CTG TCT |
|  | CAG GTG AAG TTG ATA GCA GAG CCG TGG GAC ATA GCC CCC |
|  | GGA GGG TAT CAA GTT GGG AAC TTT CCG CCC CTG TTC GCG |
|  | GAG TGG AAC GAT CAT TTC AGG GAC GCC GCA AGA CGC TTC |
|  | TGG TTG CAC TAC GAT CTG CCT CTC GGC GCT TTT GCA GGT |
|  | CGG TTT GCG GCT AGT AGT GAC GTA TTC AAG CGC AAC GGA |
|  | CGG CTT CCG TCT GCC GCA ATC AAC CTT GTA ACC GCA CAC |
|  | GAC GGC TTC ACA TTG CGG GAC TGC GTA TGT TTC AAT CAT |
|  | AAG CAT AAC GAG GCC AAT GGT GAG GAA AAC CGG GAT GGA |
|  | ACC AAC AAT AAC TAT AGT AAT AAT CAT GGT AAA GAA GGT |
|  | CTG GGT GGA TCA CTC GAC TTG GTC GAG CGC CGA CGG GAT |
|  | TCC ATA CAT GCA TTG CTT ACT ACC CTC CTC CTC TCC CAA |
|  | GGA ACC CCA ATG TTG CTT GCT GGA GAT GAG CAC GGT CAC |
|  | AGC CAA CAT GGG AAT AAT AAT GCT TAT TGT CAG GAT AAC |
|  | CAA CTC ACG TGG TTG GAT TGG AGT CAA GCA AGT TCA GGC |
|  | CTG ACC GCT TTT ACG GCA GCG TTG ATA CAT CTG CGC AAA |
|  | CGC ATT CCT GCG CTC GTT GAA AAC AGA TGG TGG GAA GAA |
|  | GGC GAC GGC AAC GTC AGA TGG TTG AAT CGA TAT GCG CAA |

TABLE 2-continued

Potential sequences related to this disclosure.

|  |  |
|---|---|
|  | CCT CTG TCA ACG GAT GAA TGG CAA AAC GGT CCT AAG CAG |
|  | CTC CAG ATA CTG CTG AGT GAT AGG TTC CTC ATT GCA ATC |
|  | AAC GCG ACC CTG GAA GTC ACG GAA ATC GTT TTG CCC GCT |
|  | GGT GAA TGG CAC GCT ATA CCG CCT TTT GCG GGT GAG GAT |
|  | AAC CCC GTT ATC ACT GCC GTG TGG CAG GGA CCA GCG CAC |
|  | GGC CTG TGT GTG TTC CAA CGA TGA (SEQ ID NO: 21) |
| Codon optimized polynucleotide coding sequence (#7) for expressing the bacterial limit dextrin alpha-1,6-glucohydrolase (GlgX) derived from *Escherichia coli* strain K-12 in mammalian cells | ATG ACT CAG CTT GCC ATC GGG AAA CCC GCC CCG CTT GGA |
|  | GCT CAT TAC GAT GGT CAA GGC GTA AAT TTC ACA CTC TTC |
|  | TCA GCA CAT GCG GAA CGA GTC GAA CTC TGT GTA TTT GAT |
|  | GCA AAC GGG CAA GAA CAT CGC TAC GAT CTT CCA GGT CAC |
|  | TCC GGG GAC ATC TGG CAT GGA TAC CTC CCC GAC GCT AGG |
|  | CCG GGA CTT AGA TAC GGG TAC CGA GTG CAT GGA CCC TGG |
|  | CAG CCA GCG GAG GGG CAT CGA TTT AAT CCA GCT AAG TTG |
|  | CTT ATC GAT CCC TGC GCT AGG CAG ATA GAC GGC GAA TTT |
|  | AAA GAT AAT CCC CTT TTG CAT GCT GGG CAT AAC GAG CCT |
|  | GAC TAT CGC GAC AAT GCT GCG ATT GCG CCG AAG TGC GTA |
|  | GTA GTA GTC GAC CAC TAT GAT TGG GAG GAC GAT GCA CCG |
|  | CCG AGG ACC CCT TGG GGG AGT ACT ATC ATA TAT GAA GCA |
|  | CAT GTT AAA GGT CTT ACA TAT CTT CAT CCC GAG ATC CCT |
|  | GTC GAA ATC CGA GGG ACT TAT AAA GCA TTG GGG CAT CCT |
|  | GTT ATG ATC AAT TAC TTG AAA CAA CTT GGC ATC ACC GCC |
|  | TTG GAA CTG CTG CCC GTG GCC CAG TTC GCC TCC GAG CCC |
|  | CGA CTG CAA AGG ATG GGA CTC TCT AAT TAT TGG GGC TAT |
|  | AAC CCC GTT GCT ATG TTC GCG TTG CAC CCG GCA TAC GCA |
|  | TGT TCT CCT GAG ACC GCG CTC GAT GAA TTT CGA GAT GCC |
|  | ATA AAA GCT CTT CAC AAG GCC GGA ATT GAA GTC ATA CTC |
|  | GAC ATT GTT CTT AAC CAC TCA GCT GAA CTT GAC TTG GAT |
|  | GGG CCG CTT TTT TCT TTG CGC GGG ATT GAT AAC AGA AGT |
|  | TAC TAC TGG ATA CGG GAA GAC GGT GAT TAT CAC AAT TGG |
|  | ACG GGT TGT GGT AAT ACC CTC AAT CTT TCC CAC CCG GCT |
|  | GTT GTG GAT TAT GCA TCT GCG TGC CTT AGG TAC TGG GTC |
|  | GAG ACC TGT CAT GTA GAT GGC TTT CGA TTT GAT CTC GCG |
|  | GCG GTT ATG GGG AGA ACG CCC GAG TTC CGG CAG GAT GCT |
|  | CCA CTT TTC ACC GCA ATA CAG AAT TGT CCT GTA CTT TCC |
|  | CAA GTT AAA CTT ATC GCG GAG CCA TGG GAC ATA GCT CCT |
|  | GGA GGG TAC CAG GTT GGA AAT TTT CCG CCC TTG TTT GCC |
|  | GAA TGG AAC GAC CAC TTC CGC GAT GCC GCT CGG AGG TTC |
|  | TGG CTC CAT TAC GAT CTC CCA CTG GGA GCT TTC GCA GGT |
|  | CGC TTT GCA GCG TCT AGC GAC GTG TTT AAG AGA AAT GGG |
|  | CGG TTG CCA TCC GCT GCG ATA AAC CTT GTT ACC GCG CAC |
|  | GAC GGC TTT ACT CTG AGA GAC TGT GTT TGT TTC AAC CAT |
|  | AAG CAC AAC GAG GCT AAT GGA GAG GAA AAC CGC GAC GGT |
|  | ACA AAT AAC AAT TAC TCT AAT AAC CAT GGC AAG GAG GGT |
|  | CTG GGC GGC AGT CTT GAC CTG GTC GAA CGA AGA CGG GAC |
|  | TCT ATT CAT GCT CTG CTC ACA ACC CTT TTG CTC AGT CAG |
|  | GGG ACA CCT ATG CTG CTG GCC GGA GAT GAG CAC GGC CAC |
|  | TCC CAG CAT GGT AAT AAC AAC GCT TAC TGC CAG GAC AAC |
|  | CAA CTT ACG TGG TTG GAT TGG TCT CAA GCA AGT AGT GGT |
|  | CTT ACT GCA TTT ACA GCA GCT CTT ATC CAC TTG CGA AAA |
|  | AGA ATA CCC GCT CTG GTG GAG AAC CGG TGG TGG GAG GAA |
|  | GGA GAC GGA AAC GTC CGG TGG CTG AAC CGC TAT GCT CAA |
|  | CCA CTT AGC ACT GAC GAG TGG CAA AAT GGC CCA AAG CAG |
|  | CTT CAA ATA CTC CTC AGC GAT CGA TTC CTG ATT GCA ATA |
|  | AAT GCC ACT CTT GAG GTC ACC GAG ATT GTC CTT CCC GCA |
|  | GGA GAA TGG CAT GCC ATA CCC CCG TTT GCT GGA GAA GAC |
|  | AAT CCA GTA ATT ACG GCT GTA TGG CAG GGA CCT GCA CAC |
|  | GGC CTG TGC GTC TTC CAA AGG TGA (SEQ ID NO: 22) |
| Codon optimized polynucleotide coding sequence (#8) for expressing the bacterial limit dextrin alpha-1,6-glucohydrolase (GlgX) derived from *Escherichia coli* strain K-12 in mammalian cells | ATG ACT CAG CTT GCG ATT GGG AAA CCT GCT CCG TTG GGC |
|  | GCT CAT TAC GAT GGA CAA GGC GTC AAC TTT ACT TTG TTT |
|  | AGC GCT CAT GCA GAG AGA GTA GAG CTG TGC GTG TTC GAT |
|  | GCG AAT GGA CAA GAG CAC AGG TAT GAC CTC CCG GGC CAC |
|  | TCA GGG GAC ATA TGG CAT GGC TAC CTC CCC GAC GCG AGA |
|  | CCG GGT TTG AGG TAT GGT TAC CGC GTT CAC GGT CCG TGG |
|  | CAG CCC GCG GAA GGC CAT CGG TTC AAT CCC GCC AAG CTC |
|  | CTC ATC GAC CCA TGT GCC CGA CAG ATT GAC GGC GAG TTT |
|  | AAA GAT AAT CCG CTC CTC CAT GCG GGT CAT AAT GAA CCG |
|  | GAC TAC CGA GAC AAT GCT GCG ATC GCA CCT AAG TGC GTC |
|  | GTT GTA GTA GAC CAT TAT GAT TGG GAA GAT GAC GCA CCA |
|  | CCA CGG ACT CCT TGG GGG AGC ACG ATA ATA TAC GAG GCA |
|  | CAT GTG AAA GGA CTC ACC TAT CTG CAT CCG GAG ATT CCC |
|  | GTA GAA ATT CGG GGC ACT TAT AAG GCG CTC GGA CAC CCC |
|  | GTT ATG ATT AAT TAC CTC AAG CAG CTG GGG ATA ACT GCA |
|  | CTC GAA TTG CTT CCA GTT GCC CAA TTT GCC AGC GAG CCT |
|  | CGA CTT CAA CGA ATG GGC CTG AGC AAC TAT TGG GGT TAT |
|  | AAT CCT GTG GCA ATG TTT GCG TTG CAC CCG GCA TAT GCG |
|  | TGC AGC CCC GAA ACG GCT TTG GAT GAG TTC CGG GAC GCA |

TABLE 2-continued

Potential sequences related to this disclosure.

|  |  |
|---|---|
|  | ATA AAG GCT CTT CAT AAG GCC GGG ATA GAA GTA ATC CTT |
|  | GAC ATT GTA CTT AAT CAT AGT GCG GAA CTG GAC TTG GAT |
|  | GGC CCT CTG TTC AGC TTG CGG GGG ATC GAC AAC AGG AGC |
|  | TAC TAT TGG ATC CGG GAG GAT GGC GAC TAC CAT AAT TGG |
|  | ACT GGA TGT GGT AAC ACA CTG AAT CTG AGT CAT CCT GCA |
|  | GTG GTT GAC TAC GCC AGT GCA TGT TTG AGA TAT TGG GTT |
|  | GAA ACC TGT CAT GTG GAC GGT TTT AGA TTC GAT CTC GCC |
|  | GCA GTA ATG GGA CGA ACA CCG GAA TTC CGA CAA GAC GCC |
|  | CCG CTT TTT ACG GCC ATA CAG AAT TGT CCC GTG CTC TCT |
|  | CAG GTT AAA CTG ATT GCT GAA CCG TGG GAT ATA GCC CCC |
|  | GGA GGG TAT CAA GTC GGC AAT TTC CCT CCG CTG TTC GCC |
|  | GAA TGG AAC GAT CAT TTT AGA GAC GCC GCT AGA AGA TTC |
|  | TGG TTG CAC TAT GAC TTG CCG CTT GGA GCT TTC GCC GGT |
|  | CGA TTT GCT GCC TCA TCA GAT GTC TTC AAG CGC AAC GGG |
|  | CGA CTG CCG TCC GCT GCA ATT AAT TTG GTG ACC GCG CAC |
|  | GAT GGA TTC ACA CTT AGG GAT TGC GTA TGT TTT AAC CAT |
|  | AAG CAC AAC GAG GCT AAT GGC GAA GAA AAT AGA GAC GGC |
|  | ACA AAT AAT AAC TAC TCC AAC AAC CAC GGG AAG GAA GGA |
|  | CTC GGT GGG AGT TTG GAT CTC GTT GAG CGG CGA CGC GAT |
|  | TCT ATT CAT GCG CTT CTG ACA ACT CTT CTT CTC TCA CAG |
|  | GGG ACG CCA ATG CTC CTT GCC GGT GAC GAG CAC GGT CAT |
|  | AGC CAA CAT GGC AAC AAT AAT GCA TAT TGT CAG GAC AAT |
|  | CAA TTG ACG TGG CTT GAC TGG TCT CAG GCA AGC AGT GGC |
|  | CTG ACT GCG TTC ACA GCA GCC CTT ATC CAT CTT CGA AAA |
|  | AGG ATC CCA GCG CTG GTG GAG AAT CGA TGG TGG GAA GAG |
|  | GGT GAC GGG AAT GTG CGC TGG CTG AAT AGA TAT GCT CAG |
|  | CCG CTG AGC ACG GAT GAA TGG CAG AAC GGA CCG AAG CAG |
|  | CTT CAA ATT CTG CTG TCA GAT CGA TTT TTG ATC GCC ATT |
|  | AAC GCA ACA CTC GAG GTG ACA GAA ATC GTA TTG CCC GCT |
|  | GGA GAG TGG CAT GCC ATA CCA CCA TTT GCT GGT GAA GAT |
|  | AAT CCG GTC ATC ACT GCG GTA TGG CAA GGT CCG GCA CAC |
|  | GGT CTG TGT GTT TTT CAA CGA TGA (SEQ ID NO: 23) |
| Codon optimized | ATG ACG CAG TTG GCA ATA GGT AAA CCA GCT CCG CTT GGA |
| polynucleotide coding | GCG CAT TAC GAC GGG CAG GGT GTG AAT TTC ACG CTG TTT |
| sequence (#9) for expressing | TCC GCC CAT GCA GAA CGC GTA GAA CTG TGC GTG TTT GAC |
| the bacterial limit dextrin | GCA AAT GGA CAG GAA CAT AGA TAC GAC CTG CCG GGT CAC |
| alpha-1,6-glucohydrolase | TCT GGC GAT ATA TGG CAC GGA TAT CTC CCA GAC GCG AGG |
| (GlgX) derived from | CCC GGT CTC CGG TAC GGT TAC CGG GTT CAT GGT CCG TGG |
| *Escherichia coli* strain K-12 | CAG CCC GCA GAA GAC CAT CGC TTT AAC CCA GCT AAG TTG |
| in mammalian cells | CTT ATC GAC CCT TGC GCC AGA CAA ATA GAC GGT GAA TTC |
|  | AAG GAT AAT CCG CTC TTG CAT GCA GGA CAC AAC GAG CCA |
|  | GAT TAC CGC GAC AAC GCG GCC ATT GCC CCC AAG TGC GTT |
|  | GTT GTA GTT GAC CAT TAT GAC TGG GAA GAC GAT GCC CCT |
|  | CCA CGC ACG CCA TGG GGC AGC ACT ATT ATC TAT GAA GCC |
|  | CAC GTT AAA GGT CTC ACT TAT TTG CAT CCC GAG ATC CCA |
|  | GTT GAG ATA CGA GGT ACG TAT AAA GCT CTC GGG CAC CCT |
|  | GTA ATG ATC AAC TAT TTG AAA CAA TTG GGA ATT ACT GCG |
|  | CTG GAG CTT TTG CCA GTT GCA CAG TTC GCG AGT GAA CCC |
|  | CGA TTG CAG CGC ATG GGT TTG AGC AAT TAT TGG GGT TAC |
|  | AAC CCT GTA GCC ATG TTC GCT CTG CAT CCA GCG TAT GCG |
|  | TGT AGT CCC GAG ACC GCT CTC GAA TTT AGG GAT GCC |
|  | ATT AAG GCA CTC CAT AAG GCA GGC ATC GAG GTC ATT CTG |
|  | GAT ATT GTA CTC AAC CAT AGC GCT GAA TTG GAC CTC GAT |
|  | GGC CCA TTG TTT TCA TTG AGG GGG ATA GAC AAT AGG AGT |
|  | TAC TAT TGG ATA CGC GAA GAC GGC GAT TAT CAT AAC TGG |
|  | ACG GGG TGT GGG AAC ACA CTG AAC CTC AGC CAT CCT GCT |
|  | GTT GTG GAT TAT GCT TCC GCG TGC CTG AGG TAT TGG GTA |
|  | GAG ACC TGC CAC GTT GAT GGA TTT CGC TTT GAT CTG GCA |
|  | GCC GTG ATG GGC CGC ACC CCT GAG TTC CGA CAG GAT GCA |
|  | CCA CTC TTT ACT GCT ATC CAA AAT TGC CCG GTT CTG TCT |
|  | CAA GTG AAA CTG ATT GCG GAA CCA TGG GAT ATC GCC CCA |
|  | GGA GGT TAT CAG GTC GGC AAC TTT CCT CCG CTC TTC GCC |
|  | GAG TGG AAC GAC CAC TTC CGA GAC GCT GCC CGC AGA TTC |
|  | TGG CTG CAC TAC GAT CTC CCA CTT GGT GCG TTT GCG GGG |
|  | CGC TTT GCA GCT TCC TCC GAT GTC TTC AAG CGG AAT GGG |
|  | AGA CTG CCT AGT GCA GCG ATC AAT CTC GTG ACG GCG CAC |
|  | GAC GGG TTC ACA CTT AGA GAC TGC GTC TGC TTT AAT CAT |
|  | AAG CAC AAT GAG GCC AAT GGG GAA GAG AAC CGG GAC GGC |
|  | ACG AAC AAT AAC TAT TCA AAT AAC CAC GGA AAG GAA GGA |
|  | CTC GGG GGC TCA CTG GAT CTT GTA GAA AGG CGA CGA GAT |
|  | TCC ATC CAC GCG CTG TTG ACA ACT CTG CTT TTG AGC CAG |
|  | GGT ACA CCA ATG TTG TTG GCA GGG GAC GAA CAT GGA CAC |
|  | AGT CAG CAC GGA AAC AAT AAT GCG TAC TGC CAG GAC AAC |
|  | CAA CTC ACG TGG CTT GAT TGG TCA CAA GCA TCC TCC GGG |
|  | CTC ACA GCT TTC ACA GCA GCA CTG ATA CAC CTG CGA AAA |
|  | CGA ATT CCA GCA CTT GTT GAA AAC CGA TGG TGG GAG GAG |
|  | GGC GAT GGA AAC GTT AGA TGG CTC AAT AGG TAC GCT CAG |

TABLE 2-continued

Potential sequences related to this disclosure.

|  |  |
|---|---|
|  | CCT TTG TCC ACG GAC GAA TGG CAG AAT GGC CCC AAG CAA |
|  | TTG CAG ATT CTC CTG TCT GAT AGG TTC CTT ATA GCA ATT |
|  | AAC GCG ACC CTC GAG GTG ACA GAA ATC GTC CTG CCC GCG |
|  | GGA GAA TGG CAC GCA ATC CCG CCG TTC GCA GGT GAG GAC |
|  | AAC CCA GTA ATA ACG GCT GTG TGG CAA GGA CCG GCT CAT |
|  | GGC CTT TGT GTT TTC CAG AGG TGA (SEQ ID NO: 24) |
| Codon optimized polynucleotide coding sequence (#10) for expressing the bacterial limit dextrin alpha-1,6-glucohydrolase (GlgX) derived from *Escherichia coli* strain K-12 in mammalian cells | ATG ACA CAA CTT GCT ATT GGC AAG CCG GCA CCA CTC GGT GCC CAT TAT GAC GGC CAG GGC GTA AAC TTC ACA CTC TTC TCC GCA CAC GCT GAA AGA GTT GAA TTG TGC GTC TTT GAC GCC AAT GGC CAG GAG CAC CGA TAT GAT CTC CCG GGA CAC TCC GGT GAT ATC TGG CAC GGA TAT CTC CCT GAT GCA AGA CCA GGG CTG CGG TAC GGC TAC CGC GTG CAC GGG CCT TGG CAG CCA GCA GAA GGA CAT CGA TTC AAT CCG GCC AAA CTG CTG ATT GAT CCG TGC GCT CGG CAG ATT GAC GGG GAG TTC AAA GAC AAC CCC CTC CTG CAT GCT GGC CAT AAC GAA CCC GAC TAT CGC GAT AAT GCC GCG ATC GCC CCG AAG TGC GTA GTG GTA GTT GAC CAC TAT GAC TGG GAA GAT GAT GCA CCA CCG CGA ACT CCG TGG GGC AGC ACA ATT ATA TAT GAA GCA CAT GTC AAA GGT CTG ACA TAT TTG CAT CCG GAA ATA CCT GTC GAA ATA CGG GGC ACT TAC AAG GCC CTT GGA CAC CCT GTA ATG ATT AAT TAC CTG AAA CAA CTC GGT ATC ACG GCA TTG GAG CTG CTG CCC GTG GCC CAG TTT GCT TCT GAG CCA CGA TTG CAA CGG ATG GGG TTG AGT AAC TAC TGG GGT TAT AAC CCC GTT GCC ATG TTT GCA CTC CAT CCC GCG TAT GCG TGC AGT CCG GAG ACG GCC CTT GAC GAG TTC CGA GAT GCA ATA AAG GCG CTC CAT AAG GCC GGA ATA GAG GTT ATT CTT GAT ATT GTC CTT AAC CAT TCT GCT GAG TTG GAT CTG GAC GGT CCC CTG TTC AGT CTT AGA GGT ATA GAC AAT CGG TCT TAT TAT TGG ATT CGA GAG GAT GGC GAC TAC CAC AAT TGG ACC GGA TGC GGA AAC ACG CTC AAC CTC AGC CAC CCA GCC GTA GTC GAT TAT GCC TCA GCT TGC CTT CGA TAT TGG GTA GAG ACA TGC CAC GTT GAT GGG TTC CGC TTT GAT TTG GCG GCA GTG ATG GGG CGG ACT CCG GAA TTT AGG CAG GAT GCT CCA CTG TTT ACA GCA ATT CAA AAT TGC CCC GTA CTT TCC CAG GTG AAA CTG ATT GCC GAG CCC TGG GAC ATA GCC CCC GGC GGG TAC CAA GTG GGC AAT TTC CCT CCT TTG TTC GCC GAG TGG AAC GAC CAC TTC CGC GAC GCT GCG CGC AGG TTT TGG CTC CAC TAT GAC TTG CCC CTC GGA GCC TTC GCA GGT CGC TTC GCG GCA AGT AGC GAT GTC TTC AAG CGC AAT GGT CGC TTG CCC TCA GCG GCT ATT AAT CTC GTG ACC GCA CAC GAC GGC TTT ACT TTG CGA GAT TGC GTT TGC TTC AAT CAC AAA CAC AAC GAA GCC AAC GGC GAG GAG AAT AGG GAT GGA ACG AAT AAC AAC TAC TCA AAC AAT CAC GGT AAA GAG GGT CTT GGG GGG AGC CTG GAT CTT GTT GAA AGA CGG CGG GAC AGT ATT CAC GCC CTC TTG ACG ACC CTT CTT CTT AGC CAG GGA ACT CCT ATG CTC TTG GCT GGC GAT GAA CAC GGT CAC TCT CAA CAT GGC AAT AAT AAT GCG TAT TGT CAG GAC AAC CAA CTC ACG TGG CTT GAT TGG AGT CAG GCT TCC TCT GGG CTT ACG GCG TTC ACG GCG GCC CTG ATC CAC CTC CGC AAG AGA ATC CCT GCT CTT GTA GAG AAC CGC TGG TGG GAA GAA GGG GAT GGA AAT GTT CGG TGG CTG AAC AGA TAC GCA CAA CCA CTG TCT ACG GAC GAG TGG CAA AAT GGT CCA AAG CAG CTC CAG ATT CTG CTT TCT GAT AGG TTC CTC ATT GCC ATT AAT GCC ACG CTT GAG GTG ACG GAG ATC GTC TTG CCG GCG GGT GAG TGG CAT GCG ATA CCG CCC TTC GCA GGG GAA GAC AAT CCG GTT ATT ACT GCG GTT TGG CAA GGC CCC GCA CAT GGG CTC TGC GTG TTT CAG AGG TGA (SEQ ID NO: 25) |
| Protein sequence of isoamylase [*Pseudomonas amyloderamosa* SB-15] Uniprot # P10342.3 | MKCPKILAALLGCAVLAGVPAMPAHAAINSMSLGASYDAQQANITFRVYSSQA TRIVLYLYSAGYGVQESATYTLSPAGSGVWAVTVPVSSIKAAGITGAVYYGYR AWGPNWPYASNWGKGSQAGFVSDVDANGDRFNPNKLLLDPYAQEVSQDPLNPS NQNGNVFASGASYRTTDSGIYAPKGVVLVPSTQSTGTKPTRAQKDDVIYEVHV RGFTEQDTSIPAQYRGTYYGAGLKASYLASLGVTAVEFLPVQETQNDANDVVP NSDANQNYWGYMTENYFSPDRRYAYNKAAGGPTAEFQAMVQAFHNAGIKVYMD VVYNHTAEGGTWTSSDPTTATIYSWRGLDNATYYELTSGNQYFYDNTGIGANF NTYNTVAQNLIVDSLAYWANTMGVDGFRFDLASVLGNSCLNGAYTASAPNCPN GGYNFDAADSNVAINRILREFTVRPAAGGSGLDLFAEPWAIGGNSYQLGGFPQ GWSEWNGLFRDSLRQAQNELGSMTIYVTQDANDFSGSSNLFQSSGRSPWNSIN FIDVHDGMTLKDVYSCNGANNSQAWPYGPSDGGTSTNYSWDQGMSAGTGAAVD QRRAARTGMAFEMLSAGTPLMQGGDEYLRTLQCNNNAYNLDSSANWLTYSWTT DQSNFYTFAQRLIAFRKAHPALRPSSWYSGSQLTWYQPSGAVADSNYWNNTSN YAIAYAINGPSLGDSNSIYVAYNGWSSSVTFTLPAPPSGTQWYRVTDTCDWND GASTFVAPGSETLIGGAGTTYGQCGQSLLLLISK (SEQ ID NO: 7) |
| Nucleic acid sequence of the LSP-CB dual promoter | GAGTTAATTTTTAAAAAGCAGTCAAAAGTCCAAGTGGCCCTTGCGAGC ATTTACTCTCTGTTTGCTCTGGTTAATAATCTCAGGAGCACAAAT TCCTTACTAGTCCTAGAAGTTAATTTTTAAAAAGCAGTCAAAAGTCCA |

TABLE 2-continued

Potential sequences related to this disclosure.

```
AGTCCAAGTGGCCCTTGCGAGCATTTACTCTCTCTGTTTGCTCTGGTT
AATAATCTCAGGAGCACAAACATTCCTTACTAGTTCTAGAGCGGCCGC
CAGTGTGCTGGAATTCGGCTTTTTTAGGGCTGGAAGCTACCTTTGACA
TCATCTCCTCTGCGAATGCATGTATAATTTCTACAGAACCTATTAGAA
AGGATCACCCAGCCTCTGCTTTTGTACAACTTTCCCTTAAAAAACTGC
CAATCCCACTGCTGTTTGGCCCAATAGTGAGAACTTTTTCTGCTGCCT
CTTGGTGCTTTTGCCTATGGCCCCTATTCTGCTGCTGAAGACACTCTT
GCCAGCATGGACTTAAACCCCTCCAGCTCTGACAATCCTCTTTCTCTT
TTGTTTTACATGAAGGGTCTGGCAGCCAAAGCAATCACTCAAAGTTCA
AACCTTATCATTTTTTGCTTTGTTCCTCTTGGCCTTGGTTTTGTACAT
CAGCTTTGAAAATACCATCCCAGGGTTAATGCTGGGGTTAATTTATAA
CTGAGAGTGCTCTAGTTTTGCAATACAGGACATGCTATAAAAATGGCT
TAAGGTTCCGCGTTACATAACTTACGGTAAATGGCCCGCCTGGCTGAC
CGCCCAACGACCCCCGCCCATTGACGTCAATAATGACGTATGTTCCCA
TAGTAACGCCAATAGGGACTTTCCATTGACGTCAATGGGTGGAGTATT
TACGGTAAACTGCCCACTTGGCAGTACATCAAGTGTATCATATGCCAA
GTACGCCCCCTATTGACGTCAATGACGGTAAATGGCCCGCCTGGCATT
ATGCCCAGTACATGACCTTATGGGACTTTCCTACTTGGCAGTACATCT
ACGTATTAGTCATCGCTATTACCATGCATGGTCGAGGTGAGCCCCACG
TTCTGCTTCACTCTCCCCATCTCCCCCCCCTCCCCACCCCCAATTTTG
TATTTATTTATTTTTTAATTATTTTGTGCAGCGAGGGGCGGGGCGGGG
CGAGGCGGAGAGGTGCGGCGGCAGCCAATCAGAGCGGCGCGCTCCGAA
AGTTTCCTTTTATGGCGAGGCGGCGGCGGCGGCGGCGGCCCTATAAAAGC
GAAGCGCGCGGCGGGCG (SEQ ID NO: 30)
```

Nucleic Acid Vectors

Another aspect of the present disclosure provides a vector comprising an isolated nucleic acid molecule comprising a nucleic acid sequence encoding a microbial polypeptide for degrading glycogen, wherein the nucleic acid is codon optimized for expression in mammalian cells or mammals such as humans.

As described herein, an AAV vector containing a universally active CMV enhanced chicken beta-actin hybrid (CB) promoter (AAV-CB-Pull) or a liver-specific promoter (AAV-LSP-Pull) and a 2.2 kb coding sequence codon optimized for expressing a type I Pullulanase (derived from *Bacillus subtilis* strain 168) in human cells were constructed. The results showed that a ten-week treatment by intravenous administration of the AAV-CB-Pull vector in infant GSD IIIa mice (at two weeks of age) effectively reduced glycogen contents in skeletal muscle and heart without provoking Pullulanase-induced immune responses (immune response is impaired in infant mice during the first few weeks after birth). When the GSD IIIa mice were treated at an adult age (ten weeks), the AAV-LSP-Pull treatment markedly reduced liver glycogen storage and effectively prevented hepatic fibrosis. In contrast, the AAV-CB-Pull treatment in adult mice induced strong cytotoxic T cell responses and eventually lost treatment efficacy 7 weeks post treatment.

As further described herein, a combination treatment with the AAV-CB-Pull at two weeks of age and the AAV-LSP-Pull at 3 months of age (CB+LSP) effectively reduced glycogen accumulation in both liver and muscle and recovered liver and muscle functions in GSD IIIa mice. Furthermore, as described herein, an AAV vector having an immunotolerant LSP-CB dual promoter (consisting of the liver-specific promoter and the ubiquitous CB promoter) encoding a microbial polypeptide or a non-microbial polypeptide prevented cytotoxic T cell responses in both GSD IIIa and GSD IV mouse models, indicating that this immunotolerant dual vector system can be used to treat diseases having multisystem involvement (e.g., Pompe disease).

It will be apparent to those skilled in the art that any suitable vector can be used to deliver the isolated nucleic acids of the disclosure to the target cell(s) or subject of interest. The choice of delivery vector can be made based on a number of factors known in the art, including age and species of the target host, in vitro vs. in vivo delivery, level and persistence of expression desired, intended purpose (e.g., for therapy or enzyme production), the target cell or organ, route of delivery, size of the isolated nucleic acid, safety concerns, and the like.

Any suitable vector known in the art can be used to deliver, and optionally, express the isolated nucleic acids of the disclosure (e.g., viral and non-viral vectors), including, virus vectors (e.g., retrovirus, adenovirus, AAV, or herpes simplex virus), lipid vectors, poly-lysine vectors, synthetic polyamino polymer vectors that are used with nucleic acid molecules, such as a plasmid, and the like. In some embodiments, the non-viral vector can be a polymer based vector (e.g., polyethyleimine (PEI), chitosan, poly (DL-Lactide) (PLA), or poly (DL-lactidie-co-glycoside) (PLGA), dendrimers, polymethacrylate) a peptide based vector, a lipid nanoparticle, a solid lipid nanoparticle, or a cationic lipid based vector.

Any viral vector that is known in the art can be used in the present disclosure. Examples of such viral vectors include, but are not limited to vectors derived from: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picornaviridae; Plasmaviridae; Prodoviridae; Polydnaviridae; Potexvirus group; Potyvirus; Poxyiridae; Reoviridae; Retroviridae; Rhabdoviridae; Group Rhizidiovirus; Siphoviri-dae; Sobemovirus group; SSV 1-Type Phages; Tectiviridae; Tenuivirus; Tetraviridae; Group Tobamovirus; Group Tobra-virus; Togaviridae; Group Tombusvirus; Group Torovirus; Totiviridae; Group Tymovirus; and plant virus satellites.

Protocols for producing recombinant viral vectors and for using viral vectors for nucleic acid delivery can be found in *Current Protocols in Molecular Biology*; Ausubel, F. M. et al. (eds.) Greene Publishing Associates; (1989) and other standard laboratory manuals (e.g., Vectors for Gene Therapy, In: *Current Protocols in Human Genetics*, John Wiley and Sons, Inc.; 1997).

In some embodiments, the viral vector is selected from the group consisting of an adenovirus vector, an AAV vector (e.g., AAV serotypes and genetically modified AAV vari-ants), a herpes simplex virus vector (e.g., HSV-1, HSV), a retrovirus vector (e.g., MMSV, MSCV), a lentivirus vector (HIV-1, HIV-2), and alphavirus vector (e.g., SFV, SIN, VEE, M1), a flavivirus vector (e.g., Kunjin, West Nile, Dengue virus), a rhabdovirus vector (e.g., Rabies, VSV), a measles virus vector (e.g., MV-Edm), a Newcastle disease virus vector, a poxvirus vector (VV), or a picornavirus vector (e.g., Coxsackievirus).

Protocols for producing recombinant viral vectors and for using viral vectors for nucleic acid delivery can be found in *Current Protocols in Molecular Biology*; Ausubel, F. M. et al. (eds.) Greene Publishing Associates; (1989) and other standard laboratory manuals (e.g., Vectors for Gene Therapy, In: *Current Protocols in Human Genetics*, John Wiley and Sons, Inc.; 1997).

Viral vectors can be those previously employed for the delivery of transgenes including, for example, retrovirus, adenovirus, AAV, herpes virus, hybrid adenovirus-AAV, and poxvirus vectors. In some embodiments, the vector is an adenovirus vector, AAV vector or hybrid adenovirus-AAV vector.

In some embodiments, the delivery vector is an adenovi-rus vector. The term "adenovirus" as used herein encom-passes all adenoviruses, including the Mastadenovirus and Aviadenovirus genera.

The various regions of the adenovirus genome have been mapped and are understood by those skilled in the art. The genomic sequences of the various Ad serotypes, as well as the nucleotide sequence of the particular coding regions of the Ad genome, are known in the art and may be accessed, e.g., from GenBank and NCBI (see, e.g., GenBank Acces-sion Nos. J0917, M73260, X73487, AF108105, L19443, NC 003266 and NCBI Accession Nos. NC 001405, NC 001460, NC 002067, NC 00454).

A recombinant adenovirus (rAd) vector genome can com-prise the adenovirus terminal repeat sequences and packag-ing signal. An "adenovirus particle" or "recombinant adeno-virus particle" comprises an adenovirus vector genome or recombinant adenovirus vector genome, respectively, pack-aged within an adenovirus capsid. Generally, the adenovirus vector genome is most stable at sizes of about 28 kb to 38 kb (approximately 75% to 105% of the native genome size). In the case of an adenovirus vector containing large dele-tions and a relatively small transgene, "stutter DNA" can be used to maintain the total size of the vector within the desired range by methods known in the art.

The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 d 1324 or other strains of adenovirus (e.g., Ad2, Ad3, Ad7, etc.) are known to those skilled in the art. Recombinant adenoviruses can be advan-tageous in certain circumstances in that they are not capable of infecting nondividing cells and can be used to infect a wide variety of cell types, including epithelial cells. Fur-thermore, the virus particle is relatively stable and amenable to purification and concentration, and as above, can be modified so as to affect the spectrum of infectivity. Addi-tionally, introduced adenoviral DNA (and foreign DNA contained therein) is not integrated into the genome of a host cell but remains episomal, thereby avoiding potential prob-lems that can occur as a result of insertional mutagenesis in situations where introduced DNA becomes integrated into the host genome (e.g., retroviral DNA). Moreover, the carrying capacity of the adenoviral genome for foreign DNA is large relative to other nucleic acid delivery vectors.

In particular embodiments, the adenovirus genome con-tains a deletion therein, so that at least one of the adenovirus gene regions does not encode a functional protein. For example, first-generation adenovirus vectors are typically deleted for the E1 genes and packaged using a cell that expresses the E1 proteins (e.g., 293 cells). The E3 region is also frequently deleted as well, as there is no need for complementation of this deletion. In addition, deletions in the E4, E2a, protein IX, and fiber protein regions have been described. The deletions can be selected to avoid toxicity to the packaging cell.

AAV have also been employed as nucleic acid delivery vectors. AAV are parvoviruses and have small icosahedral virions, 18-26 nanometers in diameter and contain a single stranded DNA molecule about 4.7 kb in size. The viruses contain either the sense or antisense strand of the DNA molecule and either strand is incorporated into the virion. Two open reading frames encode a series of Rep and Cap polypeptides. Rep polypeptides (Rep50, Rep52, Rep68 and Rep78) are involved in replication, rescue and integration of the AAV genome, although significant activity may be observed in the absence of all four Rep polypeptides. The Cap proteins (VP1, VP2, VP3) form the virion capsid. Flanking the rep and cap open reading frames at the 5' and 3' ends of the genome are 145 basepair inverted terminal repeats (ITRs), the first 125 basepairs of which are capable of forming Y- or T-shaped duplex structures. It has been shown that the ITRs represent the minimal cis sequences required for replication, rescue, packaging and integration of the AAV genome. Typically, in recombinant AAV (rAAV) vectors, the entire rep and cap coding regions are excised and replaced with a transgene of interest.

Wild-type AAV can integrate their DNA into non-dividing cells, and exhibit a high frequency of stable integration into human chromosome 19. A rAAV vector genome will typi-cally comprise the AAV terminal repeat sequences and packaging signal. An "AAV particle" or "rAAV particle" comprises an AAV vector genome or rAAV vector genome, respectively, packaged within an AAV capsid. The rAAV vector itself need not contain AAV genes encoding the capsid and Rep proteins. In particular embodiments of the disclosure, the rep and/or cap genes are deleted from the AAV genome. In a representative embodiment, the rAAV vector retains only the terminal AAV sequences (ITRs) necessary for integration, excision, and replication.

Sources for the AAV capsid genes can include naturally isolated serotypes, including but not limited to, AAV1, AAV2, AAV3 (including 3a and 3b), AAV4, AAV5, AAV6, AAV7, AAV8, AAVrh8, AAV9, AAV10, AAVrh10, AAV11, AAV12, AAV13, AAVrh39, AAVrh43, AAVcy.7 as well as bovine AAV, caprine AAV, canine AAV, equine AAV, ovine AAV, avian AAV, primate AAV, non-primate AAV, and any other virus classified by the International Committee on Taxonomy of Viruses (ICTV) as an AAV. In particular embodiments, the AAV capsids are chimeras either created by capsid evolution or by rational capsid engineering from the naturally isolated AAV variants to capture desirable serotype features such as enhanced or specific tissue tropism and host immune response escape, including but not limited to AAV-DJ, AAV-HAE1, AAV-HAE2, AAVM41, AAV-1829, AAV2 Y/F, AAV2 T/V, AAV2i8, AAV2.5, AAV9.45, AAV9.61, AAV-B1, AAV-AS, AAV9.45A-String (e.g., AAV9.45-AS), AAV9.45Angiopep, AAV9.47-Angiopep, and AAV9.47-AS, AAV-PHP.B, AAV-PHP.eB, and AAV-PHP.S.

Because of packaging limitations, the total size of the rAAV genome can be less than about 5.2, 5.0, 4.8, 4.6 or 4.5 kb in size. The rAAV genome refers to the two inverted terminal repeats (ITRs) from the same AAV serotype or from two different AAV serotypes as well as the gene expression cassette comprising one or more promoters, a codon optimized nucleic acid sequence encoding a microbial polypeptide, and a poly A tail.

Any suitable method known in the art can be used to produce AAV vectors. In one particular method, AAV stocks can be produced by co-transfection of a rep/cap vector plasmid encoding AAV packaging functions and the vector plasmid containing the recombinant AAV genome into human cells infected with the helper adenovirus.

In other particular embodiments, the adenovirus helper virus is a hybrid helper virus that encodes AAV Rep and/or capsid proteins. Hybrid helper Ad/AAV vectors expressing AAV rep and/or cap genes and methods of producing AAV stocks using these reagents are known in the art. The hybrid Ad of the disclosure can express the AAV capsid proteins (i.e., VP1, VP2, and VP3). Alternatively, or additionally, the hybrid adenovirus can express one or more of AAV Rep proteins (i.e., Rep40, Rep52, Rep68 and/or Rep78). The AAV sequences can be operatively associated with a tissue-specific promoter, a ubiquitous promoter, a constitutive or an inducible promoter, or combinations thereof.

The AAV rep and/or cap genes can alternatively be provided by a packaging cell that stably expresses the genes. In still further embodiments, the delivery vector is a hybrid Ad-AAV delivery vector, for example, as described in the working Examples and in U.S. Pat. No. 7,858,367 (incorporated by reference herein in its entirety for its teaching of how to make and use hybrid Ad-AAV delivery vectors). Briefly, the hybrid Ad-AAV vector comprises an adenovirus vector genome comprising adenovirus (i) 5' and 3' cis-elements for viral replication and encapsidation and, further, (ii) a recombinant AAV vector genome comprising the AAV 5' and 3' inverted terminal repeats (ITRs), an AAV packaging sequence, and a heterologous sequence(s) flanked by the AAV ITRs, where the recombinant AAV vector genome is flanked by the adenovirus 5' and 3' cis-elements. The adenovirus vector genome can further be deleted, as described above.

Another vector for use in the present disclosure comprises Herpes Simplex Virus (HSV). Herpes simplex virions have an overall diameter of 150 to 200 nm and a genome consisting of one double-stranded DNA molecule that is 120 to 200 kilobases in length. Glycoprotein D (gD) is a structural component of the HSV envelope that mediates virus entry into host cells. The initial interaction of HSV with cell surface heparin sulfate proteoglycans is mediated by another glycoprotein, glycoprotein C (gC) and/or glycoprotein B (gB). This is followed by interaction with one or more of the viral glycoproteins with cellular receptors. Glycoprotein D of HSV binds directly to Herpes virus entry mediator (HVEM) of host cells. HVEM is a member of the tumor necrosis factor receptor superfamily. Finally, gD, gB and the complex of gH and gL act individually or in combination to trigger pH-independent fusion of the viral envelope with the host cell plasma membrane.

HSV can be modified for the delivery of transgenes to cells by producing a vector that exhibits only the latent function for long-term gene maintenance. HSV vectors are useful for nucleic acid delivery because they allow for a large DNA insert of up to or greater than 20 kilobases; they can be produced with extremely high titers; and they have been shown to express transgenes for a long period of time in the central nervous system as long as the lytic cycle does not occur.

In other embodiments of the present disclosure, the delivery vector of interest is a retrovirus. Retroviruses normally bind to a species specific cell surface receptor, e.g., CD4 (for HIV); CAT (for MLV-E; ecotropic Murine leukemic virus E); RAM1/GLVR2 (for murine leukemic virus-A; MLV-A); GLVR1 (for Gibbon Ape leukemia virus (GALV) and Feline leukemia virus B (FeLV-B)). The development of specialized cell lines (termed "packaging cells") which produce only replication-defective retroviruses has increased the utility of retroviruses for gene therapy, and defective retroviruses are characterized for use in gene transfer for gene therapy purposes. A replication-defective retrovirus can be packaged into virions which can be used to infect a target cell through the use of a helper virus by standard techniques.

Yet another suitable vector is a poxvirus vector. These viruses contain more than 100 proteins. Extracellular forms of the virus have two membranes while intracellular particles only have an inner membrane. The outer surface of the virus is made up of lipids and proteins that surround the biconcave core. Poxviruses are very complex antigenically, inducing both specific and cross-reacting antibodies after infection. Poxvirus can infect a wide range of cells. Poxvirus gene expression is well studied due to the interest in using vaccinia virus as a vector for expression of transgenes.

In addition to viral transfer methods, such as those illustrated above, non-viral methods can also be employed. Many non-viral methods of gene transfer rely on normal mechanisms used by mammalian cells for the uptake and intracellular transport of macromolecules. In particular embodiments, non-viral delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present disclosure. Naked plasmids can be introduced into muscle cells by injection into the tissue. Expression can extend over many months, although the number of positive cells is typically low (Wolff et al., (1989) *Science* 247:247). Cationic lipids have been demonstrated to aid in introduction of DNA into some cells in culture (Feigner and Ringold, (1989) Nature 337:387). Injection of cationic lipid plasmid DNA complexes into the circulation of mice has been shown to result in expression of the DNA in lung (Brigham et al., (1989) *Am. J. Med. Sci.* 298:278). One advantage of plasmid DNA is that it can be introduced into non-replicating cells.

In a representative embodiment, a nucleic acid molecule (e.g., a plasmid) can be entrapped in a lipid particle bearing positive changes on its surface and, optionally, tagged with antibodies against cell surface antigens of the target tissue.

Liposomes that consist of amphiphilic cationic molecules are useful non-viral vectors for nucleic acid delivery in vitro and in vivo. The positively charged liposomes are believed to complex with negatively charged nucleic acids via electrostatic interactions to form lipid:nucleic acid complexes. The lipid:nucleic acid complexes have several advantages as gene transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency.

Amphiphilic cationic lipid:nucleic acid complexes can be used for in vivo transfection both in animals and in humans and can be prepared to have a long shelf-life.

Administering an immunosuppressive agent in combination with gene therapy could be another approach to help prevent or reduce cytotoxic T cell and/or antibody mediated immune responses towards gene therapy. Methods of delivering a recombinant nucleic acid molecule comprising a nucleic acid sequence encoding a microbial polypeptide for degrading glycogen for therapeutic methods are described in more detail below.

An isolated nucleic acid molecule can be carried by a delivery vector as described in the preceding section. Those skilled in the art will appreciate that the isolated nucleic acid encoding the microbial polypeptides for degrading glycogen can be operably associated with appropriate expression control sequences, e.g., transcription/translation control signals or secretory signal sequences, which can be included in the isolated nucleic acid or by a vector backbone. For example, specific initiation signals can be required for efficient translation of inserted protein coding sequences. These exogenous translational control sequences, which can include the ATG initiation codon and adjacent sequences, can be of a variety of origins, both natural and synthetic.

A variety of promoter/enhancer elements can be used depending on the level and tissue-specific expression desired. The promoter can be tissue-specific or ubiquitous and can be constitutive or inducible, depending on the pattern of the therapeutic gene expression desired. The promoter can be native or foreign and can be a natural or a synthetic sequence. By foreign, it is intended that the transcriptional initiation region is not found in the wild-type host into which the transcriptional initiation region is introduced.

The promoter can be chosen so that it will function in the target cell(s) of interest. Tissue-specific promoters refer to promoters that have activity in only certain cell types. The use of a tissue-specific promoter in a nucleic acid expression cassette can restrict unwanted transgene expression in the unaffected tissues as well as facilitate persistent transgene expression by escaping from transgene induced host immune responses.

Ubiquitous promoters refer to promoters that are strongly active in a wide range of cells and tissues, including, but not limited to, the liver, kidney, skeletal muscle, cardiac muscle, smooth muscle, diaphragm muscle, brain, spinal cord, endothelial cells, intestinal cells, pulmonary cells (e.g., smooth muscle or epithelium), peritoneal epithelial cells and fibroblasts.

Ubiquitous promoters include, but are not limited to, a CMV major immediate-early enhancer/chicken beta-actin promoter, a cytomegalovirus (CMV) major immediate-early promoter, an Elongation Factor 1-α (EF1-α) promoter, a simian vacuolating virus 40 (SV40) promoter, a PyK promoter, a human ubiquitin C gene (Ubc) promoter, a MFG promoter, a human beta actin promoter, a CAG promoter, a EGR1 promoter, a FerH promoter, a FerL promoter, a GRP78 promoter, a GRP94 promoter, a HSP70 promoter, a β-kin promoter, a murine phosphoglycerate kinase (mPGK) or human PGK (hPGK) promoter, a ROSA promoter, human Ubiquitin B promoter, a Rous sarcoma virus promoter, or any other natural or synthetic ubiquitous promoters.

Constitutive promoters refer to unregulated promoters that allow for continual transcription of its associate gene. In some embodiments, a constitutive promoter can also be a ubiquitous promoter.

Inducible promoters refer to promoters that can be regulated by positive or negative control. Factors that can regulate an inducible promoter include, but are not limited to, chemical agents (e.g., the metallothionein promoter or a hormone inducible promoter), temperature, and light.

Liver-specific promoters include, but are not limited to, the α1-microglobulin/bikunin enhancer/thyroid hormone-binding globulin promoter, the human albumin (hALB) promoter, the thyroid hormone-binding globulin promoter, the α-1-anti-trypsin promoter, the bovine albumin (bAlb) promoter, the murine albumin (mAlb) promoter, the human α1-antitrypsin (hAAT) promoter, the ApoEhAAT promoter composed of the ApoE enhancer and the hAAT promoter, the transthyretin (TTR) promoter, the liver fatty acid binding protein promoter, the hepatitis B virus (HBV) promoter, the DC172 promoter consisting of the hAAT promoter and the α1-microglobulin enhancer, the DC190 promoter containing the human albumin promoter and the prothrombin enhancer, and other natural and synthetic liver-specific promoters.

Muscle specific promoters include, but are not limited to, the MHCK7 promoter, the muscle creatine kinase (MCK) promoter/enhancer, the slow isoform of troponin I (TnIS) promoter, the MYODI promoter, the MYLK2 promoter, the SPc5-12 promoter, the desmin (Des) promoter, the unc45b promoter, and other natual and synthetic muscle-specific promoters.

Skeletal muscle-specific promoters include, but are not limited to, the HSA promoter, the human α-skeletal actin promoter.

Heart-specific promoters include, but art not limited to, the MYH6 promoter, the TNNI3 promoter, the cardiac troponin C (cTnC) promoter, the alpha-myosin heavy chain (α-MHC) promoter, and the MYBPC3 promoter.

Neuron-specific promoters include, but are not limited to the synapsin I (SYN) promoter, the calcium/calmodulin-dependent protein kinase promoter, the tubulin alpha I promoter, the enolase promoter, and the platelet-derived growth factor beta chain promoter.

The tissue-specific promoters can be operably linked to one or more (e.g., 2, 3, 4, 5, 6, 7, or 8) enhancer elements or combined to form a tandem promoter (e.g., liver-specific/muscle-specific tandem promoter, liver-specific/neuron-specific tandem promoter, or muscle-specific/neuron-specific tandem promoter). When two or more tissue-specific promoters are present, the isolated nucleic acid can be targeted to two or more different tissues at the same time.

In some embodiments, the vector can comprise one or more immunotolerant promoters (e.g., an immunotolerant liver-specific promoter or an immunotolerant dual promoter). As used herein, the term "immunotolerant" refers to unresponsiveness to an antigen (e.g., a vector, a therapeutic protein, a bacterial GDE, etc.). An immunotolerant promoter can reduce, ameliorate, or prevent transgene-induced immune responses that can be associated with gene therapy. Assays known in the art to measure immune responses, such as immunohistochemical detection of cytotoxic T cell responses, can be used to determine whether one or more promoters can confer immunotolerant properties.

In some embodiments, the vector can comprise an immunotolerant dual promoter having a liver-specific promoter and a ubiquitous promoter. In some embodiments, the liver-specific promoters that can be used in the immunotolerant dual promoter system include, but are not limited to, the α1-microglobulin/bikunin enhancer/thyroid hormone-binding globulin promoter, the human albumin (hALB) promoter, the thyroid hormone-binding globulin promoter, the α-1-anti-trypsin promoter, the bovine albumin (bAlb) promoter, the murine albumin (mAlb) promoter, the human α1-antitrypsin (hAAT) promoter, the ApoEhAAT promoter composed of the ApoE enhancer and the hAAT promoter, the transthyretin (TTR) promoter, the liver fatty acid binding protein promoter, the hepatitis B virus (HBV) promoter, the DC172 promoter consisting of the hAAT promoter and the α1-microglobulin enhancer, the DC190 promoter containing the human albumin promoter and the prothrombin enhancer, and other natural and synthetic liver-specific promoters.

In some embodiments, the ubiquitous promoters that can be used in the immunotolerant dual promoter system include, but are not limited to, a CMV major immediate-early enhancer/chicken beta-actin promoter, a cytomegalovirus (CMV) major immediate-early promoter, an Elongation Factor 1-α (EF1-α) promoter, a simian vacuolating virus 40 (SV40) promoter, a PyK promoter, a human ubiquitin C gene (Ubc) promoter, a MFG promoter, a human beta actin promoter, a CAG promoter, a EGR1 promoter, a FerH promoter, a FerL promoter, a GRP78 promoter, a GRP94 promoter, a HSP70 promoter, a β-kin promoter, a murine phosphoglycerate kinase (mPGK) or human PGK (hPGK) promoter, a ROSA promoter, human Ubiquitin B promoter, a Rous sarcoma virus promoter, or any other natual or synthetic ubiquitous promoters.

In some embodiments, the immunotolerant dual promoter comprises a α1-microglobulin/bikunin enhancer/thyroid hormone-binding globulin promoter and a CMV enhancer/beta-actin (CB) promoter. In some embodiments, the immunotolerant dual promoter comprises a α1-microglobulin/bikunin enhancer/thyroid hormone-binding globulin promoter and a CMV enhancer/beta-actin (CB) promoter. The α1-microglobulin/bikunin enhancer/thyroid hormone-binding globulin promoter can have the nucleic acid sequence as set forth in SEQ ID NO: 31, or can have at least 50%, 60%, 70%, 80%, 85%, 86%, 87%, 88%, 89%, 90%, 91%, 92%, 93%, 94%, 95%, 96%, 97%, 98%, or 99% sequence identity to the nucleic acid sequence set forth in SEQ ID NO:31. The CMV enhancer/chicken β-actin promoter can have the nucleic acid sequence as set forth in SEQ ID NO: 32, or can have at least 50%, 60%, 70%, 80%, 85%, 86%, 87%, 88%, 89%, 90%, 91%, 92%, 93%, 94%, 95%, 96%, 97%, 98%, or 99% sequence identity to the nucleic acid sequence set forth in SEQ ID NO:32.

In some embodiments, the immunotolerant dual promoter has a nucleic acid sequence as set forth in SEQ ID NO:30, or has at least 50%, 60%, 70%, 80%, 85%, 86%, 87%, 88%, 89%, 90%, 91%, 92%, 93%, 94%, 95%, 96%, 97%, 98%, or 99% sequence identity to the nucleic acid sequence set forth in SEQ ID NO:30. The nucleic acid sequence set forth in SEQ ID NO:30 is shown in Table 2, and the un-bolded portion of the sequence represents the α1-microglobulin/bikunin enhancer/thyroid hormone-binding globulin promoter and the bolded portion of the sequence represents the CMV enhancer/chicken R-actin promoter.

The dual promoters can be engineered into the gene expression cassette such that the 3' end of the liver-specific promoter is operably linked to the 5' end of the ubiquitous promoter or the 3' end of the ubiquitous promoter is operably linked to the 5' end of the liver-specific promoter. Delivering a therapeutic gene under the control of the dual promoters described herein has the surprising advantage of preventing a transgene-induced T cell response of a therapeutic transgene product for gene therapy of human genetic diseases that affect multiple tissues (e.g., GSD III or GSD IV).

Thus, the disclosure relates to methods and compositions of the use of an immunotolerant dual promoter system consisting of a liver-specific promoter and a ubiquitous promoter to prevent host immune responses against a therapeutic transgene product for gene therapy of human genetic diseases that affect multiple tissues. The disclosure also relates to gene replacement therapy approaches to deliver a functional therapeutic gene under the control of the said immunotolerant dual promoter with a viral or non-viral vector.

The transgene under control of the immunotolerant dual promoter system described herein can encode a variety of therapeutic proteins/enzymes and polypeptides, including microbial polypeptides for degrading glycogen and non-microbial proteins to treat human genetic diseases that affect multiple tissues. Therapeutic proteins and polypeptides that can be used with the immunotolerant dual promoter system described herein include, but are not limited to, cluster of differentiation 39 (CD39) protein, cluster of differentiation 73 (CD73) protein, Recombinant Anti-Inflammation fusion protein (RAIN) (CD73-39 fusion), interleukin-1 inhibitor, tumor necrosis factor-a inhibitor, interleukin-12 inhibitor, interleukin-1 receptor antagonist, interleukin-18 binding protein, soluble tumor necrosis factor-α receptor p55 or soluble tumor necrosis factor-α protein 75, dominant negative IκB kinase-β, inter leukin-4, interleukin-10, interleukin-13, interferon-R, vasoactive intestinal polypeptide, cystic fibrosis transmembrane regulator protein (CFTR), dystrophin, utrophin, blood coagulation (clotting) factor (e.g., Factor XIII, Factor IX, Factor X, Factor VIII, Factor Vila, protein C, Factor VII, B domain-deleted Factor VIII, or a longer half-life variant of a coagulation factor), retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, lysosomal acid α-glucosidase (GAA; also known as acid maltase), α-galactosidase A, β-galactosidase, β-hexosaminidase A, β-hexosaminidase B, $GM_2$ activator protein, glucocerebrosidase, arylsulfatase A, galactosylceramidase, acid sphingomyelinase, acid ceramidase, acid lipase, α-L-iduronidase, iduronate sulfatase, heparan N-sulfatase, α-N-acetylglucosaminidase, glucosaminide acetyltransferase, N-acetylglucosamine-6-sulfatase, arylsulfatase B, β-glucuronidase, α-mannosidase, R-mannosidase, α-L-fucosidase, N-aspartyl-β-glucosaminidase, N-acetylgalactosamine 4-sulfatase, α-neuraminidase, lysosomal protective protein, α-N-acetyl-galactosaminidase, N-acetylglucosamine-1-phosphotransferase, glycogen branching enzyme (GDE), a microbial polypeptide for degrading glycogen, glycogen debranching enzyme (GDE), cystine transport protein, sialic acid transport protein, the CLN3 gene product, palmitoyl-protein thioesterase, saposin A, saposin B, saposin C, and saposin D, hypoxanthine guanine phosphoribosyl transferase, P-25 glucocerebrosidase, sphingomyelinase, lysosomal hexosaminidase, branched chain keto acid dehydrogenase, a hormone, a growth factor, insulin-like growth factor 1 or 2, platelet derived growth factor, epidermal growth factor, nerve growth factor, neurotrophic factor-3 and -4, brain-derived neurotrophic factor, glial derived growth factor, transforming growth factor α and β, a cytokine, interferon-a, interferon-γ, inter leukin-2, interleukin-12, granulocyte-macrophage colony stimulating factor, lymphotoxin, a suicide gene product, herpes simplex virus thymidine kinase, cytosine deaminase, diphtheria toxin, cytochrome P450, deoxycytidine kinase, tumor necrosis factor, a drug resistance protein, a tumor suppressor protein (e.g., p53, Rb, Wt-1, NFI, Von Hippel-Lindau (VHL), SERCA2a, adenomatous polyposis coli (APC)), VEGF, microdystrophin, lysosomal acid lipase, arylsulfatase A and B, ATP7A and B, a peptide with immunomodulatory properties, a tolerogenic or immunogenic peptide or protein Tregitope or hCDRI, insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome IC), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, or a gene product implicated in lysosomal storage diseases (e.g., sulfatases, N-acetylglucosamine-1-phosphate transferase, cathepsin A, GM2-AP, NPC1, VPC2, a sphingo lipid activator protein), and any other peptide or protein that has a therapeutic effect in a subject in need thereof.

In some embodiments, the nucleic acid sequence encoding a therapeutic protein under the control of a dual promoter has a coding sequence that is less than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, or 5.5 kilobases (kb).

The promoter can further be "specific" for these cells and tissues, in that it can only show significant activity in the specific cell or tissue type. In some embodiments, the tissue-specific promoter is a liver-specific promoter, a muscle-specific promoter, a neuron-specific promoter, or a combination thereof.

The isolated nucleic acid can be operatively associated with an ubiquitous promoter, for example, a cytomegalovirus (CMV) major immediate-early promoter, an Elongation Factor 1-α (EF1-α) promoter, a simian vacuolating virus 40 (SV40) promoter, a PyK promoter, a human ubiquitin C gene (Ubc) promoter, a MFG promoter, a human beta actin promoter, a CAG promoter, a EGR1 promoter, a FerH promoter, a FerL promoter, a GRP78 promoter, a GRP94 promoter, a HSP70 promoter, a β-kin promoter, a murine phosphoglycerate kinase (mPGK) or human PGK (hPGK) promoter, a ROSA promoter, human Ubiquitin B promoter, a Rous sarcoma virus promoter, or any other natual or synthetic ubiquitous promoters. A hybrid promoter containing the CMV major immediate-early enhancer and chicken beta-actin (CB) promoter is also suitable. Driving heterologous nucleotide transcription with the CMV promoter can result in down-regulation of expression in immunocompetent animals. Accordingly, it can be advantageous to operably associate the isolated nucleic acid molecule with a modified CMV promoter that does not result in this down-regulation of transgene expression. In some embodiments, the ubiquitous promoter is a CMV enhancer/chicken β-actin promoter.

The vector can comprise a ubiquitous promoter and/or a tissue-specific promoter operably linked to the nucleic acid molecule. The term "operably linked" means joined as part of the same nucleic acid molecule, suitably positioned and oriented for transcription to be initiated from the promoter. A nucleic acid molecule that is operably linked to a promoter can be under transcriptional initiation regulation of the promoter.

The isolated nucleic acids of the disclosure can comprise two or more coding sequences. In embodiments wherein there is more than one coding sequence, the coding sequences can be operatively associated with separate promoters or, alternatively, with a single upstream promoter and one or more downstream internal ribosome entry site (IRES) sequences (e.g., the picornavirus EMC IRES sequence).

In some embodiments, the isolated nucleic acid encoding the microbial polypeptides for degrading glycogen can be operably associated with or fused to a secretory signal sequence (e.g., for secreting the microbial polypeptide to the blood circulation that subsequently can be taken up by other tissues).

The secretory signal sequence can be derived in whole or in part from the secretory signal of a secreted polypeptide (e.g., from the precursor) and/or can be in whole or in part synthetic. The secretory signal sequence can be from any species of origin, including mammals, plants, yeast, bacteria, protozoa or fungi. The length of the secretory signal sequence can be from about 10-15 to 50-60 amino acids in length. Further, known secretory signals from secreted polypeptides can be altered or modified (e.g., by substitution, deletion, truncation or insertion of amino acids) as long as the resulting secretory signal sequence functions to enhance secretion of an operably linked lysosomal polypeptide.

Exemplary secreted proteins (and their secretory signals) include but are not limited to: erythropoietin, coagulation Factor IX, cystatin, lactotransferrin, plasma protease C1 inhibitor, apolipoproteins (e.g., APO A, C, E), MCP-1, α-2-HS-glycoprotein, α-1-microgolubilin, complement (e.g., C1Q, C3), vitronectin, lymphotoxin-α, azurocidin, VIP, metalloproteinase inhibitor 2, glypican-1, pancreatic hormone, clusterin, hepatocyte growth factor, insulin, α-1-antichymotrypsin, growth hormone, type IV collagenase, guanylin, properdin, proenkephalin A, inhibin β (e.g., A chain), prealbumin, angiocenin, lutropin (e.g., β chain), insulin-like growth factor binding protein 1 and 2, proactivator polypeptide, fibrinogen (e.g., β chain), gastric triacylglycerol lipase, midkine, neutrophil defensins 1, 2, and 3, α-1-antitrypsin, matrix gla-protein, α-tryptase, bile-salt-activated lipase, chymotrypsinogen B, elastin, IG lambda chain V region, platelet factor 4 variant, chromogranin A, WNT-1 proto-oncogene protein, oncostatin M, β-neoendorphin-dynorphin, von Willebrand factor, plasma serine protease inhibitor, serum amyloid A protein, nidogen, fibronectin, rennin, osteonectin, histatin 3, phospholipase A2, cartilage matrix Protein, GM-CSF, matrilysin, neuroendocrine protein 7B2, placental protein 11, gelsolin, IGF 1 and 2, M-CSF, transcobalamin I, lactase-phlorizin hydrolase, elastase 2B, pepsinogen A, MIP 1-β, prolactin, trypsinogen II, gastrin-releasing peptide II, atrial natriuretic factor, secreted alkaline phosphatase, pancreatic α-amylase, secretogranin I, β-casein, serotransferrin, tissue factor pathway inhibitor, follitropin β-chain, coagulation factor XII, growth hormone-releasing factor, prostate seminal plasma protein, interleukins (e.g., 2, 3, 4, 5, 9, 11), inhibin (e.g., alpha chain), angiotensinogen, thyroglobulin, IG heavy or light chains, plasminogen activator inhibitor-1, lysozyme C, plasminogen activator, antileukoproteinase 1, statherin, fibulin-1, isoform B, uromodulin, thyroxine-binding globulin, axonin-1, endometrial α-2 globulin, interferon (e.g., alpha, beta, gamma), β-2-microglobulin, procholecystokinin, pro-gastricsin, prostatic acid phosphatase, bone sialoprotein II, colipase, Alzheimer's amyloid A4 protein, PDGF (e.g., A or B chain), coagulation factor V, triacylglycerol lipase, hap-toglobuin-2, corticosteroid-binding globulin, triacylglycerol lipase, prorelaxin H2, follistatin 1 and 2, platelet glycopro-tein IX, GCSF, VEGF, heparin cofactor II, antithrombin-III, leukemia inhibitory factor, interstitial collagenase, pleiotro-phin, small inducible cytokine A1, melanin-concentrating hormone, angiotensin-converting enzyme, pancreatic trypsin inhibitor, coagulation factor VIII, α-fetoprotein, α-lactalbumin, senogelin II, kappa casein, glucagon, thy-rotropin beta chain, transcobalamin II, thrombospondin 1, parathyroid hormone, vasopressin copeptin, tissue factor, motilin, MPIF-1, kininogen, neuroendocrine convertase 2, stem cell factor procollagen α1 chain, plasma kallikrein keratinocyte growth factor, as well as any other secreted hormone, growth factor, cytokine, enzyme, coagulation fac-tor, milk protein, immunoglobulin chain, and the like.

In other particular embodiments, the secretory signal sequence is derived in part or in whole from a secreted polypeptide that is produced by liver cells.

In some embodiments of the disclosure, the total size of the gene expression cassette comprising the isolated nucleic acid molecule is less than about 5.0, 4.8, 4.7, 4.6, 4.5, 4.3, 4.2, 4.0, 3.8, 3.7, 3.6, 3.5, 3.2, 3.0, 2.8, 2.5, 2.2, 2.0, or 1.8 kb in length. A gene expression cassette can comprise, for example, one or more promoters, an isolated nucleic acid molecule comprising a nucleic acid sequence encoding a microbial polypeptide, and a polyadenylation sequence (poly A sequence). Relatively small gene expression cas-settes can be particularly advantageous for delivery by, e.g., AAV vectors.

In some embodiments, the vector comprising an isolated nucleic acid molecule comprising a nucleic acid sequence encoding a microbial polypeptide having fewer than about 4.0 kilobases (e.g., about 0.5, 1.0, 1.5, 2.0, 2.2, 2.4, 2.6, 2.8, 3.0, 3.2, 3.4, 3.6, 3.8, or 3.9 kbs), wherein a counterpart human nucleic acid sequence has a coding sequence that is greater than about 4.0 kilobases (e.g., 4.1, 4.2, 4.4, 4.6, 4.8, 5.0, 5.5, 6.0, 6.5, or 7.0 kbs), and wherein the nucleic acid sequence encoding the microbial polypeptide is codon-optimized for expression in a human cell. A counterpart human nucleic acid sequence of a microbial nucleic acid sequence refers to a human nucleic acid sequence that encodes a polypeptide that has the same or similar catalytic function as a polypeptide encoded by a microbial nucleic acid sequence (e.g., a human nucleic acid sequence encoding a GDE capable of degrading glycogen is a counterpart of a microbial nucleic acid sequence encoding an enzyme capable of degrading glycogen).

Another aspect of the present disclosure provides an isolated cell comprising a vector comprising a codon-opti-mized microbial polypeptide for degrading glycogen.

Gene Therapy Methods, Pharmaceutical Formulations, and Modes of Administration

Another aspect of the present disclosure provides a phar-maceutical formulation comprising the microbial polypep-tide for degrading glycogen. In some embodiments, the present disclosure provides a pharmaceutical composition comprising an isolated nucleic acid or vector of the disclo-sure in a pharmaceutically-acceptable carrier and, option-ally, other medicinal agents, pharmaceutical agents, carriers, adjuvants, dispersing agents, diluents, and the like. For injection, the carrier will typically be a liquid, such as sterile pyrogen-free water, pyrogen-free phosphate-buffered saline solution, bacteriostatic water, or Cremophor EL® (BASF, Parsippany, N.J.). For other methods of administration, the carrier can be either solid or liquid.

By "pharmaceutically acceptable" it is meant a material that is not biologically or otherwise undesirable, i.e., the material can be administered to a subject along with the isolated nucleic acid or vector without causing any undesir-able biological effects such as toxicity. Thus, such a phar-maceutical composition can be used, for example, in trans-fection of a cell ex vivo or in administering an isolated nucleic acid or vector directly to a subject.

In the case of a viral vector, virus particles can be contacted with the cells at the appropriate multiplicity of infection according to standard transduction methods appro-priate for the particular target cells. Titers of virus to administer can vary, depending upon the target cell type and the particular virus vector, and can be determined by those of skill in the art. Typically, at least about $10^3$ virus particles, at least about $10^5$ particles, at least about $10^7$ particles, at least about $10^9$ particles, at least about $10^{11}$ particles, or at least about $10^{12}$ particles are administered to the cell. In exemplary embodiments, about $10^7$ to about $10^{15}$ particles, about $10^7$ to about $10^{13}$ particles, about $10^8$ to about $10^2$ particles, about $10^{10}$ to about $10^{15}$ particles, about $10^{11}$ to about $10^{15}$ particles, about $10^{12}$ to about $10^{14}$ particles, or about $10^{12}$ to about $10^{13}$ particles are administered.

The cell to be administered the vectors of the disclosure can be of any type, including but not limited to neuronal cells (including cells of the peripheral and central nervous systems), retinal cells, epithelial cells (including dermal, gut, respiratory, bladder, pulmonary, peritoneal and breast tissue epithelium), muscle (including cardiac, smooth muscle, including pulmonary smooth muscle cells, skeletal muscle, and diaphragm muscle), pancreatic cells (including islet cells), kidney cells, hepatic cells (including parenchyma), cells of the intestine, fibroblasts (e.g., skin fibroblasts such as human skin fibroblasts), fibroblast-derived cells, endothe-lial cells, intestinal cells, germ cells, lung cells (including bronchial cells and alveolar cells), prostate cells, stem cells, progenitor cells, dendritic cells, and the like. Alternatively, the cell is a cancer cell (including tumor cells). Moreover, the cells can be from any species of origin, as indicated above.

Another aspect of the present disclosure provides a method of treating a deficiency of a polypeptide for degrad-ing glycogen in a subject, comprising administering to the subject a therapeutically effective amount of an isolated nucleic acid encoding a microbial polypeptide for degrading glycogen, a vector comprising an isolated nucleic acid encoding a microbial polypeptide for degrading glycogen or pharmaceutical composition comprising an isolated nucleic acid encoding a microbial polypeptide for degrading glyco-gen. The subject can be suffering from a GSD (e.g., GSD III).

Administration of the nucleic acid or delivery vectors of the present disclosure to a human subject or an animal can be by any means known in the art. The subject can be a mammalian subject, more particularly a human subject. In other embodiments, the subject is in need of treatment, for example, has been diagnosed with or is suspected of having a deficiency of a polypeptide for degrading glycogen.

Dosages will depend upon the mode of administration, the severity of the disease or condition to be treated, the individual subject's condition, the particular vector, and the gene to be delivered, and can be determined in a routine manner. In some embodiments, the isolated nucleic acid molecule or vector is administered to the subject in a therapeutically effective amount, as that term is defined above.

With respect to viral vectors, at least about $10^3$ virus particles, at least about $10^5$ virus particles, at least about $10^7$ virus particles, at least about $10^9$, at least about $10^{11}$ virus particles, or at least about $10^{12}$ virus particles are administered to the subject per treatment. Exemplary doses are virus titers of about $10^7$ to about $10^{15}$ particles, about $10^7$ to about $10^{14}$ particles, about $10^8$ to about $10^{13}$ particles, about $10^{10}$ to about $10^{15}$ particles, about $10^{11}$ to about $10^{15}$ particles, about $10^{12}$ to about $10^{14}$ particles, or about $10^{12}$ to about $10^{13}$ particles.

In some embodiments, more than one administration (e.g., two, three, four, or more administrations) can be employed to achieve therapeutic levels of nucleic acid expression. In some embodiments, more than one administration of the same vector can be employed to achieve the durability of therapeutic levels of nucleic acid expression (e.g., two, three, or four administrations of an AAV-LSP-Pull vector).

In other embodiments, more than one administration of a different vector can be employed to achieve therapeutic levels of nucleic acid expression in different affected tissues (e.g., administration of an AAV-CB-Pull vector and administration of an AAV-LSP-Pull vector). Administration of more than one different types of vectors can include, for example, vectors of the same serotype carrying different elements (e.g., administration of an AAV9-CB-Pull vector and administration of an AAV9-LSP-Pull vector) or vectors of different serotypes carrying different elements (e.g., administration of an AAV9-CB-Pull vector and administration of an AAV8-LSP-Pull vector). Administration of more than one different vector can also refer to administering, for example, and AAV vector and an Ad vector carrying similar or different elements.

More than one administration can be co-administering more than one vector at the same time or administering one vector and then subsequently administering two, three, four, or more vectors at a time period of minutes, hours, days, weeks, or months after the initial administration.

In some embodiments, tissue-restricted gene expression using a single or a tandem tissue-specific promoter can prevent, reduce, or suppress bacterial enzyme induced immune responses towards gene therapy. The term "immune response" as used herein refers to host immunity (cytotoxic T cell and/or antibody mediated immune responses) during gene therapy against transgene expression and/or viral vectors (e.g., AAV). In other embodiments, an immune response to the gene therapy approaches described herein can be prevented, reduced, or suppressed by administering an immunosuppressive agent instead of relying on tissue-restricted gene expression. An immunosuppressive agent can include, but is not limited to, agents acting on B cells, T cells, plasma cells. Examples are proteasome inhibitors (e.g., bortezomib, carfilzomib, Ixazomib), corticosteroids (e.g., hydrocortisone, cortisone, ethamethasoneb, prednisone, prednisolone, triamcinolone, dexamethasone, fludrocortisone, bethamethasone, triamcinolone, methylprednisolone), Janus kinase inhibitors (e.g., ruxolitinib, tofacitinib, oclacitinib, baricitinib), calcinerurin inhibitors (e.g., cyclosporine, tacrolimus), mTOR inhibitors (e.g., rapamycin sirolimus, temsirolimus, everolimus, ridaforolimus), inosine monophosphate dehydrogenase (IMDH) inhibitors (e.g., mycophenolic acid), methotrexate, biologic drugs (e.g., etanercept), or monoclonal antibodies (e.g., rituximab, adalimumab, infliximab, efalizumab). In some embodiments, more than one immunosuppressive agent can be administered in combination with gene therapy.

In other embodiments, an immune response to the gene therapy approaches described herein can be prevented, reduced, or suppressed by performing plasmapheresis in combination with or as an alternative to administering one or more immunosuppressive agents. Plasmapheresis is a procedure that can remove harmful antibodies from the blood.

In other embodiments, an immune response to the gene therapy approaches described herein can be prevented, reduced, or suppressed by utilizing vectors that express a therapeutic enzyme under the control of an immunotolerant dual promoter (e.g., the LSP-CB dual promoter).

In some embodiments, the gene therapy methods described herein can be enhanced by administering an inhibitor of glycogen synthase in combination with a nucleic acid or delivery vector of the present disclosure. In humans, glycogen synthase 1 (encoded by the GYS1 gene) regulates glycogen/glucose levels in the muscle and other tissues and glycogen synthase 2 (encoded by the GYS2 gene) regulates glycogen/glucose levels in the liver. Glycogen synthase inhibitors include, but are not limited to, small molecule drugs or RNA interference (RNAi) polynucleotides (e.g., double stranded RNA (dsRNA), antisense oligonucleotides (ASO), small interfering RNA (siRNA), short hairpin RNA (shRNA), microRNA (miRNAs) oligonucleotides, and aptamers, and the like, as described by Pursell, N. et al. (2018) *Molecular Therapy* 26(7):1771-1782)).

Modes of administration include oral, rectal, transmucosal, topical, transdermal, inhalation, parenteral, e.g., intravenous, subcutaneous, intradermal, intramuscular (i.e., administration to cardiac, skeletal, diaphragm and/or smooth muscle), and intraarticular administration, and the like, as well as direct tissue (e.g., muscle) or organ injection (e.g., into the liver, into the brain for delivery to the central nervous system), alternatively, intrathecal, direct intramuscular (e.g., into cardiac, skeletal, or diaphragm muscle), intraventricular, intravenous, intraperitoneal, intranasal, or intraocular. Additional modes of administration can include intraarterially, intraperitoneally, or directly into utero. Administration to the liver (discussed below) is another representative mode of administration.

Injectables can be prepared in conventional forms, either as liquid solutions or suspensions, solid forms suitable for solution or suspension in liquid prior to injection, or as emulsions. An injection medium will typically be an aqueous liquid that contains the additives usual for injection solutions, such as stabilizing agents, salts or saline, and/or buffers.

In some embodiments, the isolated nucleic acid molecule or vector is delivered to the liver of the subject. Administration to the liver can be achieved by any method known in the art, including, but not limited to intravenous administration, intraportal administration, intrabiliary administration, intra-arterial administration, injection into the liver parenchyma, and intrasplenic injection.

Intramuscular delivery and intracardiac delivery to skeletal muscle or cardiac muscle, respectively, or direct injection into diaphragm muscle can be used. In other particular embodiments, intraperitoneal administration is used to deliver the isolated nucleic acid or vector to diaphragm muscle.

In particular embodiments, the isolated nucleic acid molecule (e.g., carried by an Ad, AAV or hybrid Ad/AAV vector) encoding a microbial polypeptide for degrading glycogen is introduced into a depot organ or tissue (e.g., liver, skeletal muscle, lung) and the polypeptide is expressed therein and secreted into the circulatory system, where it is optionally delivered to other target tissues, in a therapeutically effective amount. Intramuscular delivery to skeletal muscle or delivery to the liver is illustrative for the practice of this embodiment of the disclosure. Alternatively, the isolated nucleic acid or vector can be administered to the brain (e.g., to treat MPS disorders such as Sly disease), where the polypeptide can be expressed and secreted by transformed or transduced cells (e.g., neurons, glial cells) and taken up by other brain cells.

Certain aspects of the disclosure are now explained further via the following non-limiting examples.

EXAMPLES

Materials and Methods for Examples 1-6

AAV Vector Construction and AAV Viral Vector Preparation:

A 2.2 kb codon optimized coding sequence (SEQ ID NO:03) for Pullulanase was synthesized at GenScript (Piscataway, N.J.) and cloned into an AAV vector (AAV-CBhGAA) (Sun, B. D. et al. (2003) *Mol. Ther.* 7(2):193-201) containing a CMV enhanced chicken beta-actin hybrid (CB) promoter to replace the human GAA cDNA, to generate the AAV-CB-Pull vector. The ScaI-KpnI fragment containing the liver-specific promoter (LSP) from the AAV-LSPhGAA vector (Franco, L. M. et al., (2005) *Mol. Ther.* 12(5):876-84) was cloned into the AAV-CB-Pull vector to replace the CB promoter, to generate the AAV-LSP-Pull vector. To generate the pAAV-MHCK7-Pull vector plasmid, the MHCK7 promoter was amplified from the AAV-MHCK7hGAApA vector (Sun, B., et al. (2008) Mol Ther, 16(8):1366-71) using primers: XbaI-MHCK7-F (5'-cccct-taagagctgcatgtctaagctagaccc-3') (SEQ ID NO: 33) and KpnI-MHCK7-R (5'-cggggtacccgctggctggctcctgagt-3') (SEQ ID NO: 34). The amplified PCR fragment was digested with XbaI and KpnI and then cloned into the pAAV-LSP-Pull vector to replace the LSP promoter. To generate the pAAV-LSP-CB-Pull vector plasmid containing the LSP-CB dual promoter, the LSP promoter was amplified from the pAAV-LSP-hGAA vector (Franco, L. M., et al. (2005) Mol Ther., 12(5):876-84) using primers: XbaI-LSP-F (5'-AGTTCTAGAGCGGCCGCCAG-3') (SEQ ID NO: 35) and AflIII-LSP-R (5'-CCCCTTAAGCCATTTTTATAG-CATGTCCTGTATTGCAAAACTA-3') (SEQ ID NO: 36); the CB promoter was amplified from the pAAV-CB-Pull vector using primers AflIII-CB-F (5'-CCCCT-TAAGGTTCCGCGTTACATAACTTACGGTAAAT-3') (SEQ ID NO: 37) and KpnI-CB-R (5'-GTCGACGGTACCGCGCAG-3') (SEQ ID NO: 38). The amplified XbaI-LSP-AflIII and AflIII-CB-KpnI fragments were ligated through the AflIII site and amplified again using primers: XbaI-LSP-F and KpnI-CB-R (see above). The amplified XbaI-LSP-CB-KpnI fragment was purified and cloned into the pAAV-LSP-Pull vector at XbaI and KpnI sites to replace the LSP promoter region. The LSP-CB dual promoter (SEQ ID NO:30) described in the Examples is a α1-microglobulin/bikunin enhancer/thyroid hormone-binding globulin promoter (SEQ ID NO:31) and a CMV enhancer/beta-actin (CB) promoter (SEQ ID NO:32).

These AAV vectors were packaged as AAV8 or AAV9 in HEK 293T cells using standard phosphate-mediated transfection and purified using iodixanol gradient ultracentrifugation (Sun, B., et al. (2008) *Mol. Ther.,* 16(8):1366-71; Hermens, W. T., et al. (1999) *Hum Gene Ther,* 10(11):1885-91; Lock, M. et al., (2010) *Human Gene Therapy,* 21(10):

1259-1271). The titer of the viral stock was determined using purified viral DNA and southern blotting with a biotin-labeled probe generated with Prime-A-Gene labeling kit (Promega, Madison, Wis.). All viral vector stocks were handled according to the Biohazard Safety Level 2 guidelines published by the National Institutes of Health.

Animals and Virus Administration:

Animal care and experiments were conducted in accordance with Duke University Institutional Animal Care and Use Committee-approved guidelines.

AAV Copy Number Determination in Mouse Tissues by Real-Time PCR:

DNA was extracted from frozen tissues using the Wizard Genomic DNA Purification Kit (Promega, Madison, Wis.). Real-time PCR was performed using SYBR Green (Roche, Basel, Switzerland) and gene-specific primer pairs for Pullulanase (primers 5'-GCCACTGGATGCCTACAACT-3' (SEQ ID NO:26) and 5'-CGTGCTGGTGCAGTGTATTG-3' (SEQ ID NO:27); and for mouse beta-actin (internal control, primers: 5'-AGAGGGAAATCGTGCGTGAC-3' (SEQ ID NO:28) and 5'-CAATAGTGATGACCTGGCCGT-3' (SEQ ID NO:29)). The AAV-CB-Pull or AAV-LSP-Pull plasmid DNA was used to generate a standard curve for viral vector copy number calculation (Yi, H. et al., (2017) *Hum Gene Ther,* 28(3):286-294; Lim, J. A., et al। (2018) *Molecular Therapy,* 26(5):382-83).

Pullulanase Activity and Glycogen Content Assay

Frozen tissues were homogenized in distilled water (1 mg/20 μL of water) using a homogenizer, followed by sonication for 15 sec and centrifugation at 18,000 g at 4° C. for 15 min. Pullulanase activity was assayed with the tissue homogenates using the Pullulanase/Limit-Dextrinase Assay Kit (PullG6 Method) (Megazyme, Chicago, Ill.) following manufacturer's instructions.

For measuring glycogen content, the 1:5 diluted tissue lysates were boiled for 3 min (to inactivate endogenous enzymes) and incubated with 0.175 U/mL (final concentration in the reaction) of amyloglucosidase (Sigma-Aldrich Co., St. Louis, Mo.) for 90 min at 37° C. The reaction mixtures were then boiled again for 3 min to stop the reaction. 30 μL of the mixtures were incubated with 1 mL of Pointe Scientific Glucose (Hexokinase) Liquid Reagents (Fisher, Hampton, N.H.) for at least 10 min at RT. The absorbance at 340 nm was read on a Shimadzu UV-1700 PharmaSpec UV-VIS Spectrophotometer. Protein concentration was determined by BCA assay and used to normalize the data (Yi, H. et al., (2017) *Hum Gene Ther,* 28(3):286-294).

Histology:

Fresh tissues were fixed in 10% neutral-buffered formalin (NBF) for 48 h. After primary immersion fixation, the samples were post-fixed with 1% periodic acid (PA) in 10% NBF for 48 h at 4° C. The samples were then washed with PBS, dehydrated with ascending grades of alcohol, cleared with xylene, and infiltrated with paraffin. For Periodic acid-Schiff (PAS) staining, sections of paraffin-embedded tissues were processed and stained using Schiff reagent as described (Lim, J. A., et al. (2018) Mol Ther., 26(5):382-83). Briefly, the slides were oxidized with freshly made 0.5% PA for 5 min and rinsed with distilled water for 1 min. The slides were then stained with Schiff reagent for 15 min and washed with tap water for 10 min. The slides were counterstained with Hematoxylin and rinsed with tap water, incubated with bluing reagent for 1 min, dehydrated, and mounted. For trichrome staining, the paraffin-embedded liver sections were processed and stained using Masson's trichrome staining kit (Sigma-Aldrich Co., St. Louis, Mo.)

following the manufacturer's protocol. The images were taken on a BZ-X710 microscope (Keyence America, Itasca, Ill.).

Immunohistochemistry for Detection of Cytotoxic T Cells:

Sections of the paraffin-embedded liver were deparaffinized and rehydrated. The antigen retrieval was by heat mediation using citrate buffer (pH 6.0). Then, the slides were incubated in 10% normal goat serum with 1% BSA in TBS for 2 hours at room temperature. The anti-CD4 or anti-CD8a monoclonal antibody (Abcam, Cambridge, Mass.) was diluted in TBS with 1% BSA and incubated overnight at 4° C. And then, the samples were washed with TBS containing 0.025% Triton X-100 and incubated in 0.3% $H_2O_2$ in TBS for 15 minutes. The HRP-conjugated secondary antibody was diluted in TBS with 1% BSA and incubated for 1 hour at room temperature. The samples were washed and developed using SignalStain DAB substrate kit (Cell Signaling Technology, Danvers, Mass.) (Sun, B. et al., (2005) *Mol Ther,* 11(6):889-98).

Western Blot:

Frozen tissues were homogenized on ice in RIPA buffer [PBS containing 1% NP40, 0.5% sodium deoxycholate, 0.1% SDS and a protease/phosphatase inhibitor cocktail (Cell Signaling Technology, Danvers, Mass.)] using a glass homogenizer. Lysates were cleared by centrifugation at 18,000 g at 4° C. for 15 minutes. The protein concentration of the supernatants was measured using the BCA assay. Equal amounts of protein were run on SDS-PAGE gels and transferred to nitrocellulose membrane. The membranes were blocked in 3% BSA/PBST, incubated with primary antibodies overnight at 4° C., washed, incubated with secondary antibodies, washed again, and developed using ECL kit (Bio-rad, Hercules, Calif.). The images were obtained by the image analyzer (Bio-rad, Hercules, Calif.). The following primary antibodies were used: rabbit anti AGL (Abcam, ab71423) and mouse anti β-actin-HRP (Sigma-Aldrich, A3854).

Plasma Enzyme Activity Measurement:

Plasma ALT, AST, and CK enzyme activities were assessed using the Liquid ALT Reagent Set, Liquid AST Reagent Set, and Creatinine Reagent Set (Pointe Scientific) per the manufacturer's protocol.

Determination of Urinary Glc4 Concentration:

Urinary Glc4 concentration was determined by stable isotope-dilution electrospray tandem mass spectrometry as previously described (Young, S. P. et al. (2003) *Biochem,* 316(2):175-80).

Accelerating Rotarod Test:

Mice were trained on a rotarod (ENV-577M, Med Associates Inc, Fairfax, Vt.) by first allowing them to stay for 3 minutes on the drum which was rotating at a constant speed of four rotations per minute (waiting mode). Mice were then trained twice on a gradually accelerating rotarod (4.0-40 rpm). Trained mice were then tested during three sessions using accelerating rotarod protocol, and the latency to fall was recorded. This routine provided at least 5 minutes of rest between the sessions (Lim, J. A., et al. (2018) Mol Ther., 26(5):382-83).

Wire-Hang Test:

Mice are placed on a ¼" mesh wire screen with either 2 or 4 limbs. Then the screen is inverted 8" above a mouse cage cushioned with bedding, and the time until the mouse drops off is recorded (Zhang, P., et al., (2012) *Hum Gene Ther,* 23(5):460-72).

Treadmill Fatigue Testing:

Treadmill testing will be performed every 1 to 2 months on a treadmill device (model LE 8709, Panlab, Spain)

according to manufacturer's instructions. Running speed can be adjusted from ~5 to 150 m/min, and the running surface can be inclined from −25° to +25° above horizontal in 5° increments depending on the mouse strain. A stimulus can be created using the electrical shock grids, and grids can be enabled or disabled individually for each lane. The testing protocol include 3 steps: Acclimation, Warm-up, and Exhaustion exercise. The test will be ended when the mouse sits on the shock grid consecutive 5 seconds on the shock grid without attempting to reengage the treadmill (Knab, A. M., et al. (2009) *Physiol Behav,* 98(4):433-40).

Statistics:

Statistical significance was determined by unpaired two-tailed Student's t-test using Prism software (GraphPad, La Jolla, Calif.); data are presented as mean±standard deviation (SD). *P<0.05 was considered statistically significant. * indicate P-values <0.05;  indicate P-values <0.01; * indicate P-values <0.001; **** indicate P-values <0.0001.

Example 1: Generation of a Mouse Model of GSD IIIa

Figure 2:
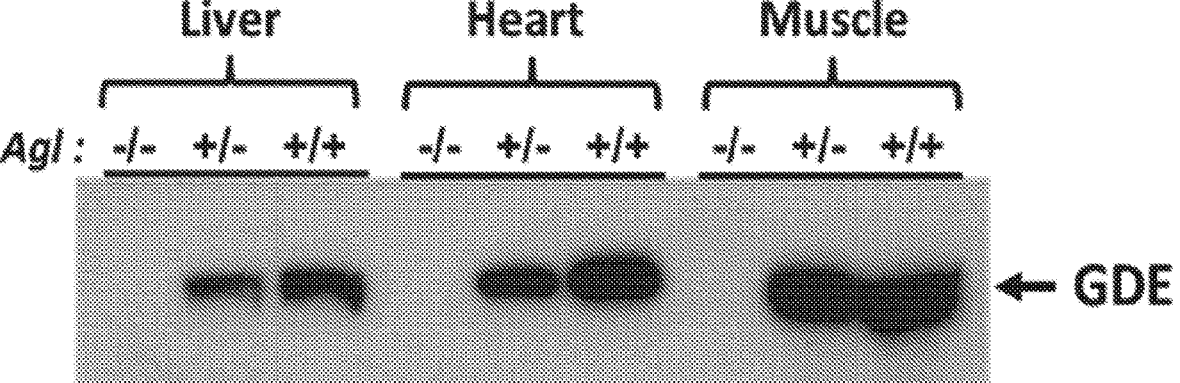
FIG. 2 illustrates Western blotting with an anti-mouse GDE antibody showing the absence of GDE protein in tissues of the homozygous Agl$^{-/-}$ mice. Data are presented as mean±SD; n=6 for each point.
Figure 3:
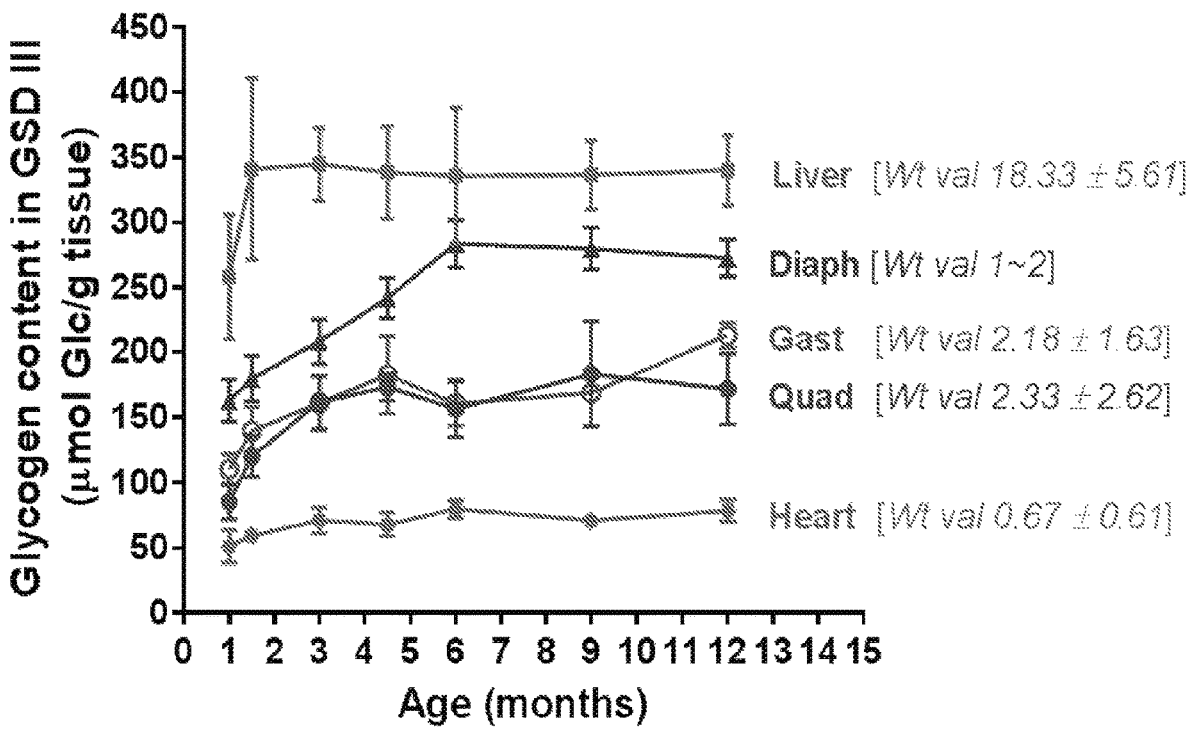
FIG. 3 illustrates patterns of glycogen accumulation in tissues of GSD IIIa mice with age. Wild-type (Wt) values were indicated. Diaph, diaphragm; Gast, gastrocnemius; Quad, quadriceps. Data are presented as mean±SD; n=6 for each point.

Heterozygous Agl mutant mice ($Agl^{Tm1a}$) in the C57BL/6N background that carry a mutant Agl allele (FIG. 1A) were purchased form the European Mouse Mutant Archive (EMMA) and crossed with the CMV-Cre mice (the Jackson Laboratory), to convert the mutant Agl allele into a knockout allele by deleting the exons 6-10 and the neo expression cassette (FIG. 1B). The resulting $Agl^{+/-}$ mice were interbred to generate homozygous $Agl^{-/-}$ mice. $Agl^{-/-}$ mice were used as breeders to produce Agl-KO mice ($Agl^{-/-}$ or GSD IIIa mice in this disclosure). No GDE protein was detected in liver, heart, and skeletal tissue of the GSD IIIa mice (FIG. 2). PAS-stained tissue sections from 3-month-old GSD IIIa mice showed massive glycogen accumulation in the liver, heart, skeletal muscles (quadriceps, gastrocnemius, soleus muscle, tongue, and diaphragm) and smooth muscle (bladder), and significant amounts in the kidney and the entire region of the brain (data not shown). FIG. 3 shows the pattern of glycogen accumulation in liver, heart, and skeletal muscles of GSD IIIa mice with age. Masson Trichrome stained liver and kidney sections from 3-month-old GSD IIIa mice revealed mild fibrosis in both tissues (data not shown). Increased liver/body weight ratio (hepatomegaly), lowered blood glucose concentration (hypoglycemia), and elevated serum AST, ALT, ALP, and CK activities were consistently observed in the affected mice at different ages, when compared to the age-matched wild-type (WT) controls (data not shown). The levels of urinary Glc4, a glucose tetrasaccharide and a biomarker being used for GSD II and GSD III (Kumlien, J. et al. (1988) *Clin. Chim. Acta,* 176 (1):39-48; Young, S. P. et al. (2003) *Anal Biochem,* 316(2): 175-80; Pompe Disease Diagnostic Working, (2008) *Mol. Genet. Metab.,* 93(3):275-81; Manwaring, V. et al. (2012) *J Inherit. Metab Dis.* 35(2):311-6), were also markedly elevated in these GSD IIIa mice compared to WT controls.

The following behavioral tests were performed in WT and GSD IIIa mice at 3 and 6 months of age, to assess the functional deficits in GSD IIIa mice. Treadmill fatigue test was used to evaluate cardiac function and exercise tolerance (Knab, A. M. et al. (2009) *Physiol Behav.* 98(4):433-440) (Knab, A. M., et al. (2009) *Physiol Behav,* 98(4):433-40); four limb wire-hang test for muscle strength (Zhang, P. et al. (2012) *Hum. Gene Ther,* 23(5):460-72; Miniarikova, J. et al. (2017) *Gene Ther.* 24(10):630-639); Rota-rod test for motor coordination and balance (Sun, B. et al. (2008) *Mol Ther* 16(8):1366-71; Sun, B. et al (2005) *Mol Ther,* 11(6):889-98).a The affected GSD IIIa mice showed a remarkable reduction in treadmill and wire-hang performance and a moderate but significant (p<0.05) decrease in Rota-rod test at 6 months of age, compared with the age-matched WT (FIG. 4). No significant difference was observed in other tests between the GSD IIIa and WT mice (data not shown). Similar results were observed when mice were tested at 3 months of age (data not shown). These data indicate that the neuromuscular dysfunction in the GSD IIIa mice is likely a result of muscle damage, rather than neurological impairment despite the widespread glycogen accumulation in the brain. At a minimum, neuromuscular dysfunction in the GSD IIIa mice can be due to peripheral nerve involvement.

Notably, based on the results described above, the GSD IIIa mouse model showed symptoms of liver and skeletal muscle defects similar to human GSD IIIa patients, such a liver fibrosis, hepatomegaly, increased plasma alanine aminotransferase (ALT) activity, elevated disease urinary Glc4, and impaired muscle functions.

Example 2: Correction of Glycogen Accumulation in Liver of GSD IIIa Mice and GSD IIIa Dogs with the Liver-Targeted AAV-LSP-Pull Vector In this experiment, the feasibility of using pullulanase-based gene therapy to reduce glycogen accumulation and the effectiveness of using a tissue-restricted gene expression approach to suppress pullulanase-induced cellular immune responses in GSD IIIa mice was tested. Ten-week-old GSD IIIa mice were intravenously injected with the AAV-CB-Pull or the AAV-LSP-Pull vector (both packaged as AAV9) at a dose of $5 \times 10^{12}$ vg/kg and euthanized two and seven weeks later to collect tissues and blood. Age-matched untreated (UT) GSD IIIa mice and WT mice were included as controls.

Figure 5A:
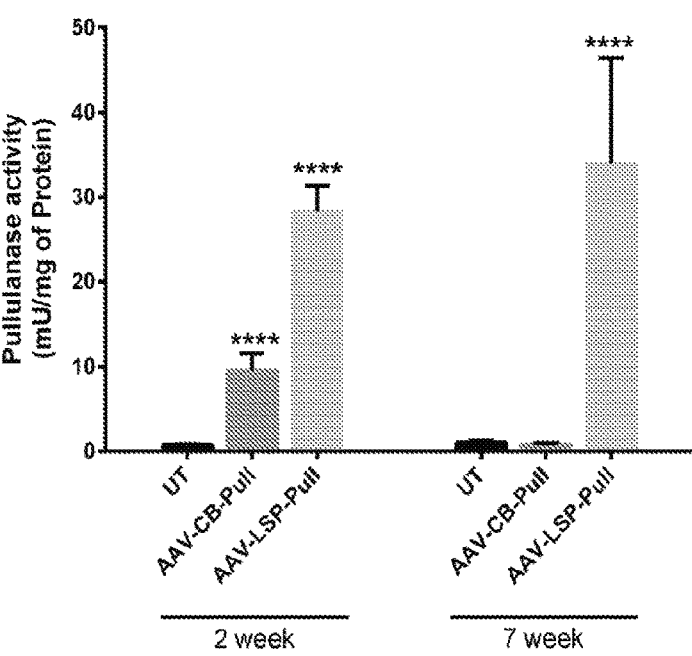
FIG. 5A-FIG. 5B show biochemical correction of glycogen storage in liver of GSD IIIa mice two or seven weeks following intravenous administration of the indicated AAV vectors.
Figure 5B:
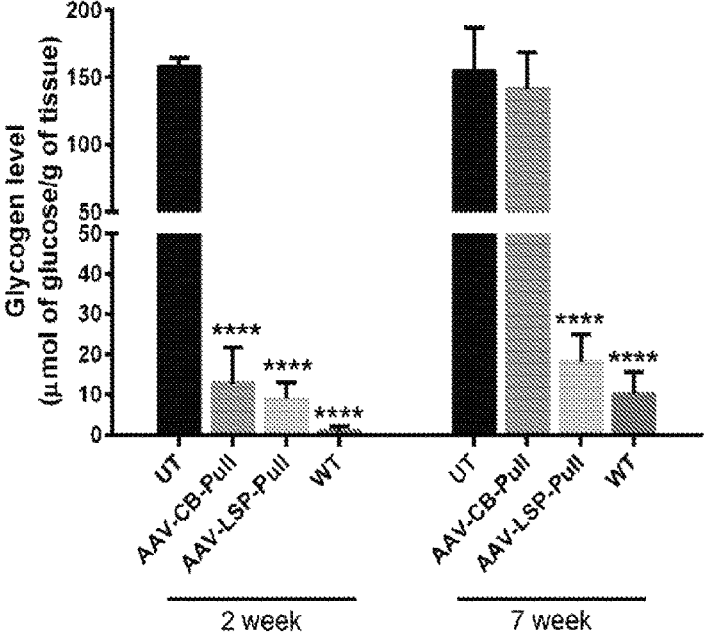
Figure 6:
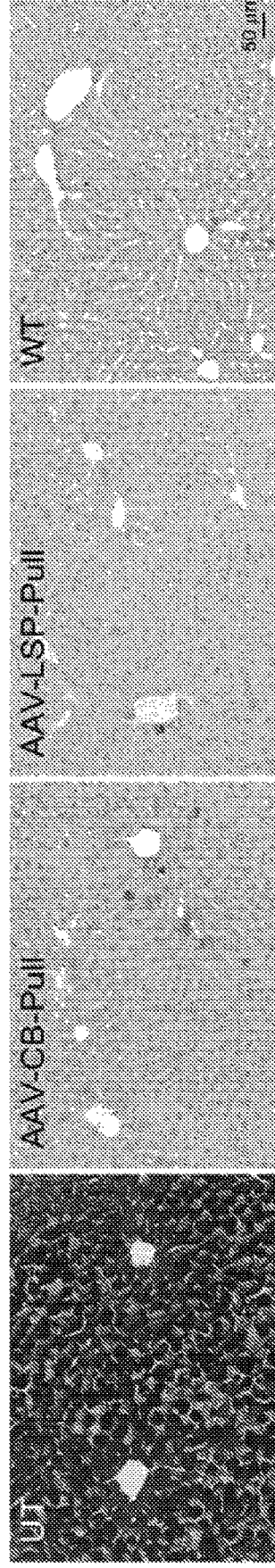
FIG. 6 shows representative PAS-stained liver sections showing clearance of glycogen storage in livers of GSD IIIa mice two weeks following AAV treatment. UT, untreated GSD IIIa mice; AAV-CB-Pull or AAV-LSP-Pull, AAV-treated GSD IIIa mice; WT, wild-type mice.
Figure 7A:
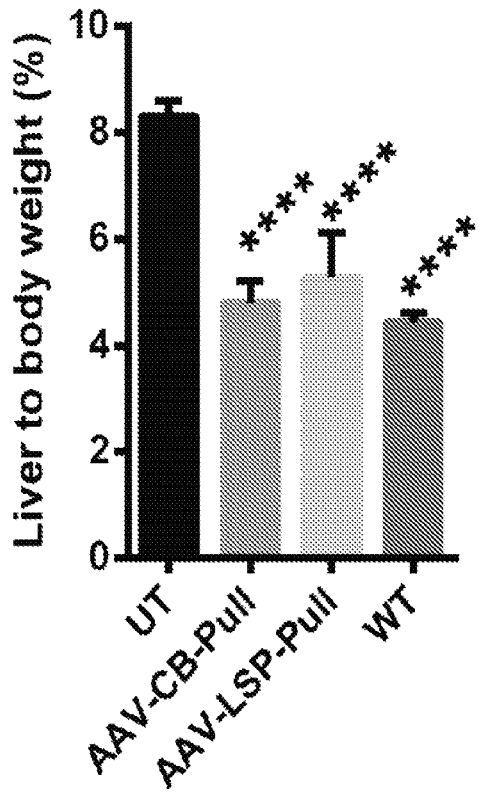
FIG. 7A-FIG. 7B illustrate correction of liver symptoms in GSD IIIa mice two weeks after AAV treatment.
Figure 7B:
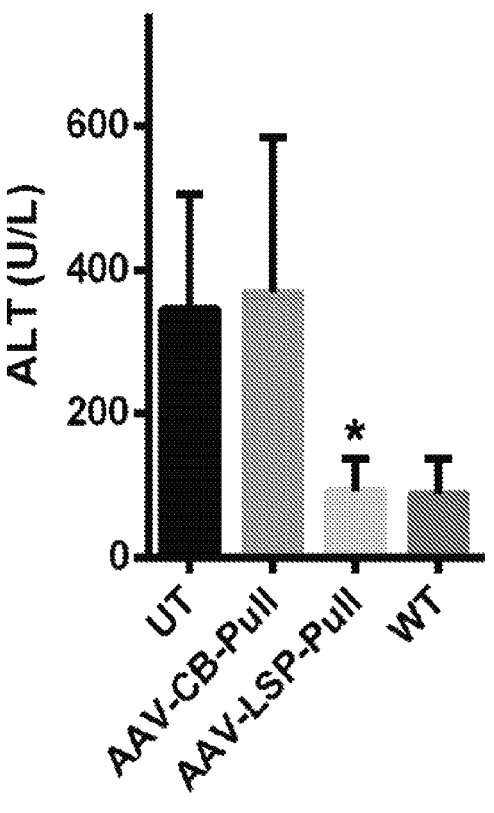
Figure 8:
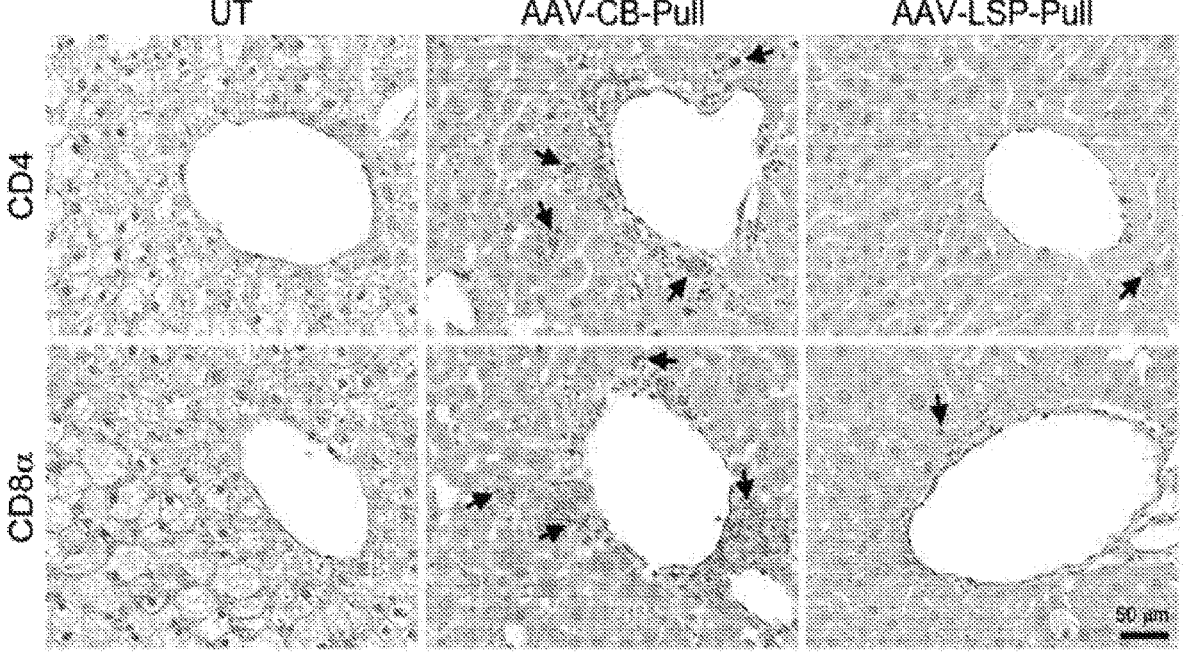
FIG. 8 shows immunohistochemical detection of CD8+ and CD4$^+$ lymphocytes in the liver of GSD IIIa mice two weeks after AAV administration. Sections of the paraffin-embedded livers from untreated (UT), AA9-CB-Pull treated, and AAV9-LSP-Pull treated GSD IIIa mice were stained with an anti-CD4 or anti-CD8α monoclonal antibody (Abcam). Foci of lymphocytes are indicated (arrows).

At two weeks after AAV injection, the AAV-LSP-Pull treatment resulted in a significantly (2-fold) higher Pullulanase activity in the liver than the AAV-CB-Pull treatment (FIG. 5A), but both treatments dramatically reduced glycogen content in the liver by >90% (FIG. 5B). Light microscopy of PAS-stained liver sections confirmed the clearance of glycogen accumulation and the restoration of normal hepatic morphology by the AAV treatments (FIG. 6). Consistent with the correction of liver glycogen, the liver/body weight ratios were reduced to the WT value by either AAV treatment (FIG. 7A) but the plasma ALT activities were decreased only in the AAV-LSP-Pull-treated mice (FIG. 7B). The lower Pullulanase activity in the liver (FIG. 5A) and the lack of the efficacy in the heart and skeletal muscle (data not shown) by the AAC-CB-Pull treatment are likely caused by the Pullulanase-induced cellular immune responses in these tissues. As expected, immunohistochemical staining of tissue sections showed multiple CD4+ and CD8+ lymphocytic infiltrates present in the AAV-CB-Pull treated liver, but barely detectable in the AAV-LSP-Pull treated liver two weeks after the AAV treatment (FIG. 8), a similar phenomenon was also observed in the heart and skeletal muscle (data not shown).

Figure 9:
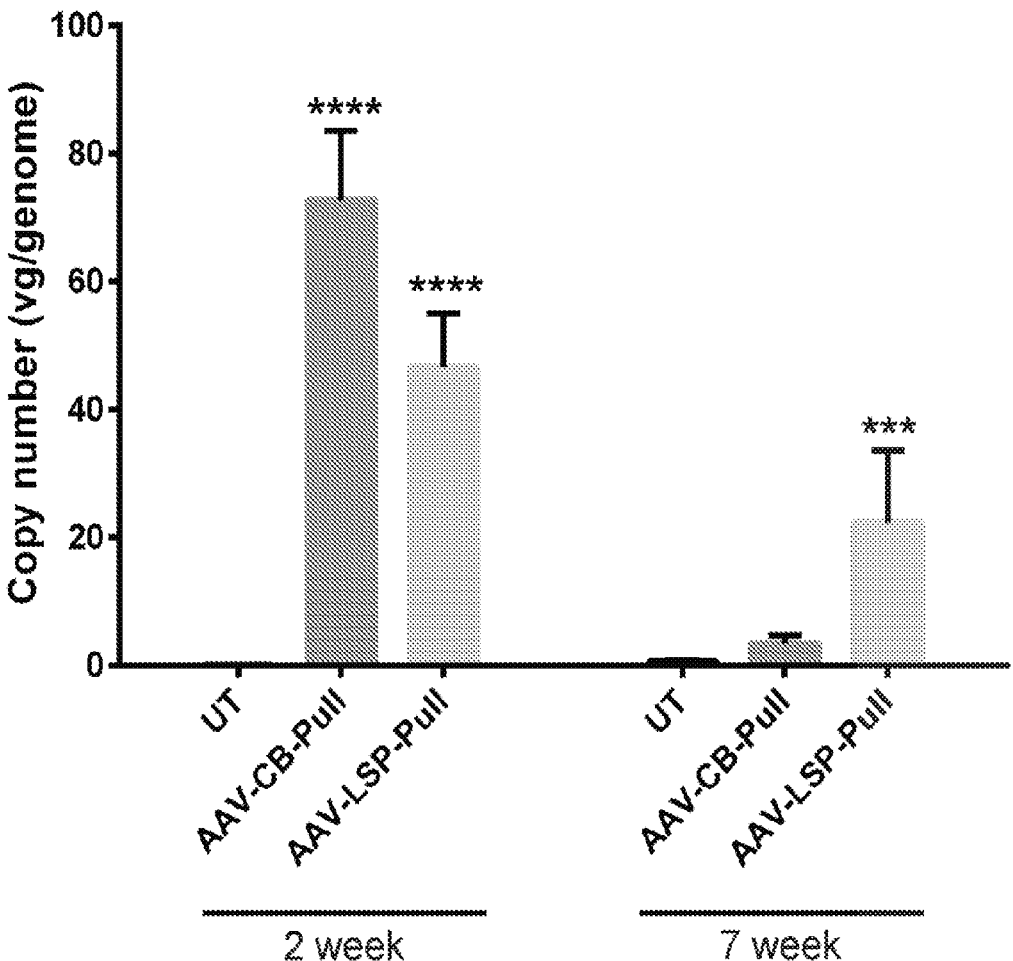
FIG. 9 illustrates AAV vector genome copy numbers in liver of GSD IIIa mice two or seven weeks after AAV treatment. UT, untreated GSD IIIa mice; AAV-CB-Pull or AAV-LSP-Pull, AAV-treated GSD IIIa mice. Data represent mean±SD. n=5 for each condition. *, p<0.001; **, p<0.0001 vs UT.
Figure 10A:
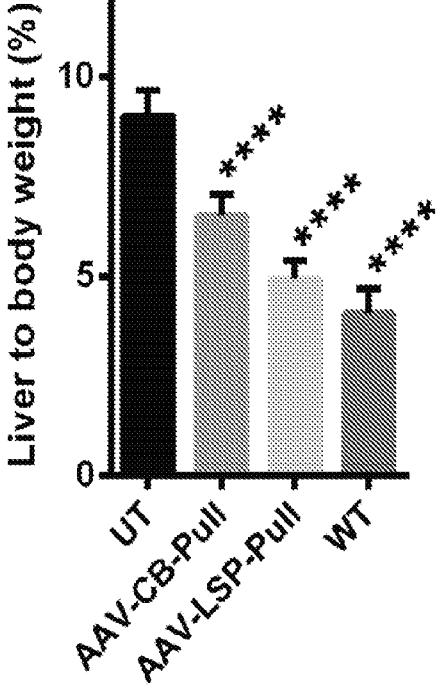
FIG. 10A-FIG. 10B illustrate the correction of liver symptoms in GSD IIIa mice seven weeks after AAV treatment.
Figure 10B:
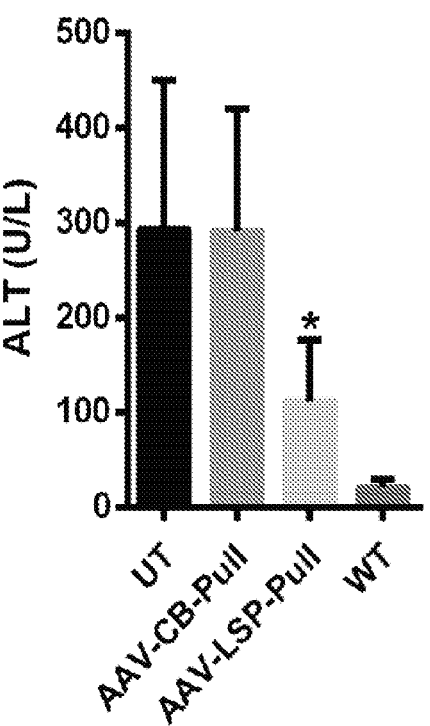
Figure 11:
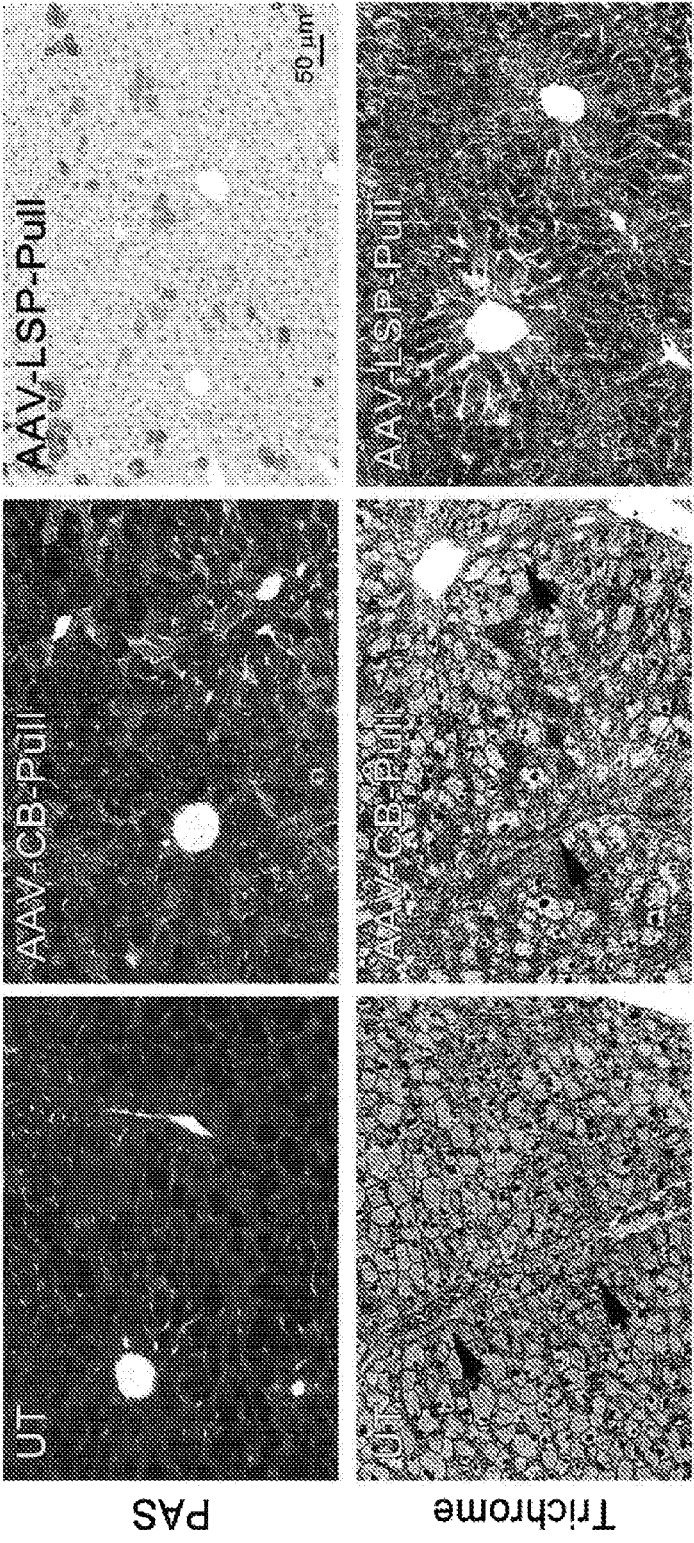
FIG. 11 shows histological correction of liver disease in GSD IIIa mice seven weeks after AAV treatment. Upper panel: PAS stained liver sections show clearance of glycogen storage by the AAV-LSP-Pull treatment. Lower panel: Trichrome stained liver sections show the absence of blue-stained fibrotic tissues (arrows) in the AAV-LSP-Pull treated liver.

At seven weeks after AAV injection, the AAV-LSP-Pull treated livers still had very high Pullulanase activities and low glycogen contents; in contrast, Pullulanase activity became undetectable and glycogen content returned to the UT level in the AAV-CB-Pull treated liver (FIG. 5A, 5B). Consistent with the enzyme activity results, AAV copy numbers were significantly lower in the AAV-CB-Pull treated livers than that in the AAV-LSP-Pull treated liver (FIG. 9). The liver/body weight ratio and plasma ALT activity in the AAC-LSP-Pull treated mice were significantly lower than those in the AAV-CB-Pull-treated or untreated mice (FIG. 10A-10B), suggesting functional improvement of liver. In addition, Trichrome-stained liver sections showed that the AAV-LSP-Pull treatment effectively prevented progression of liver fibrosis seven weeks after AAV injection (FIG. 11).

These results demonstrate that gene therapy with the liver-targeted AAV-LSP-Pull vector can effectively prevent Pullulanase-induced cytotoxic T cell immune responses and correct liver disease in GSD IIIa mice.

The efficacy of AAV-LSP-Pull treatment in correcting liver glycogen storage was further tested in a naturally occurring GSD IIIa dog model (Yi, H., et al. (2012) Dis Model Mech, 5(6):804-11; Yi, H., et al. (2014) J Mol Med (Berl), 92(6): 641-50; Brooks, E. D., et al. (2016) *Comp Med,* 66(1):41-51). Twelve-week-old GSD IIIa dogs (n=2) were intravenously injected with the AAV-LSP-Pull vector packaged as AAV9 at a dose of $3.8 \times 10^{12}$ vg/kg. Age-matched untreated (UT) GSD IIIa dogs were used as untreated controls (n=3). Two weeks after AAV treatment, liver and muscle biopsies were performed on both the AAV-treated and untreated GSD IIIa dogs following overnight fasting, to analyze the Pullulanase expression by Western blot and glycogen content in these tissues. Pre- and post-treatment radiographic imaging was done on the two treated dogs to measure the size of liver.

Figure 12A:
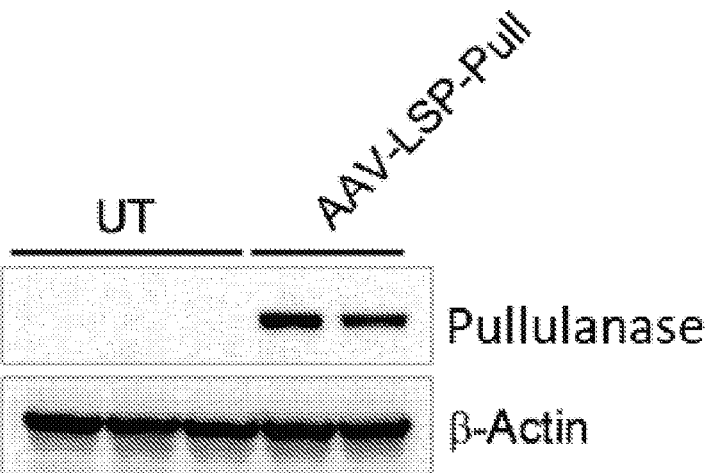
FIG. 12A-FIG. 12B show AAV9-LSP-Pull reduced glycogen contents in liver of GSD IIIa dogs two weeks after vector injection.
Figure 12B:
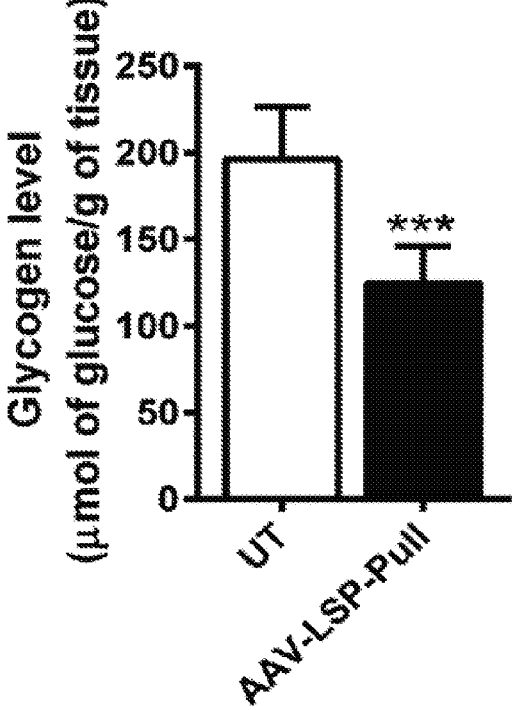
Figure 13A:
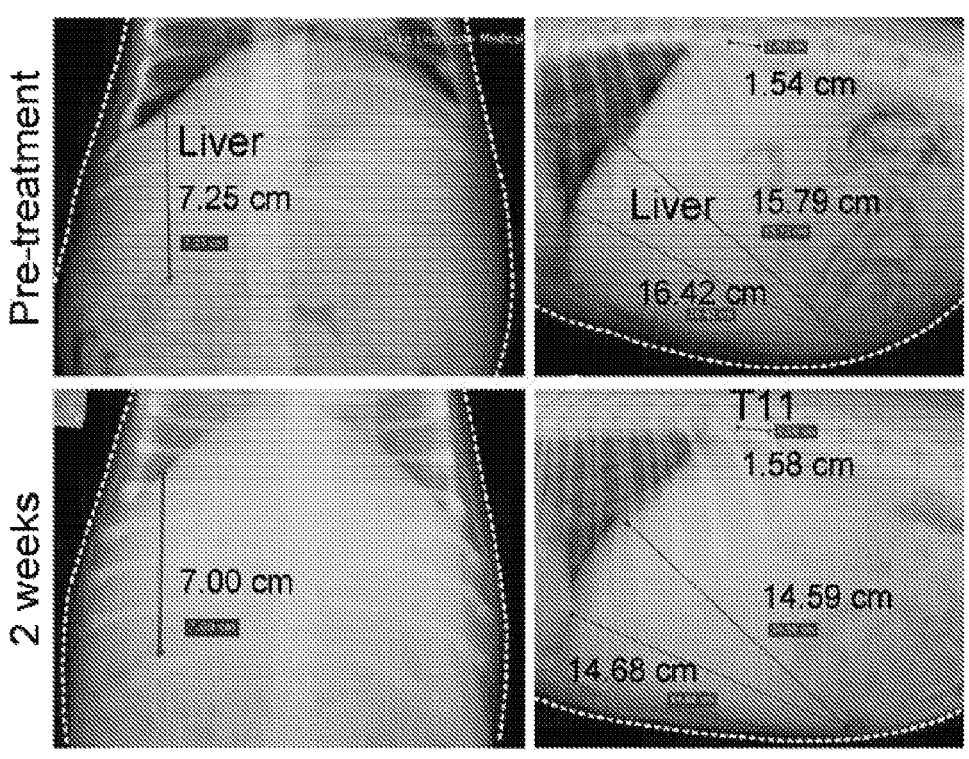
FIG. 13A-FIG. 13B show AAV9-LSP-Pull significantly reduced liver size in GSD IIIa dogs two weeks after AAV treatment.
Figure 13B:
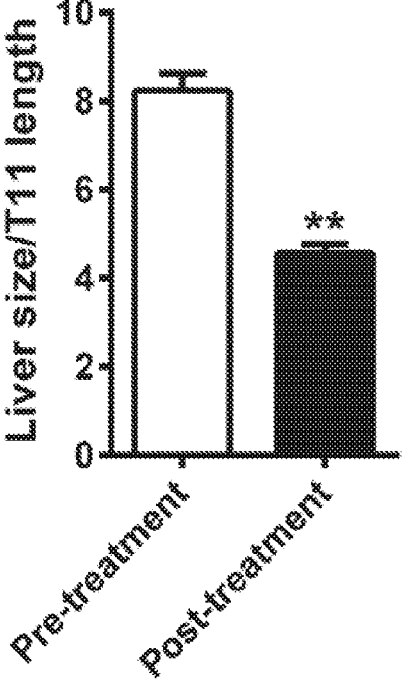

Two weeks after AAV-LSP-Pull treatment, Pullulanase expression was detected in the livers from both treated dogs (FIG. 12A); glycogen content was significantly reduced (–35%) in the AAV-treated livers compared to the UT livers (FIG. 12B). No Pullulanase expression and glycogen reduction were observed in the skeletal muscle of the AAV-treated mice (not shown). Radiographic images of GSD IIIa dogs showed abnormal shape of the abdomen (yellow dot lines) with unusual curvatures before treatment due to hepatomegaly; two weeks after gene therapy, liver size was obviously reduced and the abdomen shape became less curvature (FIG. 13A). The liver size was significantly reduced (–35%) two weeks after AAV treatment compared to that at pretreatment (FIG. 13B).

These data indicate that gene therapy with an AAV vector expressing Pullulanase is a feasible treatment approach for GSD III and the Pullulanase-induced cellular immune responses can be overcome by tissue-restricted gene expression. This liver-targeted gene therapy approach is suitable for treating GSD IIb patients (–15% of total GSD III patients) who have disease limited to the liver. For treatment of GSD IIIa patients, a supplementary therapy (muscle-directed gene therapy with the AAV-MHCK7-Pull vector) can be used to correct muscle specific symptoms along with the AAV-LSP-Pull treatment.

Figure 14A:
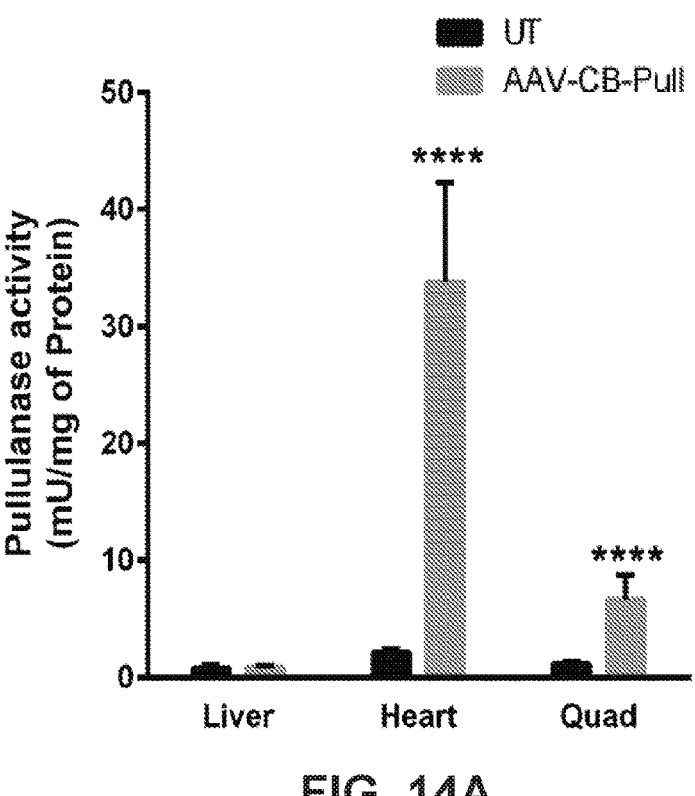
FIG. 14A-FIG. 14B show biochemical correction of glycogen storage in tissues of GSD IIIa mice ten weeks after intravenous administration of AAV vectors at two weeks of age.
Figure 14B:
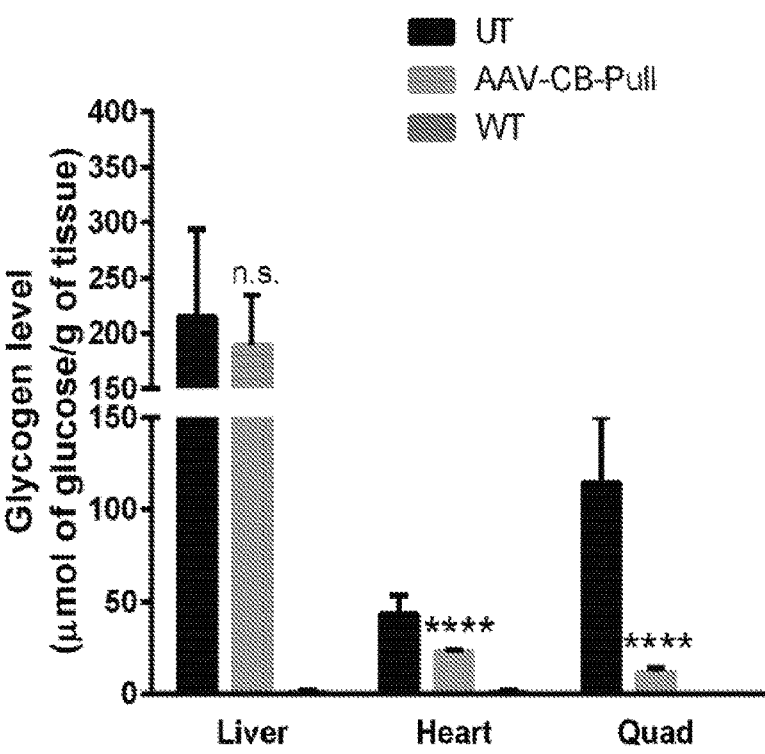
Figure 15:
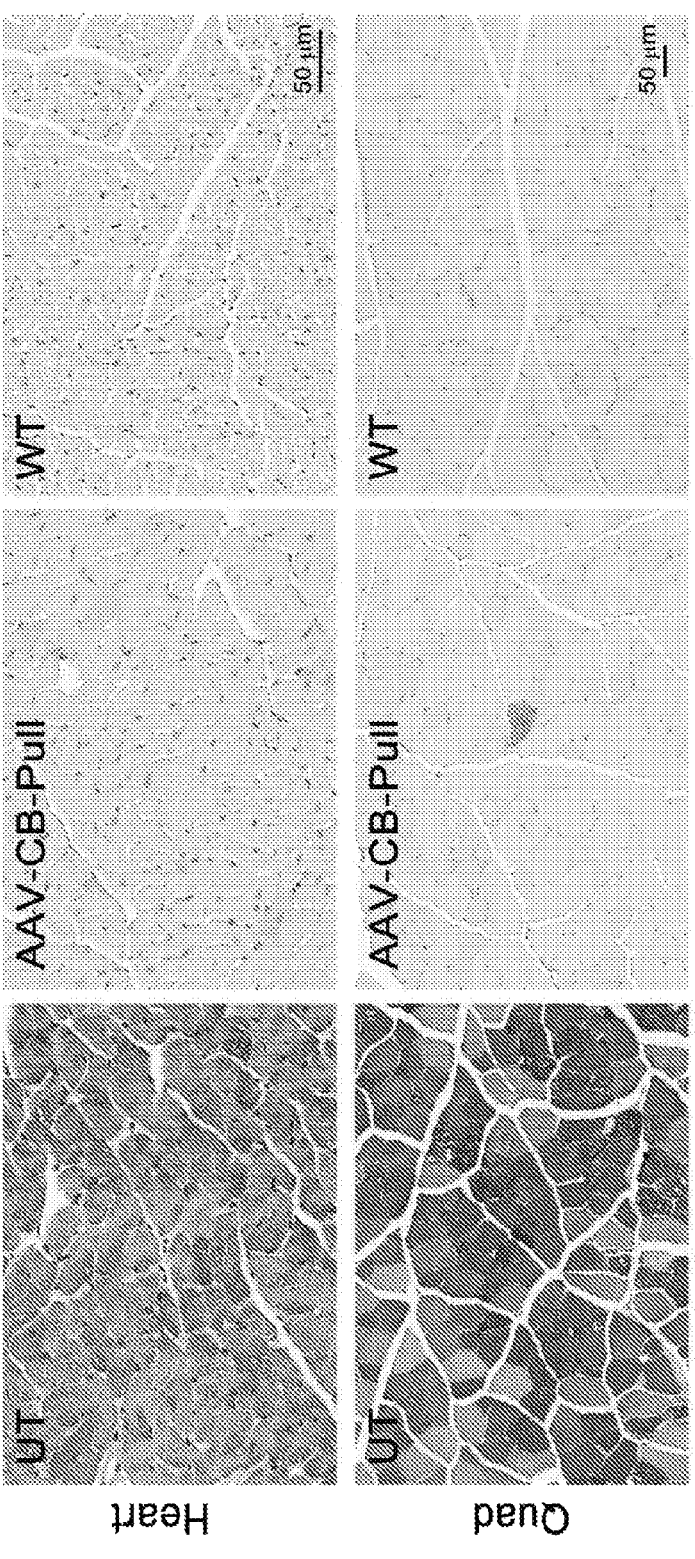
FIG. 15 shows representative PAS-stained tissue sections showing clearance of glycogen storage in the heart and skeletal muscle of GSD IIIa mice ten weeks following AAV administration at two weeks of age. UT, untreated GSD IIIa mice; AAV-CB-Pull, AAV-treated GSD IIIa mice; WT, wild-type mice; Quad, quadriceps.
Figure 16C:
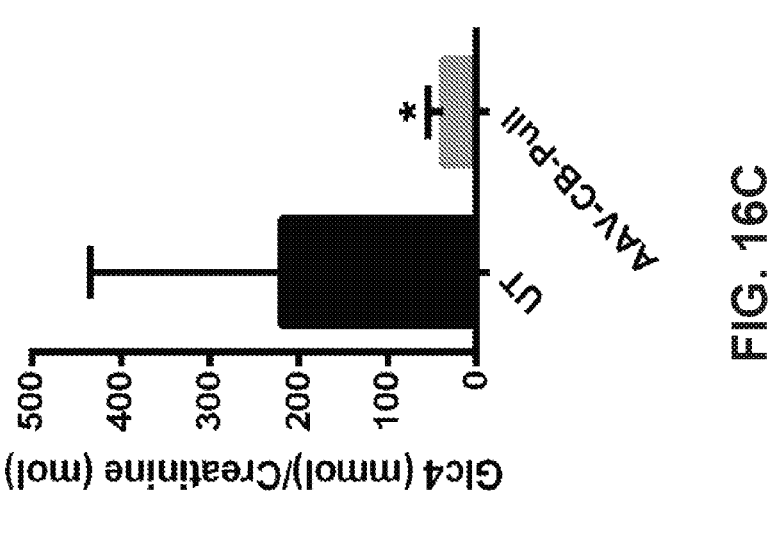
FIG. 16A-FIG. 16C show the effect of AAV-CB-Pull treatment on plasma enzyme activities and urinary Glc4 levels in the GSD IIIa mice ten weeks after intravenous administration of AAV vectors at two weeks of age.
Figure 16B:
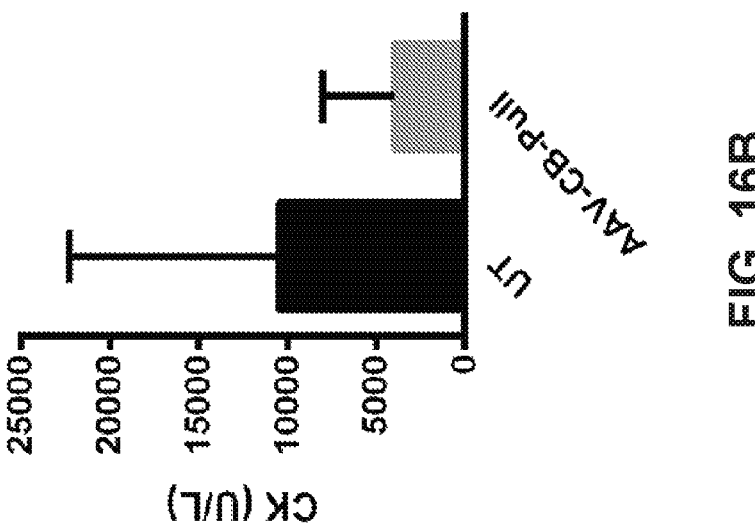
Figure 16A:
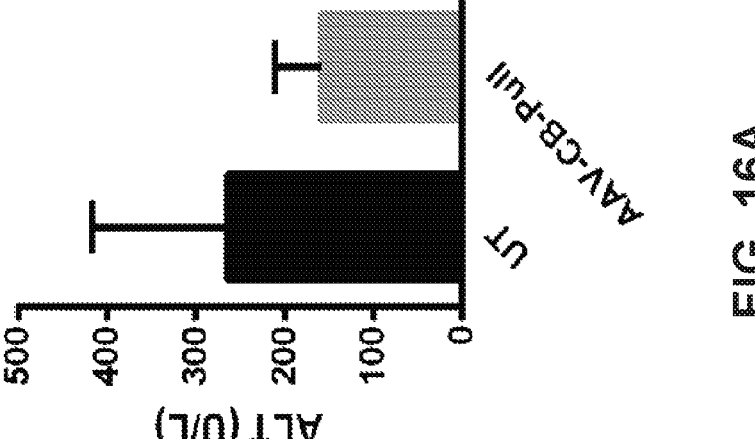

Example 3. Neonatal Gene Therapy with the AAV-CB-Pull Vector Achieved Long-Term Systemic Correction of Glycogen Storage in GSD IIIa Mice Immune response is impaired in neonatal mice during the first few weeks after birth (Ramachandran, P. S., et al. (2017) *Human Gene Ther.,* 28(2):154-167) and GSD animals often accumulate very low levels of glycogen in muscle tissues at this stage. The AAV-CB-Pull vector packaged as AAV9 was intravenously injected into 14-day-old GSD IIIa mice at a dose of $5 \times 10^{12}$ vg/kg. Age-matched untreated mice were included as UT controls. All mice were euthanized 10 weeks after AAV injection following overnight fasting. The AAV treatment resulted in highly elevated Pullulanase activities in the heart and skeletal muscle (quadriceps) (FIG. 14A) and markedly reduced glycogen contents in these tissues (FIG. 14B). Consistent with measured glycogen contents, PAS stained tissue sections confirmed the clearance of glycogen accumulation in heart and skeletal muscle (FIG. 15). Plasma ALT and CK activities and urinary Glc4 levels were lowered by the AAV-CB-Pull treatment (FIG. 16A-16C). The failure of the AAV-CB-Pull treatment to correct liver in this experiment is likely caused by the rapid growth of liver during the 10-week experimental time. This study demonstrated a long-term benefit of neonatal gene therapy with the AAV-CB-Pull vector in GSD IIIa mice.

Example 4. Testing the Ability of the AAV-MHCK7-Pull Vector to Achieve Long-Term Efficacy in Reversing Muscular Defects in GSD IIIa Mice (for Patients with GSD IIIa)

Systemic administration of the AAV-MHCK7-Pull vector can achieve long-term correction of cardiac and skeletal muscles in GSD IIIa mice and a high dose of vector administration is required for the correction of skeletal muscles. The AAV-MHCK7-Pull vector was packaged as AAV9 in this experiment. This experiment includes 2 groups starting with n=12 mice per group: Group 1: no treatment; Group 2: AAV-MHCK7-Pull treatment. The AAV-MHCK7-Pull vector at $5 \times 10^{13}$ vg/kg was intravenously injected into ten-week-old GSD IIIa mice. Mice from each group were euthanized after 12 weeks following overnight fasting to collect tissues and blood. Functional tests including treadmill and wire-hang were performed at 3, 4, and 5 months of age. Gender- and age-matched untreated GSD III mice were used as controls. Fresh tissue specimens were either immediately frozen on dry ice and stored at $-80°$ C. until used for biochemical analyses, or fixed immediately for histology.

Figure 17A:
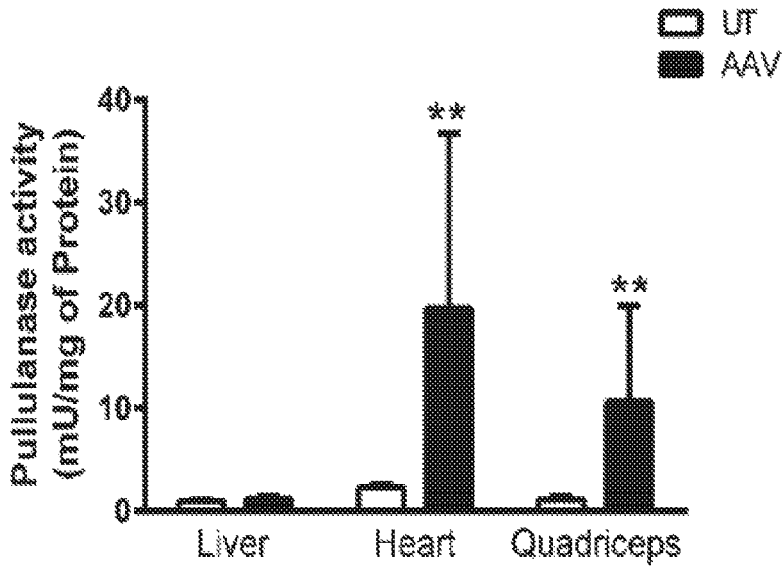
FIG. 17A-FIG. 17B show biochemical correction of muscle defects in GSD IIIa mice by AAV9-MHCK7-Pull treatment.
Figure 17B:
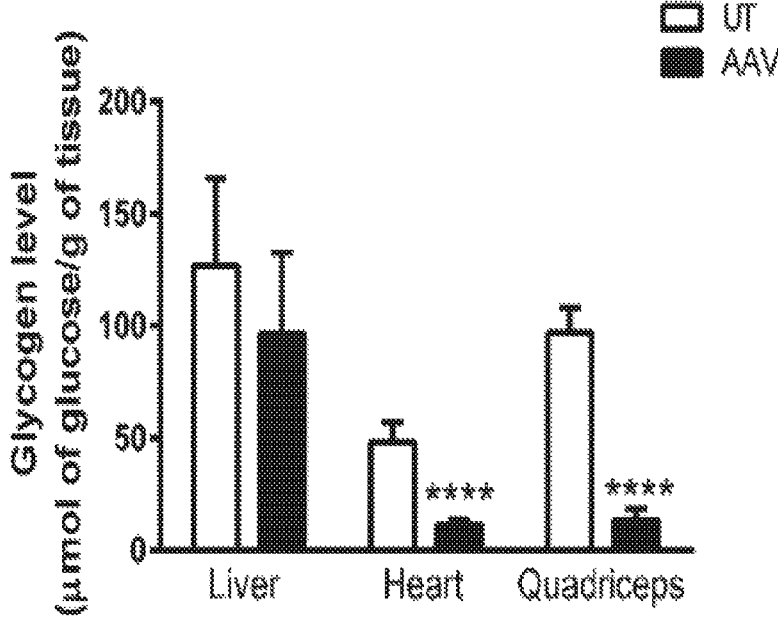
Figure 18A:
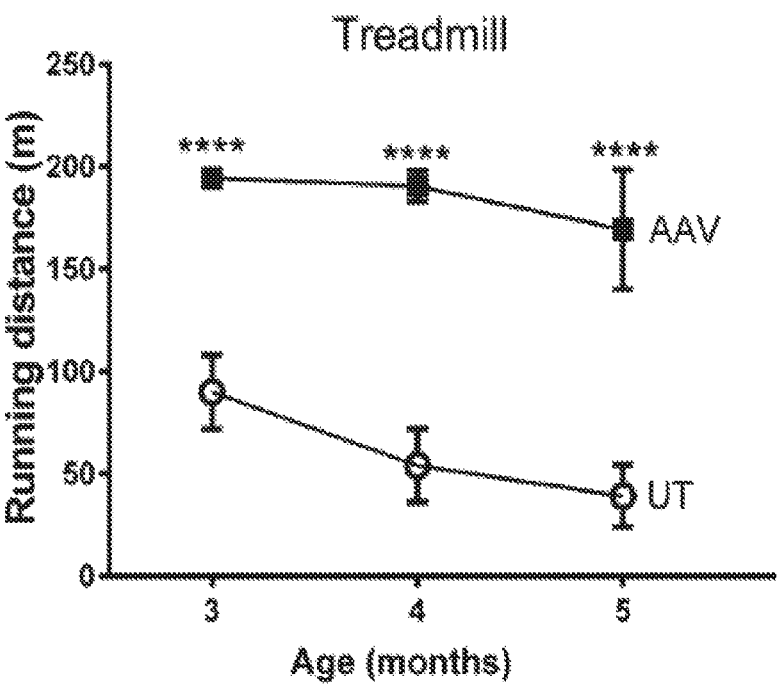
FIG. 18A-FIG. 18B show improvement of muscle function by the AAV-MHCK7-Pull treatment.
Figure 18B:
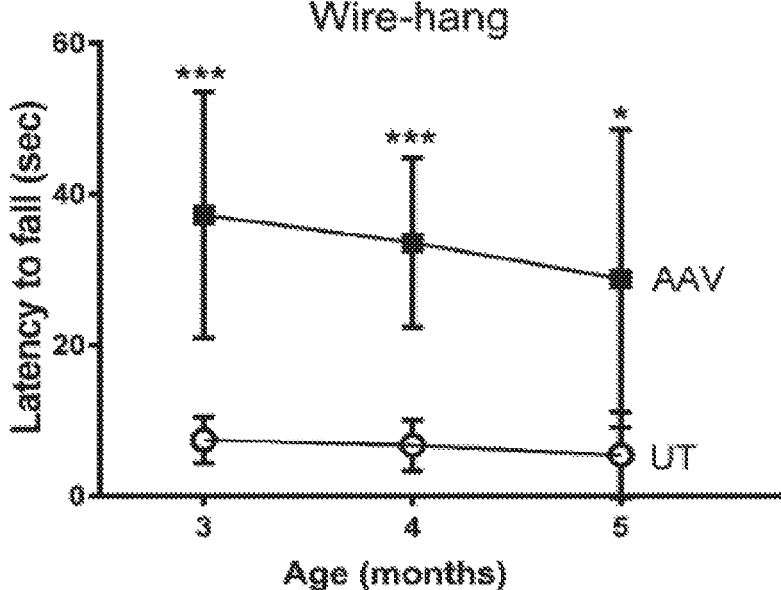

Twelve weeks after AAV treatment, Pullulanase activity was significantly increased in the heart and skeletal muscle, but not in the liver, of the AAV-treated mice (FIG. 17A). Consistent with the enzyme activity results, AAV treatment significantly reduced glycogen levels in the heart and quadriceps while glycogen content in the liver was not significantly changes (FIG. 17B). Treadmill test was used for evaluating exercise intolerance. The running distance was dramatically increased for the AAV-treated mice compared to the untreated mice (FIG. 18A). Wire-hang test was performed to assess limb muscle strength by measuring the time of latency to fall. The AAV-treated mice showed significantly increased hanging time compared to the untreated mice throughout the treatment period (FIG. 18B).

Figure 19A:
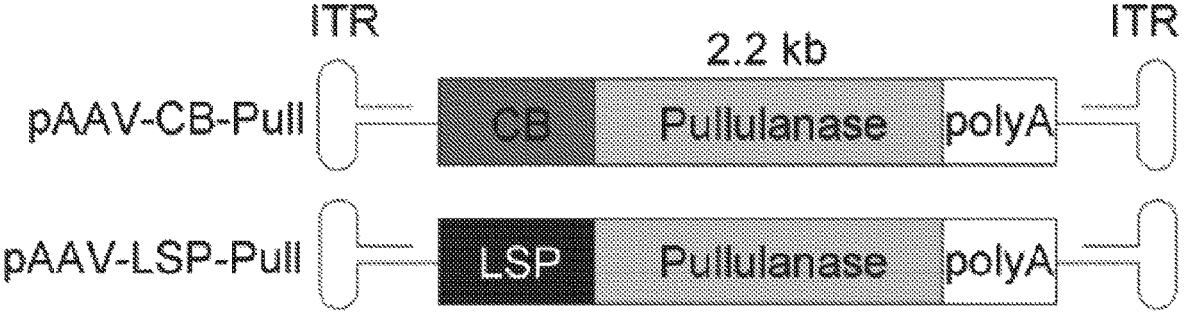
FIG. 19A-FIG. 19E show AAV-mediated gene delivery of Pullulanase in the liver and muscles of GSD IIIa mice.
Figure 19B:
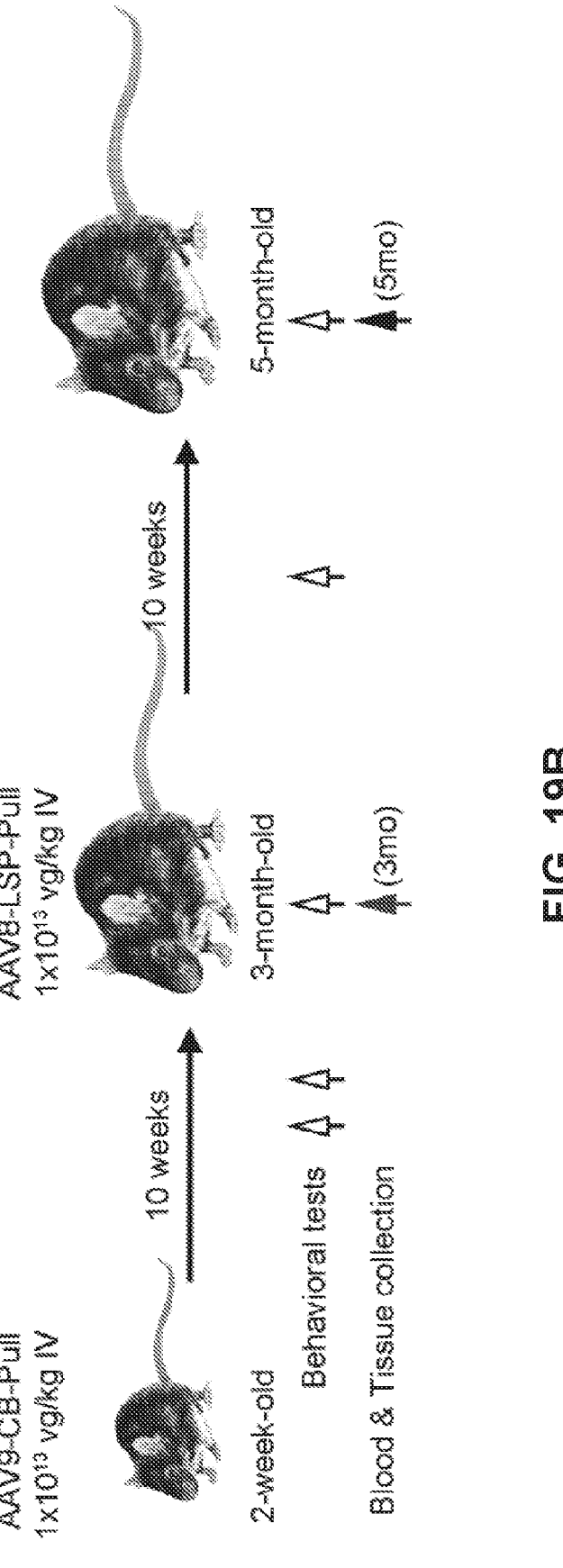

Example 5: Combination Treatment with AAV9-CB-Pull and AAV8-LSP-Pull Corrects Glycogen Storage in Both Liver and Muscle Tissues of GSD IIIa Mice Because GSD IIIa manifests mainly in liver, heart and skeletal muscles, the study focused on these tissues. The AAV vector plasmids pAAV-CB-Pull and pAAV-LSP-Pull (FIG. 19A) were packaged into AAV9 (AAV9-CB-Pull) and AAV8 (AAV8-LSP-Pull), respectively. Two-week-old GSD IIIa mice were intravenously injected with AAV9-CB-Pull at a dose of $1 \times 10^{13}$ vg/kg. After 10 weeks, half of the mice were sacrificed to evaluate the efficacy of AAV9-CB-Pull treatment in different tissues at 3 months of age (FIG. 19B, 3 mo, gray arrow) and the other half were further treated with AAV8-LSP-Pull ($1 \times 10^{13}$ vg/kg) for another 10 weeks to correct liver abnormalities (FIG. 19B, 5 mo, black arrow). Behavioral tests were performed to evaluate muscle functions during the treatments at 2, 2.5, 3, 4, and 5 months old age (FIG. 19B, open arrows).

Figure 19C:
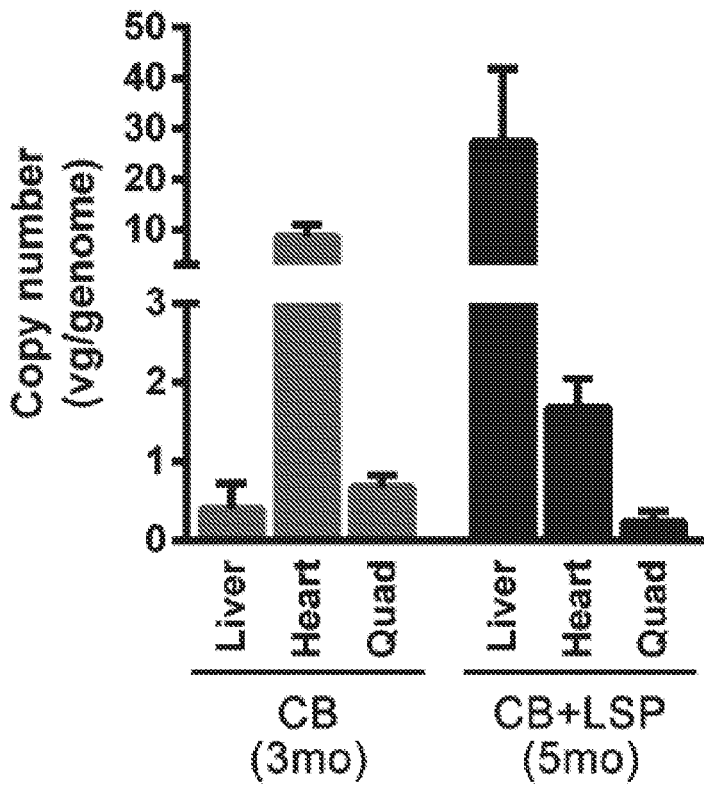
Figure 19D:
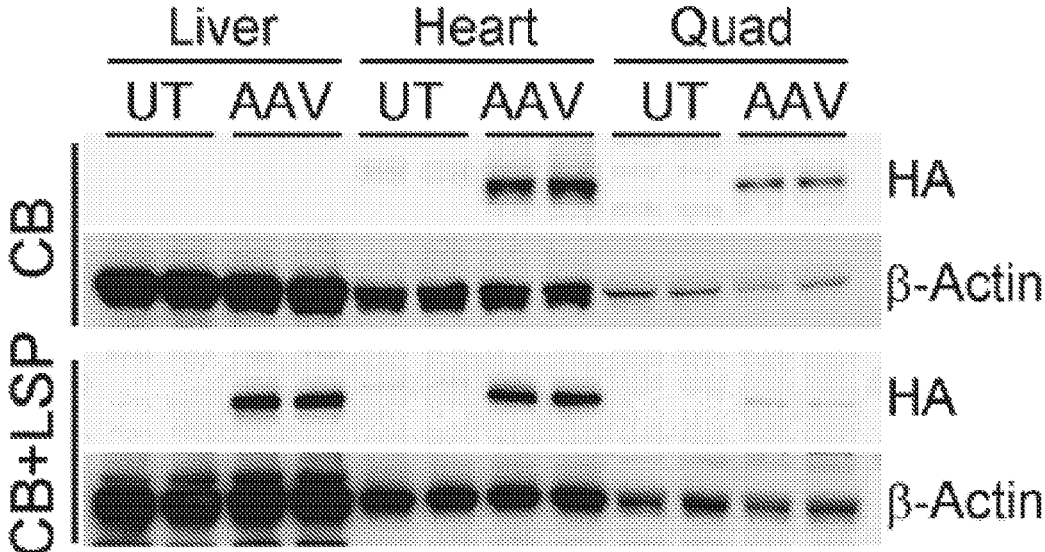
Figure 19E:
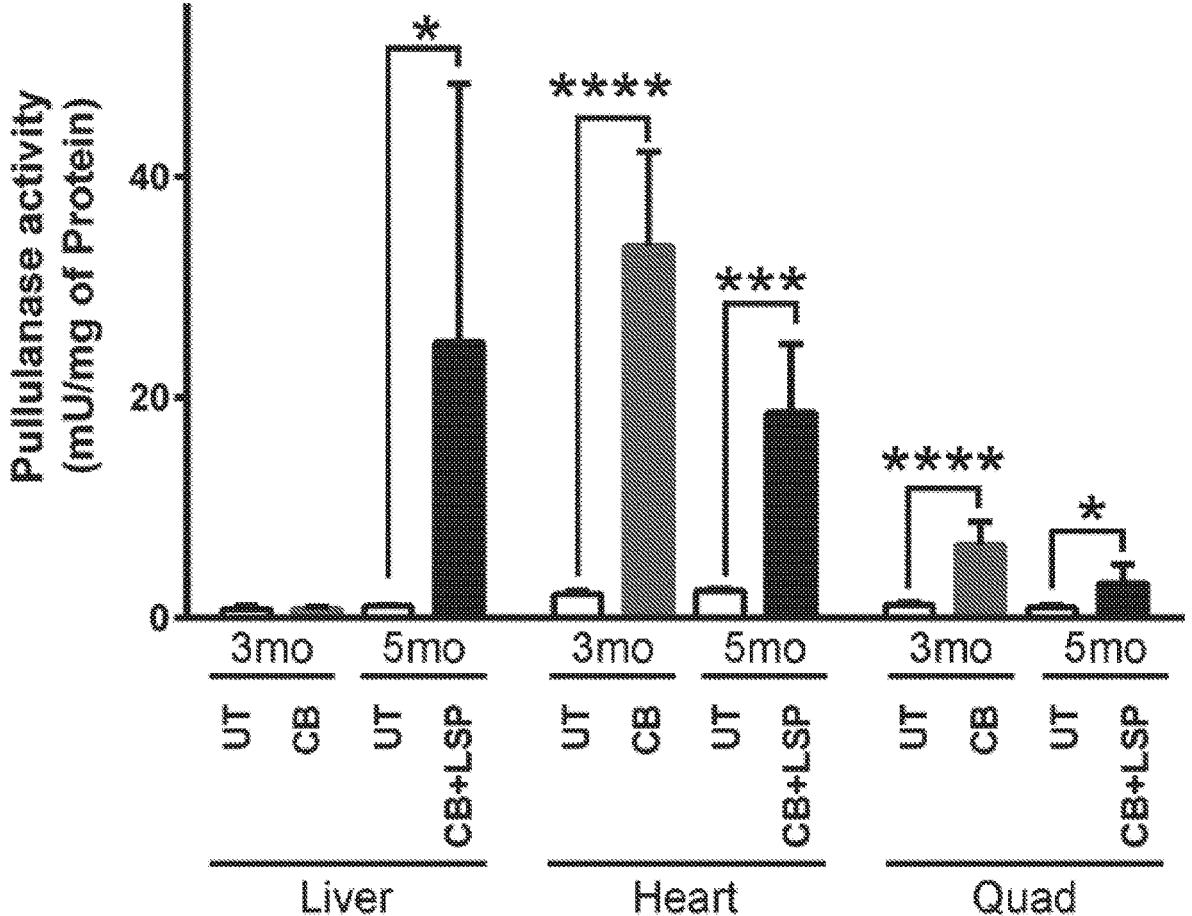
Figure 20A:
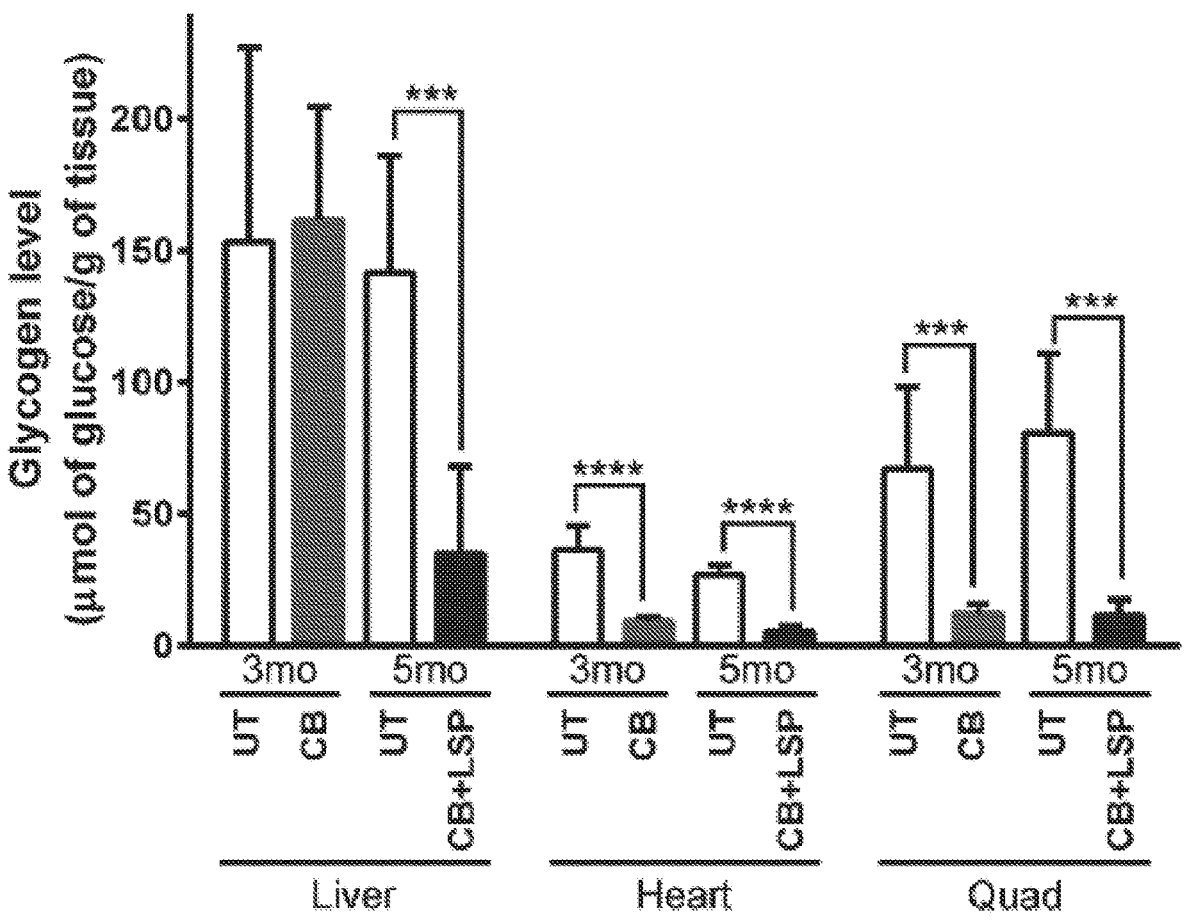
FIG. 20A-FIG. 20D show AAV-mediated pullulanase expression reduced glycogen accumulation in the liver and muscles and reversed liver fibrosis in GSD IIIa mice.

To evaluate the transduction efficiency of the AAV vectors in liver and muscles, we first checked AAV genome copy numbers using real-time-PCR and protein expression with Western blot. Ten weeks after the AAV9-CB-Pull (CB) treatment, AAV copy numbers were high in the heart ($8.69 \pm 2.22$ vg/genome) and low in the quadriceps ($0.68 \pm 0.15$) and liver ($0.40 \pm 0.32$) (FIG. 19C). Protein level was high in the heart, moderate in the quadriceps, and undetectable in the liver (FIG. 19D). Consistent with the Western blot results, Pullulanase enzyme activity was profoundly high in the heart ($33.77 \pm 8.51$ mU/mg) and readily detectable in the quadriceps ($6.64 \pm 2.11$ mU/mg) but undetectable in the liver at 3 months age (FIG. 19E). However, 10 weeks after the secondary treatment with AAV8-LSP-Pull (CB+LSP), the AAV genome copy number, protein expression, and enzyme activity were all significantly increased in the liver (FIG. 19C, FIG. 19D, FIG. 19E, black bars); enzyme activity was lowered in the heart ($18.69 \pm 6.19$ mU/mg) and still detectable in the skeletal muscle (FIG. 19E, black bars). Both the CB and CB+LSP combination treatments significantly decreased glycogen contents in the heart ($-75 \sim 80\%$) and skeletal muscle ($-80\%$) compared to those in the untreated mice (FIG. 20A). Glycogen level did not change significantly in the CB treated liver but decreased remarkably ($-75\%$) in the CB+LSP treated liver (FIG. 20A).

Figure 20B:
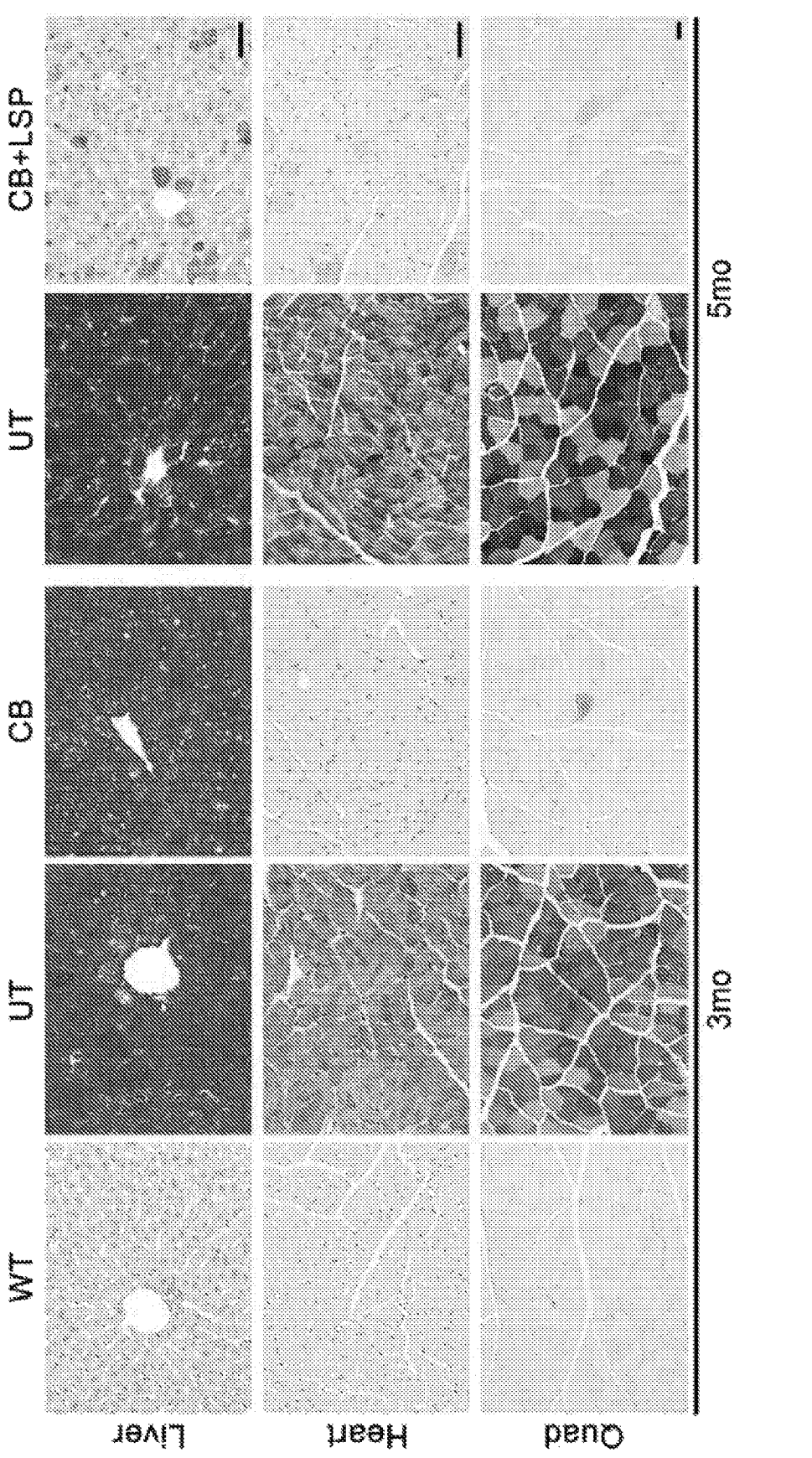
Figure 20C:
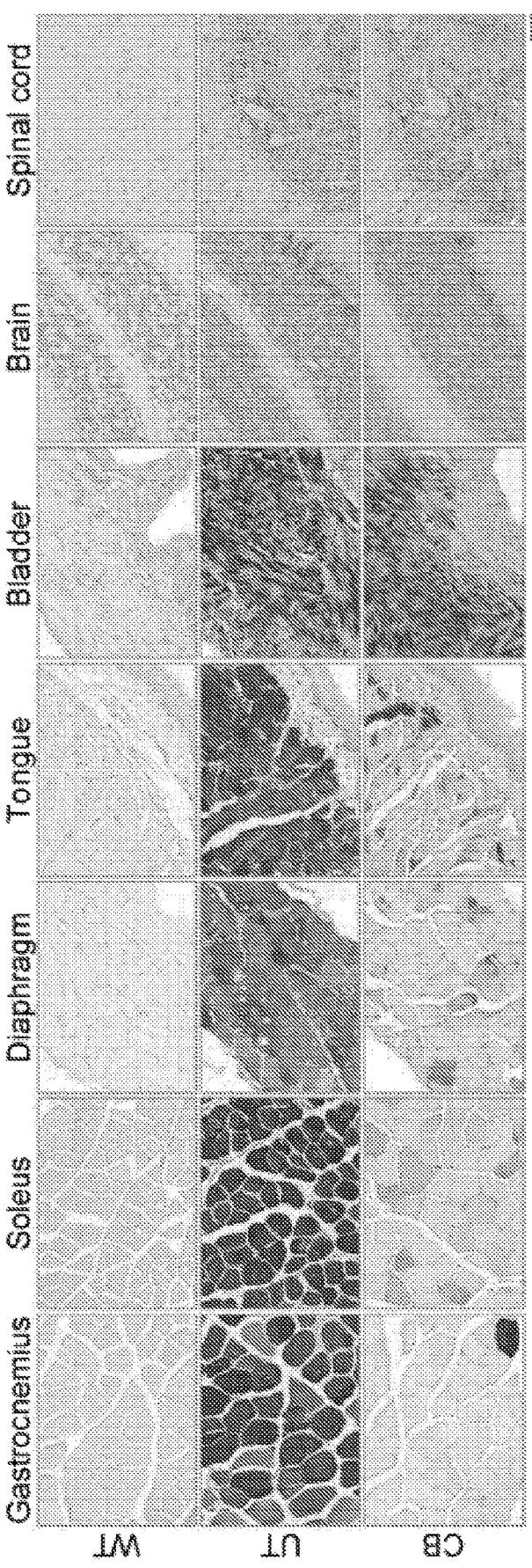

PAS staining of tissue sections confirmed the glycogen content results. CB treatment effectively cleared glycogen accumulation in the heart and skeletal muscles (quadriceps, gastrocnemius, soleus, diaphragm, and tongue), but had no effect on the liver, smooth muscle (bladder), brain (cerebellum), or the spinal cord (FIG. 20B and FIG. 20C, CB). Additional treatment with the second AAV8-LSP-Pull vector cleared glycogen accumulation in the liver (FIG. 20B, CB+LSP).

Figure 20D:
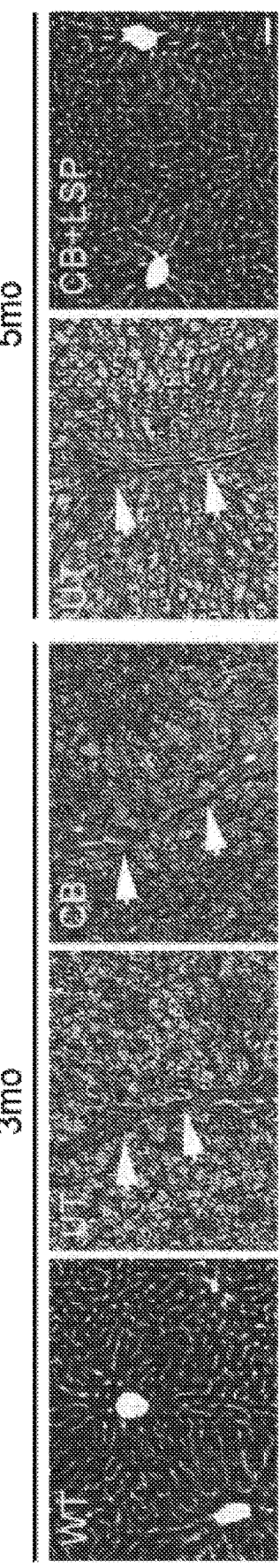

Another hepatic disease manifestation in GSD III is progressive liver fibrosis. The liver fibrosis status was evaluated in the untreated and AAV treated GSD IIIa mice by trichrome staining. Untreated GSD IIIa liver showed similar early stage (stage 1-2) fibrosis with appearance of blue on staining at both 3 and 5 months of age (FIG. 20D, white arrows). The early (on postnatal day 14) treatment with AAV9-CB-Pull, which did not change the glycogen level in the liver, did not prevent liver fibrosis (FIG. 20D). There was no obvious fibrotic tissues in the CB+LSP treated liver (FIG. 20D), indicating that the secondary AAV8-LSP-Pull treatment can reverse and prevent early stage liver fibrosis in adult GSD IIIa mice.

Figure 21A:
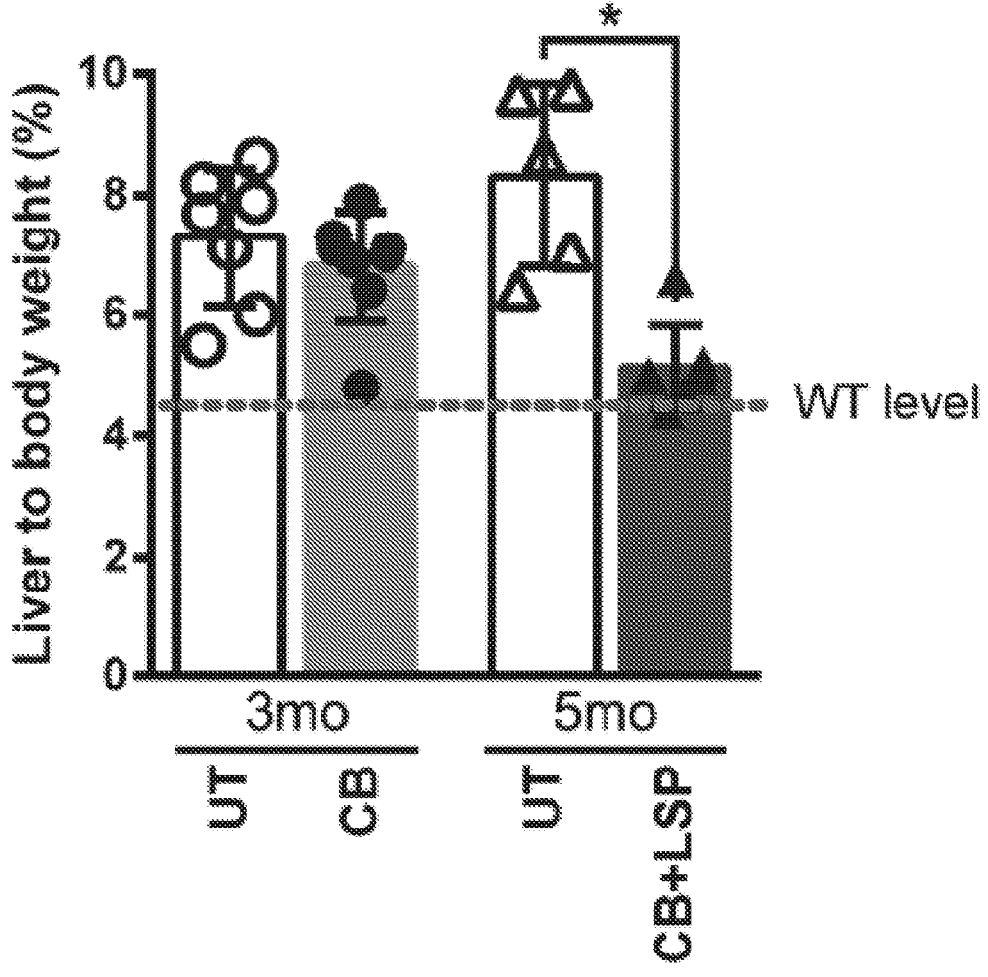
FIG. 21A-FIG. 21D show that pullulanase improved liver and muscle function.
Figure 21B:
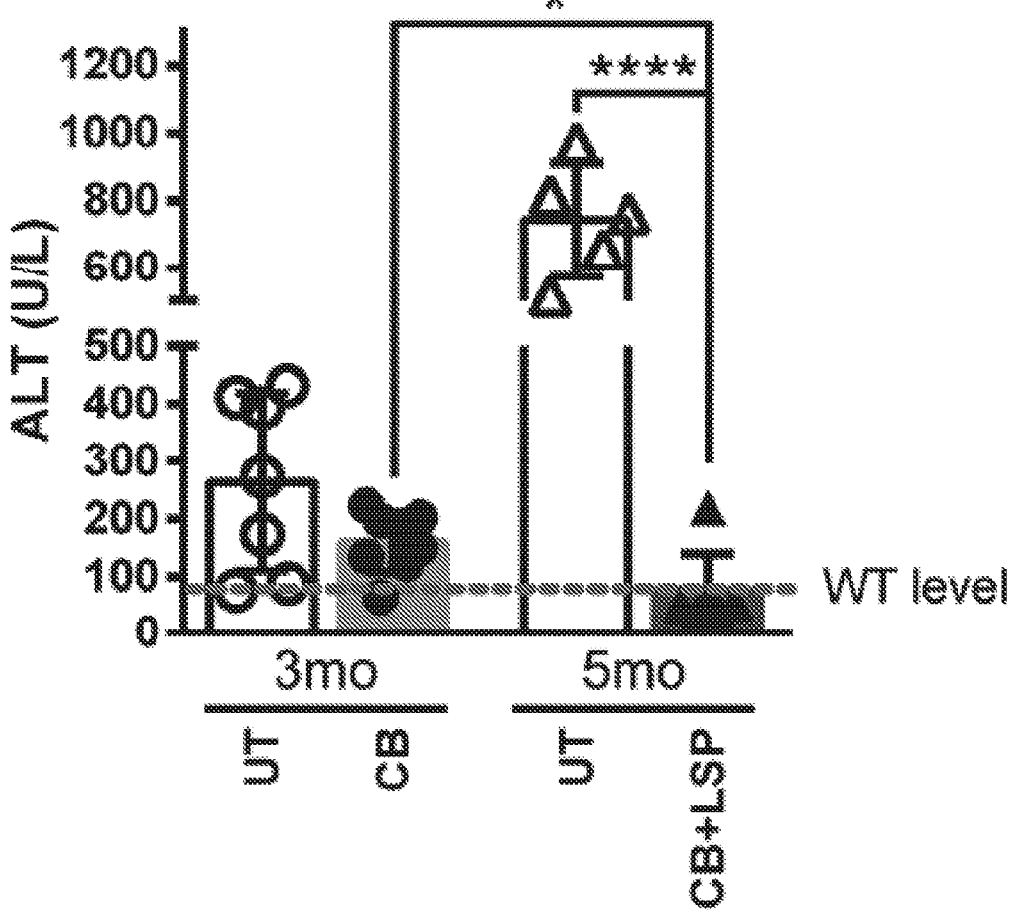

Hepatomegaly is one of the most common symptoms of GSD III patients. Therefore, the liver size using the liver-to-bodyweight ratio was measured. The liver-to-bodyweight ratio clearly increased in the untreated GSD IIIa mice (7-8%) compared to WT level (about 4%) (FIG. 21A). Consistent with the Pullulanase activity and glycogen data, the liver size remained unchanged in the CB treated mice but was normalized to the WT level in the CB+LSP treated mice (FIG. 21A). Furthermore, the activity of ALT in the plasma, which is commonly used for monitoring liver damage, was reduced to the WT level in CB+LSP treated mice (FIG. 21B). The CB treated mice showed a slightly decreased in plasma ALT activity compared with the untreated mice at 3 months of age (p=0.09, FIG. 21B). A significant increase in plasma ALT level in the untreated GSD IIIa mice from 3 month of age (264.0±153.4 U/L) to 5 months of age (744.0±170.4 U/L), which indicated progressive liver damage during that time (FIG. 21B).

Figure 21C:
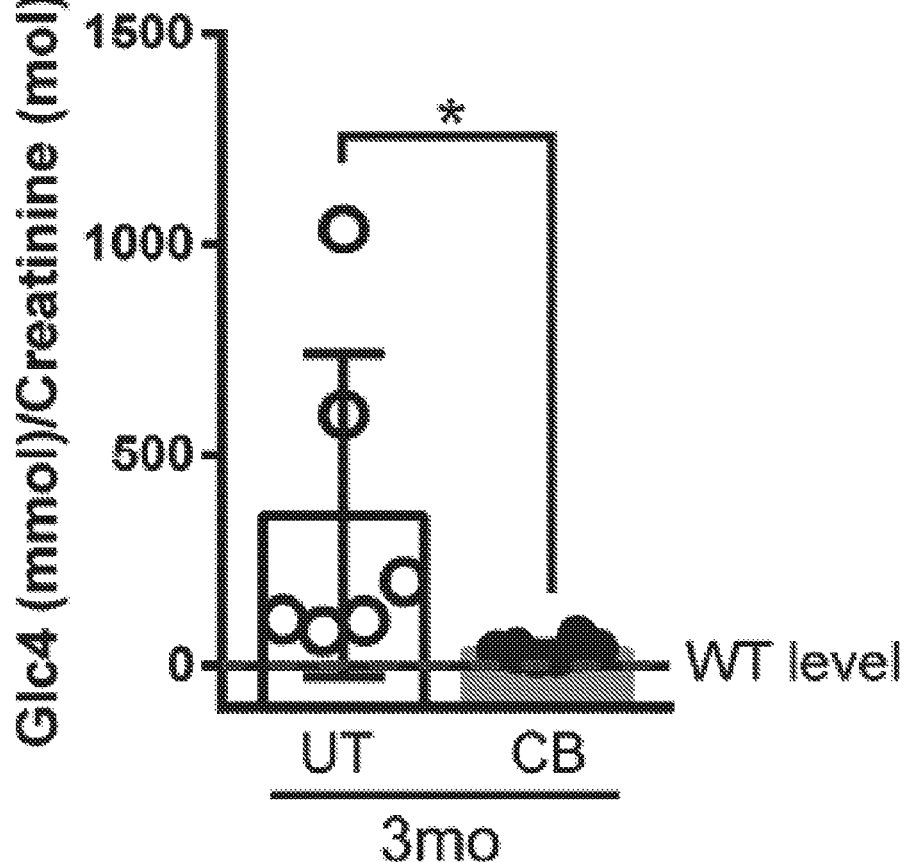

Urinary Glc4, a known disease biomarker for Pompe disease (GSD II) that is often correlated with the levels of glycogen accumulation in skeletal muscle, has been indicated as a potential biomarker for GSD III. The concentration of urinary Glc4 was reduced to the WT level in the CB treated GSD IIIa mice at 3 months of age (FIG. 21C).

Figure 21D:
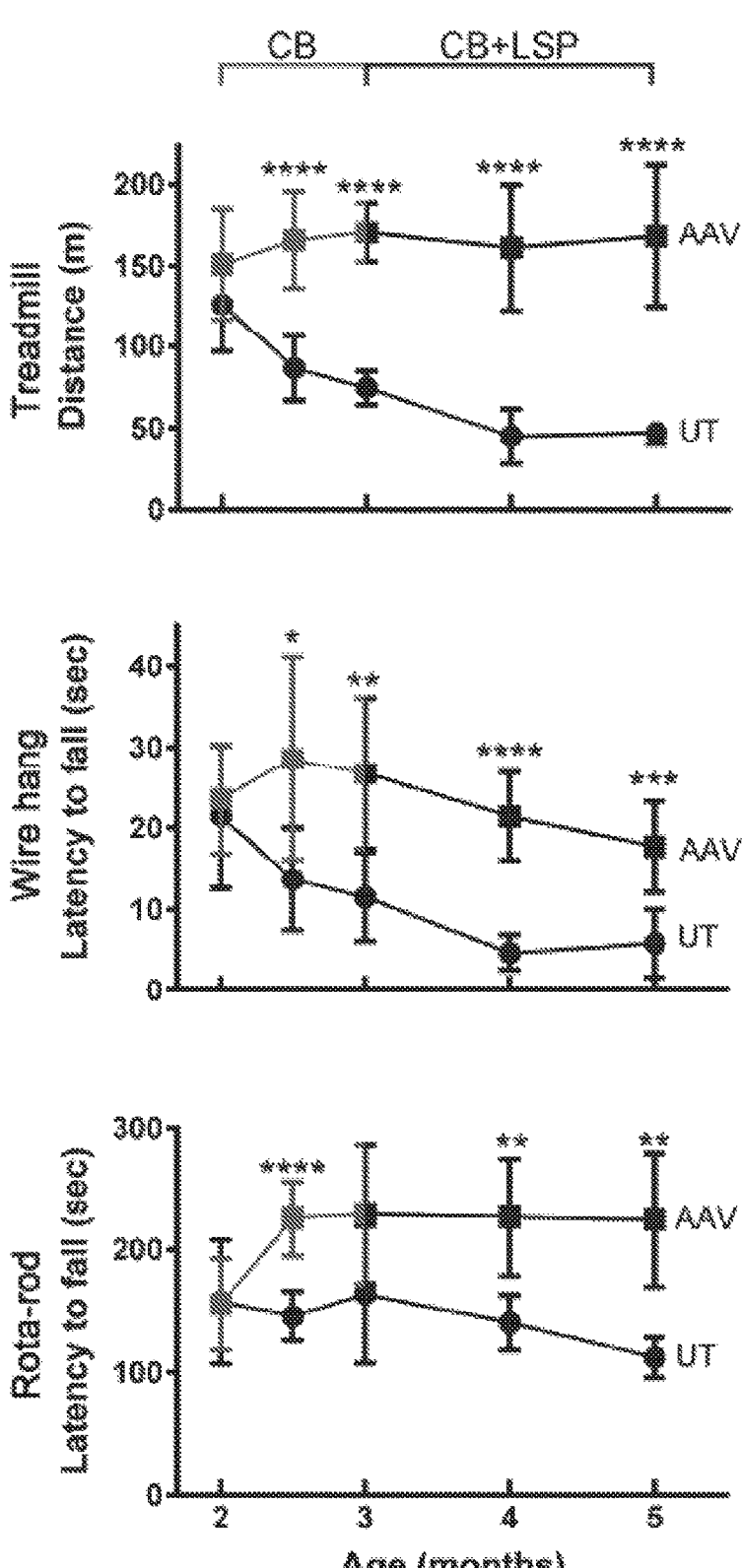

The behavioral tests including treadmill, inverted wire hang, and Rota-rod have been broadly used for assessment of muscle function in mice. After AAV treatments, all the three tests showed significant improvement of muscle function (FIG. 21D). Notably, the running distance improved dramatically in the treadmill test after AAV treatments (FIG. 21D).

The improved performance in the Rota-rod test after Pullulanase treatments (FIG. 21D) could be the result of skeletal muscle recovery because the treatment did not apparently affect the glycogen accumulation in the brain and spinal cord (FIG. 20C). Thus, the combination treatment with AAV9-CB-Pull at an infant age (2 weeks) and AAV8-LSP-Pull at an adult age (3 months) effectively reduced glycogen accumulation in both liver and muscle and recovered liver function and improved muscle strength.

In addition to the Pullulanase used in this study, other bacterial enzymes with a similar glycogen degrading activity can also possibly be used for GSD III gene therapy, such as type I Pullulanase derived from other bacteria species and strains 38 and the bacterial GDE encoded by the glgX gene in *Escherichia coli*. See FIG. 22-FIG. 28 (corresponding to SEQ ID NOs: 01-07, respectively) and Table 2.

Example 6: Gene Therapy with an AAV Vector Expressing Pullulanase Under the Control of an Immunotolerant LSP-CB Dual Promoter in GSD IIIa Mice In this study, the effectiveness of the use of a dual promoter consisting of a liver-specific promoter and the ubiquitous CB promoter to prevent immune responses against Pullulanase and correct genetic defects in both liver and muscle tissues of GSD IIIa mice was investigated.

Figure 29A:
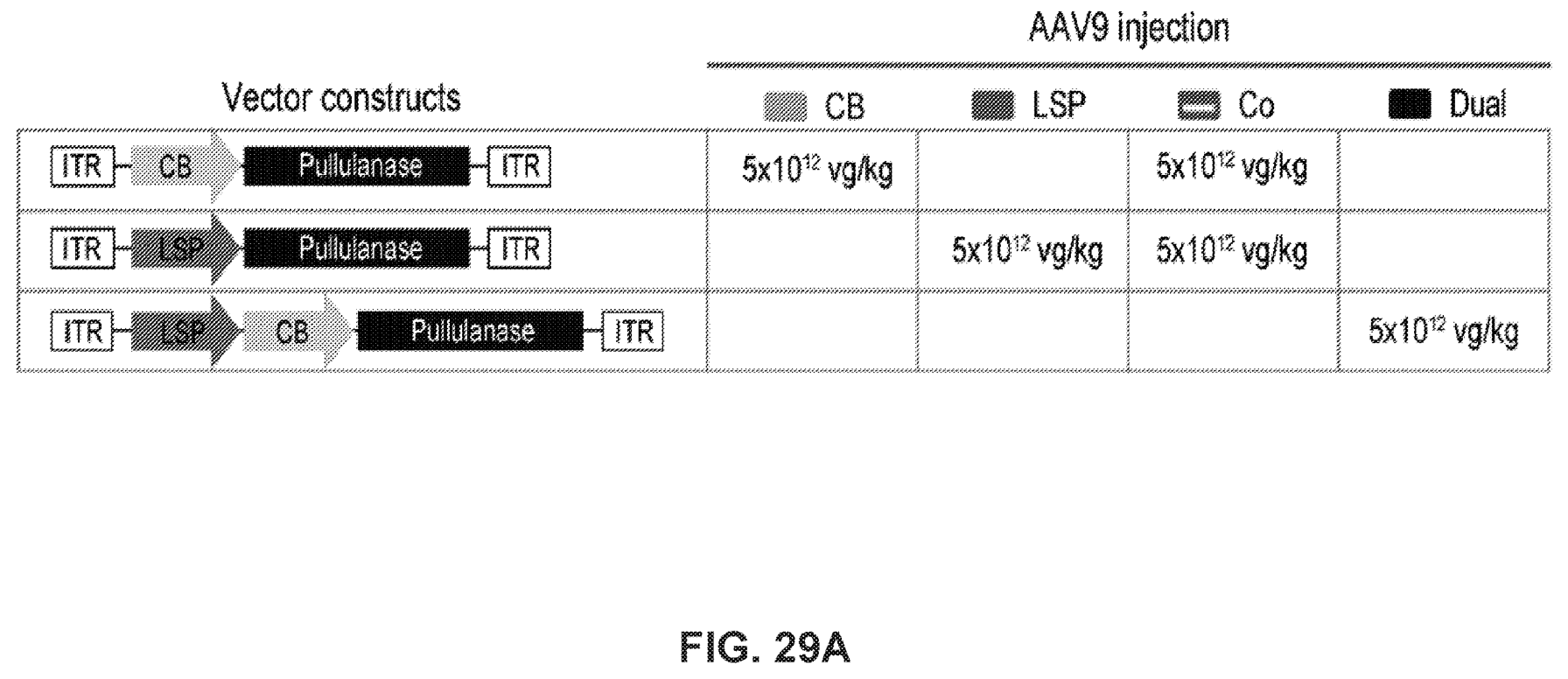

The AAV9-LSP-Pull, AAV9-CB-Pull, and AAV9-LSP-CB-Pull were all packaged as AAV9. Ten-week-old GSD IIIa mice were intravenously injected with AAV9-LSP-Pull, AAV9-CB-Pull, AAV9-LSP-Pull+AAV9-CB-Pull, or AAV9-LSP-CB-Pull at a dose of $5.0 \times 10^{12}$ vg/kg (FIG. 29A). After ten weeks, the mice were sacrificed to collect tissues and blood. The mice were examined for the treadmill test at 2, 3, 4, and 5 months of age. Gender- and age-matched untreated GSD IIIa mice were used as controls. Fresh tissue specimens were either immediately frozen on dry ice and stored at −80° C. until used for biochemical analyses, or fixed immediately for histology.

AAV vector genome copy numbers were evaluated by real-time PCR in the liver, heart, and quadriceps ten weeks after AAV treatment. AAV copy numbers were markedly high in all the tested tissues of the AAV-LSP-CB-Pull (Dual) treated mice and moderate elevated in the liver of AAV-LSP-Pull (LSP) treated mice. Very low AAV genome copies were detected in the heart and skeletal muscle of the treated LSP treated mice and in all the tissues from mice treated with AAV-CB-Pull alone (CB) or co-treated with LSP and CB (Co) (FIG. 29B).

Figure 30A:
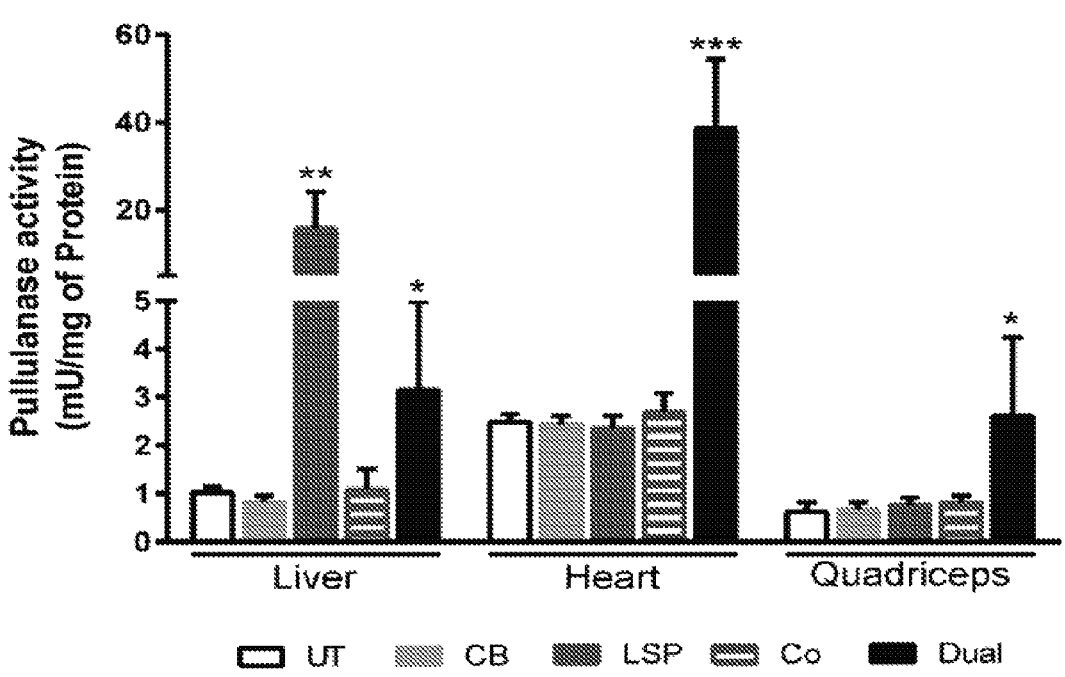
FIG. 30A-FIG. 30B show long-term Pullulanase expression and glycogen reduction by the LSP-CB dual promoter in the major affected tissues of GSD IIIa mice.
Figure 30B:
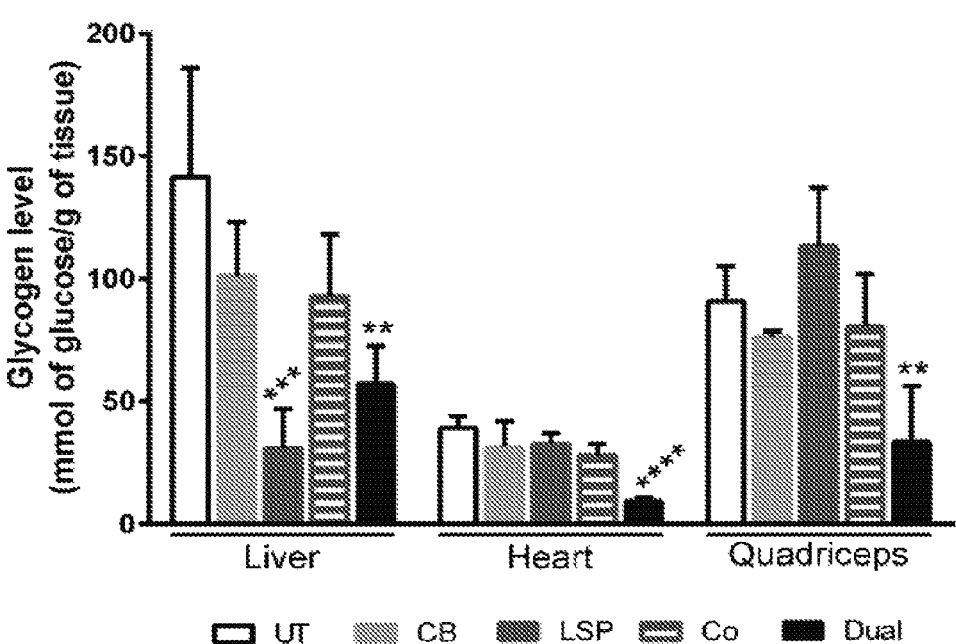
Figure 31:
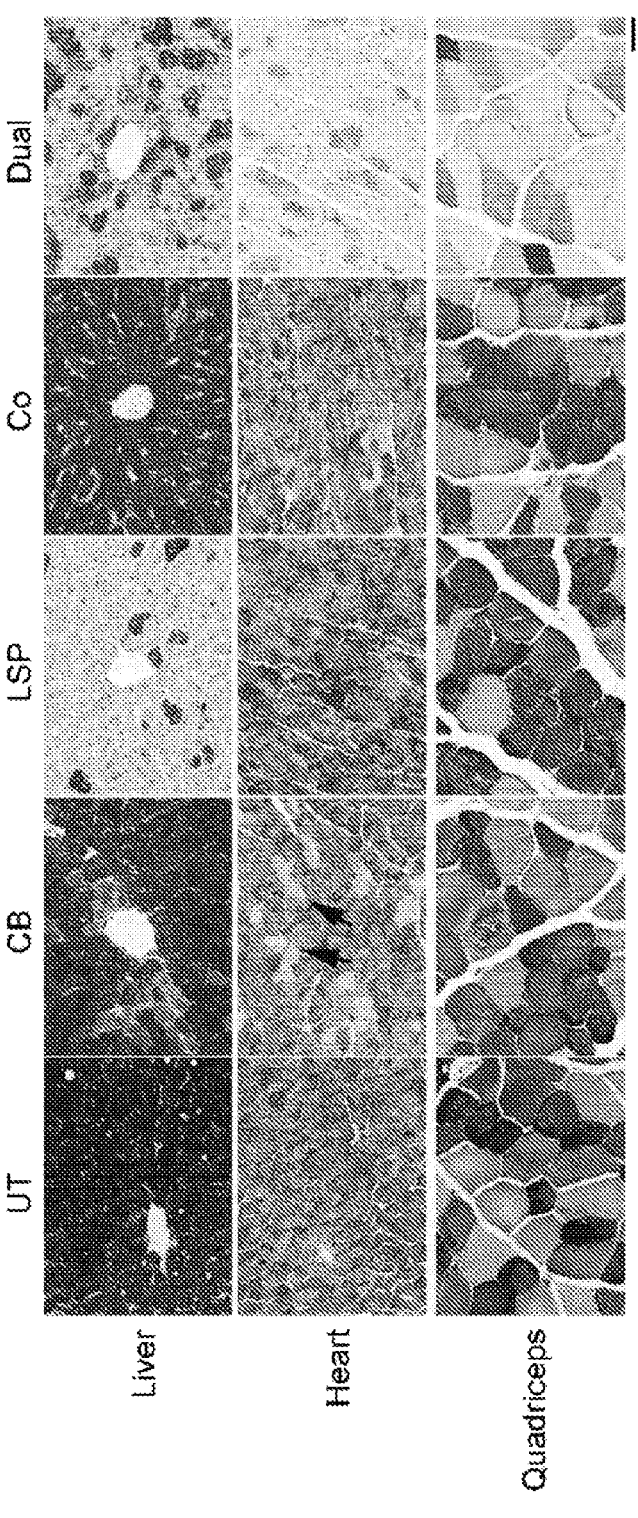
FIG. 31 shows PAS-stained tissue sections, which confirmed the clearance of glycogen accumulation in tissues of GSD IIIa mice ten weeks after AAV-LSP-CB-Pull treatment. UT, untreated GSD IIIa mice; CB, AAV9-CB-Pull injection; LSP, AAV9-LSP-Pull injection; Co, AAV9-CB-Pull+AAV9-LSP-Pull co-injection; Dual, AAV9-LSP-CB-Pull injection. Scale bar=50 μm. The images represent at least three mice in each group

Pullulanase activities were highly elevated in all the tested tissues (liver, heart, and skeletal muscle) by the LSP-CB dual promoter treatment. Pullulanase activity was increased only in the liver of LSP treated mice. There is no significantly increase in Pullulanase activity in any tissues of the CB treated and LSP+CB co-treated mice (FIG. 30A). Consistent with the Pullulanase activity results, glycogen contents were significantly in all the tissues of the LSP-CB dual promoter treated mice, but only in the liver of LSP treated mice. No glycogen reduction was observed in any tissues of the CB treated and LSP+CB co-treated mice (FIG. 30B). PAS-staining of tissue sections confirmed the reduction of glycogen accumulation in those tissues by the dual promoter treatment (FIG. 31).

Figure 32A:
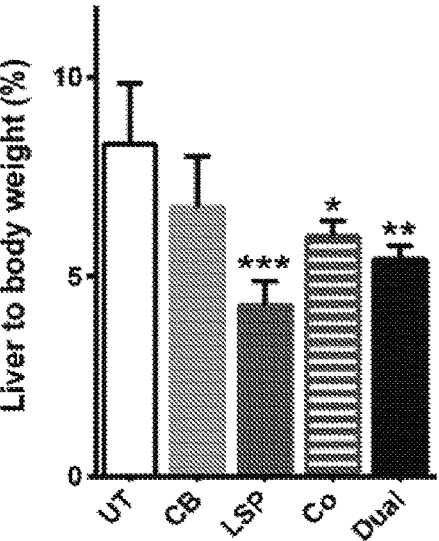
FIG. 32A-FIG. 32D show the LSP-CB dual promoter is as effective as the LSP promoter in correcting liver abnormalities in GSD IIIa mice.
Figure 32B:
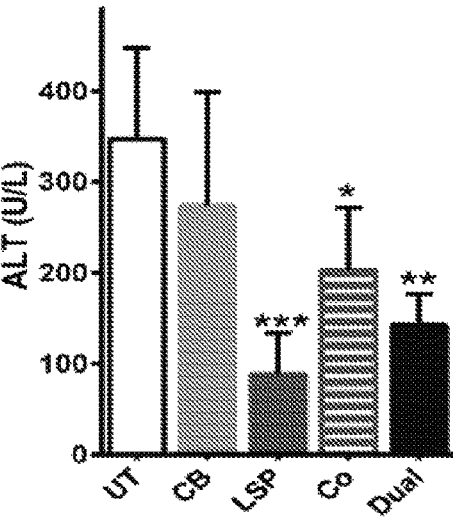
Figure 32C:
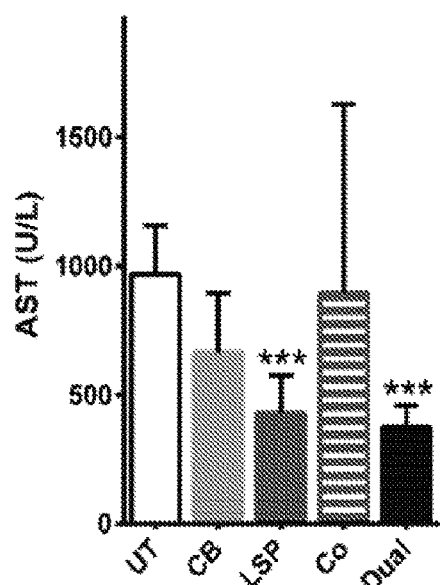
Figure 32D:
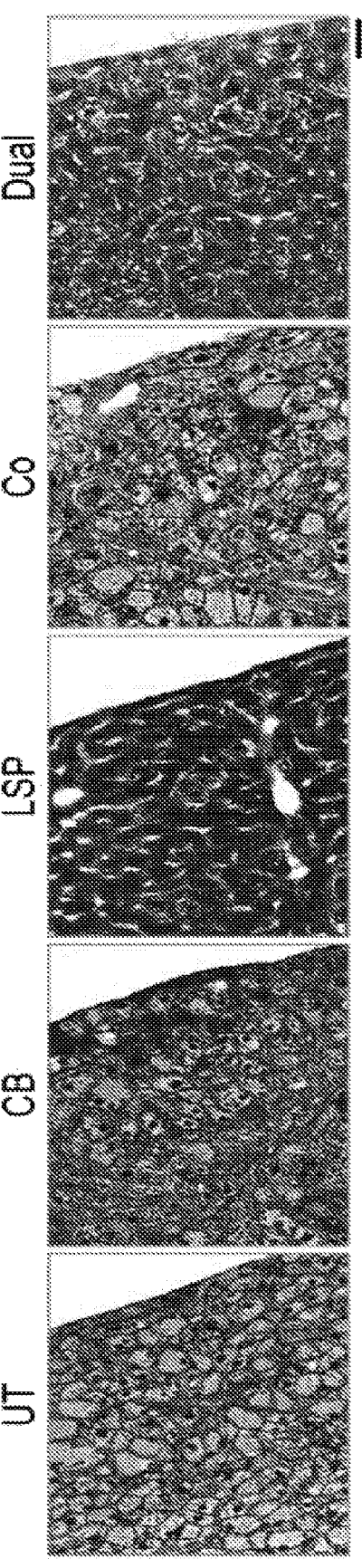

The ratio of liver to body weight was measured to determine liver size. The ratio reduced significantly in the LSP and LSP-CB dual promoter treated mice but showed no significant change in the CB treated to the untreated mice. Co-injected mice showed a decrease in liver size but to a lesser extent than the LSP or LSP-CB dual promoter treated mice (FIG. 32A). The activities of alanine aminotransferase (ALT) and aspartate aminotransferase (AST) in plasma were measured to evaluate liver function. Both LSP and LSP-CB dual promoter treatments significantly decreased ALT and AST levels. Co-injected mice showed slightly decreased in ALT level but not in AST level, compared to the UT mice. CB treatment had no effect on the plasma ALT and AST activities (FIG. 32B and FIG. 32C). Trichrome staining was used to detect liver fibrosis. Significant fibrotic tissues were observed in the livers from UT, CB treated, and co-treated mice. In contrast, LSP and LSP-CB dual promoter treatments fully prevented liver fibrosis in the GSD IIIa mice (FIG. 32D).

Figure 33:
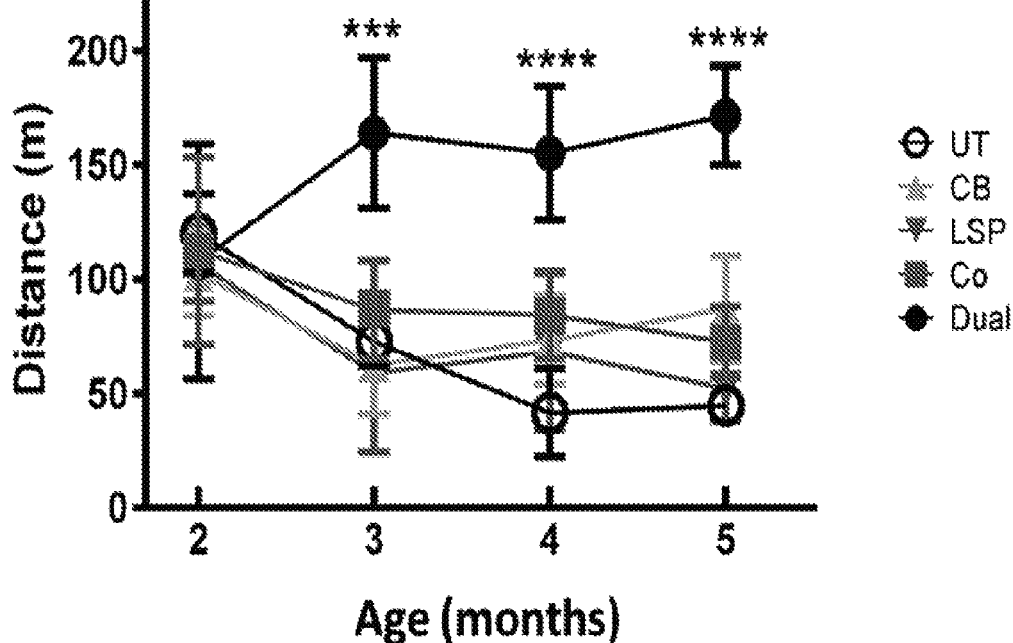
FIG. 33 is a graph showing that AAV-LSP-CB-Pull treatment significantly improved muscle function in GSD IIIa mice as evidenced by treadmill test. The graph represents the maximum running distance. Data shown as mean±SD. n=5 for each group at each time point. Student's test. *p<0.001, and **p<0.0001 vs UT.

Treadmill test was used for evaluating exercise intolerance in the untreated and AAV treated GSD IIIa mice. Only the LSP-CB dual promoter treated mice showed significantly improved running distance and other treatment groups showed no differences compared to the UT mice (FIG. 33).

Figure 34:
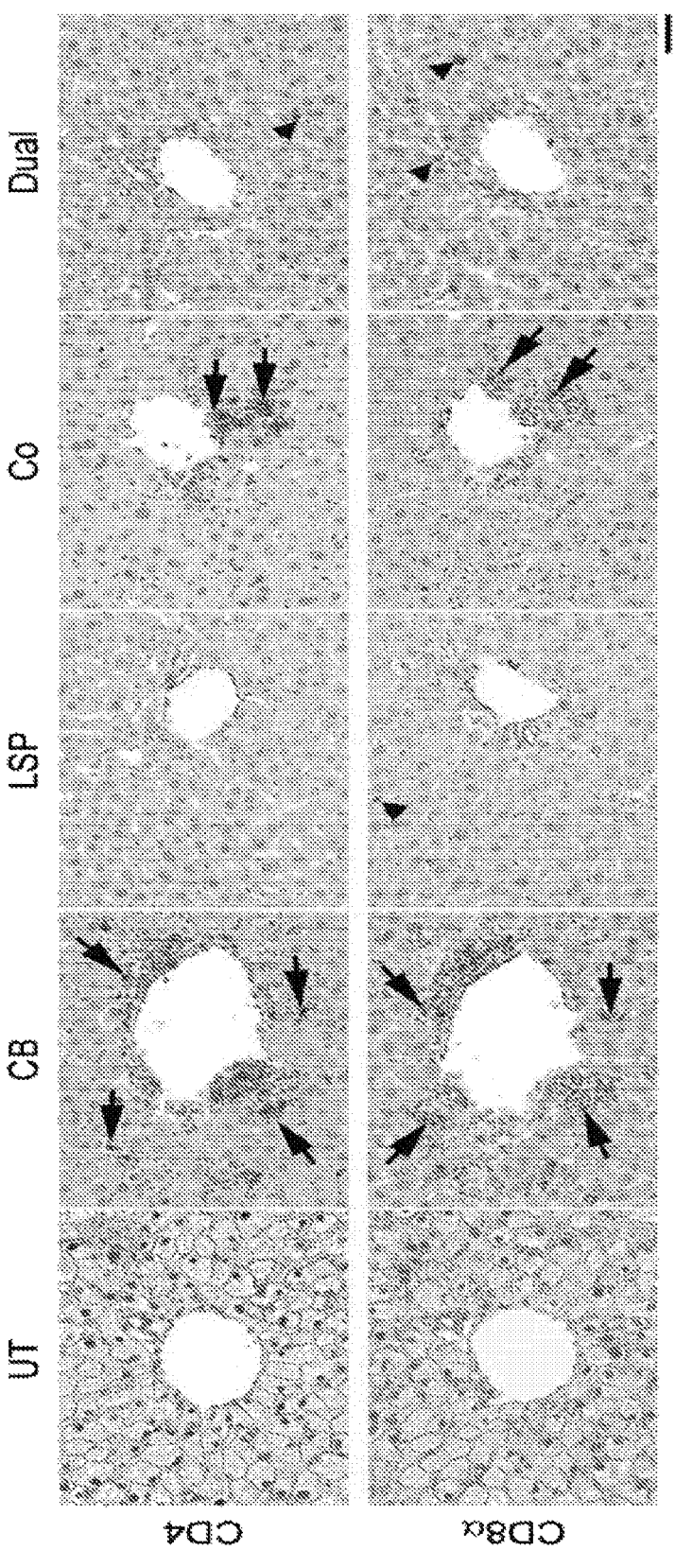
FIG. 34 shows immunohistochemical detection of cytotoxic T cell immune responses in liver of GSD IIIa mice. Paraffin-embedded liver sections two weeks following AAV treatment were stained with anti-CD4 or CD8α antibodies. Infiltration of CD4+ or CD8+ lymphocytes (black arrows) increased in the CB-treated and Co-treated livers but barely visible in LSP- and LSP-CB-treated livers (arrowheads). The images represent at least three mice in each group. Scale bar=50 μm.

Immunohistochemical detection of cytotoxic T cell responses showed that infiltration of CD4+ or CD8+ lymphocytes increased in the CB-treated and Co-treated livers but were barely visible in LSP treated and LSP-CB dual promoter treated livers (FIG. 34).

This study demonstrated that the LSP-CB dual promoter effectively prevented Pullulanase-induced immune responses in GSD IIIa mice, leading to persistent Pullulanase expression and glycogen correction of the genetic defects in all the affected tissues (e.g., the liver and muscle tissues). These data indicate that this immunotolerant LSP-CB dual promoter technology can be used for gene therapy for human inherited diseases with broad tissue involvement.

Example 7: Gene Therapy with an AAV Vector Under the Control of an Immunotolerant LSP-CB Dual Promoter in a Mouse Model of GSD IV The immunotolerant and therapeutic properties of an AAV vector having a dual promoter, as described above in Example 6, was further investigated in a mouse model for adult polyglucosan body disease APBD harboring the homozygous Y329S mutation in the Gbe1 gene. The affected mice are designated as Gbe1$^{ys/ys}$ mice and they are phenotypically very similar to APBD patients with residual GBE activity and widespread, progressive increase of PG deposition in all tissues, including the CNS (Akman, H. O., et al., (2015) Hum Mol Genet, 24(23):6801-10).

Glycogen branching enzyme (GBE) is the enzyme that introduces branches to the growing glycogen molecule during the synthesis of glycogen in animals. GBE deficiency causes glycogen storage disease type IV (GSD IV), which is characterized by the accumulation of a poorly soluble amylopectin-like glycogen, called polyglucosan bodies (PBs), in liver, skeletal muscle, heart, and the central nervous system (CNS). GSD IV is clinically variable. The classical form of GSD IV is characterized by failure to thrive, hepatosplenomegaly, and progressive liver cirrhosis, which normally lead to death by 5 years of age. In addition to the hepatic presentation, four neuromuscular forms can be distinguished based on the ages at onset: fatal perinatal neuromuscular type, congenital muscular type, childhood neuromuscular type, and adult neuromuscular type (Bruno, C. et al. (2004) Neurology, 63(6):1053-8; Moses, S. W. et al., (2002) Curr Mol Med, 2(2):177-88; Bao, Y. et al. (1996) J Clin Invest, 97(4):941-8). Most early onset GSD IV patients die in infancy or early childhood due to severe hypotonia, respiratory distress, cardiomyopathy and/or liver dysfunction. Adult onset GSD IV constitutes the majority of adult polyglucosan body disease (APBD) (Bruno, C. et al. (2004) Neurology, 63(6):1053-8; Moses, S. W. et al., (2002) Curr Mol Med, 2(2):177-88; Bao, Y. et al. (1996) J Clin Invest, 97(4):941-8). Y329S is the most common mutation in the GBE1 gene in APBD patients of Ashkenazi Jewish ancestry (Lossos, A. et al. (1998) Ann Neurol, 44(6):867-72). APBD can present as an isolated myopathy or as a multisystem disorder with intracellular accumulation of PG in the central and peripheral nervous systems and in all muscles (Mochel, F., et al. (2012) Ann Neurol, 72(3):433-441; Klein, C. J., (1993) GeneReviews®). There is currently no definitive treatment for GSD IV, though liver transplantation has been successful in some cases to alleviate liver symptoms (Ban, H. R., et al. (2009) Eur J Pediatr, 152:S71-S76; Selby, R., et al. (1993) Eur J Pediatr, 152:S71-S76; Davis, M. K. and Weinstein, D. A. (2008) Pediatr Transplant, 12(2):137-45).

It has been shown that a single intravenous injection of 5×10$^{13}$ vg/kg AAV-hGBE vector packaged as AAV serotype 9 (AAV9) into 2-week-old Gbe1$^{ys/ys}$ mice almost completely prevented PB formation in skeletal muscles, and partially corrected glycogen accumulation in the brain for up to 9 months of age (Yi, H. et al. (2017) Hum Gene Ther, 28(3):286-294). However, when the same vector was administered into adult mice, no hGBE expression or glycogen reduction was observed in any tissues at 6 months post vector treatment (unpublished data). This discrepancy was likely caused by a stronger cellular immune response towards human protein (hGBE) in adult mice. Thus, a novel method using an immunotolerant dual promoter (LSP-CB) consisting of a liver-specific promoter and a universally active promoter to prevent hGBE-induced cytotoxic T cell response in Gbe1$^{ys/ys}$ mice was investigated.

Materials and Methods

Figure 35:
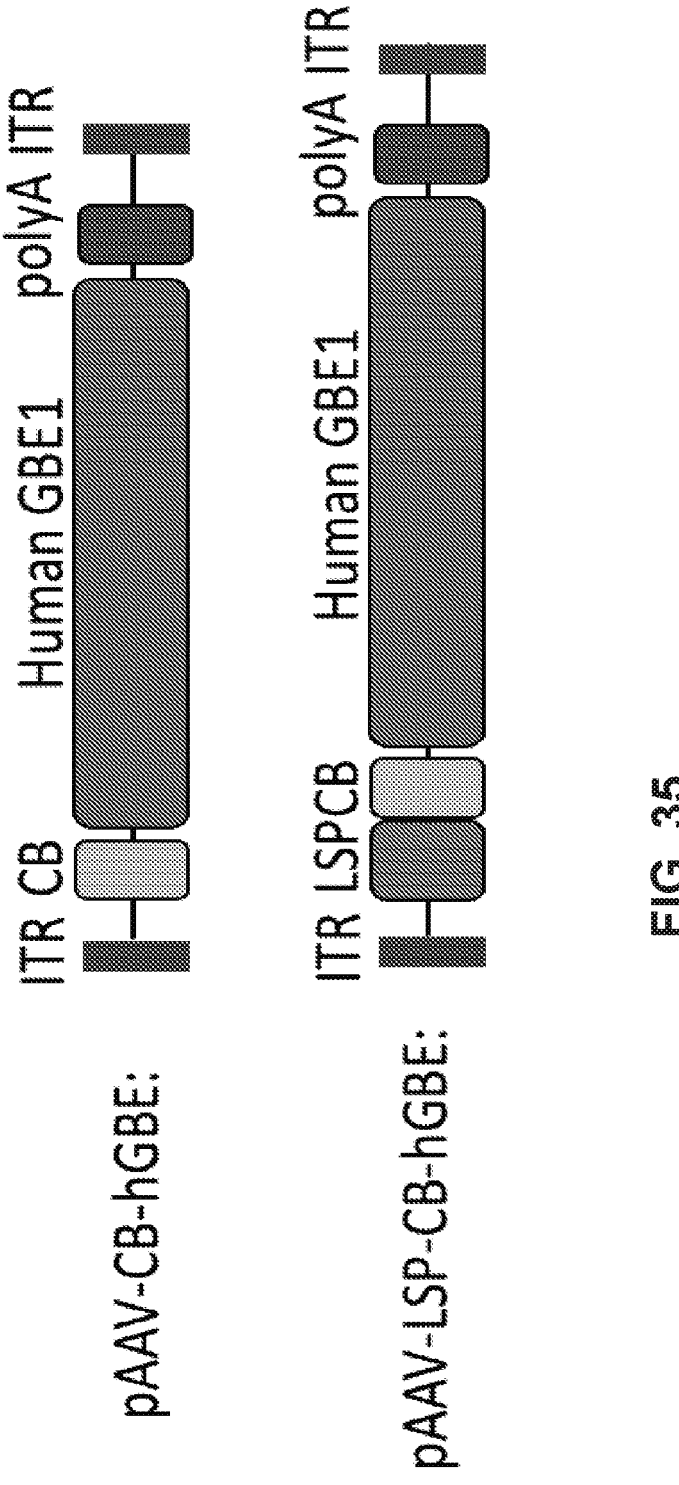
FIG. 35 is a schematic depicting the AAV vectors used in Example 9. The AAV-CB-hGBE vector contains a ubiquitous CMV-enhanced chicken beta-actin hybrid promoter (CB) and the AAV-LSPCB-hGBE vector contains a dual LSP and CB fusion promoter. ITR, inverted repeats; polyA, human growth hormone polyA signal sequence.

Preparation of AAV vector plasmids. The pAAV-CB-hGBE vector, which contains a CMV-enhanced chicken beta-actin hybrid promoter (CB), was described previously (Yi, H. et al. (2017) Hum Gene Ther, 28(3):286-294); to construct the pAAV-LSP-CB-hGBE vector, the XbaI-KpnI fragment containing the LSP-CB dual promoter from the AAV-LSP-CB-Pull promoter was subcloned into the pAAV-CB-hGBE vector, to replace the CB promoter. Both AAV vectors had a human growth hormone polyA signal sequence (FIG. 35).

Expression of GBE in HEK293 cells: Cells plated in 10-cm plates were transfected with 10 µg of plasmid per plate. Cells were harvested 48 hours after transfection. For Western blotting, cells were lysed in RIPA buffer; for GBE activity assay, cells were homogenized in cold water (Yi, H. et al. (2017) Hum Gene Ther, 28(3):286-294).

AAV packaging, purification, and mouse injection: Both AAV vectors were packaged as AAV9 in HEK293T cells using phosphate triple transfection method and purified using iodixanol gradient ultracentrifugation (Yi, H. et al. (2017) Hum Gene Ther, 28(3):286-294). Two-month-old Gbe1$^{ys/ys}$ mice were intravenously injected with the AAV-CB-hGBE or AAV-LSPCB-hGBE at a dose of 2×10$^{13}$ vg/kg (n=3 each group), and liver, heart and muscle (quadriceps) tissues were collected 2 weeks later.

GBE activity assay and Western blotting: All procedures were described previously (Yi, H. et al. (2017) Hum Gene Ther, 28(3):286-294).

Immunohistochemical staining: Fresh liver specimens were fixed in 10% neutral formalin and the paraffin-embedded tissue sections were stained with an anti-CD4 or anti CD8a antibody (Abcam).

Results

Figure 36A:
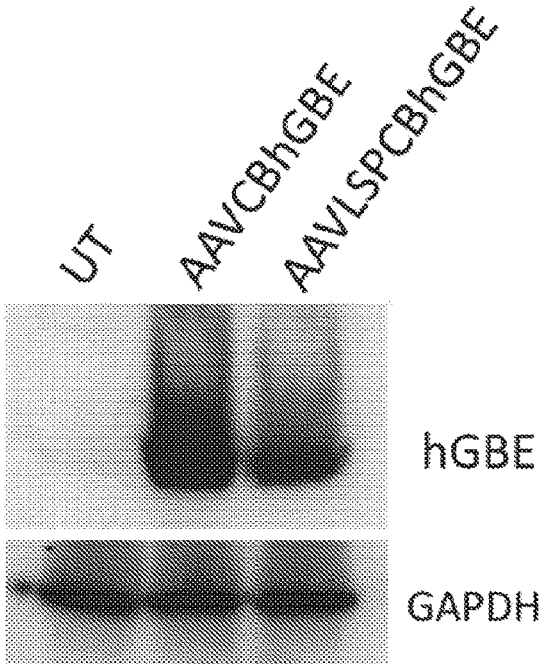
FIG. 36A-FIG. 36B show AAV-CB-hGBE and AAV-LSPCB-hGBE plasmids are over-expressed hGBE in HEK293 cells. Cells in 10-cm plates were transfected with 10 µg plasmid per plate. Cells were harvested 48 h after transfection.
Figure 36B:
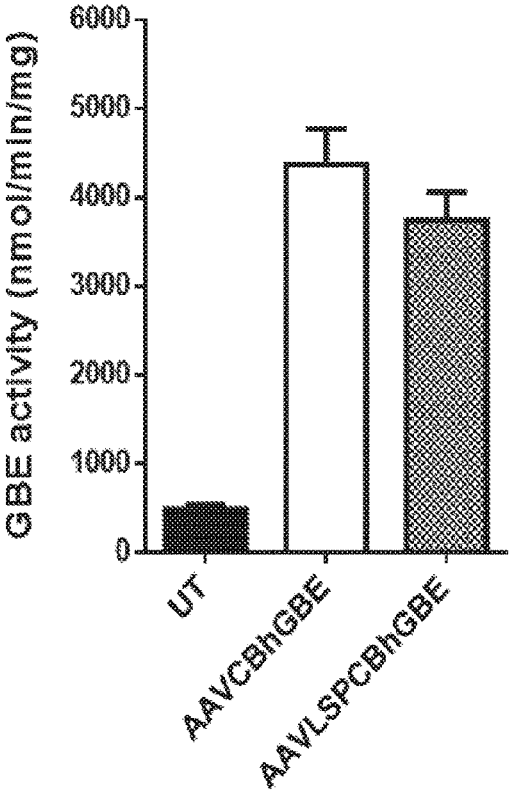

Forty-eight hours after transfection of HEK293 cells, both AAV-CB-hGBE and AAV-LSPCB-hGBE vectors resulted in high-level hGBE expression as determined by the Western blot and GBE activity assays (FIG. 36A and FIG. 36B). This suggests that both CB promoter and LSPCB dual promoter are highly active in the non-liver cells.

Two weeks post AAV injection, the GBE activities were markedly higher in the liver, heart, and skeletal muscle of the AAV-LSPCB-hGBE treated Gbe1$^{ys/ys}$ mice than those of the AAV-CB-hGBE treated mice or the untreated mice (FIG. 37).

Figure 38:
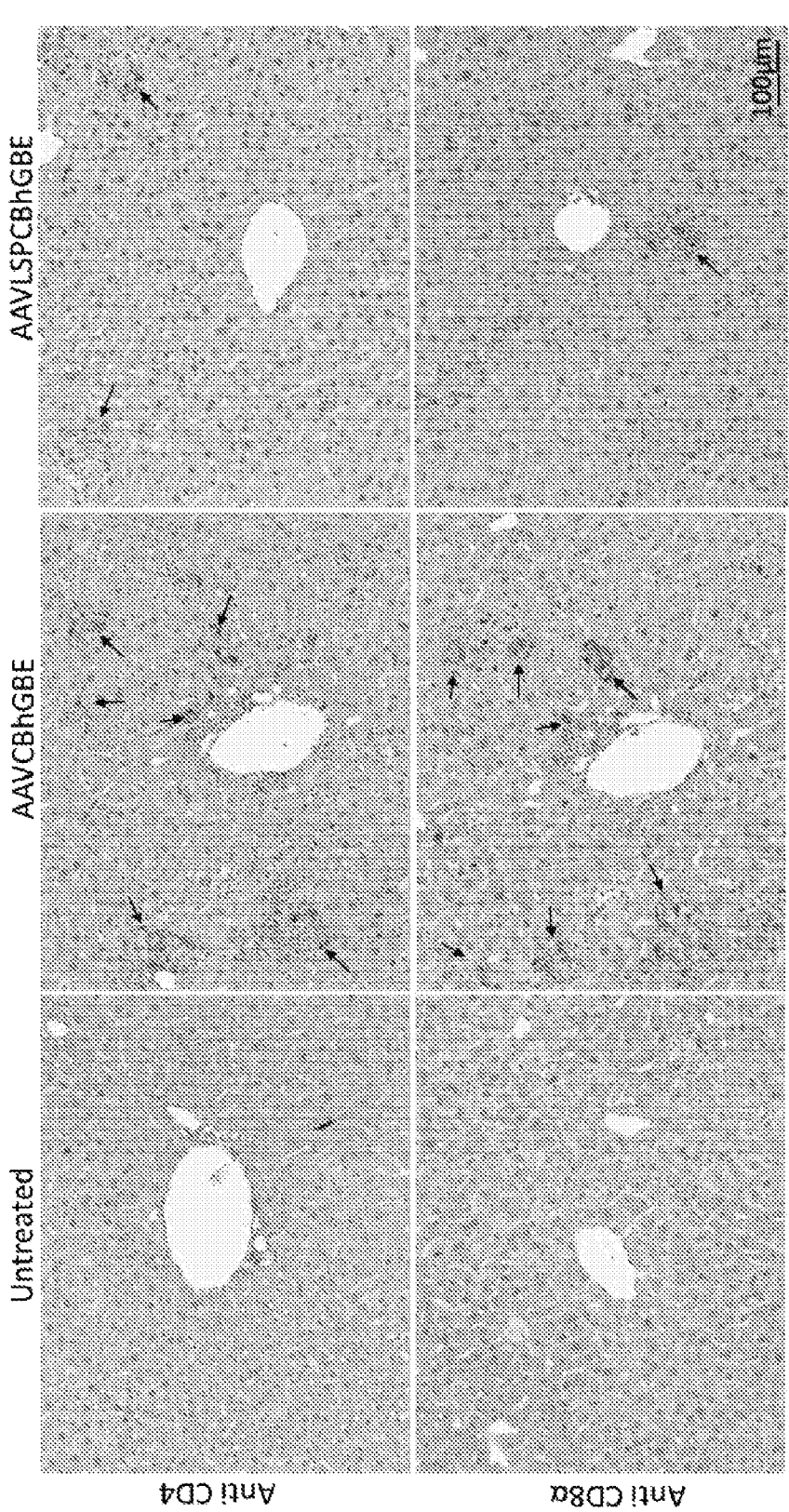
FIG. 38 shows immunohistochemical detection of cellular immune responses in liver of Gbe1$^{ys/ys}$ mice two weeks post AAV administration. AAV-CB-hGBE treatment apparently induced significant cellular immune response as shown by heavily stained CD4$^+$ and CD8$^+$ foci of lymphocytes (arrows), while AAV-LSPCB-hGBE showed apparently fewer CD4$^+$ and CD8$^+$ cells. The images represent at least three mice in each group.

Immunohistochemical stained liver sections revealed that multiple CD4+ and CD8+ lymphocytic infiltrates were present in the AAV-CB-hGBE treated liver but barely detectable in the AAV-LSPCB-hGBE treated liver (FIG. 38).

These results demonstrate that the cellular immunity against hGBE expressed from the CB promoter was associated with waning hGBE levels in the AAV-CB-hGBE treated mice. Our data indicate that the use of the LSPCB dual promoter can prevent transgene-induced immune responses and achieve long-term efficacy of gene therapy in the Gbe1$^{ys/ys}$ mice.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

---

We claim:

1. A nucleic acid molecule, comprising:
a nucleic acid sequence encoding a microbial polypeptide
    for degrading glycogen,
    wherein the nucleic acid sequence is codon-optimized
        for expression in a mammalian cell;
    wherein the microbial polypeptide is a type I Pullula-
        nase from *Bacillus subtilis* or a limit dextrin alpha-
        1,6-glucohydrolase (GlgX) from *Escherichia coli,*
    wherein the type I Pullulanase is encoded by SEQ ID
        NOs: 3 and 8-16 and the GlgX is encoded by SEQ ID
        NOs: 6 and 17-25.

2. The nucleic acid molecule of claim 1, wherein the encoded microbial polypeptide has debranching enzyme activity that can cleave the α-1, 6-glycosidic bonds in glycogen and/or limit dextrin.

3. A vector comprising the nucleic acid molecule of claim 1, wherein the vector comprises a promoter operably linked to the nucleic acid molecule, and wherein the promoter drives the expression of the microbial polypeptide.

4. The vector of claim 3, wherein the promoter operably linked to the nucleic acid molecule comprises (i) a tissue-specific promoter, (ii) a ubiquitous promoter, or (iii) a dual promoter.

5. The vector of claim 4, wherein the dual promoter comprises a liver-specific promoter and a ubiquitous promoter.

6. A vector, comprising a gene expression cassette comprising one or more promoters, the nucleic acid molecule of claim 1, and a polyadenylation sequence.

7. The vector of claim 6, wherein the gene expression cassette contains a nucleotide sequence having about 4.5 kb or less.

8. The vector of claim 3, wherein the vector is an adeno-associated virus (AAV) vector.

9. The vector of claim 4, wherein the tissue-specific promoter comprises a liver-specific promoter, a muscle-specific promoter, a neuron-specific promoter, or a combination of any of the two or more thereof.

10. The vector of claim 5, wherein the liver-specific promoter is an α1-microglobulin/bikunin enhancer/thyroid hormone-binding globulin promoter.

11. The vector of claim 10, wherein the α1-microglobulin/bikunin enhancer/thyroid hormone-binding globulin promoter comprises the sequence set forth in SEQ ID NO:31.

12. The vector of claim 4, wherein the ubiquitous promoter comprises a CMV enhancer/chicken β-actin promoter.

13. The vector of claim 4, wherein the dual promoter comprises an α1-microglobulin/bikunin enhancer/thyroid hormone-binding globulin promoter and a CMV enhancer/beta-actin (CB) promoter.

14. The vector of claim 4, wherein the dual promoter comprises the sequence set forth in SEQ ID NO:30.

\* \* \* \* \*